United States Patent
Söll et al.

(10) Patent No.: US 10,876,142 B2
(45) Date of Patent: *Dec. 29, 2020

(54) COMPOSITIONS AND METHODS FOR MAKING SELENOCYSTEINE CONTAINING POLYPEPTIDES

(71) Applicant: Yale University, New Haven, CT (US)

(72) Inventors: Dieter Söll, Guilford, CT (US);
Caroline Aldag, Mannheim (DE);
Michael Hohn, Scotch Plains, NJ (US);
Takahito Mukai, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 191 days.

This patent is subject to a terminal disclaimer.

(21) Appl. No.: 15/724,678

(22) Filed: Oct. 4, 2017

(65) Prior Publication Data

US 2018/0105854 A1   Apr. 19, 2018

Related U.S. Application Data

(63) Continuation-in-part of application No. 15/202,194, filed on Jul. 5, 2016, now Pat. No. 10,240,158, which is a continuation-in-part of application No. 14/131,382, filed as application No. PCT/US2012/046252 on Jul. 11, 2012, now Pat. No. 9,464,288.

(60) Provisional application No. 61/506,338, filed on Jul. 11, 2011.

(51) Int. Cl.
 C12P 21/00    (2006.01)
 C12N 15/113   (2010.01)
 C12N 15/11    (2006.01)

(52) U.S. Cl.
 CPC .............. *C12P 21/00* (2013.01); *C12N 15/11* (2013.01); *C12N 15/113* (2013.01)

(58) Field of Classification Search
 None
 See application file for complete search history.

(56) References Cited

U.S. PATENT DOCUMENTS

| | | |
|---|---|---|
| 5,700,660 A | 12/1997 | Leonard |
| 6,503,729 B1 | 1/2003 | Bult |
| 7,723,069 B2 | 5/2010 | Soll |
| 9,090,928 B2 | 7/2015 | Park |
| 9,464,288 B2 | 10/2016 | Soll |
| 2003/0082575 A1 | 5/2003 | Schultz |
| 2014/0154744 A1 | 6/2014 | Soll |
| 2017/0002347 A1 | 1/2017 | Soll |

FOREIGN PATENT DOCUMENTS

| | | |
|---|---|---|
| EP | 2246428 | 11/2010 |
| JP | 2008061538 | 3/2008 |
| WO | 0044906 | 8/2000 |
| WO | 2006107813 | 10/2006 |

OTHER PUBLICATIONS

Aldag, et al., "Probing the role of the proximal heme ligand in cytochrome P450cam by recombinant incorporation of selenocysteine", PNAS, 106:5481-6 (2009).
Ambrogelly, et al., "Pyrrolysine is not hardwired for cotranslational insertion at UAG codons", PNAS, 104:3141-6 (2007).
Arner, "Recombinant expression of mammalian selenocysteine-containing thioredoxin reductase and other selenoproteins in *Escherichia coli*", Methods Enzymol., 347:226-35 (2002).
Arner, "Selenoproteins—What unique properties can arise with selenocysteine in place of cysteine", Exp. Cell Res., 316:1296-1303 (2010).
Ataide, et al., "Stationary-phase expression and aminoacylation of a transfer-RNA-like small RNA", EMBO Rep, 6:742-7 (2005).
Bain, et al., "Ribosome-mediated incorporation of a non-standard amino acid into a peptide through expansion of the genetic code", Nature, 356:537-9 (1992).
Beld, et al., "Selenoglutathione: efficient oxidative protein folding by a diselenide", Biochemistry; 46:5382-90 (2007).
Biou, et al., "The 2.9 A crystal structure of T. thermophilus seryl-tRNA synthetase complexed with tRNA(Ser)", Science, 263:1404-10 (1994).
Bock, et al., "Selenocysteine in: The Aminoacyl-tRNA Synthetases", Ibba, M., Francklyn, C. and Cusack, S., Eds.,, pp. 320-327, Landes Bioscience, Georgetown, TX (2005).
Borrel, et al., "Unique characteristics of the pyrrolysine system in the 7th order of methanogens: implications for the evolution of a genetic code expansion cassette", Archaea, 374146 (2014).
Bröcker, et al., "Recoding the genetic code with selenocysteine", Angew. Chem. Int. Ed. Engl., 53, 319-23 (2014).
Campbell, et al., "UGA is an additional glycine codon in uncultured SR1 bacteria from the human microbiota", PNAS, 110:5540-5 (2013).
Cooley, et al., "Post-transcriptional nucleotide addition is responsible for the formation of the 5' terminus of histidine tRNA", PNAS, 79:6475-9 (1982).
Cravedi, et al., "Evolution of the Selenoproteome in Helicobacter pylori and Epsilonproteobacteria", Genome Biol Evol, 7:2692-2704 (2015).

(Continued)

*Primary Examiner* — Kagnew H Gebreyesus
(74) *Attorney, Agent, or Firm* — Pabst Patent Group LLP

(57) ABSTRACT

Non-naturally occurring tRNA$^{Sec}$ and methods of using them for recombinant expression of proteins engineered to include one or more selenocysteine residues are disclosed. The non-naturally occurring tRNA$^{Sec}$ can be used for recombinant manufacture of selenocysteine containing polypeptides encoded by mRNA without the requirement of an SECIS element. In some embodiments, selenocysteine containing polypeptides are manufactured by co-expressing a non-naturally occurring tRNA$^{Sec}$ a recombinant expression system, such as *E. coli*, with SerRS, EF-Tu, SelA, or PSTK and SepSecS, and an mRNA with at least one codon that recognizes the anticodon of the non-naturally occurring tRNA$^{Sec}$.

22 Claims, 31 Drawing Sheets

Specification includes a Sequence Listing.

(56) References Cited

OTHER PUBLICATIONS

Fan, et al., "Efficient Expression of Glutathione Peroxidase with Chimeric tRNA in Amber-less *Escherichia coli*", ACS Synth Biol., 7:249-57 (2018).
Fan, et al., "Manipulating Cellular Activities Using an Ultrasound-Chemical Hybrid Tool", ACS Synth Biol. 6L2021-7 (2017).
Fischer, et al., "The pathway to GTPase activation of elongation factor SelB on the ribosome", Nature, 540:80-5 (2016).
Gupta, et al., "Reconstitution of selenocysteine incorporation reveals intrinsic regulation by SECIS elements", J. Mol. Biol., 425:2415-22 (2013).
Hamashima, et al., "Alternative genetic code for amino acids and transfer RNA revisited", Biomol Concepts, 4:309-18 (2013).
Hamashima, et al., "Expansion of Noncanonical V-Arm-Containing tRNAs in Eukaryotes", Mol Biol Evol, 33:530-40 (2016).
Haruna, et al., "Engineering the elongation factor Tu for efficient selenoprotein synthesis", Nucleic Acids Res, 42:9976-83 (2014).
Himeno, et al., "Conversion of aminoacylation specificity from tRNA(Tyr) to tRNA(Ser) in vitro", Nucleic Acids Res, 18:6815-9 (1990).
Hou, et al., "A simple structural feature is a major determinant of the identity of a transfer RNA", Nature, 333:140-5 (1988).
Hubert, et al., "The 9/4 secondary structure of eukaryotic selenocysteine tRNA: more pieces of evidence", RNA, 4:1029-33 (1998).
Isaacs, et al., "Precise manipulation of chromosomes in vivo enables genome-wide codon replacement", Science, 333:348-53 (2011).
Itoh, et al., "Crystal structure of human selenocysteine tRNA", Nucleic Acids Res, 37:6259-6268 (2009).
Itoh, et al., "Decameric SelA'tRNA(Sec) ring structure reveals mechanism of bacterial selenocysteine formation", Science, 340:75-78 (2013b).
Itoh, et al., "Tertiary structure of bacterial selenocysteine tRNA", Nucleic Acids Res, 41:6729-38 (2013).
Ivanova, et al., "Stop codon reassignments in the wild",Science, 344:909-13 (2014).
Jewett, et al., "An integrated cell-free metabolic platform for protein production and synthetic biology", Mol. Syst. Biol., 4:220 (2008).
Kang, et al., "Ribosomal synthesis of nonstandard peptides", Biochem. Cell Biol., 86:92-99 (2008).
Katz, et al., "Non-canonical roles of tRNAs and tRNA mimics in bacterial cell biology", Mol Microbiol, 101(4):545-58 (2016).
Kim, et al., "Selenium utilization in thioredoxin and catalytic advantage provided by selenocysteine", Biochem Biophys Res Commun, 461:648-52 (2015).
Komatsoulis, et al., "Recognition of tRNA(Cys) by *Escherichia coli* cysteinyl-tRNA synthetase", Biochemistry, 32:7435-44 (1993).
Kumar, et al., "Selenite is a substrate for calf thymus thioredoxin reductase and thioredoxin and elicits a large non-stoichiometric oxidation of NADPH in the presence of oxygen.", Eur J Biochem, 207:435-9 (1992).
Lacourciere, et al., "Direct detection of potential selenium delivery proteins by using an *Escherichia coli* strain unable to incorporate selenium from selenite into proteins", PNAS, 99:9150-3 (2002).
Lajoie, et al., "Genomically recoded organisms expand biological functions", Science 342:357-60 (2013).
Larkin, et al., "Clustal W and Clustal X version 2.0.", Bioinformatics, 23:2947-8 (2007).
Laslett, et al., "ARAGORN, a program to detect tRNA genes and tmRNA genes in nucleotide sequences", Nucleic Acids Res, 32:11-16 (2004).
Liu, et al., "Adaptation to tRNA acceptor stem structure by flexible adjustment in the catalytic domain of class I tRNA synthetases", RNA, 18:213-21 (2012).
Liu, et al., "Adding new chemistries to the genetic code", Annu. Rev, Biochem., 79:413-44 (2010).
Llado, et al., "*Silvibacterium bohemicum* gen. nov. sp. nov., an acidobacterium isolated from coniferous soil in the Bohemian Forest National Park", Syst Appl Microbiol, 39:14-19 (2016).
Malyshev, et al., "A semi-synthetic organism with an expanded genetic alphabet", Nature, 509:385-8 (2014).

Marck, et al., "tRNomics: analysis of tRNA genes from 50 genomes of Eukarya, Archaea, and Bacteria reveals anticodon-sparing strategies and domain-specific features", RNA, 8:1189-1232 (2002).
Markowitz, et al., "IMG/M 4 version of the integrated metagenome comparative analysis system", Nucleic Acids Res, 42:D568-573 (2014).
Masson and Miller, "Expression of synthetic suppressor tRNA genes under the control of a synthetic promoter", Gene, 47:179-83 (1986).
McClain, et al., "Changing the identity of a tRNA by introducing a G-U wobble pair near the 3' acceptor end", Science, 240:793-6 (1988).
Mehta, et al., "Efficiency of mammalian selenocysteine incorporation", J. Biol. Chem., 279:37852-9 (2004).
Meinnel, et al., "Fast purification of a functional elongator tRNAmet expressed from a synthetic gene in vivo", Nucleic Acids Res., 16:8095-6 (1988).
Miller, et al., "A synthetic tRNA for EF-Tu mediated selenocysteine incorporation in vivo and in vitro," FEBS Letters, 589:2194-2199 (2015).
Mizutani, et al., "The dual identities of mammalian tRNA(Sec) for SerRS and selenocysteine synthase", Mol Biol Rep, 25:211-6 (1998).
Möhlhausen, et al., "A novel nuclear genetic code alteration in yeasts and the evolution of codon reassignment in eukaryotes", Genome Res, 26:945-955 (2016).
Mukai, et al., "Facile Recoding of Selenocysteine in Nature", Angew Chem Int Ed Engl, 55: 5337-41 (2016).
Mukai, et al., "RNA-Dependent Cysteine Biosynthesis in Bacteria and Archaea", MBio, 8, e00561-00517 (2017B).
Mukai, et al., "Transfer RNAs with novel cloverleaf structures," Nucleic Acids Research, 45(5):2776-2785 (2017).
Mustoe, et al., "Noncanonical secondary structure stabilizes mitochondrial tRNA(Ser(UCN)) by reducing the entropic cost of tertiary folding", J Am Chem Soc, 137:3592-9 (2015).
Naganuma, et al., "The selective tRNA aminoacylation mechanism based on a single G•U pair", Nature, 510:507-11 (2014).
Nozawa, et al., "Pyrrolysyl-tRNA synthetase-tRNA(Pyl) structure reveals the molecular basis of orthogonality", Nature, 457:1163-7 (2009).
Orellana, et al., "The additional guanylate at the 5' terminus of *Escherichia coli* tRNAHis is the result of unusual processing by RNase P.", Mol Cell Biol, 6:525-9 (1986).
Paleskava, et al., "Thermodynamic and kinetic framework of selenocysteyl-tRNASec recognition by elongation factor SelB", J. Biol. Chem., 285:3014-20 (2010).
Pallanck, et al., "The anticodon and discriminator base are major determinants of cysteine tRNA identity in vivo", J Biol Chem, 267:7221-3 (1992).
Santesmasses, et al., "Computational identification of the selenocysteine tRNA (tRNASec) in genomes", PLoS Comput Biol, 13, e1005383 (2017).
Seebeck, et al., "Artificial lantipeptides from in vitro translations", Chem. Commun. (Camb.), 47:6141-3 (2011).
Silva, et al., "Formation of a Ternary Complex for Selenocysteine Biosynthesis in Bacteria", J Biol Chem, 290:29178-29188 (2015).
Sprinzl, et al., "Compilation of tRNA sequences and sequences of tRNA genes", Nucleic Acids Research, 26(1):148-153 (1998).
Suzuki, et al., "The 'polysemous' codon—a codon with multiple amino acid assignment caused by dual specificity of tRNA identity", EMBO J, 16:1122-34 (1997).
Swart, et al., "Genetic Codes with No Dedicated Stop Codon: Context-Dependent Translation Termination", Cell, 166:691-702 (2016).
Tamura, et al., "Selenite reduction by the thioredoxin system: kinetics and identification of protein-bound selenide",Biosci Biotechnol Biochem, 75:1184-7 (2011).
Thyer, et al., "Evolving tRNA(Sec) for efficient canonical incorporation of selenocysteine", J Am Chem Soc, 137:46-49 (2015).
Tisné, et al., "NMR and biochemical characterization of recombinant human tRNA(Lys)3 expressed in *Escherichia coli*: identification of posttranscriptional nucleotide modifications required for efficient initiation of HIV-1 reverse transcription", RNA, 6:1403-1412 (2000).

(56) References Cited

OTHER PUBLICATIONS

Turanov, et al., "Genetic code supports targeted insertion of two amino acids by one codon", Science, 323:259-261 (2009).
Wu, et al., "The long extra arms of human tRNA((Ser)Sec) and tRNA(Ser) function as major identify elements for serylation in an orientation-dependent, but not sequence-specific manner", Nucleic Acids Res, 21:5589-5594 (1993).
Xu, et al., "Biosynthesis of selenocysteine on its tRNA in eukaryotes", PLoS Biol, 5, e4 (2007).
Xu, et al., "Wobble decoding by the *Escherichia coli* selenocysteine insertion machinery", Nucleic Acids Res., 41:9800-9811 (2013).
Aldag, et al., "Rewiring translation for elongation-factor Tu-dependent selenocysteine incorporation", Angew Chem Int Ed., 52:1441-45 (2013).
Alessi, et al., "dentification of the sites in MAP kinase kinase-1 phosphorylated by p74raf-1", EMBO J., 13:1610-9 (1994).
Altschul et al., "Basic local alignment search tool", J. Mol. Biol., 215(3):403-410 (1990).
Ambrogelly, et al., "Cys-tRNACys formation and cysteine biosynthesis in methanogenic archaea: two faces of the same problem?", Cell. Mol. LifeSci., 61:2437-45 (2004).
Arslan, et al., "Structurally modified firefly luciferase, Effects of amino acid substitution at position 286", Journal of the American Chemical Society, 119(45):10877-10887 (1997).
Bajaj, et al., "Mutagenesis-based definitions and probes of residue burial in proteins", PNAS, 102(45):16221-6 (2005).
Balch, et al., "Transport of coenzyme M (2-mercaptoethanesulfonic acid) in Methanobacterium ruminantium", J. Bacteriol, 137:264 (1979).
Basurko, et al., Phosphoserine aminotransferase, the second step-catalyzing , enzyme for serine biosynthesis\, IUBMB Life, 48:525-9 (1999).
Bentin, et al. "Photoreactive bicyclic amino acids as substrates for mutant *Escherichia coli* phenylalanyl-tRNA synthetases", J. Biol. Chem. 279:19839-45 (2004).
Bernard, et al., "Positive-selection vectors using the F plasmid ccdB killer gene", Gene, 148:71-4 (1994).
Bilokapic, et al., "The unusual methanogenic seryl-tRNA synthetase recognizes tRNASer species from all three kingdoms of life", Eur. Journ. Biochemistry, 271(4):694-702 (2004).
Blight, et al., "Direct charging of tRNA(CUA) with pyrrolysine in vitro and in vivo", Nature, 431(7006):333-5 (2004).
Boyington, et al., "Crystal structure of formate dehydrogenase H: catalysis involving Mo, molybdopterin, selenocysteine, and an Fe4S4 cluster", Science, 275:1305-08 (1997).
Buchner, et al., "A method for increasing the yield of properly folded recombinant fusion proteins: single-chain Immunotoxins from renaturation of bacterial inclusion bodies", Anal. Biochem., 205: 263-270 (1992).
Bunjun, et al., "A dual-specificity aminoacyl-tRNA synthetase in the deep-rooted eukaryote Giardia lamblia", PNAS, 97:12997-13002 (2000).
Calendar and Berg, "Purification and physical characterization of tyrosyl ribonucleic acid synthetases from *Escherichia coli* and Bacillus subtilis" , Biochemistry, 5(5):1681-90 (1966a).
Calendar and Berg, "The catalytic properties of tyrosyl ribonucleic acid synthetases from *Escherichia coli* and Bacillus subtilis" , Biochemistry, 5(5):1690-5 (1966b).
Carlson, et al., "Transfer RNAs that insert selenocysteine", Methods Enzymol, 347:24-39 (2002).
Chatterji and Pachter, "Large multiple organism gene finding by collapsed Gibbs sampling", J Comput Biol., 12(6):599-608 (2005).
Dale, et al., "The affinity of elongation factor Tu for an aminoacyl-tRNA is modulated by the esterified amino acid", Biochemistry 43:6159-66 (2004).
Daly and Hearn, "Expression of heterologous proteins in Pichia pastoris: a useful experimental tool in protein engineering and production", J. Mol. Recognit., 18(2):119-38 (2005).

Das and Vothknecht, "Phenylalanyl-tRNA synthetase from the archaeon Methanobacterium thermoautotrophicum is an (alphabeta)2 heterotetrameric protein", Biochimie, 81(11):1037-9 (1999).
Datsenko, et al., "One-step inactivation of chromosomal genes in *Escherichia coli* K-12 using PCR products", PNAS, 97:6640-5 (2000).
Debinski, et al., "A wide range of human cancers express interleukin 4 (IL4) receptors that can be targeted with chimeric toxin composed of IL4 and Pseudomonas exotoxin", J. Biol. Chem., 268:14065-14070 (1993).
Diamond, et al., "Dietary selenium affects methylation of the wobble nucleoside in the anticodon of selenocysteine tRNA ([Ser]Sec).", J. Biol. Chem., 268:14215-23 (1993).
Eargle, et al., "Dynamics of Recognition between tRNA and elongation factor Tu", J Mol Biol., 377(5):1382-1405 (2008).
Ellman, et al., "Biosynthetic method for introducing unnatural amino acids site-specifically into proteins", Methods Enzymol., 202:301-36 (1991).
Engelhard, et al., "The insect tracheal system: a conduit for the systemic spread of Autographa californica M nuclear polyhedrosis virus", Proc. Natl. Acad. Sci. USA, 91:3224-3227 (1994).
Fabrega, et al., "An aminoacyl tRNA synthetase whose sequence fits into neither of the two known classes", Nature, 411:110-4 (2001).
Fleer, et al., "High-level secretion of correctly processed recombinant human interleukin-1 beta in Kluyveromyces lactis", Gene, 107:285-95 (1991).
Florens, et al., A proteomic view of the Plasmodium falciparum life cycle Nature, 419, 520-6 (2002).
Fromm, et al., "Expression of genes transferred into monocot and dicot plant cells by electroporation" Proc. Natl. Acad. Sci. USA, 82, 5824-8 (1985).
Fukunaga and Yokoyama, "Structural insights into the first step of RNA-dependent cysteine biosynthesis in archaea", Nat Struct Mol Biol., 14:272-9 (2007).
Giometti, et al., "Global analysis of a "simple" proteome: Methanococcus jannaschii", J. Chromatogr. B Anal. Technol. Biomed. Life Sci., 782(1-2):227-43 (2002).
Harrington, et al., "Formation of de novo centromeres and construction of first-generation human artificial microchromosomes", Nat Genet., 15:345-355 (1997).
Hitzeman, et al., "Isolation and characterization of the yeast 3-phosphoglycerokinase gene (PGK) by an immunological screening technique", J. Biol. Chem., 255:12073-80 (1980).
Hofer, et al., "An engineered selenocysteine defines a unique class of antibody derivatives",PNAS, 105(34):12451-6 (2008).
Hohn, et al., "Emergence of the universal genetic code imprinted in an RNA record", PNAS,103(48):18095-100 (2006).
Hohsaka, et al., "Five-base codons for incorporation of nonnatural amino acids into proteins", Nucleic Acids Res., 29:3646-51 (2001).
Holland and Holland, "Isolation and identification of yeast messenger ribonucleic acids coding for enolase, glyceraldehyde-3-phosphate dehydrogenase, and phosphoglycerate kinase", Biochem., 17:4900-7 (1978).
Ibba, et al., "The adaptor hypothesis revisited", Trends Biochem. Sci., 25:311-6 (2000).
Jacob, et al., "Sulfur and selenium: the role of oxidation state in protein structure and function", Angew. Chem, Int. Ed. Engl., 42:4742-58 (2003).
Jansen, et al., "Drag&Drop cloning in yeast", Gene, 344:43-51 (2005).
Johansson, et al., "Selenocysteine in proteins—properties and biotechnological use", Biochim Biophys Acta., 1726:1-13 (2005).
Kamtekar, et al., "Toward understanding phosphoseryl-tRNACys formation: the crystal structure of Methanococcus maripaludis phosphoseryl-tRNA synthetase", PNAS, 104(8):2620-5 (2007).
Karlin and Altschul, "Applications and statistics for multiple high-scoring segments in molecular sequences", Proc. Nat'l. Acad. Sci. USA, 90:5873-5787 (1993).
Kim, et al., "Sequence Divergence of Seryl-tRNA Synthetases in Archaea", J. Bacteriol., 180:6446-49 (1998).
Klein, et al., "High velocity microprojectiles for delivering nucleic acids into living cells", Nature, 327:70-73 (1987).

(56) References Cited

OTHER PUBLICATIONS

Kreitman and Pastan, "Purification and characterization of IL6-PE4E, a recombinant fusion of interleukin 6 with Pseudomonas exotoxin", Bioconjug. Chem., 4:581-585 (1993).
Kryukov, et al, "Characterization of mammalian selenoproteomes", Science, 300:1439-43 (2003).
LaRiviere, et al., "Uniform binding of aminoacyl-tRNAs to elongation factor Tu by thermodynamic compensation", Science, 294(5540):165-8 (2001).
Lee, et al., "The discriminator base influences RNA structure at the end of the acceptor stem and possibly its interaction with proteins", PNAS, 90(15):7149-52 (1993).
Li, et al., "Cysteinyl-tRNA formation: the last puzzle of aminoacyl-tRNA synthesis", FEBS Lett., 462:302 (1999).
Li, et al., "Usage of an intronic promoter for stable gene expression in *Saccharomyces cerevisiae*", Lett Appl Microbial., 40(5):347-52 (2005).
Ling, et al., "Phenylalanyl-tRNA synthetase editing defects result in efficient mistranslation of phenylalanine codons as tyrosine", RNA.,13(11):1881-6 (2007b).
Ling, et al., "Pathogenic mechanism of a human mitochondrial tRNAPhe mutation associated with myoclonic epilepsy with ragged red fibers syndrome", PNAS, 104 (39):15299-304 (2007a).
Lipman, et al., "Synthesis of cysteinyl-tRNA(Cys) by a genome that lacks the normal cysteine-tRNA synthetase" Biochemistry 39:7792-8 (2000).
Liu, et al., "Catalytic mechanism of Sep-tRNA:Cys-tRNA synthase: sulfur transfer is mediated by disulfide and persulfide", J. Biol, Chem., 287:5426-33 (2012).
Logan and Shenk, "Adenovirus tripartite leader sequence enhances translation of mRNAs late after infection" Proc. Natl. Acad. Sci. USA, 81:3655-3659 (1984).
Maccoss, et al., "Probability-based validation of protein identifications using a modified SEQUEST algorithm", Anal. Chem., 74:5593-9 (2002).
Margelevicius and Venclovas, "PSI-BLAST-ISS: an intermediate sequence search tool for estimation of the position-specific alignment reliability", BMC Bioinformatics, 6:185 (2005).
Min, et al., "Transfer RNA-dependent amino acid biosynthesis: an essential route to asparagine formation", Proc. Natl. Acad. Sci. U.S.A., 99:2678 (2002).
Mino and Ishikawa, "A novel O-phospho-L-serine sulfhydrylation reaction catalyzed by O-acetylserine sulfhydrylase from Aeropyrum pernix K1", FEBS Lett., 551:133-8 (2003).
Mizutani, et al., "Possible incorporation of phosphoserine into globin readthrough protein via bovine opal suppressor phosphoseryl-tRNA", FEBS Lett., 207(1):162-6 (1986).
Moore, "On the Determination of Cystine as Cysteic Acid", J. Biol. Chem., 238:235-7 (1963).
Needleman and Wunsch, "A general method applicable to the search for similarities in the amino acid sequence of two proteins", J. Mol. Biol., 4(3):443-53 (1970).
Nissen, et al., "Crystal structure of the ternary complex of Phe-tRNAPhe, EF-Tu, and a GTP analog", Science, 270(5241)1464-72 (1995).
Normanly, et al., "Changing the identity of a transfer RNA", Nature, 321:213-9 (1986).
Palioura, et al., "The human SepSecS-tRNASec complex reveals the mechanism of selenocysteine formation", Science, 325:321-5 (2009).
Park, et al., "Design and evolution of new catalytic activity with an existing protein scaffold", Science 311(5760):535-8 (2006).
Park, et al., "Expanding the genetic code of *Escherichia coli* with phasphoserine", Science, 33(6046):1151-4 (2011).
Pearson and Lipman, "Improved tools for biological sequence comparison", Proc. Nat'l. Acad. Sci. USA, 85:2444-8 (1988).
Polycarpo, et al., "Activation of the pyrrolysine suppressor tRNA requires formation of a ternary complex with class I and class II lysyl-tRNA synthetases", Mol.Cell, 12:287-94 (2003).
Polycarpo, et al., "An aminoacyl-tRNA synthetase that specifically activates pyrrolysine", Proc. Natl. Acad. Sci. U.S.A., 101;12450 (2004).
Raffa, "Diselenium, instead of disulfide, bonded analogs of conotoxins: novel synthesis and pharmacotherapeutic potential", Life Sci., 87(15-16):451-6 (2010).
Riaz and Mehmood, "Selenium in Human Health and Disease: A Review", JPMI, 26(02):120-33 (2012).
Rothman, et al., "Caged phosphoproteins", J Am Chem Soc., 127(3):846-7 (2005).
Ruan, et al., "Cysteinyl-tRNA(Cys) formation in Methanocaldococcus jannaschii: the mechanism is still unknown", J. Bacteriol. 186, 8-14 (2004).
Rudinger, et al., "Antideterminants present in minihelix(Sec) hinder its recognition by prokaryotic elongation factor Tu", EMBO J., 15(3):650-57 (1996).
Sadygov and Yates, A hypergeometric probability model for protein identification and validation using tandem mass spectral data and protein sequence databases\, Anal. Chem., 75:3792-8 (2003).
Sandig, et al., "Gene transfer into hepatocytes and human liver tissue by baculovirus vectors", Hum. Gene Ther., 7:1937-1945 (1996).
Sauerwald, et al., "RNA-dependent cysteine biosynthesis in archaea", Science, 307(5717):1969-72 (2005).
Schon, et al., "The selenocysteine-inserting opal suppressor serine tRNA from *E. coli* is highly unusual in structure and modification", Nucleic Acids Res., 17(18):7159-65 (1989).
Schrader, et al. "Understanding the sequence of tRNA binding to EF-TU using tRNA mutagenesis", J Mol Biol, 386(5):1255-64 (2009).
Sebolt-Leopold, et al., "Targeting the mitogen-activated protein kinase cascade to treat cancer", Nat Rev Cancer, 4:937-47 (2004).
Shchedrina, et al., "Identification and characterization of a selenoprotein family containing a diselenide bond in a redox motif", PNAS, 104(35):13919-24 (2007).
Sherrer, et al., "Characterization and evolutionary history of an archaeal kinase involved in selenocysteinyl-tRNA formation", Nucleic Acids Res., 36(4): 1247-59 (2008b).
Sherrer, et al., "Divergence of selenocysteine tRNA recognition by archaeal and eukaryotic O-phosphoseryl-tRNASec kinase", Nucleic Acids Res, 36:1871-80 (2008a).
Smith and Waterman, "Comparison of Biosequences", Adv. Appl. Math., 2:482-89 (1981).
Stathopoulos, et al., "Cysteinyl-tRNA synthetase is not essential for viability of the archaeon Methanococcus maripaludis", Proc. Natl. Acad. Sci. U.S.A., 98:14292-7 (2001).
Stathopoulos, et al., "One polypeptide with two aminoacyl-tRNA synthetase activities", Science, 287(5452):479-82 (2000).
Studier, "Protein production by auto-induction in high density shaking cultures", Protein Expr Purif.,41(1):207-34 (2005).
Tabb, et al., "DTASelect and Contrast: tools for assembling and comparing protein identifications from shotgun proteomics", J. Proteome Res., 1:21-6 (2002).
Takamatsu, et al., "Expression of bacterial chloramphenicol acetyltransferase gene in tobacco plants mediated by TMV-RNA", EMBO J., 6:307-311 (1987).
Tapiero, et al., "The antioxidant role of selenium and seleno-compounds", Biomed Pharmacother., 57:134-44 (2003).
Tomari, et al., "The role of tightly bound ATP in *Escherichia coli* tRNA nucleotidyltransferase", Genes Cells, 5:68998 (2000).
Tumbula, et al., "Transformation of Methanococcus maripaludis and identification of a PstI-like restriction system", FEMS Microbiol. Lett., 121:309-14 (1994).
Van Heeke and Schuster, "Expression of human asparagine synthetase in *Escherichia coli*", J. Biol. Chem., 264:5503-5509 (1989).
Varshney, et al., "Direct analysis of aminoacylation levels of tRNAs in vivo. Application to studying recognition of *Escherichia coli* initiator tRNA mutants by glutaminyl-tRNA synthetase", J. Biol. Chem. 266:24712 (1991).
Wang, et al., "Expanding the genetic code of *Escherichia coli*", Science, 292(5516):498-500 (2001).

(56) References Cited

OTHER PUBLICATIONS

Wanner, "Molecular genetic studies of a 10.9-kb operon in *Escherichia coli* for phosphonate uptake and biodegradation", FEMS Microbiol Lett., 79(1-):133-9 (1992).
White, "The biosynthesis of cysteine and homocysteine in Methanococcus jannaschii", Biochim. Biophys. Acta, 1624:46-53 (2003).
Whitman, et al., "Isolation and characterization of 22 mesophillic methanococci", Syst. Appl. Microbiol. 7:235-40 (1986).
Wolfson and Uhlenbeck, "Modulation of tRNAAla identity by inorganic pyrophosphatase", Proc. Natl. Acad. Sci. U.S.A., 99:5965-70 (2002).
Wu and Gross, "The length and the secondary structure of the D-stem of human selenocysteine tRNA are the major identity determinants for serine phosphorylation", EMBO J., 13:241-8 (1994).
Xu, et al., "New developments in selenium biochemistry: selenocysteine biosynthesis in eukaryotes and archaea", Biol TraceElem Res., 119(3):234-41 (2007).
Yoshizawa and Böck, "The many levels of control on bacterial selenoprotein synthesis", Biochim Biophys Acta., 1790:1404-14 (2009).
Yuan, et al., "Distinct genetic code expansion strategies for selenocysteine and pyrrolysine are reflected in different aminoacyl-tRNA formation systems", FEBS Lett., 584(2):342-9 (2010).
Yuan, et al., "RNA-dependent conversion of phosphoserine forms selenocysteine in eukaryotes and archaea", PNAS, 103:18923-7 (2006).
Zhang and Hou, "Synthesis of cysteinyl-tRNACys by a prolyl-tRNA synthetase", RNA Biol., 1:35-41 (2004).
Zhang, et al., "Aminoacylation of tRNA with phosphoserine for synthesis of cysteinyl-tRNA(Cys", Nat. Struct Mol. Biol., 15(5):507-14 (2008).
Zhu, et al., Shotgun Proteomics of Methanococcus jannaschii and insights into methanogenesis\, J. Proteome Res., 3:538 (2004).

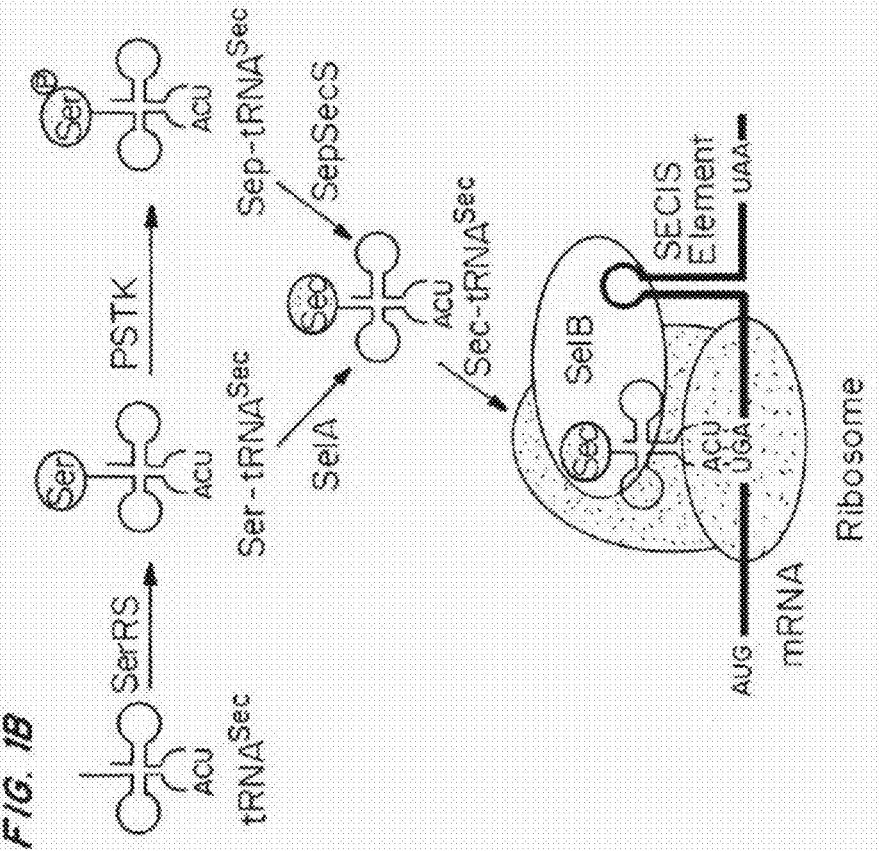
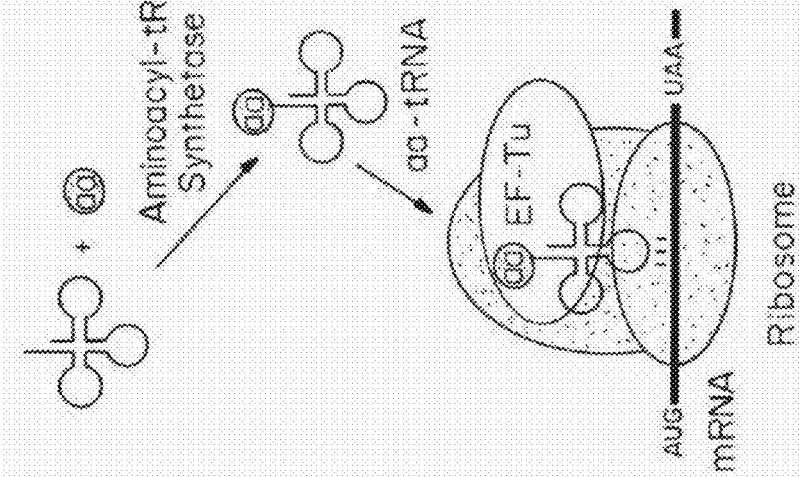
FIG. 1A
FIG. 1B

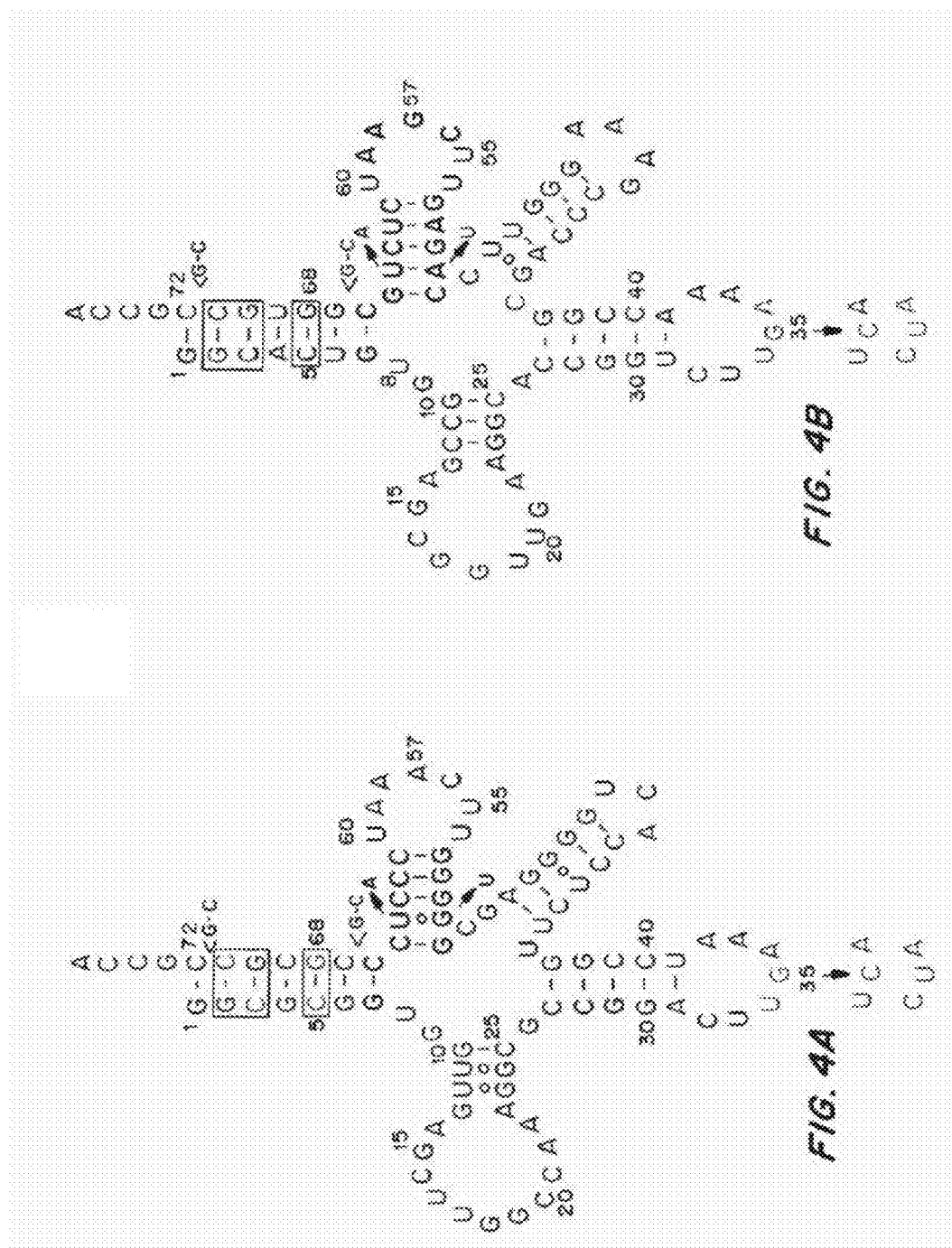

1: vector
2: 8/4-1 (CUA)
3: 9/3-2
4: 9/3-1 (CUA)
5: 8/4-3
6: 8/4-4
7: 8/4-5
8: 8/4-6
9: 8/4-7
10: 8/4-8 allo-tRNA$^{UTu}$

| pTrc99A | vector | As SelA | Tb PSTK | Hs PSTK |
|---|---|---|---|---|
| pSecUAG-A | + | + | + | + |
| FDH_H 8 | Am | Am | Am | Am |
| FDH_H 11 | Am | Am | Am | Am |
| FDH_H 140 | Am | Am | Am | Am |
| IPTG 10 μM | ● | ● | ○ | ● |
| IPTG 100 μM | ● | | | ● |

FIG. 12B

| pTrc99A | vector | Tb PSTK + SepCysS | Hs PSTK + SepCysS |
|---|---|---|---|
| allo-tRNA | + | + | + |
| FDH_H 140 | Am | Am | Am |
| IPTG 10 μM | | ○ | ● |

FIG. 12C

| pSecUAG-A | + | − | − | + | − | − |
|---|---|---|---|---|---|---|
| pSecUAG-A + AsselD | − | + | − | − | + | − |
| pSecUAG-AD | − | − | + | − | − | + |
| FDH<sub>H</sub> 8 | Am | Am | Am | Am | Am | Am |
| 11 | Am | Am | Am | Am | Am | Am |
| 15 | Am | Am | Am | Am | Am | Am |
| 42 | Cys | Cys | Cys | Am | Am | Am |
| 140 | Am | Am | Am | Am | Am | Am |

FIG. 13A

| pSecUAG-A | + | − | + | − |
|---|---|---|---|---|
| pSecUAG-A + AsselD | − | + | − | + |
| FDH<sub>H</sub> 8 | Am | Am | Am | Am |
| 11 | Am | Am | Am | Am |
| 15 | Am | Am | Am | Am |
| 42 | Cys | Cys | Am | Am |
| 140 | Am | Am | Am | Am |

FIG. 13B pSecUAG-AD

| FDH<sub>H</sub> 8 | Cys | Am | Ser | Cys | Cys | Cys | Ser | Am | Am | Am |
|---|---|---|---|---|---|---|---|---|---|---|
| 11 | Cys | Am | Cys | Ser | Cys | Cys | Am | Ser | Am | Am |
| 15 | Cys | Am | Cys | Cys | Ser | Cys | Am | Am | Ser | Am |
| 42 | Cys | Am | Cys | Cys | Cys | Ser | Am | Am | Am | Ser |
| 140 | Opal | Am | Am | Am | Am | Am | Am | Am | Am | Am |

FIG. 13C

|  | Second base | | | | |
|---|---|---|---|---|---|
| | U | C | A | G | |
| U | UUU, UUC } PHE<br>UUA, UUG } LEU | UCU, UCC, UCA, UCG } SER | UAU, UAC } TYR<br>UAA, UAG } STOP | UGU, UGC } CYS<br>UGA } STOP<br>UGG } TRP | U C A G |
| C | CUU, CUC, CUA, CUG } LEU | CCU, CCC, CCA, CCG } PRO | CAU, CAC } HIS<br>CAA, CAG } GLN | CGU, CGC, CGA, CGG } ARG | U C A G |
| A | AUU, AUC, AUA } ILE<br>AUG } MET or START | ACU, ACC, ACA, ACG } THR | AAU, AAC } ASN<br>AAA, AAG } LYS | AGU, AGC } SER<br>AGA, AGG } ARG | U C A G |
| G | GUU, GUC, GUA, GUG } VAL | GCU, GCC, GCA, GCG } ALA | GAU, GAC } ASP<br>GAA, GAG } GLU | GGU, GGC, GGA, GGG } GLY | U C A G |

First base / Third base

FIG. 18A

| Phe [ UUU, UUC→GAA 1<br>Leu [ UUA—UAA 15/1, UUG—CAA 5/2 | Ser [ UCU←AGA 1, UCC→GGA 8, UCA—UGA 6, UCG—CGA 5 | Tyr [ UAU, UAC→GUA 13<br>stop [ UAA—UUA 9/2, UAG—CUA 2 | Cys [ UGU, UGC→GCA 17<br>stop [ UGA—UCA 8<br>Trp [ UGG |
|---|---|---|---|
| Leu [ CUU, CUC→GAG 3, CUA—UAG 1, CUG—CAG 1 | Pro [ CCU, CCC, CCA, CCG | His [ CAU, CAC→GUG 1<br>Gln [ CAA, CAG | Arg [ CGU, CGC→GCG 139, CGA, CGG |
| Ile [ AUU, AUC, AUA—UAU 186<br>Met [ AUG | Thr [ ACU, ACC, ACA, ACG | Asn [ AAU, AAC<br>Lys [ AAA—UUU 1, AAG | Ser [ AGU, AGC→GCU 12<br>Arg [ AGA—UCU 1, AGG—CCU 1 |
| Val [ GUU, GUC→GAC 1, GUA, GUG | Ala [ GCU, GCC, GCA, GCG | Asp [ GAU←AUC 11, GAC→GUC 161<br>Glu [ GAA—UUC 12, GAG—CUC 5 | Gly [ GGU, GGC→GCC 44, GGA, GGG |

FIG. 18B

SEQUENCE LISTING

```
<160> NUMBER OF SEQ ID NOS: 95

<210> SEQ ID NO 1
<211> LENGTH: 95
<212> TYPE: RNA
<213> ORGANISM: Escherichia coli

<400> SEQUENCE: 1
ggaagaucgu cgucuccggu gaggcggcug gacuucaaau ccaguugggg ccgccagcgg      60
ucccgggcag guucgacucc ugugaucuuc cgcca                                 95

<210> SEQ ID NO 2
<211> LENGTH: 93
<212> TYPE: RNA
<213> ORGANISM: Methanococcus maripaludis

<400> SEQUENCE: 2
ggcacggggu gcuuaucuug guagaugagg gcggacuuca gauccgucga guuccguugg      60
aauucggggu ucgauucccc cccugcgccg cca                                   93
```

```
<210> SEQ ID NO 3
<211> LENGTH: 90
<212> TYPE: RNA
<213> ORGANISM: Homo sapiens

<400> SEQUENCE: 3
gcccggauga uccucagugg ucuggggugc aggcuucaaa ccuguagcug ucuagggaca    60
gagugguuca auuccaccuu ucgggcgcca                                    90

<210> SEQ ID NO 4
<211> LENGTH: 88
<212> TYPE: RNA
<213> ORGANISM: Escherichia coli

<400> SEQUENCE: 4
ggaagugugg ccgagcgguu gaaggcaccg gucuugaaaa ccggcgaccc gaaagdgguuc   60 cagaguucga aucucugcgc uuccgcca                                      88

<210> SEQ ID NO 5
<211> LENGTH: 90
<212> TYPE: RNA
<213> ORGANISM: Methanococcus maripaludis

<400> SEQUENCE: 5
gcagaggugg uugagcuugg ccaaaggcgc cggacuugaa auccgguucu ccacugggga   60
gcggggguuc aaaucccucc cucugcgcca                                    90

<210> SEQ ID NO 6
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 6
ggaagaugug gccgagcggu ugaaggcacc ggucuucaaa accggcgacc cgaaagdgguu   60 ccagaguucg aaucucugca ucuuccgcca                                    90

<210> SEQ ID NO 7
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 7
ggaagaugug gccgagcggu ugaaggcacc ggucucuaaa accggcgacc cgaaagdgguu   60 ccagaguucg aaucucugca ucuuccgcca                                    90

<210> SEQ ID NO 8
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 8
ggaagaugug gccgagcggu ugaaggcacc ggucuuuaaa accggcgacc cgaaagdgguu   60 ccagaguucg aaucucugca ucuuccgcca                                    90
```

<210> SEQ ID NO 9
<211> LENGTH: 88
<212> TYPE: RNA
<213> ORGANISM: Artificial Sequence
<220> FEATURE:
<223> OTHER INFORMATION: synthetic polynucleotide - tRNA

<400> SEQUENCE: 9
ggcacugugg ccgagcgguu gaaggcaccg gucuucaaaa ccggcgaccc gaaaggguuc    60
cagaguucga aucucugcgg ugccgcca                                      88

<210> SEQ ID NO 10
<211> LENGTH: 88
<212> TYPE: RNA
<213> ORGANISM: Artificial Sequence
<220> FEATURE:
<223> OTHER INFORMATION: synthetic polynucleotide - tRNA

<400> SEQUENCE: 10
ggcacugugg ccgagcgguu gaaggcaccg gucucuaaaa ccggcgaccc gaaagg guuc    60 cagaguucga aucucugcgg ugccgcca                                      88

<210> SEQ ID NO 11
<211> LENGTH: 88
<212> TYPE: RNA
<213> ORGANISM: Artificial Sequence
<220> FEATURE:
<223> OTHER INFORMATION: synthetic polynucleotdie - tRNA

<400> SEQUENCE: 11
ggcacugugg ccgagcgguu gaaggcaccg gucuuuaaaa ccggcgaccc gaaagg guuc    60 cagaguucga aucucugcgg ugccgcca                                      88

<210> SEQ ID NO 12
<211> LENGTH: 88
<212> TYPE: RNA
<213> ORGANISM: Artificial Sequence
<220> FEATURE:
<223> OTHER INFORMATION: synthetic polynucleotide - tRNA

<400> SEQUENCE: 12
ggcacugugg ccgagcgguu gaaggcaccg gucuugaaaa ccggcgaccc gaaagg guuc    60 cagaguucga aucucugcgg ugccgcca                                      88

<210> SEQ ID NO 13
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 13
ggcgcggugg uugagcuugg ccaaaggcgc cggacuucaa auccgguucu ccacugggga    60
gcggggguuc aaaucccucc cgcgccgcca                                    90

<210> SEQ ID NO 14
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 14

```
ggcgcggugg uugagcuugg ccaaaggcgc cggacucuaa auccgguucu ccacugggga    60
gcggggguuc aaaucccucc cgcgccgcca                                    90
```

<210> SEQ ID NO 15
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 15

```
ggcgcggugg uugagcuugg ccaaaggcgc cggacuuuaa auccgguucu ccacugggga    60
gcggggguuc aaaucccucc cgcgccgcca                                    90
```

<210> SEQ ID NO 16
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 16

```
ggcgcggugg uugagcuugg ccaaaggcgc cggacuugaa auccgguucu ccacugggga    60
gcggggguuc aaaucccucc cgcgccgcca                                    90
```

<210> SEQ ID NO 17
<211> LENGTH: 93
<212> TYPE: RNA
<213> ORGANISM: Artificial Sequence
<220> FEATURE:
<223> OTHER INFORMATION: synthetic polynucleotide - tRNA

<400> SEQUENCE: 17

```
ggaagaaugg ugccguccgg ugaaggcgcc ggucucuaaa accggucgac ccgaaagggu    60
ucgcaggguu cgacucccug cauacuuccg cca                                93
```

<210> SEQ ID NO 18
<211> LENGTH: 95
<212> TYPE: DNA
<213> ORGANISM: Artificial Sequence
<220> FEATURE:
<223> OTHER INFORMATION: synthetic polynucleotide - encoding tRNA

<400> SEQUENCE: 18

```
ggaagatggt cgtctccggt gaggcggctg gactctaaat ccagttgggg ccgccagcgg    60
tcccggtcag gttcgactcc ttgcatcttc cgcca                              95
```

<210> SEQ ID NO 19
<211> LENGTH: 91
<212> TYPE: RNA
<213> ORGANISM: Artificial Sequence
<220> FEATURE:
<223> OTHER INFORMATION: synthetic polynucleotide - consensus 8/4
      allo-tRNA
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (5)..(5)
<223> OTHER INFORMATION: r is a or g
<220> FEATURE:
<221> NAME/KEY: misc_feature -continued

```
<222> LOCATION: (6)..(6)
<223> OTHER INFORMATION: r is a or g
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (8)..(8)
<223> OTHER INFORMATION: r is a or g
<220> FEATURE:
<221> NAME/KEY: misc_feature
<222> LOCATION: (9)..(17)
<223> OTHER INFORMATION: n is a, c, g, or u
<220> FEATURE:
<221> NAME/KEY: misc_feature
<222> LOCATION: (20)..(20)
<223> OTHER INFORMATION: y is u or c
<220> FEATURE:
<221> NAME/KEY: misc_feature
<222> LOCATION: (21)..(30)
<223> OTHER INFORMATION: n is a, c, g, or u
<220> FEATURE:
<221> NAME/KEY: misc_feature
<222> LOCATION: (32)..(32)
<223> OTHER INFORMATION: n is a, c, g, or u
<220> FEATURE:
<221> NAME/KEY: misc_feature
<222> LOCATION: (33)..(33)
<223> OTHER INFORMATION: y is u or c
<220> FEATURE:
<221> NAME/KEY: misc_feature
<222> LOCATION: (35)..(37)
<223> OTHER INFORMATION: n is a, c, g, or u
<220> FEATURE:
<221> NAME/KEY: misc_feature
<222> LOCATION: (40)..(40)
<223> OTHER INFORMATION: n is a, c, g, or u
<220> FEATURE:
<221> NAME/KEY: misc_feature
<222> LOCATION: (42)..(64)
<223> OTHER INFORMATION: n is a, c, g, or u
<220> FEATURE:
<221> NAME/KEY: misc_feature
<222> LOCATION: (65)..(65)
<223> OTHER INFORMATION: r is a or g
<220> FEATURE:
<221> NAME/KEY: misc_feature
<222> LOCATION: (66)..(66)
<223> OTHER INFORMATION: n is a, c, g, or u
<220> FEATURE:
<221> NAME/KEY: misc_feature
<222> LOCATION: (67)..(67)
<223> OTHER INFORMATION: r is a or g
<220> FEATURE:
<221> NAME/KEY: misc_feature
<222> LOCATION: (70)..(70)
<223> OTHER INFORMATION: y is u or c
<220> FEATURE:
<221> NAME/KEY: misc_feature
<222> LOCATION: (72)..(72)
<223> OTHER INFORMATION: r is a or g
<220> FEATURE:
<221> NAME/KEY: misc_feature
<222> LOCATION: (74)..(74)
<223> OTHER INFORMATION: n is a, c, g, or u
<220> FEATURE:
<221> NAME/KEY: misc_feature
<222> LOCATION: (75)..(75)
<223> OTHER INFORMATION: y is u or c
<220> FEATURE:
<221> NAME/KEY: misc_feature
<222> LOCATION: (77)..(77)
<223> OTHER INFORMATION: y is u or c
<220> FEATURE:
<221> NAME/KEY: misc_feature
<222> LOCATION: (78)..(78)
<223> OTHER INFORMATION: n is a, c, g, or u
<220> FEATURE:
```

```
<221> NAME/KEY: misc_feature
<222> LOCATION: (79)..(79)
<223> OTHER INFORMATION: y is u or c
<220> FEATURE:
<221> NAME/KEY: misc_feature
<222> LOCATION: (80)..(80)
<223> OTHER INFORMATION: y is u or c
<220> FEATURE:
<221> NAME/KEY: misc_feature
<222> LOCATION: (81)..(81)
<223> OTHER INFORMATION: n is a, c, g, or u
<220> FEATURE:
<221> NAME/KEY: misc_feature
<222> LOCATION: (82)..(82)
<223> OTHER INFORMATION: y is u or c
<220> FEATURE:
<221> NAME/KEY: misc_feature
<222> LOCATION: (83)..(83)
<223> OTHER INFORMATION: y is u or c
<220> FEATURE:
<221> NAME/KEY: misc_feature
<222> LOCATION: (85)..(85)
<223> OTHER INFORMATION: y is u or c
<220> FEATURE:
<221> NAME/KEY: misc_feature
<222> LOCATION: (88)..(88)
<223> OTHER INFORMATION: n is a, c, g, or u

<400> SEQUENCE: 19
ggrgrrnrnn nnnnnnnggy nnnnnnnnnn gnyunnnaan cnnnnnnnnn nnnnnnnnn      60 nnnnrnrguy cranycynyy nyycyccncc a                                    91

<210> SEQ ID NO 20
<211> LENGTH: 95
<212> TYPE: RNA
<213> ORGANISM: Artificial Sequence
<220> FEATURE:
<223> OTHER INFORMATION: synthetic polynucleotide - consensus 9/3
      allo-tRNA
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (5)..(17)
<223> OTHER INFORMATION: n is a, c, g, or u
<220> FEATURE:
<221> NAME/KEY: misc_feature
<222> LOCATION: (18)..(18)
<223> OTHER INFORMATION: y is u or c
<220> FEATURE:
<221> NAME/KEY: misc_feature
<222> LOCATION: (21)..(31)
<223> OTHER INFORMATION: n is a, c, g, or u
<220> FEATURE:
<221> NAME/KEY: misc_feature
<222> LOCATION: (32)..(32)
<223> OTHER INFORMATION: r is a or g
<220> FEATURE:
<221> NAME/KEY: misc_feature
<222> LOCATION: (33)..(33)
<223> OTHER INFORMATION: n is a, c, g, or u
<220> FEATURE:
<221> NAME/KEY: misc_feature
<222> LOCATION: (34)..(34)
<223> OTHER INFORMATION: y is u or c
<220> FEATURE:
<221> NAME/KEY: misc_feature
<222> LOCATION: (36)..(38)
<223> OTHER INFORMATION: n is a, c, g, or u
<220> FEATURE:
```

```
<221> NAME/KEY: misc_feature
<222> LOCATION: (41)..(41)
<223> OTHER INFORMATION: n is a, c, g, or u
<220> FEATURE:
<221> NAME/KEY: misc_feature
<222> LOCATION: (42)..(42)
<223> OTHER INFORMATION: y is u or c
<220> FEATURE:
<221> NAME/KEY: misc_feature
<222> LOCATION: (43)..(69)
<223> OTHER INFORMATION: n is a, c, g, or u
<220> FEATURE:
<221> NAME/KEY: misc_feature
<222> LOCATION: (70)..(70)
<223> OTHER INFORMATION: r is a or g
<220> FEATURE:
<221> NAME/KEY: misc_feature
<222> LOCATION: (78)..(78)
<223> OTHER INFORMATION: r is a or g
<220> FEATURE:
<221> NAME/KEY: misc_feature
<222> LOCATION: (78)..(78)
<223> OTHER INFORMATION: y is u or c
<220> FEATURE:
<221> NAME/KEY: misc_feature
<222> LOCATION: (82)..(82)
<223> OTHER INFORMATION: y is u or c
<220> FEATURE:
<221> NAME/KEY: misc_feature
<222> LOCATION: (83)..(87)
<223> OTHER INFORMATION: n is a, c, g, or u
<220> FEATURE:
<221> NAME/KEY: misc_feature
<222> LOCATION: (88)..(88)
<223> OTHER INFORMATION: y is u or c
<220> FEATURE:
<221> NAME/KEY: misc_feature
<222> LOCATION: (89)..(89)
<223> OTHER INFORMATION: y is u or c
<220> FEATURE:
<221> NAME/KEY: misc_feature
<222> LOCATION: (92)..(92)
<223> OTHER INFORMATION: r is a or g

<400> SEQUENCE: 20
ggrrnnnnnn nnnnnnnygg nnnnnnnnnn nrnyunnnaa nynnnnnnnn nnnnnnnnnn    60
nnnnnnnnnr gguucrayuc cynnnnnyyc crcca                              95

<210> SEQ ID NO 21
<211> LENGTH: 91
<212> TYPE: RNA
<213> ORGANISM: Artificial Sequence
<220> FEATURE:
<223> OTHER INFORMATION: synthetic polynucleotide - consensus 8/4
      tRNASer
<220> FEATURE:
<221> NAME/KEY: misc_feature
<222> LOCATION: (2)..(5)
<223> OTHER INFORMATION: n is a, c, g, or u
<220> FEATURE:
<221> NAME/KEY: misc_feature
<222> LOCATION: (6)..(6)
<223> OTHER INFORMATION: r is a or g
<220> FEATURE:
<221> NAME/KEY: misc_feature
<222> LOCATION: (7)..(7)
<223> OTHER INFORMATION: y is u or c
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (10)..(17)
<223> OTHER INFORMATION: n is a, c, g, or u
<220> FEATURE:
```

```
<221> NAME/KEY: misc_feature
<222> LOCATION: (20)..(20)
<223> OTHER INFORMATION: y is u or c
<220> FEATURE:
<221> NAME/KEY: misc_feature
<222> LOCATION: (21)..(30)
<223> OTHER INFORMATION: n is a, c, g, or u
<220> FEATURE:
<221> NAME/KEY: misc_feature
<222> LOCATION: (32)..(32)
<223> OTHER INFORMATION: n is a, c, g, or u
<220> FEATURE:
<221> NAME/KEY: misc_feature
<222> LOCATION: (33)..(33)
<223> OTHER INFORMATION: y is u or c
<220> FEATURE:
<221> NAME/KEY: misc_feature
<222> LOCATION: (34)..(34)
<223> OTHER INFORMATION: y is u or c
<220> FEATURE:
<221> NAME/KEY: misc_feature
<222> LOCATION: (35)..(37)
<223> OTHER INFORMATION: n is a, c, g, or u
<220> FEATURE:
<221> NAME/KEY: misc_feature
<222> LOCATION: (40)..(40)
<223> OTHER INFORMATION: n is a, c, g, or u
<220> FEATURE:
<221> NAME/KEY: misc_feature
<222> LOCATION: (42)..(67)
<223> OTHER INFORMATION: n is a, c, g, or u
<220> FEATURE:
<221> NAME/KEY: misc_feature
<222> LOCATION: (69)..(69)
<223> OTHER INFORMATION: n is a, c, g, or u
<220> FEATURE:
<221> NAME/KEY: misc_feature
<222> LOCATION: (72)..(72)
<223> OTHER INFORMATION: r is a or g
<220> FEATURE:
<221> NAME/KEY: misc_feature
<222> LOCATION: (74)..(75)
<223> OTHER INFORMATION: n is a, c, g, or u
<220> FEATURE:
<221> NAME/KEY: misc_feature
<222> LOCATION: (77)..(81)
<223> OTHER INFORMATION: n is a, c, g, or u
<220> FEATURE:
<221> NAME/KEY: misc_feature
<222> LOCATION: (82)..(82)
<223> OTHER INFORMATION: y is u or c
<220> FEATURE:
<221> NAME/KEY: misc_feature
<222> LOCATION: (83)..(86)
<223> OTHER INFORMATION: n is a, c, g, or u

<400> SEQUENCE: 21
gnnnnrynan nnnnnnnggy nnnnnnnnnn gnyynnnaan cnnnnnnnnn nnnnnnnnnn      60
nnnnnnngnu cranncnnnn nynnnncgcc a                                    91

<210> SEQ ID NO 22
<211> LENGTH: 92
<212> TYPE: DNA
<213> ORGANISM: Unknown
<220> FEATURE:
<223> OTHER INFORMATION: Origin - Marine viral communities from the Deep
      Pacific Ocean - MSP-121 (Metagenome Std Draft M1679 Malaspina
      viral metagenome MSP-121, ASSEMBLY_DATE=20130718)

<400> SEQUENCE: 22
gggagcaggt atgtgtctgg ggacacgagc ggtcttctaa accgcgtggg ccgtggttct      60
gtcacggtcg ggttcgattc cccctgctcc cg                                   92
```

-continued

```
<210> SEQ ID NO 23
<211> LENGTH: 85
<212> TYPE: DNA
<213> ORGANISM: Unknown
<220> FEATURE:
<223> OTHER INFORMATION: Origin - Forest soil microbial communities from
      Davy Crockett National Forest, Groveton, Texas, USA - Texas A
      ecozone_OM3H0_M2 (Texas A ecozone_OM3H0_M2,
      ASSEMBLY_DATE=20130221)

<400> SEQUENCE: 23
ggagtggtgt gcccggctgg tgccgggagc agtttcctaa actgccgacg ctgcgaggcg    60
tagggttcga ttccccacca ttccg                                         85

<210> SEQ ID NO 24
<211> LENGTH: 88
<212> TYPE: DNA
<213> ORGANISM: Unknown
<220> FEATURE:
<223> OTHER INFORMATION: Origin - Wetland microbial communities from the
      San Francisco Bay, California, USA, that impact long-term carbon
      sequestration - White_ThreeSqA_D1

<400> SEQUENCE: 24
ggagggtggt cgctgttggt gcagcgggcg ggcctagaac ccgctggagc ctcaccgggc    60
taaggttcga ttcctccacc ctccgcca                                      88

<210> SEQ ID NO 25
<211> LENGTH: 87
<212> TYPE: DNA
<213> ORGANISM: Unknown
<220> FEATURE:
<223> OTHER INFORMATION: Origin - Forest soil microbial communities from
      Harvard Forest LTER, USA - PH H12_O (Forest soil microbial
      communities from Harvard Forest LTER, USA - PH H12_O,
      ASSEMBLY_DATE=20140709)

<400> SEQUENCE: 25
ggagagggca agagtgacgg ttcactcacc cgtctcagaa acgggtaacg tctatccggg    60
cgttgggttc aattcccgcc ctctccg                                       87

<210> SEQ ID NO 26
<211> LENGTH: 86
<212> TYPE: DNA
<213> ORGANISM: Unknown
<220> FEATURE:
<223> OTHER INFORMATION: Origin - Switchgrass rhizosphere microbial
      communities from Kellogg Biological Station, Michigan, USA - S6
      (KBS Switchgrass S6, ASSEMBLY_DATE=20140130)

<400> SEQUENCE: 26
ggggtggggt tccggctggt gccggtcgcg ggctttaaac ccgtcaggac gctgcgacgc    60
gtaaggttcg attcctcccc actccg                                        86

<210> SEQ ID NO 27
<211> LENGTH: 87
<212> TYPE: DNA
<213> ORGANISM: Unknown
<220> FEATURE:
<223> OTHER INFORMATION: Origin - Soil microbial communities from Great
      Prairies - Wisconsin Native Prairie soil

<400> SEQUENCE: 27
gggcgggggt tccgtctggt gacggtcgcg ggctttaaac ccgtcaggac gctgtgcagg    60
cgttaggttc gattcctccc ccgtcca                                       87
```

```
<210> SEQ ID NO 28
<211> LENGTH: 90
<212> TYPE: DNA
<213> ORGANISM: Unknown
<220> FEATURE:
<223> OTHER INFORMATION: Origin - Oil polluted marine microbial
      communities from Coal Oil Point, Santa Barbara, California, USA -
      Santa Barbara Oil Seep Sample 6 (Crude oil metagenome 6,
      ASSEMBLY_DATE=20131204)

<400> SEQUENCE: 28
ggaggggaac ttctatctgg tgatagacgg gaacttaaaa ttccttgaaa tgcctcgccg    60
cattgggttc gattcccttc ccctccgcca                                     90

<210> SEQ ID NO 29
<211> LENGTH: 85
<212> TYPE: DNA
<213> ORGANISM: Unknown
<220> FEATURE:
<223> OTHER INFORMATION: Origin - Arabidopsis thaliana rhizosphere
      microbial communities from the Joint Genome Institute, USA, that
      affect carbon cycling - Inoculated plant M3 PM (Arabidopsis
      thaliana rhizosphere microbial communities from the Joint Genome
      Institute, USA, that

<400> SEQUENCE: 29
ggagggcggc tgctgctggt gcagcgggtg gactcaaaat ccactggagc ctgtcggggc    60
tagggttcga ttcccccgcc ctccg                                          85

<210> SEQ ID NO 30
<211> LENGTH: 88
<212> TYPE: DNA
<213> ORGANISM: Unknown
<220> FEATURE:
<223> OTHER INFORMATION: Origin - Bog forest soil microbial communities
      from Calvert Island, British Columbia, Canada - ECP12_OM1 (Bog
      Forest metaG ECP12OM1, ASSEMBLY_DATE=20140815)

<400> SEQUENCE: 30
ggagagtaga tttcatgcgg ttatgaaatg cgtctcaaaa acgcagaggg ggctacacac    60
ccccagggtt caactcccct actctccg                                       88

<210> SEQ ID NO 31
<211> LENGTH: 90
<212> TYPE: DNA
<213> ORGANISM: Artificial Sequence
<220> FEATURE:
<223> OTHER INFORMATION: synthetic polynucleotide - encoding tRNA

<400> SEQUENCE: 31
ggaggggaac ttctatctgg tgatagacgg gaactctaaa ttccttgaaa tgcctcgccg    60
cattgggttc gattcccttc ccctccgcca                                     90

<210> SEQ ID NO 32
<211> LENGTH: 91
<212> TYPE: DNA
<213> ORGANISM: Artificial Sequence
<220> FEATURE:
<223> OTHER INFORMATION: synthetic polynucleotide - encoding tRNA

<400> SEQUENCE: 32
ggaggttgaa cttctatctg gtgatagacg ggaactctaa attccttgaa atgcctcgcc    60
gcattgggtt cgattccctt ctcctccgcc a                                   91
```

<210> SEQ ID NO 33
<211> LENGTH: 91
<212> TYPE: DNA
<213> ORGANISM: Artificial Sequence
<220> FEATURE:
<223> OTHER INFORMATION: synthetic polynucleotide - encoding tRNA

<400> SEQUENCE: 33
ggaggtggaa cttctatctg gtgatagacg ggaactctaa attccttgaa atgcctcgcc    60
gcattgggtt cgattccctt cccctccgcc a                                   91

<210> SEQ ID NO 34
<211> LENGTH: 90
<212> TYPE: DNA
<213> ORGANISM: Artificial Sequence
<220> FEATURE:
<223> OTHER INFORMATION: synthetic polynucleotide - encoding tRNA

<400> SEQUENCE: 34 ggagggaac ttctgtctgg tggcagacgg gaactctaaa ttccttgaaa tgcctcgccg    60
cattgggttc gattcccttc ccctccgcca                                     90

<210> SEQ ID NO 35
<211> LENGTH: 90
<212> TYPE: DNA
<213> ORGANISM: Artificial Sequence
<220> FEATURE:
<223> OTHER INFORMATION: synthetic polynucleotide - encoding tRNA

<400> SEQUENCE: 35 ggacggggt tccgtctggt gacggtcgcg ggctctaaac ccgtcaggac gctgtgcagg     60
cgttaggttc gattcctccc ccgtccgcca                                     90

<210> SEQ ID NO 36
<211> LENGTH: 90
<212> TYPE: DNA
<213> ORGANISM: Artificial Sequence
<220> FEATURE:
<223> OTHER INFORMATION: synthetic polynucleotide - encoding tRNA

<400> SEQUENCE: 36 ggacggggt tccgtctggt ggcggtcgcg ggctctaaac ccgtcaggac gctgtgcagg     60
cgttaggttc gattcctccc ccgtccgcca                                     90

<210> SEQ ID NO 37
<211> LENGTH: 89
<212> TYPE: DNA
<213> ORGANISM: Artificial Sequence
<220> FEATURE:
<223> OTHER INFORMATION: synthetic polynucleotide - encoding tRNA

<400> SEQUENCE: 37
ggagtggggt tccggctggt gccggtcgcg ggctctaaac ccgtcaggac gctgcgacgc    60
gtaaggttcg attcctcccc actccgcca                                      89

<210> SEQ ID NO 38
<211> LENGTH: 93
<212> TYPE: DNA
<213> ORGANISM: Artificial Sequence
<220> FEATURE:
<223> OTHER INFORMATION: synthetic polynucleotide - encoding tRNA

<400> SEQUENCE: 38
ggagggcatt tcagtcggt actggacgcc gtctctaaaa cggttgcagg gtcttagtca    60
gctctgggag ttcgactctc ctgccctccg cca                                93

<210> SEQ ID NO 39
<211> LENGTH: 93
<212> TYPE: DNA
<213> ORGANISM: Artificial Sequence
<220> FEATURE:
<223> OTHER INFORMATION: synthetic polynucleotide - encoding tRNA

<400> SEQUENCE: 39
ggagggcact tcagtcggt actggacgcc gtctctaaaa cggttgcagg gtcttagtca    60
gctctgggag ttcgactctc ctgccctccg cca                                93

<210> SEQ ID NO 40
<211> LENGTH: 93
<212> TYPE: DNA
<213> ORGANISM: Artificial Sequence
<220> FEATURE:
<223> OTHER INFORMATION: synthetic polynucleotide - encoding tRNA

<400> SEQUENCE: 40
ggagggcatc tcagtcggt actggacgcc gtctctaaaa cggttgcagg gtcttagtca    60
gctctgggag ttcgactctc ctgccctccg cca                                93

<210> SEQ ID NO 41
<211> LENGTH: 93
<212> TYPE: DNA
<213> ORGANISM: Artificial Sequence
<220> FEATURE:
<223> OTHER INFORMATION: synthetic polynucleotide - encoding tRNA

<400> SEQUENCE: 41
ggagggcaaa tcagtcggt actggacgcc gtctctaaaa cggttgcagg gtcttagtca    60
gctctgggag ttcgactctc ctgccctccg cca                                93

<210> SEQ ID NO 42
<211> LENGTH: 93
<212> TYPE: DNA
<213> ORGANISM: Artificial Sequence
<220> FEATURE:
<223> OTHER INFORMATION: synthetic polynucleotide - encoding tRNA

<400> SEQUENCE: 42
ggagggcaat tcagtcggt actggacgcc gtctctaaaa cggttgcagg gtcttagtca    60
gctctgggag ttcgactctc ctgccctccg cca                                93

<210> SEQ ID NO 43
<211> LENGTH: 92
<212> TYPE: RNA
<213> ORGANISM: Artificial Sequence
<220> FEATURE:
<223> OTHER INFORMATION: synthetic polynucleotide - consensus SelC*
      tRNACys  sequence
<220> FEATURE:
<221> NAME/KEY: misc_feature
<222> LOCATION: (1)..(1)
<223> OTHER INFORMATION: r is a or g
<220> FEATURE:
<221> NAME/KEY: misc_feature
<222> LOCATION: (9)..(9)
<223> OTHER INFORMATION: y is u or c
<220> FEATURE:

```
<221> NAME/KEY: misc_feature
<222> LOCATION: (12)..(12)
<223> OTHER INFORMATION: y is u or c
<220> FEATURE:
<221> NAME/KEY: misc_feature
<222> LOCATION: (20)..(20)
<223> OTHER INFORMATION: r is a or g
<220> FEATURE:
<221> NAME/KEY: misc_feature
<222> LOCATION: (25)..(25)
<223> OTHER INFORMATION: n is a, c, g, or u
<220> FEATURE:
<221> NAME/KEY: misc_feature
<222> LOCATION: (26)..(26)
<223> OTHER INFORMATION: y is u or c
<220> FEATURE:
<221> NAME/KEY: misc_feature
<222> LOCATION: (29)..(29)
<223> OTHER INFORMATION: n is a, c, g, or u
<220> FEATURE:
<221> NAME/KEY: misc_feature
<222> LOCATION: (32)..(32)
<223> OTHER INFORMATION: k is a or u
<220> FEATURE:
<221> NAME/KEY: misc_feature
<222> LOCATION: (37)..(37)
<223> OTHER INFORMATION: n is a, c, g, or u
<220> FEATURE:
<221> NAME/KEY: misc_feature
<222> LOCATION: (40)..(40)
<223> OTHER INFORMATION: r is a or g
<220> FEATURE:
<221> NAME/KEY: misc_feature
<222> LOCATION: (41)..(41)
<223> OTHER INFORMATION: y is u or c
<220> FEATURE:
<221> NAME/KEY: misc_feature
<222> LOCATION: (42)..(42)
<223> OTHER INFORMATION: n is a, c, g, or u
<220> FEATURE:
<221> NAME/KEY: misc_feature
<222> LOCATION: (46)..(46)
<223> OTHER INFORMATION: y is u or c
<220> FEATURE:
<221> NAME/KEY: misc_feature
<222> LOCATION: (47)..(47)
<223> OTHER INFORMATION: y is u or c
<220> FEATURE:
<221> NAME/KEY: misc_feature
<222> LOCATION: (48)..(48)
<223> OTHER INFORMATION: n is a, c, g, or u
<220> FEATURE:
<221> NAME/KEY: misc_feature
<222> LOCATION: (50)..(50)
<223> OTHER INFORMATION: y is u or c
<220> FEATURE:
<221> NAME/KEY: misc_feature
<222> LOCATION: (53)..(56)
<223> OTHER INFORMATION: n is a, c, g, or u
<220> FEATURE:
<221> NAME/KEY: misc_feature
<222> LOCATION: (58)..(58)
<223> OTHER INFORMATION: r is a or g
<220> FEATURE:
<221> NAME/KEY: misc_feature
<222> LOCATION: (60)..(60)
<223> OTHER INFORMATION: n is a, c, g, or u
<220> FEATURE:
<221> NAME/KEY: misc_feature
<222> LOCATION: (61)..(61)
<223> OTHER INFORMATION: r is a or g
<220> FEATURE:
<221> NAME/KEY: misc_feature
<222> LOCATION: (88)..(88)
<223> OTHER INFORMATION: y is u or c

<400> SEQUENCE: 43
rggggcaayg gygcugggcr ccccnyggnc ukcaaan rggaggaggu ucgauucccc uugccccyuc ca 92

<210> SEQ ID NO 44
<211> LENGTH: 75
<212> TYPE: RNA
<213> ORGANISM: Artificial Sequence
<220> FEATURE:
<223> OTHER INFORMATION: synthetic polynucleotide - consensus 8/4
      tRNAHis
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (3)..(3)
<223> OTHER INFORMATION: y is u or c
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (5)..(5)
<223> OTHER INFORMATION: r is a or g
<220> FEATURE:
<221> NAME/KEY: misc_feature
<222> LOCATION: (6)..(7)
<223> OTHER INFORMATION: n is a, c, g, or u
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: misc_feature
<222> LOCATION: (11)..(11)
<223> OTHER INFORMATION: n is a, c, g, or u
<220> FEATURE:
<221> NAME/KEY: misc_feature
<222> LOCATION: (17)..(17)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (25)..(25)
<223> OTHER INFORMATION: y is u or c
<220> FEATURE:
<221> NAME/KEY: misc_feature
<222> LOCATION: (26)..(26)
<223> OTHER INFORMATION: n is a, c, g, or u
<220> FEATURE:
<221> NAME/KEY: misc_feature
<222> LOCATION: (27)..(27)
<223> OTHER INFORMATION: y is u or c
<220> FEATURE:
<221> NAME/KEY: misc_feature
<222> LOCATION: (28)..(30)
<223> OTHER INFORMATION: n is a, c, g, or u
<220> FEATURE:
<221> NAME/KEY: misc_feature
<222> LOCATION: (31)..(31)
<223> OTHER INFORMATION: r is a or g
<220> FEATURE:
<221> NAME/KEY: misc_feature
<222> LOCATION: (32)..(32)
<223> OTHER INFORMATION: y is u or c
<220> FEATURE:
<221> NAME/KEY: misc_feature
<222> LOCATION: (38)..(38)
<223> OTHER INFORMATION: n is a, c, g, or u
<220> FEATURE:
<221> NAME/KEY: misc_feature
<222> LOCATION: (39)..(39)
<223> OTHER INFORMATION: y is u or c -continued

```
<220> FEATURE:
<221> NAME/KEY: misc_feature
<222> LOCATION: (40)..(44)
<223> OTHER INFORMATION: n is a, c, g, or u
<220> FEATURE:
<221> NAME/KEY: misc_feature
<222> LOCATION: (48)..(48)
<223> OTHER INFORMATION: y is u or c
<220> FEATURE:
<221> NAME/KEY: misc_feature
<222> LOCATION: (49)..(49)
<223> OTHER INFORMATION: n is a, c, g, or u
<220> FEATURE:
<221> NAME/KEY: misc_feature
<222> LOCATION: (50)..(50)
<223> OTHER INFORMATION: r is a or g
<220> FEATURE:
<221> NAME/KEY: misc_feature
<222> LOCATION: (56)..(56)
<223> OTHER INFORMATION: r is a or g
<220> FEATURE:
<221> NAME/KEY: misc_feature
<222> LOCATION: (57)..(57)
<223> OTHER INFORMATION: r is a or g
<220> FEATURE:
<221> NAME/KEY: misc_feature
<222> LOCATION: (58)..(58)
<223> OTHER INFORMATION: n is a, c, g, or u
<220> FEATURE:
<221> NAME/KEY: misc_feature
<222> LOCATION: (63)..(63)
<223> OTHER INFORMATION: n is a, c, g, or u
<220> FEATURE:
<221> NAME/KEY: misc_feature
<222> LOCATION: (65)..(66)
<223> OTHER INFORMATION: n is a, c, g, or u
<220> FEATURE:
<221> NAME/KEY: misc_feature
<222> LOCATION: (67)..(67)
<223> OTHER INFORMATION: y is u or c
<220> FEATURE:
<221> NAME/KEY: misc_feature
<222> LOCATION: (68)..(68)
<223> OTHER INFORMATION: y is u or c
<220> FEATURE:
<221> NAME/KEY: misc_feature
<222> LOCATION: (69)..(69)
<223> OTHER INFORMATION: r is a or g
<220> FEATURE:
<221> NAME/KEY: misc_feature
<222> LOCATION: (71)..(71)
<223> OTHER INFORMATION: n is a, c, g, or u

<400> SEQUENCE: 44
ncyrrnnang nuguaanggu ngcaynynnn ryuguganyn nnnnggaynr gguucrrnyc    60
cynunnyyrg nacca                                                    75

<210> SEQ ID NO 45
<211> LENGTH: 98
<212> TYPE: RNA
<213> ORGANISM: Artificial Sequence
<220> FEATURE:
<223> OTHER INFORMATION: synthetic polynucleotide - consensus 8/4
      tRNASec sequence
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (5)..(12)
<223> OTHER INFORMATION: n is a, c, g, or u
<220> FEATURE:
<221> NAME/KEY: misc_feature
<222> LOCATION: (14)..(14)
<223> OTHER INFORMATION: n is a, c, g, or u
```

```
<220> FEATURE:
<221> NAME/KEY: misc_feature
<222> LOCATION: (15)..(15)
<223> OTHER INFORMATION: y is u or c
<220> FEATURE:
<221> NAME/KEY: misc_feature
<222> LOCATION: (17)..(17)
<223> OTHER INFORMATION: y is u or c
<220> FEATURE:
<221> NAME/KEY: misc_feature
<222> LOCATION: (22)..(22)
<223> OTHER INFORMATION: r is a or g
<220> FEATURE:
<221> NAME/KEY: misc_feature
<222> LOCATION: (23)..(23)
<223> OTHER INFORMATION: n is a, c, g, or u
<220> FEATURE:
<221> NAME/KEY: misc_feature
<222> LOCATION: (25)..(28)
<223> OTHER INFORMATION: n is a, c, g, or u
<220> FEATURE:
<221> NAME/KEY: misc_feature
<222> LOCATION: (32)..(32)
<223> OTHER INFORMATION: n is a, c, g, or u
<220> FEATURE:
<221> NAME/KEY: misc_feature
<222> LOCATION: (35)..(35)
<223> OTHER INFORMATION: w is a or u
<220> FEATURE:
<221> NAME/KEY: misc_feature
<222> LOCATION: (40)..(40)
<223> OTHER INFORMATION: n is a, c, g, or u
<220> FEATURE:
<221> NAME/KEY: misc_feature
<222> LOCATION: (44)..(45)
<223> OTHER INFORMATION: n is a, c, g, or u
<220> FEATURE:
<221> NAME/KEY: misc_feature
<222> LOCATION: (47)..(70)
<223> OTHER INFORMATION: n is a, c, g, or u
<220> FEATURE:
<221> NAME/KEY: misc_feature
<222> LOCATION: (73)..(73)
<223> OTHER INFORMATION: y is u or c
<220> FEATURE:
<221> NAME/KEY: misc_feature
<222> LOCATION: (81)..(81)
<223> OTHER INFORMATION: y is u or c
<220> FEATURE:
<221> NAME/KEY: misc_feature
<222> LOCATION: (85)..(85)
<223> OTHER INFORMATION: y is u or c
<220> FEATURE:
<221> NAME/KEY: misc_feature
<222> LOCATION: (88)..(90)
<223> OTHER INFORMATION: n is a, c, g, or u
<220> FEATURE:
<221> NAME/KEY: misc_feature
<222> LOCATION: (92)..(92)
<223> OTHER INFORMATION: y is u or c

<400> SEQUENCE: 45
ggrannnnnn nngnycyggu grncnnnncg gncuwcaaan ccgnnunnnn nnnnnnnnnn      60
nnnnnnnnnn ggyguucga yuccyccnnn uyccgcca                              98

<210> SEQ ID NO 46
<211> LENGTH: 90
<212> TYPE: RNA
<213> ORGANISM: Unknown
<220> FEATURE:
<223> OTHER INFORMATION: putative tRNA

<400> SEQUENCE: 46
ggagggcauc uucaguaggu acuggacgcc gucugagaaa cgguugcagg gucuuaguca     60
```
gcucugggag uucgacucuc cugcccuccg                                       90

<210> SEQ ID NO 47
<211> LENGTH: 90
<212> TYPE: RNA
<213> ORGANISM: Unknown
<220> FEATURE:
<223> OTHER INFORMATION: putative tRNA

<400> SEQUENCE: 47
ggaggggaac uucuaucugg ugauagacgg gaacuuaaaa uuccuugaaa ugccucgccg      60 cauugggüuc gauucccuuc cccuccgcca                                      90

<210> SEQ ID NO 48
<211> LENGTH: 89
<212> TYPE: RNA
<213> ORGANISM: Artificial Sequence
<220> FEATURE:
<223> OTHER INFORMATION: synthetic polynucleotide - tRNA

<400> SEQUENCE: 48
ggggaguaau gugcgguggu ccgcaccgua gucugcgaaa cuauugguuc guuuauacga      60 auggggüuca auuccccugc ucuccacca                                       89

<210> SEQ ID NO 49
<211> LENGTH: 86
<212> TYPE: RNA
<213> ORGANISM: Artificial Sequence
<220> FEATURE:
<223> OTHER INFORMATION: synthetic polynucleotide - tRNA

<400> SEQUENCE: 49 ggggugggu uccggcuggu gccggucgcg ggcuuuaaac ccgucaggac gcugcgacgc       60
guaagguucg auuccucccc acuccg                                          86

<210> SEQ ID NO 50
<211> LENGTH: 87
<212> TYPE: RNA
<213> ORGANISM: Artificial Sequence
<220> FEATURE:
<223> OTHER INFORMATION: synthetic polynucleotide - tRNA

<400> SEQUENCE: 50
gggcgggggu uccgucuggu gacggucgcg ggcuuuaaac ccgucaggac gcugugcagg      60
cguuagguuc gauuccuccc ccgucca                                         87

<210> SEQ ID NO 51
<211> LENGTH: 85
<212> TYPE: RNA
<213> ORGANISM: Artificial Sequence
<220> FEATURE:
<223> OTHER INFORMATION: synthetic polynucleotide - tRNA

<400> SEQUENCE: 51
ggagggcguc ucgcuggcgc gagaagcggu cuuauaaacc gcaaaugucu ugacgggcau      60 uggggüccga uccccccgcc cuccg                                           85

<210> SEQ ID NO 52
<211> LENGTH: 85
<212> TYPE: RNA
<213> ORGANISM: Artificial Sequence
<220> FEATURE:
<223> OTHER INFORMATION: synthetic polynucleotide - tRNA

<400> SEQUENCE: 52
ggagggcgac aggccggugc cuggagccga cuuauaaucg gcgaauccuu cgcaggggau    60
agcgguucga cuccgccgcc cuccg    85

<210> SEQ ID NO 53
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 53
ggagggagau cccggcuggu gccuggagcc gacuuauaau cggucgaucc cguuccgggg    60
aucgcgguuc aaauccgccu cccuccgcca    90

<210> SEQ ID NO 54
<211> LENGTH: 87
<212> TYPE: RNA
<213> ORGANISM: Artificial Sequence
<220> FEATURE:
<223> OTHER INFORMATION: synthetic polynucleotide - tRNA

<400> SEQUENCE: 54 ggagggguguc acgcuggugc gugggccggu cuuauaaacc ggagauuccu ugccgggaau    60
ggaguucgau ucucccaccc uccgcca    87

<210> SEQ ID NO 55
<211> LENGTH: 88
<212> TYPE: RNA
<213> ORGANISM: Artificial Sequence
<220> FEATURE:
<223> OTHER INFORMATION: synthetic polynucleotide - tRNA

<400> SEQUENCE: 55 ggggggacaca acucgugggu gcgagaguug gucuuauaaa ccaauggcgu cguugcagcg    60
acgcaagguu caauuccuuu gucccccg    88

<210> SEQ ID NO 56
<211> LENGTH: 88
<212> TYPE: RNA
<213> ORGANISM: Artificial Sequence
<220> FEATURE:
<223> OTHER INFORMATION: synthetic polynucleotide - tRNA

<400> SEQUENCE: 56
ggaggguguc uagcuggugc uaggaccggc cuuauaagcc ggauuaccuu ccacggguau    60 uggguccga uccccccacc cuccgcca    88

<210> SEQ ID NO 57
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 57
ggaggggaac uucuaucugg ugauagacgg gaacucuaaa uuccuugaaa ugccucgccg    60
cauuggguuc gauucccuuc cccuccgcca    90

<210> SEQ ID NO 58

```
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 58 ggacggggu uccgucuggu gacggucgcg ggcucuaaac ccgucaggac gcugugcagg      60
cguuagguuc gauuccuccc ccguccgcca                                     90

<210> SEQ ID NO 59
<211> LENGTH: 16
<212> TYPE: RNA
<213> ORGANISM: Artificial Sequence
<220> FEATURE:
<223> OTHER INFORMATION: synthetic polynucleotide

<400> SEQUENCE: 59
ucuaucuggu gauaga                                                    16

<210> SEQ ID NO 60
<211> LENGTH: 51
<212> TYPE: RNA
<213> ORGANISM: Artificial Sequence
<220> FEATURE:
<223> OTHER INFORMATION: synthetic polynucleotide - SECIS-like element
      in the selAB mRNA

<400> SEQUENCE: 60
uuaaacgccc uucuccgugu gagagggccu ugaucagcca gguuuccuau g             51

<210> SEQ ID NO 61
<211> LENGTH: 93
<212> TYPE: DNA
<213> ORGANISM: Artificial Sequence
<220> FEATURE:
<223> OTHER INFORMATION: synthetic polynucleotide - encoding tRNA

<400> SEQUENCE: 61
ggagggcatc ttcagtaggt actggacgcc gtctctaaaa cggttgcagg gtcttagtca    60
gctctgggag ttcgactctc ctgccctccg cca                                 93

<210> SEQ ID NO 62
<211> LENGTH: 89
<212> TYPE: DNA
<213> ORGANISM: Artificial Sequence
<220> FEATURE:
<223> OTHER INFORMATION: synthetic polynucleotide - encoding tRNA

<400> SEQUENCE: 62
ggggtggggt tccggctggt gccggtcgcg ggctctaaac ccgtcaggac gctgcgacgc    60
gtaaggttcg attcctcccc actccgcca                                      89

<210> SEQ ID NO 63
<211> LENGTH: 91
<212> TYPE: DNA
<213> ORGANISM: Artificial Sequence
<220> FEATURE:
<223> OTHER INFORMATION: synthetic polynucleotide - encoding tRNA

<400> SEQUENCE: 63
ggaagatggt gccgtccggt gaaggcgccg gtctctaaaa ccggtcgacc cgaaagggtt    60
cgcagggttc gactccctgc atcttccgcc a                                   91
```

<210> SEQ ID NO 64
<211> LENGTH: 22
<212> TYPE: DNA
<213> ORGANISM: Artificial Sequence
<220> FEATURE:
<223> OTHER INFORMATION: syunthetic polypeptide - a weak Shine-Dalgarno
      sequence of the E. coli prfA gene

<400> SEQUENCE: 64
tttacagggt gcatttacgc ct                                            22

<210> SEQ ID NO 65
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 65
ccactccaag aattgcaaaa aggccatccg tcagg                               35

<210> SEQ ID NO 66
<211> LENGTH: 36
<212> TYPE: DNA
<213> ORGANISM: Artificial Sequence
<220> FEATURE:
<223> OTHER INFORMATION: synthetic polynucleotide

<400> SEQUENCE: 66
cgtgtgcttc tcaaagagcg caacgcaatt aatgtg                              36

<210> SEQ ID NO 67
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 67
tttgagaagc acacggtcac                                                20

<210> SEQ ID NO 68
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 68
caattcttgg agtggtgaat c                                              21

<210> SEQ ID NO 69
<211> LENGTH: 53
<212> TYPE: DNA
<213> ORGANISM: Artificial Sequence
<220> FEATURE:
<223> OTHER INFORMATION: synthetic polynucleotide

<400> SEQUENCE: 69
tcccacagcc gccagttccg ctggcggcat ttacccgac gcactttgcg ccg            53

<210> SEQ ID NO 70
<211> LENGTH: 19
<212> TYPE: DNA
<213> ORGANISM: Artificial Sequence
<220> FEATURE:

<223> OTHER INFORMATION: synthetic polynucleotide

<400> SEQUENCE: 70
aggccctttc gtcttcaag                                                  19

<210> SEQ ID NO 71
<211> LENGTH: 38
<212> TYPE: DNA
<213> ORGANISM: Artificial Sequence
<220> FEATURE:
<223> OTHER INFORMATION: synthetic polynucleotide

<400> SEQUENCE: 71
aagacgaaag ggcctcacgt gttgacaatt aatcatcg                             38

<210> SEQ ID NO 72
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 72
ctggcggctg tgggatcagg gctcctcggt cgcag                                35

<210> SEQ ID NO 73
<211> LENGTH: 17
<212> TYPE: DNA
<213> ORGANISM: Artificial Sequence
<220> FEATURE:
<223> OTHER INFORMATION: synthetic polynucleotide

<400> SEQUENCE: 73
cacacaggaa acagacc                                                    17

<210> SEQ ID NO 74
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 74
tgttttggcg gatgagagaa g                                               21

<210> SEQ ID NO 75
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 75
ttttaagaag gagatataca t                                               21

<210> SEQ ID NO 76
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 76
tcacacagga aacagacc                                                   18

```
<210> SEQ ID NO 77
<211> LENGTH: 463
<212> TYPE: PRT
<213> ORGANISM: Escherichia coli

<400> SEQUENCE: 77

Met Thr Thr Glu Thr Arg Phe Leu Tyr Ser Gln Leu Pro Ala Ile Asp
1               5                   10                  15

Arg Leu Leu Arg Asp Ser Ser Phe Leu Ser Leu Arg Asp Thr Tyr Gly
            20                  25                  30

His Thr Arg Val Val Glu Leu Leu Arg Gln Met Leu Asp Glu Ala Arg
        35                  40                  45

Glu Val Ile Arg Gly Ser Gln Thr Leu Pro Ala Trp Cys Glu Asn Trp
50                  55                  60

Ala Gln Glu Val Asp Ala Arg Leu Thr Lys Glu Ala Gln Ser Ala Leu
65                  70                  75                  80

Arg Pro Val Ile Asn Leu Thr Gly Thr Val Leu His Thr Asn Leu Gly
                85                  90                  95

Arg Ala Leu Gln Ala Glu Ala Ala Val Glu Ala Val Ala Gln Ala Met
            100                 105                 110

Arg Ser Pro Val Thr Leu Glu Tyr Asp Leu Asp Asp Ala Gly Arg Gly
        115                 120                 125

His Arg Asp Arg Ala Leu Ala Gln Leu Leu Cys Arg Ile Thr Gly Ala
130                 135                 140

Glu Asp Ala Cys Ile Val Asn Asn Asn Ala Ala Ala Val Leu Leu Met
145                 150                 155                 160

Leu Ala Ala Thr Ala Ser Gly Lys Glu Val Val Val Ser Arg Gly Glu
                165                 170                 175

Leu Val Glu Ile Gly Gly Ala Phe Arg Ile Pro Asp Val Met Arg Gln
            180                 185                 190

Ala Gly Cys Thr Leu His Glu Val Gly Thr Thr Asn Arg Thr His Ala
        195                 200                 205

Asn Asp Tyr Arg Gln Ala Val Asn Glu Asn Thr Ala Leu Leu Met Lys
210                 215                 220

Val His Thr Ser Asn Tyr Ser Ile Gln Gly Phe Thr Lys Ala Ile Asp
225                 230                 235                 240

Glu Ala Glu Leu Val Ala Leu Gly Lys Glu Leu Asp Val Pro Val Val
                245                 250                 255

Thr Asp Leu Gly Ser Gly Ser Leu Val Asp Leu Ser Gln Tyr Gly Leu
            260                 265                 270

Pro Lys Glu Pro Met Pro Gln Glu Leu Ile Ala Ala Gly Val Ser Leu
        275                 280                 285

Val Ser Phe Ser Gly Asp Lys Leu Leu Gly Gly Pro Gln Ala Gly Ile
290                 295                 300

Ile Val Gly Lys Lys Glu Met Ile Ala Arg Leu Gln Ser His Pro Leu
305                 310                 315                 320

Lys Arg Ala Leu Arg Ala Asp Lys Met Thr Leu Ala Ala Leu Glu Ala
                325                 330                 335

Thr Leu Arg Leu Tyr Leu His Pro Glu Ala Leu Ser Glu Lys Leu Pro
            340                 345                 350

Thr Leu Arg Leu Leu Thr Arg Ser Ala Glu Val Ile Gln Ile Gln Ala
        355                 360                 365

Gln Arg Leu Gln Ala Pro Leu Ala Ala His Tyr Gly Ala Glu Phe Ala
370                 375                 380
```

| | | | | | | | | | | | | | | |
|---|---|---|---|---|---|---|---|---|---|---|---|---|---|---|
|Val|Gln|Val|Met|Pro|Cys|Leu|Ser|Gln|Ile|Gly|Ser|Gly|Ser|Leu|Pro|
|385| | | |390| | | |395| | | |400| | | |

Val Asp Arg Leu Pro Ser Ala Ala Leu Thr Phe Thr Pro His Asp Gly
           405                     410                    415

Arg Gly Ser His Leu Glu Ser Leu Ala Ala Arg Trp Arg Glu Leu Pro
         420                     425                     430

Val Pro Val Ile Gly Arg Ile Tyr Asp Gly Arg Leu Trp Leu Asp Leu
           435                     440                   445

Arg Cys Leu Glu Asp Glu Gln Arg Phe Leu Glu Met Leu Leu Lys
     450                    455                  460

```
<210> SEQ ID NO 78
<211> LENGTH: 1392
<212> TYPE: DNA
<213> ORGANISM: Escherichia coli

<400> SEQUENCE: 78
atgacaaccg aaacgcgttt cctctatagt caacttccgg ctattgatcg cttattgcgc    60
gatagctcct tcctttcttt gcgtgatact tatggtcaca cccgcgtggt ggaattgttg   120
cgtcagatgc tcgacgaagc gcgagaagtg attcgtggca ccagacgct gcctgcgtgg   180 tgtgaaaact gggcgcaaga agtcgatgcc cggttgacga agaagcgca gagcgcgctg   240 cgtccggtga tcaacctgac gggaaccgtg ctgcatacca accttgggcg agctttacag   300
gcggaagccg cggtggaagc cgttgcgcag gctatgcgtt cgccagtgac cctcgagtat   360
gatctggacg acgccggacg cggacatcgc gatcgggcgc tggcgcagct gctgtgccgt   420 attacgggg cggaagatgc ctgtatcgtc aataacaatg cggcggcggt gttattgatg   480
ttggcggcca ctgccagcgg aaaagaggtg gtggtatctc gcggcgaact ggtgagatt   540 ggcggcgcgt ttcgtattcc cgatgttatg cgtcaggcag gctgcaccct acacgaagta   600
gggaccacca accgcacgca cgcgaatgat tatcgtcagg cggtgaatga aataccgca   660 ctgttgatga agtacatac cagtaactac agcattcagg ggttcaccaa agcgatagat   720
gaagcggaac tggtggcgct cggcaaagag ctggatgttc cgtagtgac tgatttaggc   780 agtggctcgc tggtcgatct tagccagtac ggtttgccga agagccaat gccgcaggag   840 ttgattgcgg cgggcgtcag tctggtgagt ttctccggcg acaagttgtt aggcgggccg   900
caggcaggaa ttattgttgg taaaaagag atgatcgccc gctgcaaag ccacccgctg   960 aagcgtgcat acgcgcgga taaaatgacc ctcgcggcgc tggaagccac gttgcgtctt  1020
tatttacacc ctgaagctct gagtgaaaaa ttaccgaccc tgcgcctgct acccgcagc  1080 gcagaggtca ttcaaatcca ggcacaacgt ttacaggccc ccttgccgc acattacggc  1140 gcggagtttg cggtacaggt tatgccatgt ctttcgcaga ttggcagtgg ttcgctgccg  1200
gttgatcgcc tgccgagcgc ggcattaacg tttacacccc atgatggacg cggtagccac  1260
cttgagtcat tagccgcccg ctggcgtgaa ttgccagtgc cggtgattgg tcgtatttat  1320
gacggacgat tgtggctgga tttacgctgc cttgaagatg agcaacggtt tttggagatg  1380
ttgttgaaat ga                                                     1392

<210> SEQ ID NO 79
<211> LENGTH: 452
<212> TYPE: PRT
<213> ORGANISM: Unknown
<220> FEATURE:
<223> OTHER INFORMATION: Aquifex aeolicus SelA (UniProtKB - O67140
      (SELA_AQUAE)
```

<400> SEQUENCE: 79

```
Met Lys Ser Leu Leu Arg Gln Ile Pro Gln Ile Ser Lys Val Val Glu
1               5                   10                  15

Ile Phe Lys Lys Lys Tyr Pro Glu Ile Tyr Val Val Lys Ala Ala Arg
            20                  25                  30

Glu Val Ala Glu Lys Tyr Arg Lys Glu Ile Glu Gly Lys Arg Lys
        35                  40                  45

Asp Leu Asn Gly Phe Leu Glu Asp Val Glu Arg Lys Ile Lys Ser Leu
    50                  55                  60

Met Lys Pro Asn Ile Lys Arg Val Ile Asn Ala Thr Gly Val Val Ile
65                  70                  75                  80

Asn Thr Asn Leu Gly Arg Ala Pro Leu Ser Lys Asp Val Ile Asn Phe
                85                  90                  95

Ile Ser Glu Ile Ala Asn Gly Tyr Ser Asn Leu Glu Tyr Asn Leu Glu
            100                 105                 110

Glu Gly Lys Arg Gly Ser Arg Ile Ala His Ile Glu Lys Tyr Leu Asn
        115                 120                 125

Glu Leu Thr Gly Ala Glu Ser Ser Phe Val Val Asn Asn Asn Ala Gly
    130                 135                 140

Ala Val Phe Leu Val Leu Asn Thr Leu Ala Glu Gly Lys Glu Val Ile
145                 150                 155                 160

Ile Ser Arg Gly Glu Leu Val Glu Ile Gly Gly Ser Phe Arg Ile Pro
                165                 170                 175

Asp Ile Met Lys Lys Ser Gly Ala Ile Leu Arg Glu Val Gly Thr Thr
            180                 185                 190

Asn Lys Thr Lys Val Ser Asp Tyr Glu Gly Ala Ile Asn Gln Asn Thr
        195                 200                 205

Ala Leu Leu Met Lys Val His Lys Ser Asn Phe Tyr Met Glu Gly Phe
    210                 215                 220

Val Glu Glu Val Lys Leu Glu Asp Leu Val Lys Leu Gly His Lys Tyr
225                 230                 235                 240

Gly Ile Pro Thr Tyr Tyr Asp Ala Gly Ser Gly Leu Leu Ile Asn Leu
                245                 250                 255

Lys Glu Phe Gly Ile Ser Val Asp Glu Pro Asn Phe Arg Asp Cys Ile
            260                 265                 270

Ser Leu Gly Ile Asp Leu Val Ser Gly Ser Gly Asp Lys Leu Leu Gly
        275                 280                 285

Gly Pro Gln Ala Gly Ile Ile Val Gly Lys Lys Asn Leu Ile Glu Lys
    290                 295                 300

Ile Lys Lys Asn Pro Ile Ala Arg Ala Leu Arg Ile Asp Lys Leu Thr
305                 310                 315                 320

Leu Ser Gly Leu Glu Met Thr Leu Lys Leu Tyr Phe Glu Lys Arg Tyr
                325                 330                 335

Glu Asp Ile Pro Val Ile Arg Met Leu Thr Gln Asp Glu Lys Ala Leu
            340                 345                 350

Arg Gln Lys Ala Lys Arg Leu Glu Lys Leu Lys Asp Ile Pro Gly
        355                 360                 365

Leu Lys Ile Ser Val Ile Lys Asp Lys Ala Lys Pro Gly Gly Gly Ser
    370                 375                 380

Leu Pro Glu Leu Glu Leu Pro Thr Tyr Cys Val Ala Ile Arg His Asp
385                 390                 395                 400

Arg Leu Ser Ser Gln Glu Leu Ser Arg Arg Leu Arg Leu Ala Glu Pro
```

```
                    405                 410                 415
Pro Ile Val Cys Arg Ile Arg Glu Asp Gln Leu Leu Phe Asp Met Arg
                420                 425                 430

Thr Val Phe His Glu Asp Leu Lys Thr Ile Lys Lys Thr Leu Gln Glu
            435                 440                 445

Leu Leu Ser Ile
    450

<210> SEQ ID NO 80
<211> LENGTH: 495
<212> TYPE: PRT
<213> ORGANISM: Aeromonas salmonicida

<400> SEQUENCE: 80

Met Pro Asn Ser Ser His Ala Pro Ala Ile Ala His Ser His Ser Gln
1               5                   10                  15

Pro Glu Ser Cys Pro Thr Ala Asp Asp Ser Leu Pro Asp Ser Leu Pro
            20                  25                  30

Asp Ser Leu Pro Gln Pro Ser Gln Gln Ala Arg Arg Leu Pro Gln
        35                  40                  45

Val Glu Gln Leu Gln Gln Pro Phe Leu Thr Gly Phe Ile Glu Ala
    50                  55                  60

Leu Ser Arg Pro Leu Val Thr Gln Ala Val Arg Asp Val Leu Ser Glu
65                  70                  75                  80

Leu Arg Gln Ser Glu Ala Phe Arg Gln His Gly Val Ala Pro Glu Gln
                85                  90                  95

Ile Glu Ala Leu Ile Ala Lys Arg Cys Gln Gln Leu Arg Gln Arg
            100                 105                 110

Gln Thr Arg Val Ile Asn Ala Thr Gly Thr Leu Val His Thr Asn Leu
        115                 120                 125

Gly Arg Ser Pro Leu Ser Arg Glu Leu Trp Asp Glu Val Arg Asp Leu
130                 135                 140

Asn Thr Gly Tyr Asn Asn Leu Glu Leu Asp Leu Ala Thr Gly Lys Arg
145                 150                 155                 160

Gly Gly Arg Lys Gly Leu Ile Ala Pro Leu Leu Arg Cys Leu Thr Gln
                165                 170                 175

Ala Glu Asp Ser Leu Val Val Asn Asn Asn Ala Ala Ser Leu Phe Leu
            180                 185                 190

Leu Leu Gln Glu Ile Ala Lys Gly Arg Glu Val Ile Val Ser Arg Gly
        195                 200                 205

Glu Gln Ile Gln Ile Gly Gly Phe Arg Ile Pro Asp Ile Leu Ala
    210                 215                 220

Leu Ser Gly Ala Lys Leu Val Glu Val Gly Thr Thr Asn Ile Thr Thr
225                 230                 235                 240

Ala Lys Asp Tyr Leu Asp Ala Ile Thr Asp Gln Thr Ala Leu Val Leu
                245                 250                 255

Met Val His Arg Ser Asn Phe Ala Ile Arg Gly Phe Thr Glu Ser Pro
            260                 265                 270

Asp Ile Gly Glu Val Ala Arg Ala Leu Pro Glu His Val Val Leu Ala
        275                 280                 285

Val Asp Gln Gly Ser Gly Leu Thr Thr Glu Glu Phe Ala Pro Asp Glu
    290                 295                 300

Thr Ser Val Arg Gln Tyr Ile Lys Ala Gly Ala Asp Leu Val Cys Tyr
305                 310                 315                 320
```

Ser Gly Asp Lys Leu Leu Gly Gly Pro Gln Ser Gly Ile Ile Ser Gly
            325                 330                 335

Arg Ser Asp Leu Ile Lys Arg Leu Glu Lys His Pro Met Met Arg Thr
        340                 345                 350

Phe Arg Pro Ser Arg Ile Val Tyr Ser Leu Leu Glu Arg Leu Leu Ile
            355                 360                 365

His Lys Leu Asn Lys Ser Pro Ile Gly Glu Gly Ile Ala Gln Arg Thr
        370                 375                 380

Leu Ser Asn Pro Ala Ala Met Gln Ala Arg Ala Asp Gln Leu Met Ala
385                 390                 395                 400

Ala Leu Pro Gly Cys Phe Val Pro Val Pro Ala Gln Leu Val Val Gly
            405                 410                 415

Gly Gly Thr Leu Pro Asp Glu Phe Tyr Pro Ala Pro Ala Leu Glu Cys
            420                 425                 430

Thr Asp Pro Arg Pro Ala Gln Gln Leu Leu Asp Ala Leu Arg Lys Leu
        435                 440                 445

Pro Val Pro Val Ile Ala Thr Val Arg Gln Gln Lys Val Leu Leu Asn
            450                 455                 460

Met Ala Thr Leu Leu Pro Thr Glu Ile Ala Leu Leu Ile Ala Gln Leu
465                 470                 475                 480

Lys Glu Leu Leu Leu Pro Thr Pro Thr Thr Ala Thr Glu Glu Pro
                485                 490                 495

<210> SEQ ID NO 81
<211> LENGTH: 1488
<212> TYPE: DNA
<213> ORGANISM: Aeromonas salmonicida

<400> SEQUENCE: 81
atgccgaact cgtctcacgc gccagccatc gcccactctc acagtcagcc cgaatcatgt      60
cccactgccg acgattcact gccagattca ctgccagatt cactgccaca gcccagccag     120
caacaagcgc gccgtctacc gcaagtggaa cagctgctgc agcaacccct tctcaccggt     180
tttatcgagg cgctgagccg cccgctggtg acccaggcgg tgcgcgatgt cctgagcgaa     240
ttgcgccaga gcgaggcatt cgccagcat ggggttgccc ccgagcaaat cgaggcactg     300
attgccaagc gttgccagca gcagctgcgc aacgtcaga cccgggtgat caacgccacc     360
ggcaccctgg tgcacaccaa tctggggcgc tcgccgctaa gtcgcgagct gtgggacgag     420
gtgcgcgacc tcaacactgg ctacaacaat ctggaactgg atctcgccac cggcaagcgc     480
ggcgggcgca aggggctgat cgccccctg ctccgttgcc tcacccaggc cgaggattcg     540
ctggtggtca caacaacgc cgcttcgctc ttcttgctgc tgcaggagat agccaagggg     600
cgcgaggtga tcgtctcgcg gggcgaacag atccagattg tggcggctt tgcattccc     660 gacattctgg cgctctccgg cgccaaactg gtggaggtgg caccaccaa tatcactacc     720 gccaaagatt acctcgatgc catcacagat cagaccgcgc tggtgctgat ggtacacaga     780
tccaatttcg ccattcgcgg ctttaccgaa tccccgata ttggcgaggt ggcccgcgcc     840
ctgcccgagc acgtggtgct ggcggtggat cagggctcgg gcttgaccac cgaggagttt     900
gcaccggacg aaacctcggt gcgtcagtac atcaaggcgg gggcggatct ggtctgctac     960
tccggcgaca gctgctgggt ggcccgcaa tcgggcatca tcagcggccg cagcgacctc    1020
atcaagcggc tggaaaaaca ccccatgatg cgcaccttcc gcccgagccg catcgtctac    1080
tccctgctgg aacgcctgct catccacaag ctcaacaagt cccccatcgg cgagggcatc    1140

-continued

```
gcccagcgca ccttgagcaa ccctgccgcc atgcaggccc gcgccgatca gctgatggcc    1200
gccctgcccg gctgctttgt gccggtcccc gcccagctgg tggtgggtgg tggcaccctg    1260
ccggacgagt tctaccctgc gcctgcgctc gaatgcaccg acccgcgtcc ggcccagcag    1320
ctgctcgatg ccctgcggaa actgccggtg ccggtcatcg ccaccgtgcg ccagcagaag    1380
gtgctgctca atatggcgac cctgctgccg accgagattg cactgcttat cgcccaactc    1440
aaggagttgc tactgcccac tccgaccact gcgaccgagg agccctga                 1488
```

<210> SEQ ID NO 82
<211> LENGTH: 455
<212> TYPE: PRT
<213> ORGANISM: Rubrobacter xylanophilus

<400> SEQUENCE: 82

```
Met Leu Asp Ala Glu Arg Gln Ser Arg Leu Arg Ser Leu Pro Ala Val
1               5                   10                  15

Asp Ala Val Leu Arg Gly Pro Ala Ala Gly Leu Ala Ala Arg His Gly
            20                  25                  30

Arg Ala Ala Val Ala Ala Ala Val Arg Glu Val Leu Glu Gly Leu Arg
        35                  40                  45

Arg Glu Ile Ala Ala Gly Gly Ser Pro Asp Val Ser Gly Arg Ala Val
    50                  55                  60

Ala Glu Gly Ala Ala Arg Leu Leu Ser Gly Arg Gly Leu Arg Arg Val
65                  70                  75                  80

Val Asn Ala Thr Gly Val Val Leu His Thr Asn Leu Gly Arg Ala Val
                85                  90                  95

Leu Ser Glu Arg Ala Ala Ala Ala Ala Arg Ala Gly Thr Ser Tyr
            100                 105                 110

Ser Asn Leu Glu Tyr Asp Leu Ser Arg Gly Arg Gly Ser Arg Tyr
        115                 120                 125

Asp His Ala Val Pro Leu Leu Arg Glu Leu Thr Gly Ala Glu Asp Ala
    130                 135                 140

Leu Val Val Asn Asn Cys Ala Gly Ala Thr Leu Leu Ala Leu Ser Ala
145                 150                 155                 160

Leu Ala Gly Glu Glu Gly Gly Pro Pro Glu Val Val Ser Arg
                165                 170                 175

Gly Gln Leu Ile Glu Ile Gly Gly Phe Arg Ile Pro Glu Val Leu
            180                 185                 190

Glu Leu Ser Gly Ala Val Leu Arg Glu Val Gly Thr Thr Asn Arg Thr
        195                 200                 205

Arg Leu Ser Asp Tyr Glu Arg Ala Leu Ser Glu Arg Thr Arg Ala Ile
    210                 215                 220

Leu Trp Val His Pro Ser Asn Phe Glu Ile Gly Phe Thr Glu Ser
225                 230                 235                 240

Ala Gly Ile Ala Glu Leu Ala Gly Leu Gly Pro Pro Val Val Ala Asp
                245                 250                 255

Leu Gly Ser Gly Ala Leu Leu Pro Leu Gly Gly Glu Pro Leu Val Gln
            260                 265                 270

Ala Ala Leu Arg Asp Gly Ala Glu Leu Ala Leu Phe Ser Gly Asp Lys
        275                 280                 285

Leu Leu Gly Gly Pro Gln Ala Gly Ile Ala Ala Gly Ser Ser Arg Leu
    290                 295                 300

Val Arg Arg Met Arg Arg His Pro Leu Val Arg Ala Leu Arg Ala Asp
305                 310                 315                 320
```

```
Lys Leu Cys Leu Ala Ala Leu Glu Ala Thr Leu Arg Ala Tyr Leu Glu
            325                 330                 335

Gly Arg Ala Glu Glu Val Pro Ala Gln Arg Met Leu Arg Glu Pro
            340                 345                 350

Leu Glu Gly Val Glu Ala Arg Ala Arg Arg Leu Ala Ser Ala Leu Ser
            355                 360                 365

Arg Glu Val Pro Gly Leu Glu Val Gly Val Val Pro Ser Val Ala Arg
            370                 375                 380

Ser Gly Gly Gly Thr Leu Pro Gly Tyr Glu Ile Pro Ser Phe Ala Ala
385                 390                 395                 400

Arg Val Leu Gly Ala Asp Ala Glu Ala Leu Ala Ala Arg Leu Arg Ala
                405                 410                 415

Ala Glu Pro Pro Val Val Gly Arg Val His Glu Gly Ala Leu Leu Leu
            420                 425                 430

Asp Ala Arg Thr Leu Leu Pro Gly Asp Glu Glu Ala Val Val Glu Ala
            435                 440                 445

Leu Arg Glu Ala Ala Arg Gly
            450                 455

<210> SEQ ID NO 83
<211> LENGTH: 1368
<212> TYPE: DNA
<213> ORGANISM: Artificial Sequence
<220> FEATURE:
<223> OTHER INFORMATION: synthetic polynucleotide

<400> SEQUENCE: 83
atgctggatg cagaacgtca gagccgtctg cgtagcctgc ctgcagttga tgcagttctg      60
cgtggtccgg cagcaggtct ggcagcacgt catggtcgtg cagcagttgc agcagcagtt     120
cgtgaagttc tggaaggtct gcgtcgtgaa attgcagccg gtggtagtcc ggatgttagc     180
ggtcgtgccg ttgcagaagg tgcagcccgt ctgctgagtg tcgtggcct gcgtcgcgtt     240 gttaatgcaa ccggtgttgt tctgcatacc aatctgggtc gtgcggttct gagcgaacgt     300
gcagccgcag cagcggcacg tgcaggcacc agctatagca atctggaata tgatctgagc     360
cgtggtcgtc gtggtagccg ttatgatcat gcagttcctc tgctgcgtga actgaccggt     420
gcagaagatg cactggttgt taataactgt gccggtgcaa ccctgctggc actgagcgca     480
ctggcaggcg aagaaggtga aggtccgcct gaagttgttg ttagtcgtgg tcagctgatt     540
gaaattggtg tggttttcg tattccggaa gtgctggaac tgagtggtgc cgttctgcgc     600
gaagttggta caaccaatcg tacccgtctg agcgattatg aacgtgcact gagtgaacgt     660
acccgtgcaa ttctgtgggt tcatccgagc aattttgaaa ttcgcggttt taccgaaagc     720
gcaggtattg cagaactggc tggtctgggt cctccggttg ttgcagatct gggtagcggt     780
gcactgctgc cgctgggtgg tgaaccgctg gttcaggcag cactgcgtga tggtgccgaa     840
ctggcactgt ttagcggtga taaactgctg ggtggaccgc aggctggtat tgccgcaggt     900
agcagccgtc tggttcgtcg tatgcgtcgt catccgctgg tgcgtgccct gcgtgcagat     960
aaactgtgcc tggcagccct ggaagcaaca ctgcgtgcat atctggaagg ccgtgccgaa    1020
gaagaagttc cggcacagcg tatgctgcgc gaaccactgg aaggtgttga agcacgtgcc    1080
cgtcgtctgg caagcgcact gagtcgtgaa gtgcctggtc tggaagttgg tgttgtgccg    1140
agcgttgcac gtagcggtgg tggcaccctg cctggttatg aaattccgag ctttgcagca    1200
cgtgttctgg gtgcagatgc agaagccctg gcagcgcgtc tgcgtgccgc agaaccgcct    1260
```

-continued

```
gttgtgggtc gtgttcatga aggtgccctg ctgctggatg cccgtaccct gctgccaggt    1320
gatgaagaag cagttgttga agcgctgcgt gaggcagccc gtggttaa                 1368
```

<210> SEQ ID NO 84
<211> LENGTH: 447
<212> TYPE: PRT
<213> ORGANISM: Unknown
<220> FEATURE:
<223> OTHER INFORMATION: Sulfurimonas honglongensis

<400> SEQUENCE: 84

```
Met Phe Leu Leu Lys Ser Ile Pro Lys Val Asp Lys Phe Ile Ala Lys
1               5                   10                  15

Lys Glu Phe Lys Thr Leu Gly Ser Ala Leu Val Met Ser Leu Thr Lys
                20                  25                  30

Glu Leu Leu Ser Glu Leu Arg Glu Asn Ile Leu Asn Gly Arg Val Thr
            35                  40                  45

Thr Phe Ser Glu Asp Leu Val Lys Glu Leu Gln Arg Tyr Thr
        50                  55                  60

Glu Leu Thr Lys Pro Ser Leu Gln Thr Leu Ile Asn Ala Thr Gly Ile
65                  70                  75                  80

Ile Val His Thr Asn Leu Gly Arg Ser Leu Ile Asp Ala Asp Ala Phe
                85                  90                  95

Asp Arg Val Lys Glu Leu Met Thr Asn Tyr Asn Asn Leu Glu Phe Asn
                100                 105                 110

Leu Glu Ser Gly Lys Arg Gly Glu Arg Tyr Ser Leu Ile Ser Lys Ser
            115                 120                 125

Val Cys Ser Leu Leu Gly Cys Glu Asp Val Leu Ile Val Asn Asn Asn
        130                 135                 140

Ala Ser Ala Val Phe Leu Ile Leu Asn Thr Phe Ala Arg Lys Lys Glu
145                 150                 155                 160

Val Val Val Ser Arg Gly Glu Leu Val Glu Ile Gly Gly Ser Phe Arg
                165                 170                 175

Val Pro Asp Val Met Lys Gln Ser Gly Ala Lys Leu Val Glu Val Gly
                180                 185                 190

Thr Thr Asn Lys Thr His Leu Tyr Asp Tyr Glu Asp Ala Ile Gly Lys
            195                 200                 205

Lys Thr Ser Met Leu Met Lys Val His Lys Ser Asn Tyr Ser Ile Glu
        210                 215                 220

Gly Phe Ser Ser Asp Val Glu Phe Gly Glu Ile Val Lys Leu Ala Cys
225                 230                 235                 240

Glu Lys Gly Leu Ile Asp Tyr Tyr Asp Met Gly Ser Gly His Leu Phe
                245                 250                 255

Asp Leu Pro Tyr Gly Leu Asp Glu Pro Ser Val Leu Asp Phe Met Lys
                260                 265                 270

Leu Asn Pro Ser Leu Leu Ser Phe Ser Gly Asp Lys Leu Leu Gly Ser
            275                 280                 285

Val Gln Ala Gly Ile Ile Val Gly Lys Lys Tyr Ile Asp Met Leu
        290                 295                 300

Lys Lys Asn Gln Leu Leu Arg Met Leu Arg Val Asp Lys Leu Thr Leu
305                 310                 315                 320

Ala Leu Leu Glu Glu Ser Phe Lys Ala Ile Leu Leu Gly Asn Lys Glu
                325                 330                 335

Gln Ile Pro Thr Ala Arg Met Leu Phe Arg Ser Thr Asp Glu Leu Arg
```

```
              340              345              350
Glu Asp Ala Met Gln Val Gln Gln Lys Leu Lys Lys Asn Ile Lys Thr
            355                  360                  365

Asn Ile Val Asp Thr Lys Thr Leu Ile Gly Gly Thr Thr Pro Asn
        370                  375                  380

Lys Thr Ile Pro Ser Val Ala Leu Val Ile Glu Ser Lys Asn Ile Lys
385                  390                  395                  400

Val Lys Lys Leu Gln Lys Leu Phe Arg Gln Lys Ser Ile Ile Gly Arg
                405                  410                  415

Ile Glu Asp Asp Glu Phe Leu Leu Asp Phe Arg Thr Ile Gln Lys Thr
            420                  425                  430

Gln Leu Gln Gln Val Val Asp Ala Ile Asp Glu Ile Thr Asp Val
            435                  440                  445

<210> SEQ ID NO 85
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 85
atgttcctgc tgaaaagcat tccgaaagtg gataagttta cgccaagaa agagtttaaa       60 accctgggta cgcactggt tatgagcctg accaaagaac tgctgagcga actgcgtgaa      120
aacattctga tggtcgtgt taccaccttt agcgaagatg aactggttaa agagctgctg      180
cagcgttata ccgaactgac caaaccgagc ctgcagaccc tgattaatgc aaccggtatt      240
attgttcata ccaatctggg tcgtagcctg attgatgcag atgcatttga tcgtgttaaa      300
gaactgatga ccaactataa caacctggaa tttaatctgg aaagcggtaa acgtggtgaa      360
cgctatagtc tgattagcaa aagcgtttgt agcctgctgg gttgtgaaga tgttctgatt      420
gtgaataata cgccagcgc agttttttctg attctgaaca cctttgcgcg taaaaaagaa      480
gttgttgtta gtcgcggtga actggtggaa attggtggta gctttcgtgt tccggatgtt      540
atgaaacaga gcggtgcaaa actggttgaa gttggcacca ccaataaaac ccatctgtat      600
gattatgaag atgccatcgg taaaaaaacg agcatgctga tgaaagtgca caaaagcaac      660
tatagcattg aaggtttag cagcgacgtg gaatttggcg aaattgttaa actggcatgt      720
gaaaaaggcc tgatcgatta ttatgatatg ggtagcggtc acctgtttga tctgccgtat      780
ggtctggatg aaccgagcgt tctggacttt atgaaactga atccgagtct gctgagcttt      840
agcggtgata aactgctggg tagtgttcag gcaggcatta ttgttggcaa aaaaaagtat      900
atcgacatgc tgaagaaaaa ccagctgctg cgtatgctgc gtgtggataa actgaccctg      960
gcactgctgg aagaaagttt taagcaatt ctgctgggca caaagagca gattccgacc     1020 gcacgtatgc tgtttcgtag caccgatgaa ctgcgcgaag atgcaatgca ggttcagcag     1080
aaactgaaaa aaaacatcaa gaccaacatc gtggatacca aaacactgat ggtggcggt     1140 acaaccccga ataaaaccat tccgagcgtt gccctggtta ttgaaagcaa aacattaag     1200 gtgaaaaaac tgcagaagct gtttcgccag aaaagtatta ttggtcgcat cgaggatgat     1260
gaatttctgc tggattttcg tacgattcag aaaacccaac tgcagcaggt tgttgatgca     1320
attgatgaaa ttaccgacgt gtaa                                           1344

<210> SEQ ID NO 86
<211> LENGTH: 347
```

<212> TYPE: PRT
<213> ORGANISM: Escherichia coli

<400> SEQUENCE: 86

Met Ser Glu Asn Ser Ile Arg Leu Thr Gln Tyr Ser His Gly Ala Gly
1               5                   10                  15

Cys Gly Cys Lys Ile Ser Pro Lys Val Leu Glu Thr Ile Leu His Ser
            20                  25                  30

Glu Gln Ala Lys Phe Val Asp Pro Asn Leu Leu Val Gly Asn Glu Thr
        35                  40                  45

Arg Asp Asp Ala Ala Val Tyr Asp Leu Gly Asn Gly Thr Ser Val Ile
    50                  55                  60

Ser Thr Thr Asp Phe Phe Met Pro Ile Val Asp Asn Pro Phe Asp Phe
65                  70                  75                  80

Gly Arg Ile Ala Ala Thr Asn Ala Ile Ser Asp Ile Phe Ala Met Gly
                85                  90                  95

Gly Lys Pro Ile Met Ala Ile Ala Ile Leu Gly Trp Pro Ile Asn Lys
            100                 105                 110

Leu Ser Pro Glu Ile Ala Arg Glu Val Thr Glu Gly Gly Arg Tyr Ala
        115                 120                 125

Cys Arg Gln Ala Gly Ile Ala Leu Ala Gly Gly His Ser Ile Asp Ala
    130                 135                 140

Pro Glu Pro Ile Phe Gly Leu Ala Val Thr Gly Ile Val Pro Thr Glu
145                 150                 155                 160

Arg Val Lys Lys Asn Ser Thr Ala Gln Ala Gly Cys Lys Leu Phe Leu
                165                 170                 175

Thr Lys Pro Leu Gly Ile Gly Val Leu Thr Thr Ala Glu Lys Lys Ser
            180                 185                 190

Leu Leu Lys Pro Glu His Gln Gly Leu Ala Thr Glu Val Met Cys Arg
        195                 200                 205

Met Asn Ile Ala Gly Ala Ser Phe Ala Asn Ile Glu Gly Val Lys Ala
    210                 215                 220

Met Thr Asp Val Thr Gly Phe Gly Leu Leu Gly His Leu Ser Glu Met
225                 230                 235                 240

Cys Gln Gly Ala Gly Val Gln Ala Arg Val Asp Tyr Glu Ala Ile Pro
                245                 250                 255

Lys Leu Pro Gly Val Glu Glu Tyr Ile Lys Leu Gly Ala Val Pro Gly
            260                 265                 270

Gly Thr Glu Arg Asn Phe Ala Ser Tyr Gly His Leu Met Gly Glu Met
        275                 280                 285

Pro Arg Glu Val Arg Asp Leu Leu Cys Asp Pro Gln Thr Ser Gly Gly
    290                 295                 300

Leu Leu Leu Ala Val Met Pro Glu Ala Glu Asn Glu Val Lys Ala Thr
305                 310                 315                 320

Ala Ala Glu Phe Gly Ile Glu Leu Thr Ala Ile Gly Glu Leu Val Pro
                325                 330                 335

Ala Arg Gly Gly Arg Ala Met Val Glu Ile Arg
            340                 345

<210> SEQ ID NO 87
<211> LENGTH: 345
<212> TYPE: PRT
<213> ORGANISM: Aeromonas salmonicida

<400> SEQUENCE: 87

```
Met Ser Ser Ile Arg Leu Thr Gln Tyr Ser His Gly Ala Gly Cys Gly
1               5                   10                  15

Cys Lys Ile Ser Pro Lys Val Leu Asp Thr Ile Leu Lys Ser Gln Ile
            20                  25                  30

Pro Gly Phe Asp Asp Pro Thr Leu Val Val Gly Asn Ser Ser Lys Asp
        35                  40                  45

Asp Ala Ala Val Val Asp Ile Gly Asn Gly Gln Gly Ile Val Ser Thr
    50                  55                  60

Thr Asp Phe Phe Met Pro Ile Val Asp Asp Pro Phe Thr Phe Gly Arg
65                  70                  75                  80

Ile Ala Ala Thr Asn Ala Ile Ser Asp Ile Tyr Ala Met Gly Gly Lys
                85                  90                  95

Pro Ile Val Ala Ile Ala Ile Leu Gly Trp Pro Ile Asn Thr Leu Ala
            100                 105                 110

Pro Glu Val Ala Gln Gln Val Ile Asp Gly Gly Arg Gln Val Cys His
        115                 120                 125

Glu Ala Gly Ile Ser Leu Ala Gly Gly His Ser Ile Asp Ala Pro Glu
    130                 135                 140

Pro Ile Phe Gly Leu Ala Val Thr Gly Ile Val Pro Leu Asn Ala Ile
145                 150                 155                 160

Lys Gln Asn Asp Thr Ala Gln Ala Gly Asp Ile Leu Tyr Leu Thr Lys
                165                 170                 175

Pro Leu Gly Ile Gly Ile Leu Thr Thr Ala Gln Lys Lys Gly Lys Leu
            180                 185                 190

Lys Pro Glu His Glu Gln Leu Ala Pro Asn Ala Met Cys Thr Leu Asn
        195                 200                 205

Lys Ile Gly Gln Arg Phe Ala Glu Leu Pro Gly Val His Ala Met Thr
    210                 215                 220

Asp Val Thr Gly Phe Gly Leu Ala Gly His Leu Leu Glu Met Cys Glu
225                 230                 235                 240

Gly Ser Gly Val Cys Ala Thr Leu Asp Phe Lys Ala Leu Pro Leu Leu
                245                 250                 255

Asp Glu Val Asp Tyr Tyr Leu Ser Glu Gly Cys Val Pro Gly Gly Thr
            260                 265                 270

Leu Arg Asn Phe Asp Ser Tyr Gly Ala Lys Leu Gly Ala Met Asp Glu
        275                 280                 285

Arg Thr Arg Asn Ile Met Cys Asp Pro Gln Thr Ser Gly Gly Leu Leu
    290                 295                 300

Val Ala Val Gly Lys Glu Ser Glu Ala Glu Leu Leu Ala Ile Ala Thr
305                 310                 315                 320

Gln Ala Gly Leu Thr Leu Ser Pro Ile Gly Gln Leu Lys Ala Tyr Thr
                325                 330                 335

Gly Asn Gln Phe Ile Glu Val Ile Gln
            340                 345

<210> SEQ ID NO 88
<211> LENGTH: 1038
<212> TYPE: DNA
<213> ORGANISM: Artificial Sequence
<220> FEATURE:
<223> OTHER INFORMATION: synthetic polynucleotide

<400> SEQUENCE: 88
gtgtcttcca ttcgtctgac ccaatacagc cacggggctg gctgcggctg caaaatttct      60
cccaaggtgc tcgacaccat tctcaagagc cagatcccgg gctttgacga cccgaccctg     120
```

```
gtggttggca acagcagcaa ggatgacgcg gccgtggtcg atatcggcaa cggtcagggc      180 attgttttcca ccaccgactt cttcatgccc atcgtcgatg atccctttac ctttggccgc    240
atcgcggcca ccaacgccat cagcgacatc tacgccatgg gcggcaagcc catcgttgcc    300
attgccatcc ttggctggcc catcaacacc ctagccccgg aagtggccca gcaggtgata    360
gatggcggcc gccaggtgtg ccatgaagcg ggcatatcct tggctggcgg ccacagtatc    420 gatgccccg agcccatctt cggtcttgct gtgaccggta tagtgccgct caatgccatc     480
aagcagaacg acacggccca ggcgggtgac atcctctacc tgaccaagcc cctcggtatc    540
ggcatcctca ccacggccca gaagaagggc aaattgaagc cagagcatga gcagctggcc    600
cccaacgcca tgtgcaccct caacaagatt ggccagcgct tgccgaact gcccggcgtg    660 cacgccatga cggatgtgac cgggtttggc ctggcgggac acctgcttga gatgtgcgaa    720
ggctcagggg tgtgtgccac cctcgatttc aaggcgctgc cactgctcga cgaagtagat    780
tactacctgt ccgagggctg cgtaccgggc ggtaccctgc gcaacttcga ttcctatggc    840
gccaagctcg gtgccatgga tgaacgcacc cgcaacatca tgtgcgatcc gcagaccagc    900
ggcggcttgc tggttgccgt cggtaaagaa agtgaagccg agctccttgc tatcgcgaca    960
caagcggggc tgaccctctc ccccataggc cagctgaaag cctataccgg aaaccagttt    1020
atcgaggtta tccaatga                                                  1038
```

<210> SEQ ID NO 89
<211> LENGTH: 1083
<212> TYPE: DNA
<213> ORGANISM: Trypanosoma brucei

<400> SEQUENCE: 89

```
atgacagttt gtcttgttct actaactggg ctgccaggag cggggaagac gacactaggc      60
aaggctctta aacagttggg ggatcacata acccatgaac tctccctcat agtcacggca    120
gtggtggaat tagatgactt tatgtgtaac gtcggtgcga gtaatgggtc ccgtgtagag    180
agtaccgttt tcgatccaag tcggtggcga gaggcgttcg aagcggctcg tcagcaact    240 cgccaggagt tggagcggtg cctaatgatg gagaggaata aagcggtaat gcacttggtt    300
tttctggtgg atccgctgcc atataggagt atgagagcat cgtactggaa aatgtgcaag    360
gaattaagtg ccaagtgtgc tgagactcac tttcatgatt catgggaagt gcagagcatt    420
gttgtcttgt tggaggtgcg gatgaacacc ccggaggagg tttgtctcca acgcaatgag    480
ctccgcgccg gaaccccgca gtatattccc ccgtatgtta ttaaggggat aagtgactcg    540
tttgaccgtg gtgacctcac tgctgtgctg ctgggtacag acggaaatat gtgggccgta    600
cttcccgggc agaagtcggc accgtggccc gttcttttac tggttgatga agtgagatgc    660
tgcgcgtcac cacccaattt gttggccacg cagttgctgg agcgtatccg aggggaagac    720
ataatgcgtg agatgacgga caacaagta agtgttttta attattacaa gtgccaagtg    780
gaagggggga agtcgaagtg tttggcgagt ggagaagcac atgacaacgt taacaactgt    840
cttcatcaag tggaccctcca catgcgggca gttgtgggac attacatggt cgagcggcag    900
agtagtggtt cactgaagcc aggcactggg caacgcgtaa gcaaatgtcg gtcgacccac    960
tacgcgggaa ttcgcgcagc aatcacgaag ggaacgagaa acacaggagg atcttttttcc    1020 gaagtgcaag gactactgca gcagttactt ttggaattcg agcatgcctt agtagatctt    1080
taa                                                                  1083
```

<210> SEQ ID NO 90
<211> LENGTH: 1077
<212> TYPE: DNA
<213> ORGANISM: Artificial Sequence
<220> FEATURE:
<223> OTHER INFORMATION: synthetic polynucleotide

<400> SEQUENCE: 90

| | | | | | |
|---|---|---|---|---|---|
| atgaaaaccg | cagaaaatat | tcgtggcacc | ggttcagatg | gtccgcgtaa | acgtggtctg | 60 |
| tgtgttctgt | gtggtctgcc | tgcagcaggt | aaaagcacct | ttgcacgtgc | cctggcacat | 120 |
| cgtctgcagc | aagaacaagg | ttgggcaatt | ggtgttgttg | catatgatga | tgttatgccg | 180 |
| gatgcatttc | tggcaggcgc | acgcgcacgt | ccggcaccga | gtcagtggaa | actgctgcgt | 240 |
| caagaactgc | tgaaatatct | ggaatatttc | ctgatggccg | tgattaatgg | ttgtcagatg | 300 |
| agcgttccgc | ctaatcgtac | cgaagcaatg | tgggaagatt | ttatcacctg | tctgaaagat | 360 |
| caggacctga | tttttagcgc | agcatttgaa | gcacagagct | gttatctgct | gaccaaaaca | 420 |
| gcagttagcc | gtccgctgtt | tctggttctg | atgataatt | tctattatca | gagcatgcgc | 480 |
| tatgaggttt | atcagctggc | acgtaaatat | agcctgggtt | tttgtcagct | gttcctggat | 540 |
| tgtccgctgg | aaacctgtct | gcagcgtaat | ggtcagcgtc | cgcaggcact | gcctccggaa | 600 |
| accattcatc | tgatgggtcg | taaactggaa | aaaccgaatc | cggaaaaaaa | tgcctgggaa | 660 |
| cataatagcc | tgaccattcc | gagtccggca | tgtgcaagcg | aagcaagcct | ggaagttacc | 720 |
| gatctgctgc | tgaccgcact | ggaaaatccg | gttaaatatg | ccgaagataa | catggaacag | 780 |
| aaagataccg | atcgcattat | ttgcagcacc | aacattctgc | ataaaaccga | tcagaccctg | 840 |
| cgtcgtattg | ttagccagac | catgaaagaa | gcaaaagatg | aacaggttct | gccgcataat | 900 |
| ctgaaactgc | tggcagaaga | actgaataaa | ctgaaagcag | aattccttga | ggatctgaaa | 960 |
| cagggcaata | aaagtatct | gtgttttcag | cagaccatcg | atattccgga | tgtgatcagc | 1020 |
| tttttccact | atgagaaaga | taacatcgtg | cagaaatact | tcagcaagca | gcattaa | 1077 |

<210> SEQ ID NO 91
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 91

| | | | | | |
|---|---|---|---|---|---|
| atgattatgg | cagtattgga | tattacaaat | gctaattttg | atgaaaccgt | taagaccgcc | 60 |
| aagcccgttt | taattgactt | ttgggcaccg | tggtagccgg | gatgcgtaca | gctcagtcct | 120 |
| gagctgcagg | ctgccgaggc | ggaactcggc | gacaaggctg | tgatagcaca | gtctaacgtg | 180 |
| gataatgcac | gtgaattggc | agtaaaattt | aagtttatgt | caatacctac | cctcatcgtt | 240 |
| ttaaagacg | gaaagaggt | ggacaggcac | acaggctata | tggataagaa | gagccttgta | 300 |
| aactttgttt | caaagcatat | ctaa | | | | 324 |

<210> SEQ ID NO 92
<211> LENGTH: 7051
<212> TYPE: DNA
<213> ORGANISM: Artificial Sequence
<220> FEATURE:
<223> OTHER INFORMATION: synthetic polynucleotide

<400> SEQUENCE: 92

| | | | | | |
|---|---|---|---|---|---|
| gtctataatc | acggcagaaa | agtccacatt | gattatttgc | acggcgtcac | actttgctat | 60 |

```
gccatagcat ttttatccat aagattagcg gatcctacct gacgctttt atcgcaactc    120
tctactgttt ctccataccc gtttgaattc ggaggggaac ttctatctgg tgatagacgg    180
gaactctaaa ttccttgaaa tgcctcgccg cattgggttc gattcccttc ccctccgcca    240
ggatctagag tcgacctgca gatccttagc gaaagctaag gatttttttt aggaattaac    300
catggatccg agcagcctga tacagattaa atcagaacgc agaagcggtc tgataaaaca    360
gaatttgcct ggcggcagta gcgcggtggt cccacctgac cccatgccga actcagaagt    420
gaaacgccgt agcgccgatg gtagtgtggg gtctccccat gcgagagtag gaactgcca     480
ggcatcaaat aaaacgaaag gctcagtcga aagactgggc ctttcgtttt atctgttgtt    540
tgtcggtgaa cgctctcctg agtaggacaa atccgccggg agcggatttg aacgttgcga    600
agcaacggcc cggagggtgg cgggcaggac gcccgccata aactgccagg catcaaatta    660
agcagaaggc catcctgacg gatggccgcg gccgcctcta aacgggtctt gagggggtttt   720
ttgctgaaac ctcaggcatt tgagaagcac acggtcacac tgcttccggt agtcaataaa    780
ccggtaaacc agcaatagac ataagcggct atttaacgac cctgccctga accgacgaca    840
agctgacgac cgggtctccg caagtggcac ttttcgggga aatgtgcgcg aaccccctat    900
ttgtttattt ttctaaatac attcaaatat gtatccgctc atgaatcatt ggataacctc    960
gataaactgg tttccggtat aggctttcag ctggcctatg ggggagaggg tcagccccgc    1020
ttgtgtcgcg atagcaagga gctcggcttc actttcttta ccgacggcaa ccagcaagcc   1080
gccgctggtc tgcggatcgc acatgatgtt gcggtgcgt tcatccatgg caccgagctt    1140
ggcgccatag gaatcgaagt tgcgcagggt accgcccggt acgcagccct cggacaggta    1200
gtaatctact tcgtcgagca gtggcagcgc cttgaaatcg agggtggcac acaccccctga   1260
gccttcgcac atctcaagca ggtgtcccgc caggccaaac ccggtcacat ccgtcatggc    1320
gtgcacgccg ggcagttcgg caaagcgctg gccaatcttg ttgagggtgc acatggcgtt    1380
gggggccagc tgctcatgct ctggcttcaa tttgcccttc ttctgggccg tggtgaggat    1440
gccgataccg aggggcttgg tcaggtagag gatgtcaccc gcctgggccg tgtcgttctg    1500
cttgatggca ttgagcggca ctataccggt cacagcaaga ccgaagatgg gctcggggggc   1560
atcgatactg tggccgccag ccaaggatat gcccgcttca tggcacacct ggcggccgcc    1620
atctataccc tgctgggcca cttccggggc tagggtgttg atgggccagc caaggatggc    1680
aatggcaacg atgggcttgc cgcccatggc gtagatgtcg ctgatggcgt tggtggccgc    1740
gatgcggcca aaggtaaagg gatcatcgac gatgggcatg aagaagtcgg tggtggaaac    1800
aatgccctga ccgttgccga tatcgaccac ggccgcgtca tccttgctgc tgttgccaac    1860
caccagggtc gggtcgtcaa agcccgggat ctggctcttg agaatggtgt cgagcaccttt   1920
gggagaaatt ttgcagccgc agccagcccc gtggctgtat gggtcagac gaatggaaga     1980
cacgattacc ccttgtttgg ctgtttctca agatgaaaca gcgtatatca ggcaaaagga    2040
gatgaccctg agcgggccat ggacagggc attatgccac aaggactctg cgggttcgaa     2100
tcacaatagc ctgtcgaaaa tgccgccagc ggaactggcg gctgtgggat cagggctcct    2160
cggtcgcagt ggtcggagtg gcagtagca actccttgag ttgggcgata agcagtgcaa     2220
tctcggtcgg cagcagggtc gccatattga gcagcacctt ctgctggcgc acggtggcga    2280
tgaccggcac cggcagtttc gcagggcat cgagcagctg ctgggccgga cgcggtcgg      2340
tgcattcgag cgcaggcgca gggtagaact cgtccggcag ggtgccacca cccaccacca    2400
```

```
gctgggcggg gaccggcaca aagcagccgg gcagggcggc catcagctga tcggcgcggg    2460
cctgcatggc ggcagggttg ctcaaggtgc gctgggcgat gccctcgccg atgggggact    2520
tgttgagctt gtggatgagc aggcgttcca gcagggagta gacgatgcgg ctcgggcgga    2580
aggtgcgcat catggggtgt ttttccagcc gcttgatgag gtcgctgcgg ccgctgatga    2640
tgcccgattg cgggccaccc agcagcttgt cgccggagta gcagaccaga tccgcccccg    2700
ccttgatgta ctgacgcacc gaggtttcgt ccggtgcaaa ctcctcggtg gtcaagcccg    2760
agccctgatc caccgccagc accacgtgct cgggcagggc gcggccacc tcgccaatat     2820 cgggggattc ggtaaagccg cgaatggcga aattggatct gtgtaccatc agcaccagcg    2880
cggtctgatc tgtgatggca tcgaggtaat cttttggcggt agtgatattg gtggtgccca   2940
cctccaccag tttggcgccg gagagcgcca gaatgtcggg aatgcgaaag ccgccaccaa    3000
tctggatctg ttcgccccgc gagacgatca cctcgcgccc cttggctatc tcctgcagca    3060
gcaagaagag cgaagcggcg ttgttgttga ccaccagcga atcctcggcc tgggtgaggc    3120 aacgagcag gggggcgatc agcccccttgc gcccgccgcg cttgccggtg gcgagatcca    3180
gttccagatt gttgtagcca gtgttgaggt cgcgcacctc gtcccacagc tcgcgactta    3240
gcggcgagcg cccccagattg gtgtgcacca gggtgccggt ggcgttgatc acccgggtct    3300
gacgttggcg cagctgctgc tggcaacgct tggcaatcag tgcctcgatt tgctcggggg    3360
caaccccatg ctggcgaaat gcctcgctct ggcgcaattc gctcaggaca tcgcgcaccg    3420
cctgggtcac cagcgggcgg ctcagcgcct cgataaaacc ggtgagaaag ggttgctgca    3480
gcagctgttc cacttgcggt agacggcgcg cttgttgctg gctgggctgt ggcagtgaat    3540
ctggcagtga atctggcagt gaatcgtcgg cagtgggaca tgattcgggc tgactgtgag    3600
agtgggcgat ggctggcgcg tgagacgagt tcggcatggt ttagttcctc accttgtcgt    3660
attatactat gccgatatac tatgccgatg attaattgtc aacacgtgtt aattcttaga    3720
aaaactcatc gagcatcaaa tgaaactgca atttattcat atcaggatta tcaataccat    3780 attttttgaaa aagccgtttc tgtaatgaag gagaaaactc accgaggcag ttccatagga    3840
tggcaagatc ctggtatcgg tctgcgattc cgactcgtcc aacatcaata caacctatta    3900
atttcccctc gtcaaaaata aggttatcaa gtgagaaatc accatgagtg acgactgaat    3960
ccggtgagaa tggcaaaagt ttatgcattt cttccagac ttgttcaaca ggccagccat     4020
tacgctcgtc atcaaaatca ctcgcatcaa ccaaaccgtt attcattcgt gattgcgcct    4080
gagcgagacg aaatacgcgg tcgctgttaa aaggacaatt acaaacagga tcgaatgca    4140 accggcgcag gaacactgcc agcgcatcaa caatattttc acctgaatca ggatattctt    4200
ctaatacctg gaatgctgtt ttcccgggga tcgcagtggt gagtaaccat gcatcatcag    4260
gagtacggat aaaatgcttg atggtcggaa gaggcataaa ttccgtcagc cagtttagtc    4320
tgaccatctc atctgtaaca tcattggcaa cgctacccttt gccatgtttc agaaacaact    4380
ctggcgcatc gggcttccca tacaatcgat agattgtcgc acctgattgc ccgacattat    4440
cgcgagccca tttataccca tataaatcag catccatgtt ggaatttaat cgcggcctag    4500
agcaagacgt ttcccgttga atatggctca tactcttcct ttttcaatat tattgaagca    4560
tttatcaggg ttattgtctc atgagcggat acatatttga atgtatttag aaaaataaac    4620
aaataggcat gcagcgctct tccgcttcct cgctcactga ctcgctacgc tcggtcgttc    4680
gactgcggcg agcggtgtca gctcactcaa aagcggtaat acgttatcc acagaatcag     4740 gggataaagc cggaaagaac atgtgagcaa aaagcaaagc accggaagaa gccaacgccg    4800
```

-continued

```
caggcgtttt tccataggct ccgccccct gacgagcatc acaaaaatcg acgctcaagc    4860
cagaggtggc gaaacccgac aggactataa agataccagg cgtttccccc tggaagctcc    4920
ctcgtgcgct ctcctgttcc gaccctgccg cttaccggat acctgtccgc ctttctccct    4980
tcgggaagcg tggcgctttc tcatagctca cgctgttggt atctcagttc ggtgtaggtc    5040
gttcgctcca agctgggctg tgtgcacgaa ccccccgttc agcccgaccg ctgcgcctta    5100
tccggtaact atcgtcttga gtccaacccg gtaagacacg acttatcgcc actggcagca    5160
gccattggta actgatttag aggactttgt cttgaagtta tgcacctgtt aaggctaaac    5220
tgaaagaaca gattttggtg agtgcggtcc tccaacccac ttaccttggt tcaaagagtt    5280
ggtagctcag cgaaccttga gaaaaccacc gttggtagcg gtggtttttc tttatttatg    5340
agatgatgaa tcaatcggtc tatcaagtca acgaacagct attccgggcc ggccggagcc    5400
tatggaaaaa cgccagcaac gcggcctttt tacggttcct ggccttttgc tggccttttg    5460
ctcacatgtt ctttcctgcg ttatcccctg attctgtgga taaccgtatt accgcctttg    5520
agtgagctga taccgctcgc cgcagccgaa cgaccgagcg cagcgagtca gtgagcgagg    5580
aagcggaaga gcgcctgatg cggtattttc tccttacgca tctgtgcggt atttcacacc    5640
gcatatggtg cactctcagt acaatctgct ctgatgccgc atagttaagc cagtatacac    5700
tccgctatcg ctacgtgact gggtcatggc tgcgccccga cacccgccaa cacccgctga    5760
cgcgccctga cgggcttgtc tgctcccggc atccgcttac agacaagctg tgaccgtctc    5820
cgggagctgc atgtgtcaga ggttttcacc gtcatcaccg aaacgcgcga ggcagcagat    5880
caattcgcgc gcgaaggcga agcggcatgc ataatgtgcc tgtcaaatgg acgaagcagg    5940
gattctgcaa accctatgct actccgtcaa gccgtcaatt gtctgattcg ttaccaatta    6000
tgacaacttg acgctacat cattcacttt ttcttcacaa ccggcacgga actcgctcgg    6060
gctggccccg gtgcatttt taaatacccg cgagaaatag agttgatcgt caaaaccaac    6120
attgcgaccg acggtggcga taggcatccg ggtggtgctc aaaagcagct tcgcctggct    6180
gatacgttgg tcctcgcgcc agcttaagac gctaatccct aactgctggc ggaaaagatg    6240
tgacagacgc gacggcgaca agcaaacatg ctgtgcgacg ctggcgatat caaaattgct    6300
gtctgccagg tgatcgctga tgtactgaca agcctcgcgt acccgattat ccatcggtgg    6360
atggagcgac tcgttaatcg cttccatgcg ccgcagtaac aattgctcaa gcagatttat    6420
cgccagcagc tccgaatagc gcccttcccc ttgcccggcg ttaatgattt gcccaaacag    6480
gtcgctgaaa tgcggctggt gcgcttcatc cgggcgaaag aaccccgtat ggcaaatat    6540 tgacggccag ttaagccatt catgccagta ggcgcgcgga cgaaagtaaa cccactggtg    6600
ataccattcg cgagcctccg gatgacgacc gtagtgatga atctctcctg gcgggaacag    6660
caaaatatca cccggtcggc aaacaaattc tcgtccctga ttttcacca cccctgacc    6720 gcgaatggtg agattgagaa tataaccttt cattcccagc ggtcggtcga taaaaaatc    6780 gagataaccg ttggcctcaa tcggcgttaa acccgccacc agatgggcat taaacgagta    6840
tcccggcagc aggggatcat tttgcgcttc agccatactt ttcatactcc cgccattcag    6900
agaagaaacc aattgtccat attgcatcag acattgccgt cactgcgtct tttactggct    6960
cttctcgcta accaaaccgg taaccccgct tattaaaagc attctgtaac aaagcgggac    7020
caaagccatg acaaaaacgc gtaacaaaag t                                    7051
```

<210> SEQ ID NO 93

<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 93

```
atgggcatgt gtgctgctcg gctagcggcg gcggcggcgg cggcccagtc ggtgtatgcc      60
ttctcggcgc gcccgctggc cggcggggag cctgtgagcc tgggctccct gcggggcaag     120
gtactactta tcgagaatgt ggcgtccctc tagggcacca cggtccggga ctacacccag     180
atgaacgagc tgcagcggcg cctcggaccc cggggcctgg tggtgctcgg cttcccgtgc     240
aaccagtttg gcatcagga gaacgccaag aacgaagaga ttctgaattc cctcaagtac     300
gtccggcctg gtggtgggtt cgagcccaac ttcatgctct cgagaagtg cgaggtgaac      360
ggtgcggggg cgcaccctct cttcgccttc ctgcgggagg ccctgccagc tcccagcgac     420
gacgccaccg cgcttatgac cgaccccaag ctcatcacct ggtctccggt gtgtcgcaac     480
gatgttgcct ggaactttga aagttcctg gtgggccctg acggtgtgcc cctacgcagg      540
tacagccgcc gcttccagac cattgacatc gagcctgaca tcgaagccct gctgtctcaa     600
gggcccagct gtgccctcga gcaccaccac caccaccact aa                         642
```

<210> SEQ ID NO 94
<211> LENGTH: 1101
<212> TYPE: DNA
<213> ORGANISM: Unknown
<220> FEATURE:
<223> OTHER INFORMATION: Parcubacteria DG_74_2 bin SepCysS

<400> SEQUENCE: 94

```
atgatctaca aacgccagaa caaaaacaaa attaacatca acccgattca ggcaggcggt       60
attctgacca agatgcacg taaaaccctg attgaatggg gtgatggtta tagcgtttgc      120
gatatttggt atagcggcaa aatcgataaa atcgaaaatc cgcagatccg caaattcatc     180
aatgaagatc tgccgaaatt tctgggtagc gatattgcac gtattattgg tggtgcacgt     240
gaaggtattt gtgcaattat gcatgcagtt gcaaaaccgg gtgatattat tctggtggat     300
gagaacaaac actataccac cattctggca gcagaaaaaa atggtctgaa agttgttgaa     360
gttccgaata gcggtcatcc ggaatacaaa attgatgtgc gcgattatga aaaactgatc     420
aaaaaacata aaccggcact gatcctgctg acctatccgg atggtaatta tggtaatatg     480
ccggatgcaa aaaactggg cgaaatcgtg atcaaatata acattccgta tctgctgaat     540
gcagcatata gcgcaggtcg tctgccggtt gatctgattg caattaatgg tgattttatt     600
gtggccagcg gtcataaaag catggcagca agcgaaccga ttggtgttct gggttttcgt     660
aaaaaatgga agacaccct gttcaaaaaa agcttcttct atccggacaa agagattgaa     720
ttcctgggcc attatcagaa aggtgcaccg atgatgaccc tgatggcaag ctttccgtat     780
gtgaaaaaac gtgttgaaga gtgggaaaaa caaatcgaga agcacgttg gtttagcgca     840
gaaatggaaa aactgggttt taaacagctg ggtgaaaaac cgcataatca cgatctgctg     900
tttttcgaat caccgcagct gtacaaaatt agccagaaac ataaagaggg tcggtttttc     960
ctgtacaaag aactgaaaaa aaaaggcatc tacggcatta accgggtct gacgaaacat     1020
tttaaactga gcacctttgc agccagcaaa gaggaactga aaaaactgct ggaagtgttc     1080
aaagagatcc tgattaaata a                                               1101
```

```
<210> SEQ ID NO 95
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 95

Leu Glu His His His His His His
1               5
```

COMPOSITIONS AND METHODS FOR MAKING SELENOCYSTEINE CONTAINING POLYPEPTIDES

CROSS-REFERENCE TO RELATED APPLICATIONS

This application is a continuation-in-part of U.S. Ser. No. 15/202,194, filed Jul. 5, 2016, which is a continuation-in-part of U.S. Ser. No. 14/131,382, now U.S. Pat. No. 9,464,288, filed Jan. 7, 2014, which is a 371 application of PCT/US2012/046252, entitled "Compositions and Methods for Making Selenocysteine Containing Polypeptides," filed Jul. 11, 2012, which claims priority to U.S. Provisional Application No. 61/506,338, entitled "System for Co-translational Selenocysteine Insertion at Any Position of a Protein" filed Jul. 11, 2011, each of which is incorporated by reference in its entirety.

STATEMENT REGARDING FEDERALLY SPONSORED RESEARCH OR DEVELOPMENT

This invention was made with government support under GM022854 and GM122560 awarded by National Institute of Health, DE-FG02-98ER20311 awarded by the Department of Energy and 0950474 awarded by the National Science Foundation. The government has certain rights in the invention.

REFERENCE TO THE SEQUENCE LISTING

The Sequence Listing submitted as a text file named "YU_5714_CIP_2_ST25.txt," created on Oct. 4, 2017, and having a size of 83,160 bytes is hereby incorporated by reference pursuant to 37 C.F.R. § 1.52(e)(5).

FIELD OF THE INVENTION

The field of the invention generally relates to compositions including tRNAs and methods of using them to manufacture recombinant selenocysteine containing polypeptides.

BACKGROUND OF THE INVENTION

Selenocysteine, commonly referred to as the twenty-first amino acid, is incorporated into at least 25 human proteins. Natural co-translational incorporation of selenocysteine (Sec) into proteins proceeds by a recoding process so that upon encountering the UGA codon in the messenger RNA the ribosome knows to recognize it as Sec instead of Stop. This process requires three components: (i) the aminoacyl-tRNA carrying selenocysteine, Sec-tRNA$^{Sec}$; (ii) the specialized elongation factor, SelB, carrying Sec-tRNA$^{Sec}$ to the ribosome, and (iii) the SECIS element, an RNA secondary structure of the mRNA just downstream of the UGA codon, that interacts with the SelB•Sec-tRNA$^{Sec}$ complex (Böck, A, Thanbichler, M, Rother, M & Resch, A (2005), eds Ibba M, Francklyn C S, & Cusack S (Landes Bioscience, Georgetown, Tex.), pp 320-327; Yoshizawa, S & Böck, A (2009) Biochim Biophys Acta 1790:1404-1414). Additionally, in order to protect the integrity of this recoding process, Sec-tRNA$^{Sec}$ is not recognized by the general elongation factor EF-Tu because of the presence of three base pairs that act as antideterminants (Rudinger, J, Hillenbrandt, R, Sprinzl, M & Giegé, R (1996) EMBO J 15:650-657). Sec-tRNA$^{Sec}$ cannot be accommodated during normal translation because it is not an acceptable substrate for EF-Tu, and the SelB•Sec-tRNA$^{Sec}$ complex will not decode in-frame UGA codons in absence of the SECIS.

Insertion of selenocysteine into a recombinant protein, for example, substitution of a naturally occurring cysteine residue for selenocysteine, can alter the function of the protein. Substituting one or more naturally occurring Cys residues in the active site of an enzyme with a Sec can increase the activity of this enzyme. Diselenide bonds have very low redox potential. Therefore, replacing disulfide bonds with diselenide or selenocysteine-cysteine bonds can lower dosage, increase half-life, increase stability, reduce toxicity, alter pharmacokinetics, change folding properties, or combinations thereof of the recombinant selenocysteine containing protein relative to a reference protein without selenocysteines, such as a naturally occurring counterpart.

However, due the presence the SECIS element as an integral part of the open reading frame (within the mRNA) encoding the protein that harbors Sec in its sequence, it is not possible to insert Sec into proteins by a standard mutational scheme or in the construction of random mutagenic libraries, and production of Sec proteins is limited to costly and inefficient methods of protein synthesis. Accordingly, there is a need for alternative methods of manufacturing selenocysteine containing polypeptides.

It is an object of the invention to provide compositions and methods for recombinant expression of proteins engineered to include one or more selenocysteine residues without the requirement of a SECIS in the mRNA encoding the protein.

It is a further object of the invention to provide non-naturally occurring proteins including one or more selenocysteine residues.

SUMMARY OF THE INVENTION tRNA$^{Sec}$ and methods of using them for recombinant expression of proteins engineered to include one or more selenocysteine residues are disclosed. Typically, tRNA$^{Sec}$ (1) can be recognized by SerRS and by EF-Tu, or variants thereof; and is characterized by one or more of the following elements: (2) when aminoacylated with serine, the Ser-tRNA$^{Sec}$ can be converted to Sec-tRNA$^{Sec}$ by SelA, or a variant thereof; (3) when aminoacylated with serine, the Ser-tRNA$^{Sec}$ can be phosphorylated by PSTK or variant thereof; (4) when aminoacylated with phosphorylated serine, the Sep-tRNA$^{Sec}$ can serve as a substrate for SepSecS or variant thereof; and combinations thereof. In some embodiments, the Ser-tRNA$^{Sec}$ is characterized by elements (1) and (2). In some embodiments, the Ser-tRNA$^{Sec}$ is characterized by elements (1), (3), and (4). In some embodiments, the Ser-tRNA$^{Sec}$ is characterized by elements (1), (2), (3), and (4). In some embodiments, the Ser-tRNA$^{Sec}$ is characterized by elements (1), (2), and (3).

Typically, the tRNA$^{Sec}$ do not require a SECIS element in an mRNA to be incorporated into a growing polypeptide chain during translation.

Typically, the tRNA$^{Sec}$ is a non-naturally occurring tRNA$^{Sec}$. The non-naturally occurring tRNA$^{Sec}$ can be a variant of a naturally occurring tRNA. In some embodiments, the tRNA$^{Sec}$ is includes or consists of a naturally occurring nucleic acid sequence.

In some embodiments, the tRNA$^{Sec}$ has a naturally occurring tRNA sequence. In some embodiments, the tRNA$^{Sec}$ is an "allo-tRNA". Allo-tRNAs typically have a 8/4 or 9/3 composition of the 12-bp amino-acid acceptor branch. Naturally and non-naturally occurring allo-tRNAs are provided and can be used in the disclosed compositions and methods.

Many naturally occurring allo-tRNA have an anticodon that recognizes a codon inconsistent with the amino acid charged to it. For example, some of the allo-tRNAs charge with serine, but have a leucine anticodon. The non-naturally occurring allo-tRNA typically have one or more insertions, deletions, or substitutions relative to the naturally occurring allo-tRNA. For example, the naturally occurring allo-tRNA can be modified to include a SerRS identity element, to have an anticodon that recognizes or hybridizes to a stop codon, or a combination thereof. In some embodiments, the variants include one more additional modifications that improve the tRNAs activity as a tRNA$^{Sec}$, for example, to improve binding to a SelA, or improve binding to a EF-Tu.

Recombinant compositions and method of using tRNA$^{Sec}$ are also provided. Exemplary tRNAs, isolated nucleic acids encoding the tRNAs, vectors thereof, and host cells expressing the tRNA are also provided. For example, an isolated nucleic acid can include a nucleic acid sequence encoding a tRNA$^{Sec}$, wherein the tRNA$^{Sec}$ is recognized by SerRS and by EF-Tu, or variants thereof, and when aminoacylated with serine the Ser-tRNA is a substrate for SelA or a variant thereof.

Consensus sequences for allo-tRNAs and exemplary naturally and non-naturally occurring allo-tRNA include SEQ ID NOS:19-42.

In some embodiments, the isolated nucleic acid includes a heterologous expression control sequence for expression of the tRNA. In some embodiments, the nucleic acid encoding the tRNA is in an expression vector. Host cells including the nucleic acid encoding the tRNA are also provided. The host cell can be, for example, a prokaryote, archaeon, or eukaryote. The nucleic acid is incorporated into the genome of the cell or expressed episomally. The host cell can be a genetically recoded organism.

Methods of manufacturing selenocysteine containing polypeptides are also disclosed. The tRNA$^{Sec}$ can be used for recombinant manufacture of selenocysteine containing polypeptides encoded by mRNA without the requirement of an SECIS element. In some embodiments, the tRNA$^{Sec}$ is co-expressed in a recombinant expression system, such as E. coli, with SerRS, EF-Tu, SelD, SelA, or PSTK and SepSecS, or a combination of SelA, PSTK and SepSecS, and an mRNA with at least one codon that recognizes the anticodon of the tRNA$^{Sec}$ to manufacture a selenocyteine containing polypeptide encoded by the mRNA.

Nucleic acids encoding selenocysteine containing polypeptides are also disclosed. The nucleic acids encode a polypeptide of interest and include a non-natural tRNA$^{Sec}$ recognition codon, for example a "stop" codon that hybridizes with the anticodon of the tRNA$^{Sec}$, such that a selenocysteine is transferred onto the growing polypeptide chain during translation. The selenocysteine containing polypeptides can be polypeptides that contain selenocysteine in nature, or polypeptides that do not contain selenocysteine in nature. For example, a non-naturally occurring tRNA recognition codon can be substituted for a cysteine codon in the naturally occurring mRNA, which changes the cysteine to a selenocysteine when the nucleic acid encoding the polypeptide is expressed recombinantly with the tRNA$^{Sec}$. Substituting one or more naturally occurring Cys residues with a Sec can increase activity, lower dosage, reduce toxicity, improve stability, increase efficacy, increase half-life or combinations thereof of a selenocysteine containing protein relative to its cysteine containing counterpart.

Methods of treating subjects in need thereof with recombinant selenocysteine containing polypeptides prepared using the disclosed compositions and methods are also disclosed. Particularly preferred proteins containing selenocysteine include antibodies and enzymes having altered binding affinity and/or pharmacokinetics.

BRIEF DESCRIPTION OF THE DRAWINGS

FIGS. 1A and 1B are illustrations showing the translation apparatus. The canonical amino acids are charged onto their respective tRNA by their cognate aminoacyl-tRNA synthetase. The aminoacyl-tRNA is then delivered by EF-Tu to the ribosome (FIG. 1A). In contrast, the Sec pathway requires several biosynthetic steps. First, tRNA$^{Sec}$ is misacylated to Ser-tRNA$^{Sec}$ by SerRS. While in bacteria Ser-tRNA$^{Sec}$ is directly converted by SelA to Sec-tRNA$^{Sec}$, archaea and eukaryotes employ an additional phosphorylation step by PSTK to form Sep-tRNA$^{Sec}$, which is then converted by SepSecS to the final product Sec-tRNA$^{Sec}$ (FIG. 1B). Sec-tRNA$^{Sec}$ is bound by elongation factor SelB and delivered to the ribosome. However, reassignment of the opal codon UGA to a Sec codon is only achieved if SelB also binds to the mRNA SECIS hairpin structure.

FIGS. 4A and 4B are depictions of the primary and secondary structures of a non-naturally occurring tRNA$^{UTu}$ with a body derived from *M. maripaludis* (FIG. 4A, tRNA$^{UTu}_{UCA}$, SEQ ID NO:16, tRNA$^{UTu}_{op}$, SEQ ID NO:13; tRNA$^{UTu}_{am}$, SEQ ID NO:14) and a non-naturally occurring tRNA$^{UTu}$ with a body derived from *E. coli* (FIG. 4B, tRNA$^{UTu}_{UCA}$, SEQ ID NO:12, tRNA$^{UTu}_{op}$, SEQ ID NO:9; tRNA$^{UTu}_{am}$, SEQ ID NO:10). Transplanted PSTK identity elements are boxed. "<" identifies potential locations of additional base pairs in the acceptor stem. "Arrow" identifies the location of other possible mutations. Specifically, the <depict one possible insertion of a G-C base pair between the 1$^{st}$ and 2$^{nd}$ base pair and a second possible insertion of a G-C pair insertion between the 6$^{th}$ and 7$^{th}$ base pair of the acceptor stem. The arrows depict a possible change in the 50:64 base pair (A-U) to a U-A pair, and substitution of the serine anticodon (UGA) with opal (UCA) or amber (CUA) anticodon.

(6B), and consensus primary and secondary structures of minor serine/histidine/cysteine/selenocysteine tRNA species (8/4) SelC*tRNA$^{Cys}$ (delta-proteobacteria) (SEQ ID NO:43) (6C), (8/4) tRNAs$^{Ser}$ (bacteria) (SEQ ID NO:21) (6D), (8/4) tRNAs' (α-proteobacteria bacteria) (SEQ ID NO:44) (6E), (8/4) tRNAs$^{Sec}$ (bacteria) (SEQ ID NO:45) (6F). The (8/4) tRNAsSer with Y20 are also classified as (8/4) allo-tRNA.

Figures 7A, 7B:
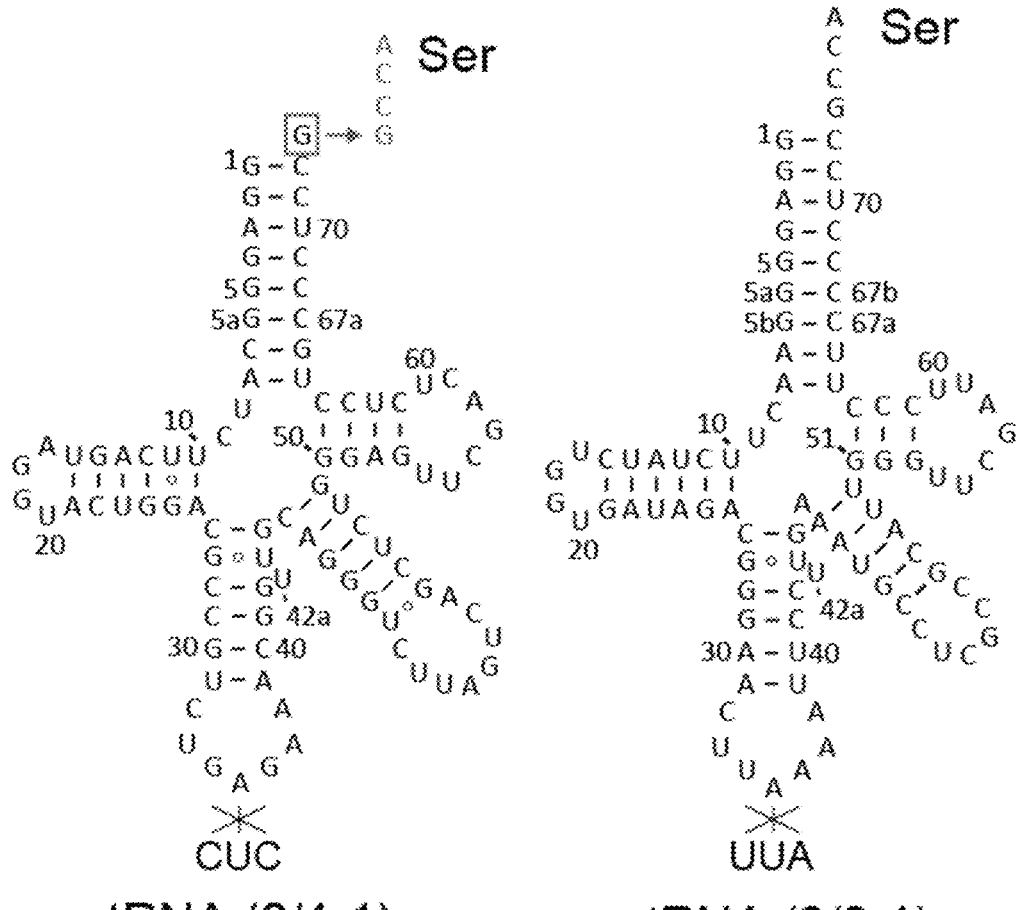
Figure 7C:
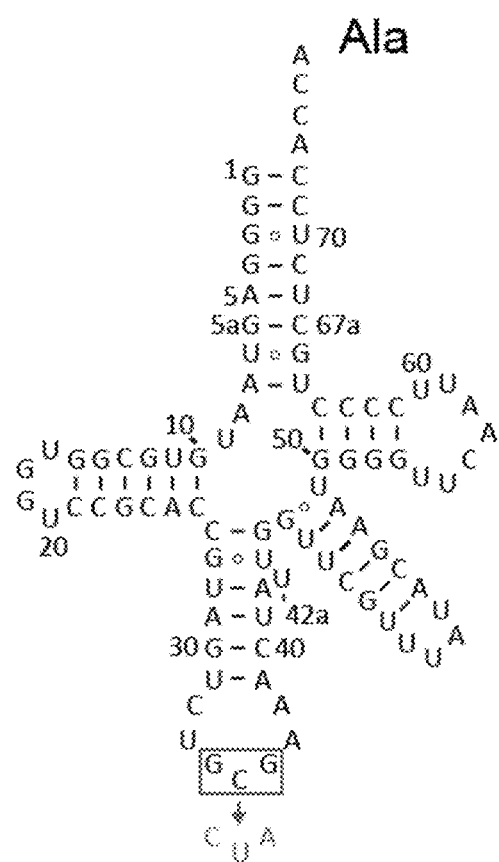
Figures 7D, 7E:
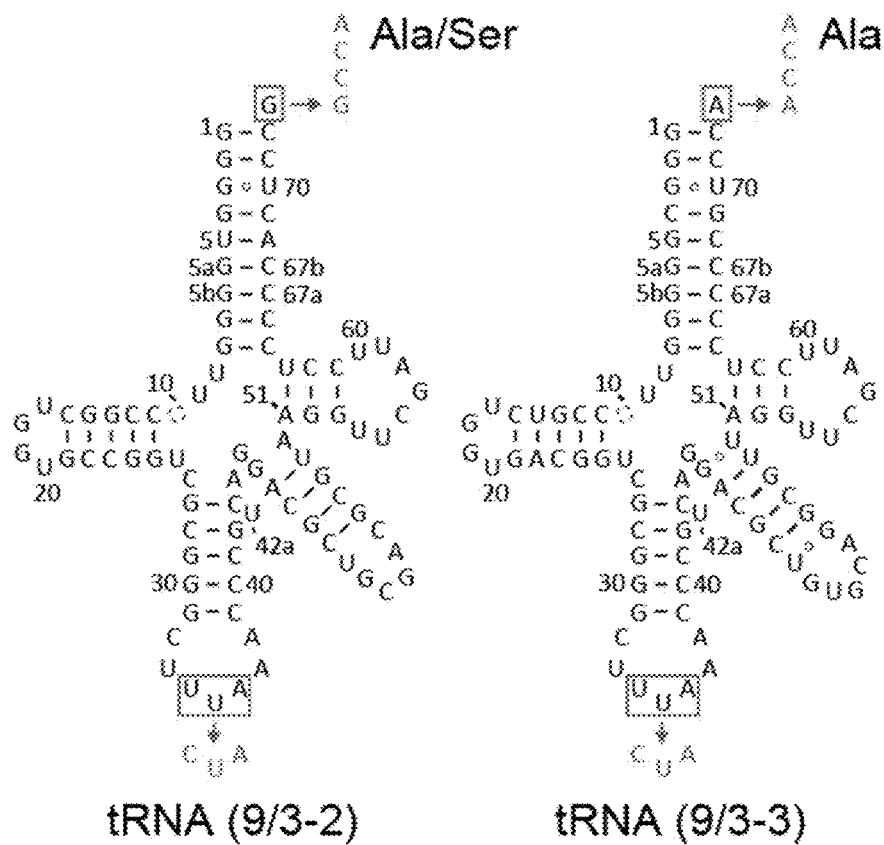
Figure 7F:
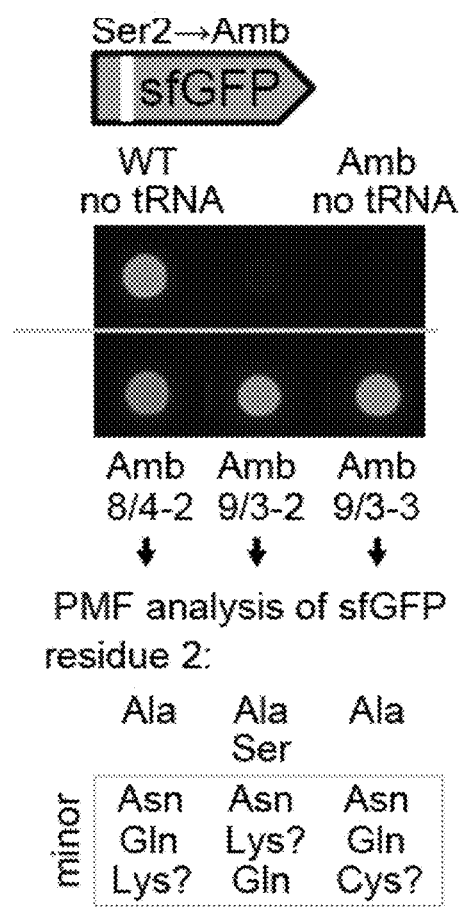
Figure 7G:
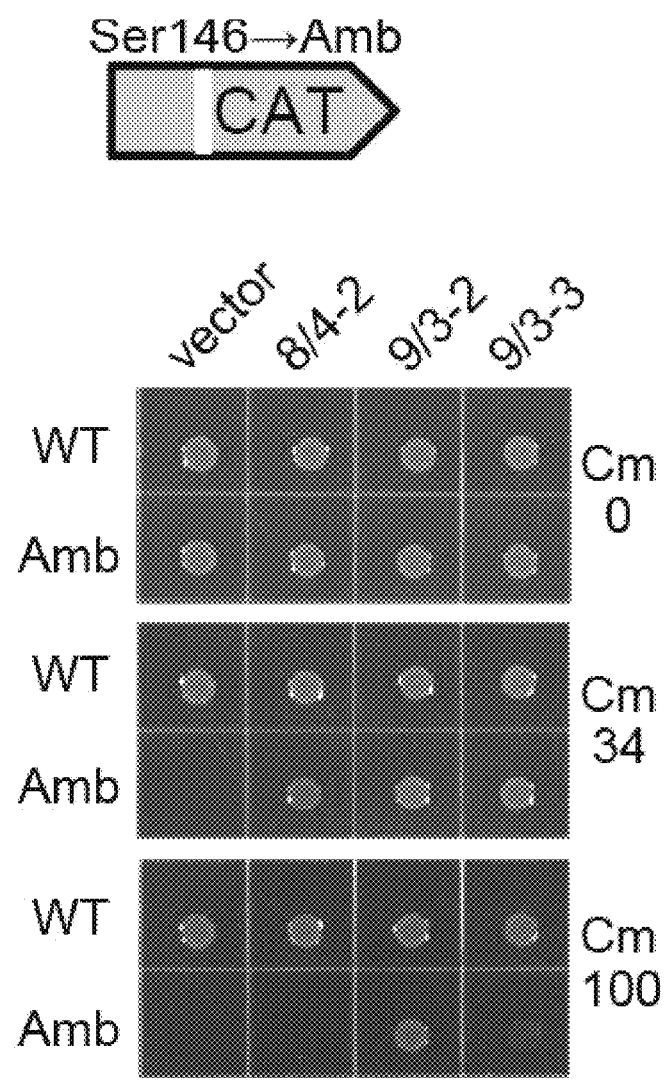

FIGS. 7A-7E are primary and secondary structures of tRNA. FIGS. 7A and 7B show missense suppressor allo-tRNAs with Ser identity and Leu anticodons: tRNA (8/4-1) (SEQ ID NO:46) (7A) and tRNA (9/3-1) (SEQ ID NO:47) (7B). FIGS. 7C-7E show amber suppressor variants of three allo-tRNA species tRNA (8/4-2) (SEQ ID NO:48) (7C), tRNA (9/3-2) (SEQ ID NO:49) (7D), and tRNA (9/3-3) (SEQ ID NO:50) (7E). Their presumed amino-acid identities are indicated. FIG. 7F is images of the results of an amber suppression experiment in E. coli DH10B using sfGFP as reporter. The amino acids incorporated into sfGFP in response to the amber codon at position 2 by allo-tRNAs are shown. FIG. 7G is images of the results of an assay testing suppression of Ser146TAG CAT by allo-tRNAs in E. coli. Pre-cultured cells were spotted onto LB agar plates with various Cm concentrations (0, 34, 100 µg/mL). The plates were incubated overnight at 37° C.

Figure 8A:
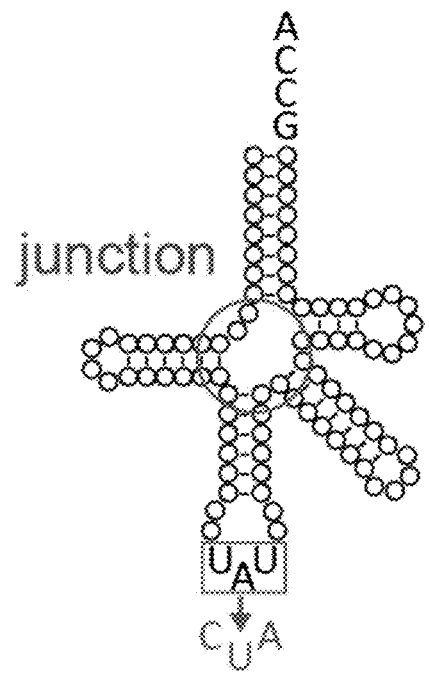
Figure 8B:
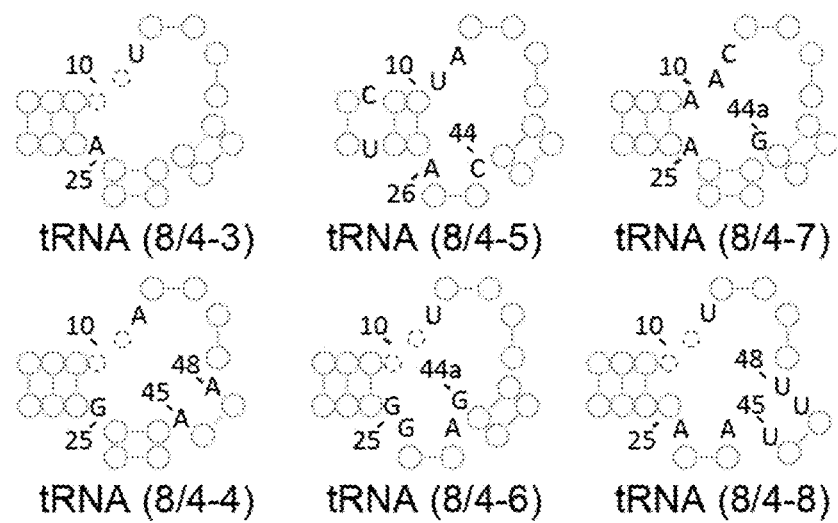
Figures 8C, 8D, 8E:
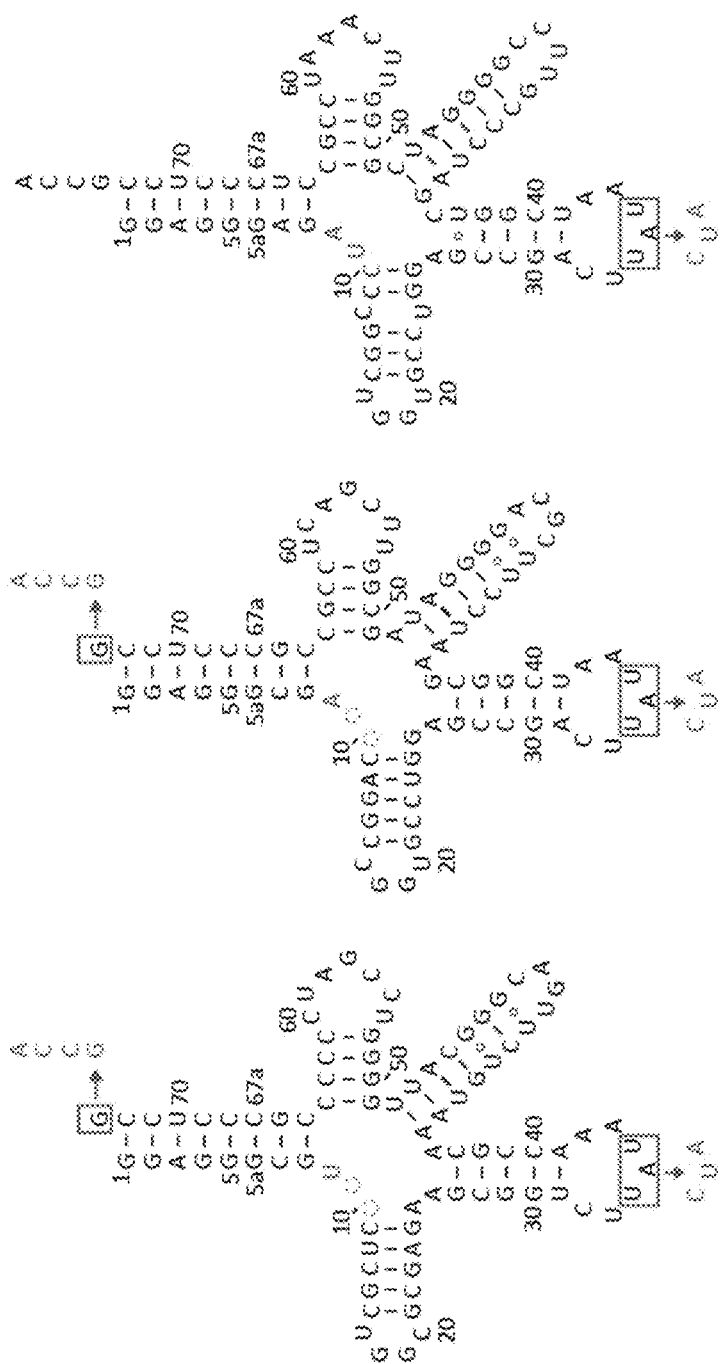
Figures 8F, 8G, 8H:
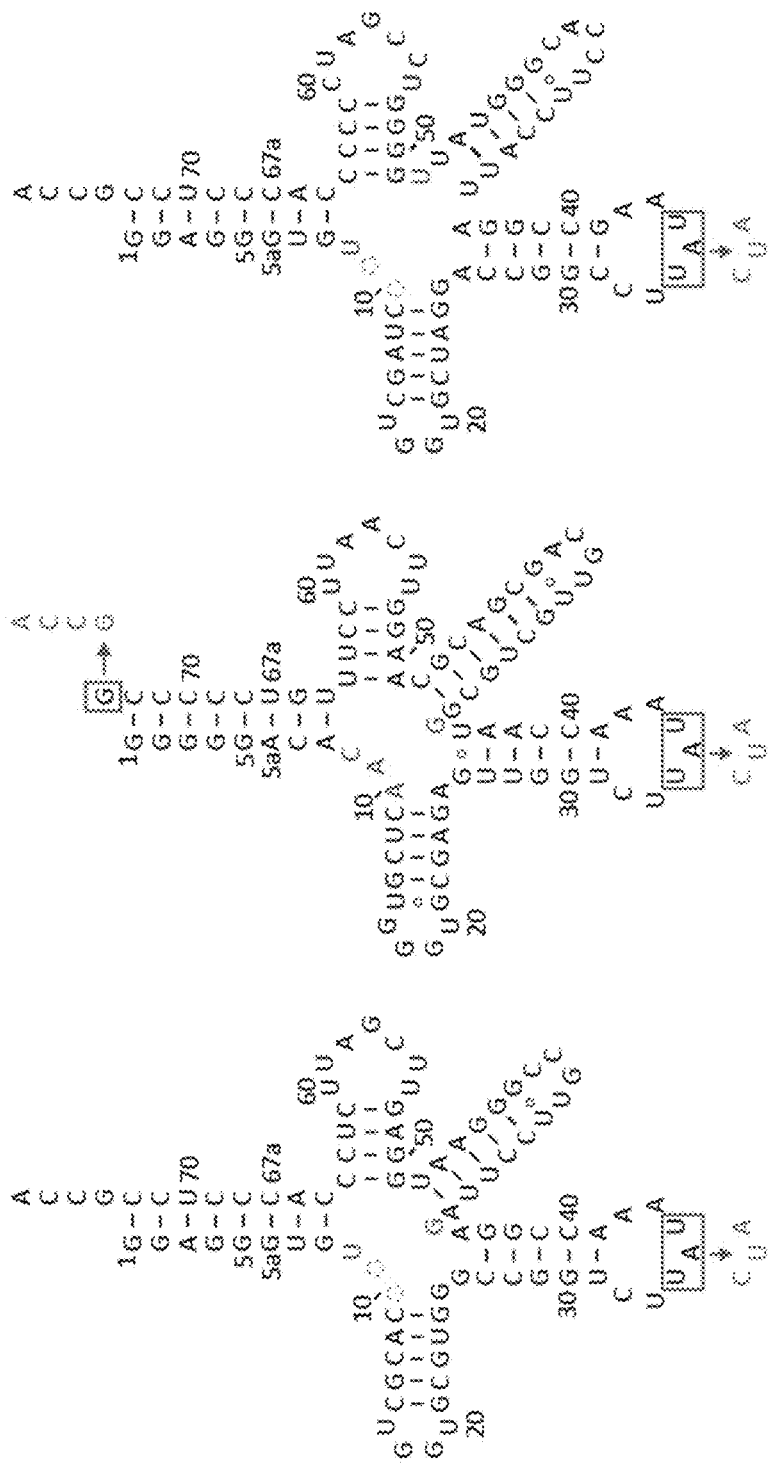
Figure 8I:
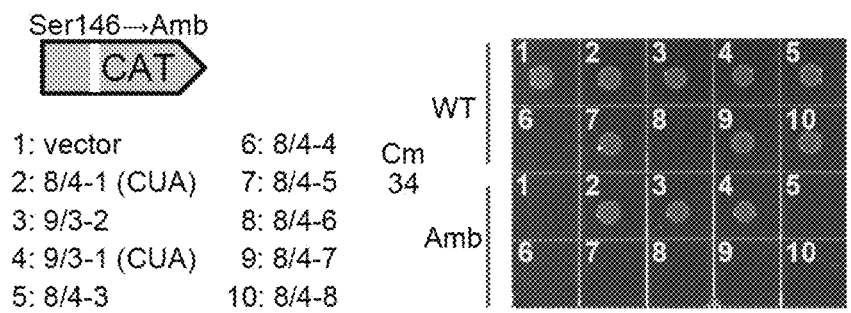

FIG. 8A is an illustration of the cloverleaf "junction" of tRNA. FIG. 8B illustrates different junction structures of six amber suppressor variants of six allo-tRNA$_{UAU}$ species. FIGS. 8C-8H are primary and secondary structures of the six allo-tRNA$_{UAU}$ variants: tRNA (8/4-3) (SEQ ID NO:51) (8C), tRNA (8/4-4) (SEQ ID NO:52) (8D), tRNA (8/4-5) (SEQ ID NO:53) (8E), tRNA (8/4-6) (SEQ ID NO:54) (8F), tRNA (8/4-7) (SEQ ID NO:55) (8G), tRNA (8/4-8) (SEQ ID NO:56) (8H). FIG. 8I is an image of the results of an assay measuring suppression of Ser146TAG CAT by allo-tRNA$_{CUA}$ variants with different junction structures. Amber suppressor variants of 8/4-1, 9/3-1 and 9/3-2 were used as positive controls. Fresh cultures of the transformants were spotted onto an agar plate with Cm at a concentration of 34 µg/mL. The plates were incubated overnight at 37° C.

Figure 9A:
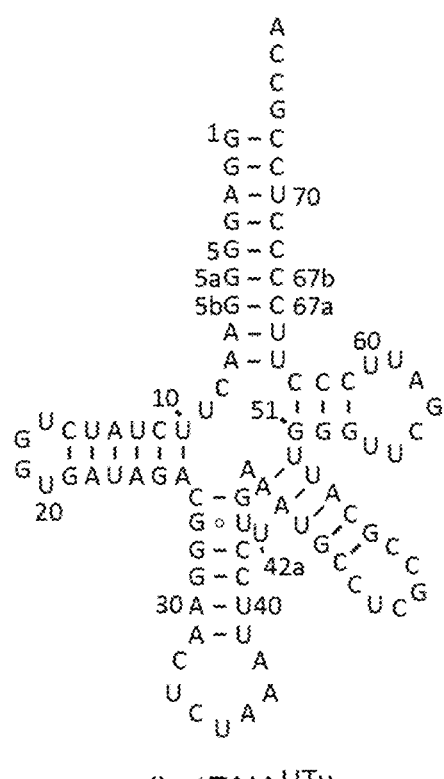
Figure 9B:
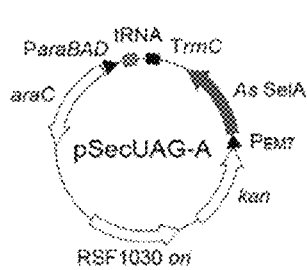
Figure 9C:
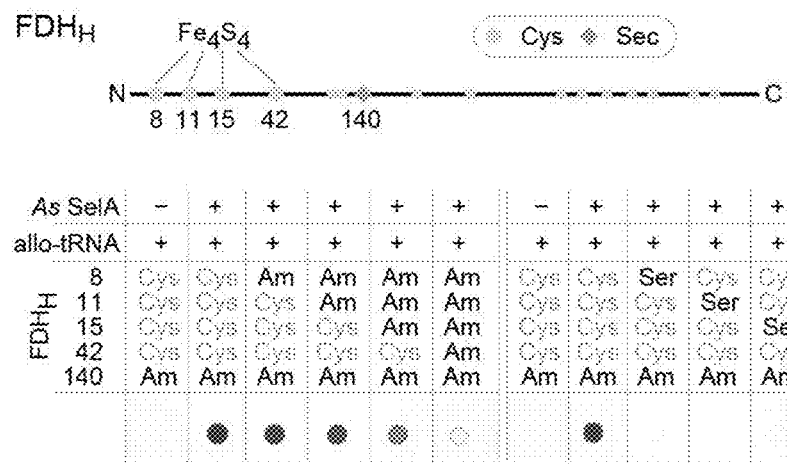
Figure 9D:
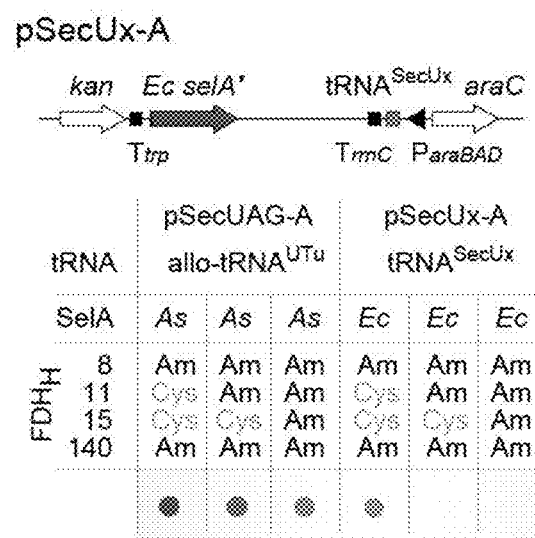
Figures 9E, 9F:
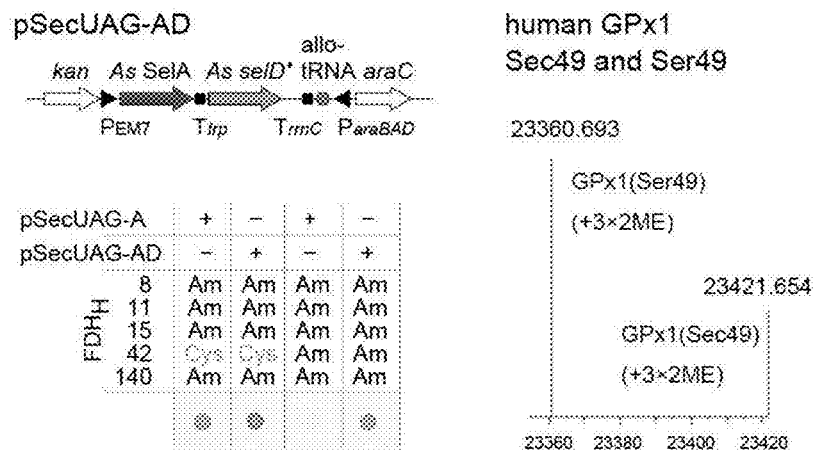
Figure 9G:
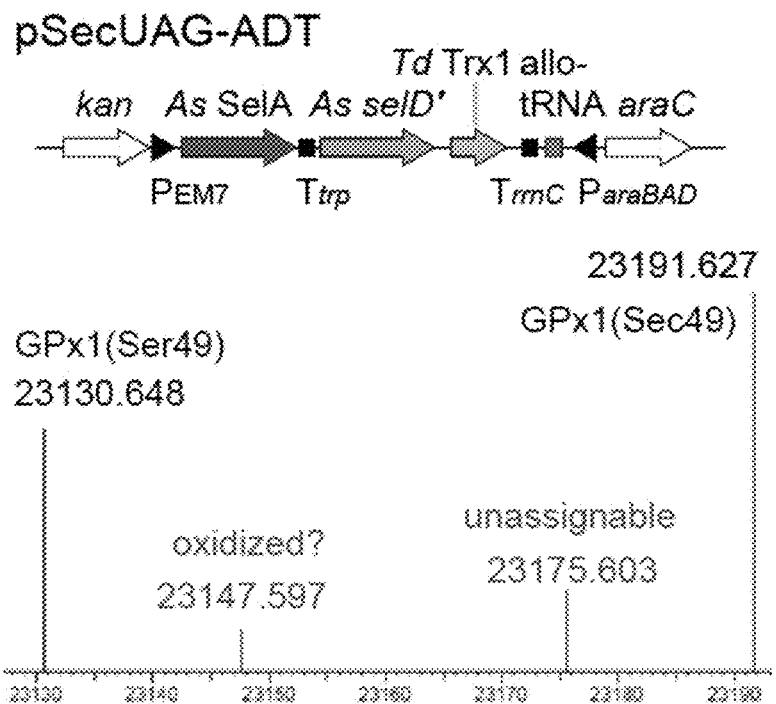

FIG. 9A is the primary and secondary structures of "allo-tRNA$^{UTu}$" (SEQ ID NO:57). FIG. 9B is a map of the pSecUAG-A plasmid used for Sec insertion in E. coli. FIGS. 9C-9E are series of images showing the results of an assay designed to test Sec insertion. Formate dehydrogenase H (FDH$_H$) encoded by the E. coli fdhF gene has a catalytic Sec residue and four Cys residues accommodating an iron sulfur cluster (Fe$_4$S$_4$). The images in FIG. 9C show FDH$_H$ expression in E. coli ΔselABC ΔfdhF (ME6) cells with allo-tRNA$^{UTu}$, with or without Aeromonas salmonicida (As) SelA, and with fdhF gene variants having UAG mutations at codon positions 8, 11, 15, 42, and 140. "Am" indicates the amber UAG codon. FDH$_H$ reduces benzyl viologen into a purple dye. The images in FIG. 9D show FDH$_H$ expression in ME6 cells with either of the allo-tRNA$^{UTu}$-As SelA pair and the tRNA$^{SecUx}$-Ec SelA pair and with fdhF gene variants having two to four UAG codons. Ec selA' in the pSecUx-A plasmid map indicates that the AUG start codon was changed to GUG with a short insertion "UAAUU" in front of it. The images in FIG. 9E show FDH$_H$ expression in ME6 cells carrying either pSecUAG-A or pSecUAG-AD and carrying fdhF gene variants having four or five UAG codons. As selD' in the pSecUAG-AD plasmid map indicates that the AUG start codon was changed to GUG. FIG. 9F is a spectrograph showing the results of intact mass spectrometry of the human GPx1(Ser49 and Sec49) mixture obtained from ME6 cells carrying pSecUAG-AD. Three exposed Cys residues of GPx1 were modified by 2-mercaptoethanol (2-ME) during purification. The calculated masses are 23,361 Da for GPx1(Ser49) with three 2-ME molecules and 23,421 Da for GPx1(Sec49) with three 2-ME molecules. FIG. 9G is a spectrograph showing the intact mass spectrometry of the human GPx1(Ser49 and Sec49) mixture obtained from ME6 cells carrying pSecUAG-ADT. Dithiothreitol (DTT) was used as the reducing agent. The calculated masses are 23,133 Da for GPx1(Ser49) and 23,193 Da for GPx1(Sec49).

Figure 10A:
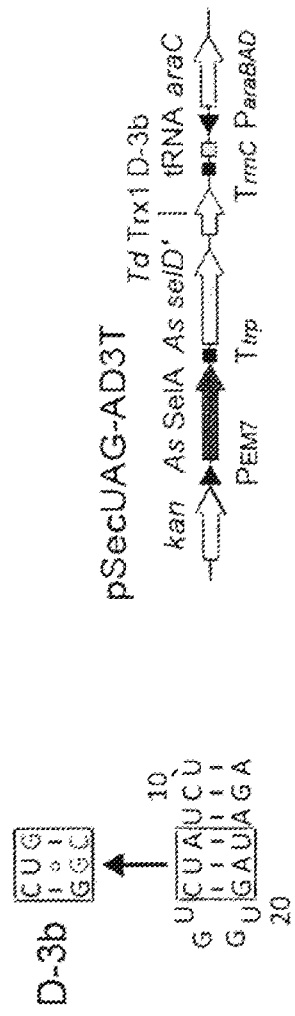
Figure 10B:
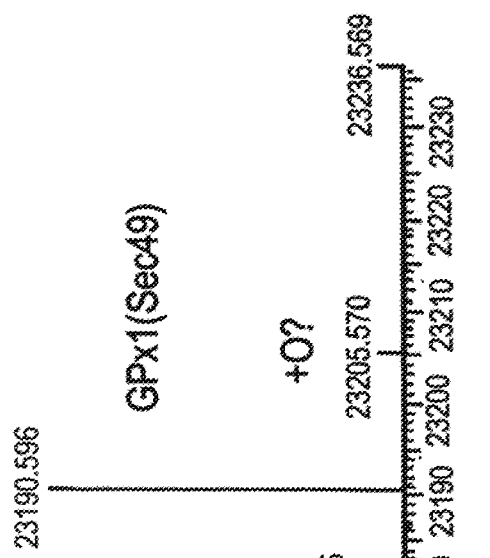
Figure 10C:
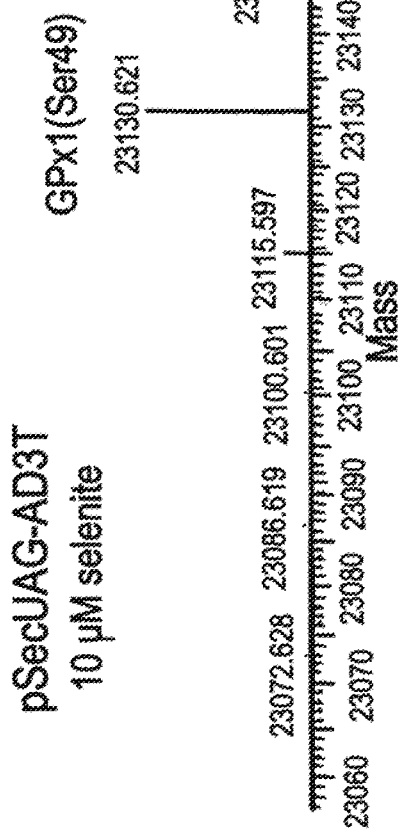

FIG. 10A is an illustration showing the development of the D-3b variant based on wildtype (UCUAUCUG-GUGAUAGA (SEQ ID NO:59)) of allo-tRNA$^{UTu}$. FIG. 10B is genetic map showing the development the pSecUAG-AD3T system. FIG. 10C is a spectrograph showing the results of intact mass spectrometry of the human GPx1 (Ser49 and Sec49) mixture obtained from ME6 cells carrying pSecUAG-AD3T. Dithiothreitol (DTT) was used as the reducing agent. The calculated masses are 23,133 Da for GPx1(Ser49) and 23,193 Da for GPx1(Sec49).

Figure 11A:
Figure 11B:
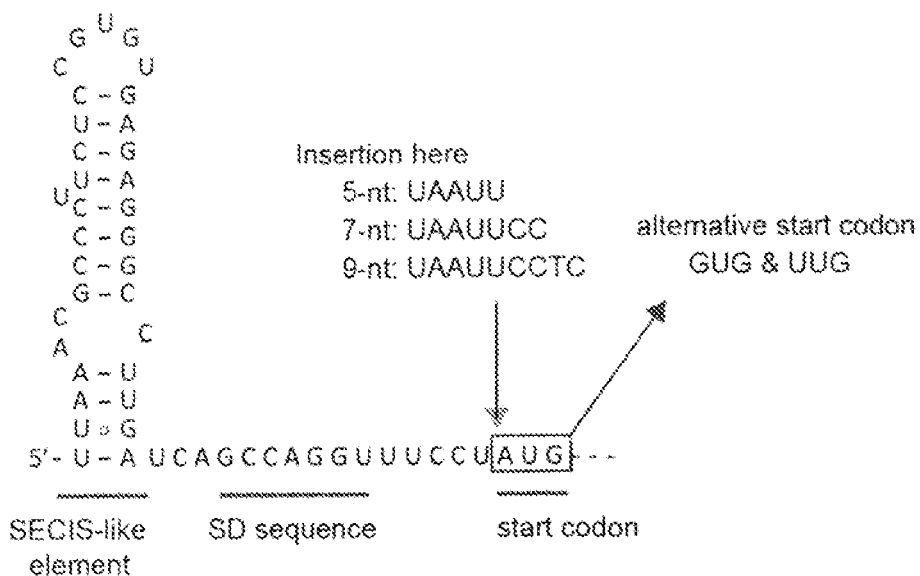
Figures 11C, 12A:
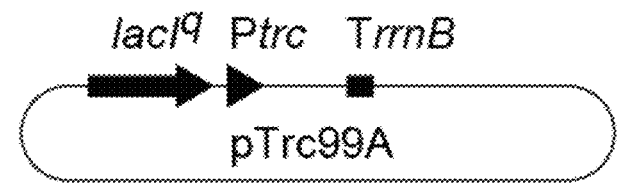

FIGS. 11A and 11B are genetic maps illustrating the cloning of the E. coli selA gene into the plasmids carrying the tRNA genes. In order to reduce the SelA expression level, the AUG start codon was changed to GUG and UUG, and a short nucleotide sequence was inserted between the Shine-Dalgarno (SD) sequence and the start codon. In wildtype E. coli, SelB binds to the SECIS-like element in the selAB mRNA for autorepression (UUAAACGCCCUU-CUCCGUGUGAGAGGGCCUUGAUCAGCCAG-GUUUCCUAUG (SEQ ID NO:60). However, ME6 strain lacks SelB and has no such regulation. FIG. 11C is a series of images showing FDH$_H$ expression in ME6 cells expressing either tRNA$^{SecUx}$ or tRNA$^{UTuX}$ and carrying the fdhF gene variants having one or two UAG codons. The E. coli selA gene variant that has the 5-nt insertion plus the GUG start codon produced the most suitable concentration of E. coli SelA molecules for both tRNA species.

FIG. 12A is a genetic map of the pTrc99A plasmid. FIG. 12B is a series of images showing the effects of additional expressions of As SelA and Trypanosoma brucei (Tb) and Homo sapiens (Hs) PSTK species from the pTrc99A plasmid. IPTG was added at a two different concentrations to induce these enzymes from the trc promoter. FDH$_H$ expression in E. coli ΔselABC ΔfdhF (ME6) cells carrying pSec-UAG-A plus one of the pTrc99A plasmids and the fdhF gene variant having mutations at codon positions 8, 11, and 140. FIG. 12C is a series of images showing FDH$_H$ expression in ME6 cells expressing allo-tRNA$^{UTu}$ and carrying one of the pTrc99A plasmids and the fdhF gene variant having a mutation at codon position 140. The SepCysS species is derived from Parcubacteria bacterium DG_74_2 bin and was cloned after the PSTK sequences in a dicistonic manner.

FIG. 13A is a series of images showing FDH$_H$ expression in ME6 cells carrying either pSecUAG-A, pSecUAG-A+ AsselD, or pSecUAG-AD and carrying fdhF gene variants having four or five UAG codons. As selD indicates the wildtype gene carrying the AUG start codon. FIG. 13B is series of images showing a repeated comparison of pSec-UAG-A and pSecUAG-A+AsselD. FIG. 13C is a series of images showing FDH$_H$ expression in ME6 cells carrying pSecUAG-AD and carrying fdhF gene variants.

FIGS. 14A-14F is a series of images showing intact mass spectrometry of the human GPx1(Ser49 and Sec49) mixture obtained from ME6 cells carrying either of pSecUAG-AD (14A and 14B), pSecUAG-ADT (14C and 14D), and pSec-UAG-AD3T (14E and 14F). Dithiothreitol (DTT) was used as the reducing agent. Possible peaks for oxidized GPx1 proteins are indicated with "+O?" (for one site) and "+2O?"

(for two sites). Another minor peak (indicated by ?) is a putative formic acid adduct of GPx1.

Figures 15A, 15B:
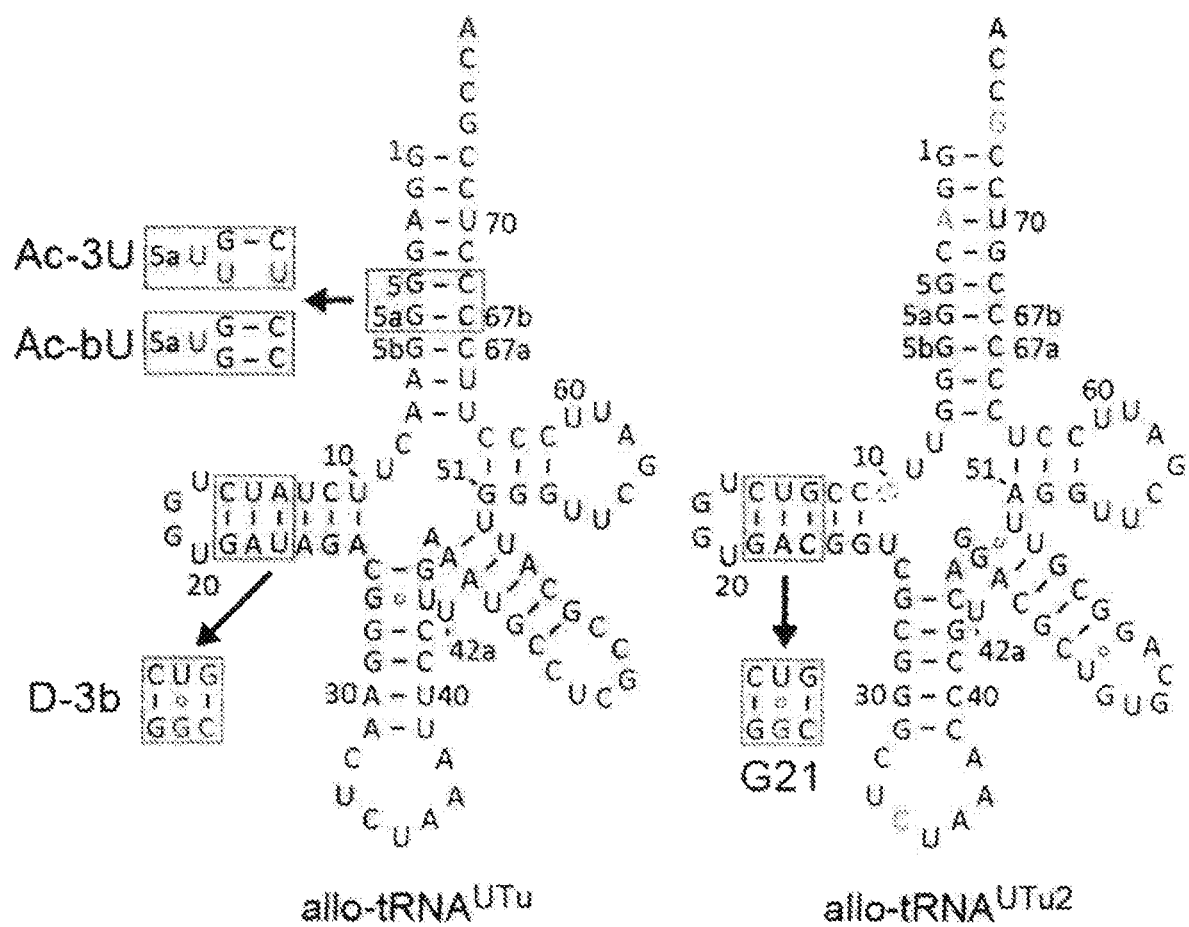
Figure 15C:
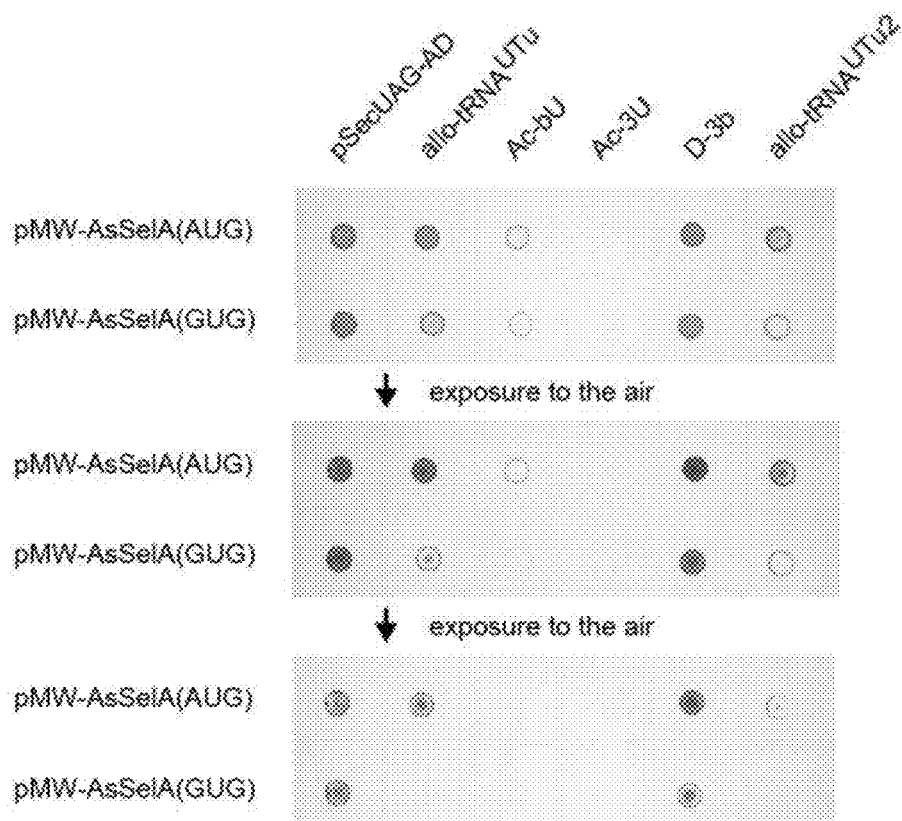
Figure 15D:
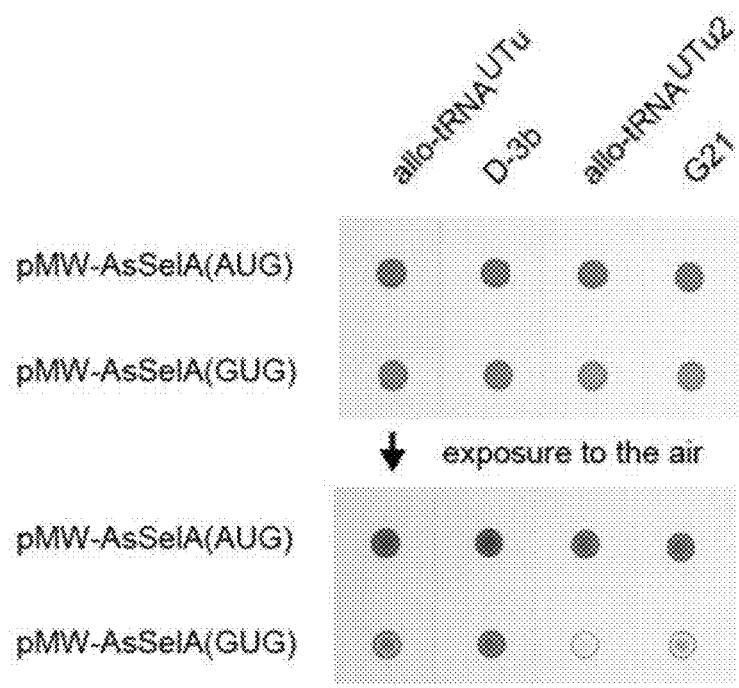

FIGS. 15A (SEQ ID NO:57) and 15B (SEQ ID NO:58) are illustrations showing the primary and secondary structure of engineered allo-tRNA$^{UTu}$ variants. A part of *Aeromonas* tRNA$^{Sec}$ structure was transplanted to allo-tRNA$^{UTu}$. Another allo-tRNA was changed to allo-tRNA$^{UTu2}$ by introducing mutations. FIG. 15C is a series of images showing the results of an assay testing FDH$_H$ expression in ME6 cells expressing As SelD, As SelA and allo-tRNA$^{UTu}$ variants and carrying the fdhF gene variant having five UAG codons. As SelA was expressed from a low-copy-number plasmid vector using the wildtype AUG start codon or an alternative GUG start codon as indicated. Only the positive control plasmid pSecUAG-AD has additional As SelA expression cassette on this high-copy-number plasmid vector. After the incubation in an anaerobic tent for the dye formation, the agar plate was exposed to the air on the lab bench for dye oxidation and bleaching. The cell spot carrying the D-3b variant and pMW-AsSelA(AUG) remained dark for the longest time under oxygen exposure. FIG. 15D is a series of images showing the results of repeating the same experiment as the 14C with the G21 variant.

Figure 16A:
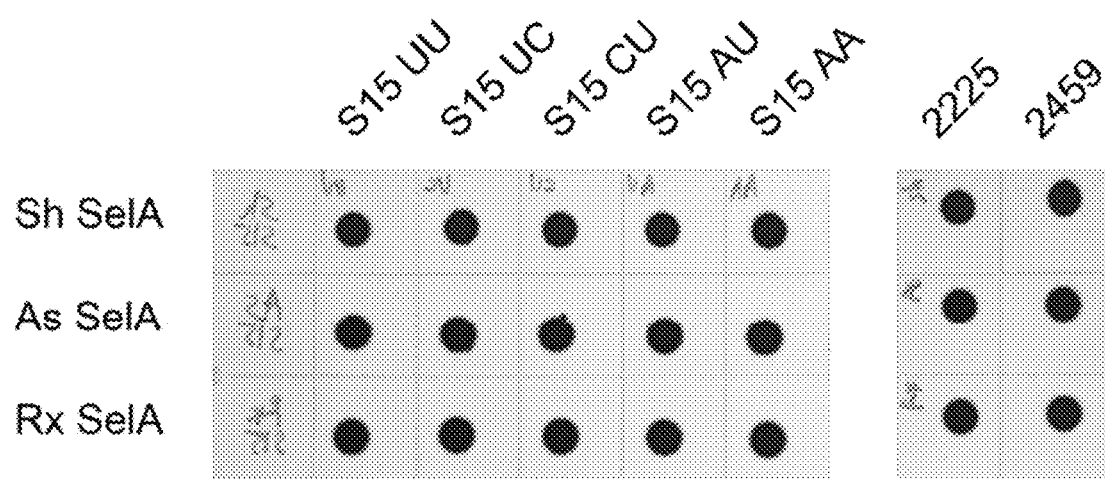
Figure 16B:
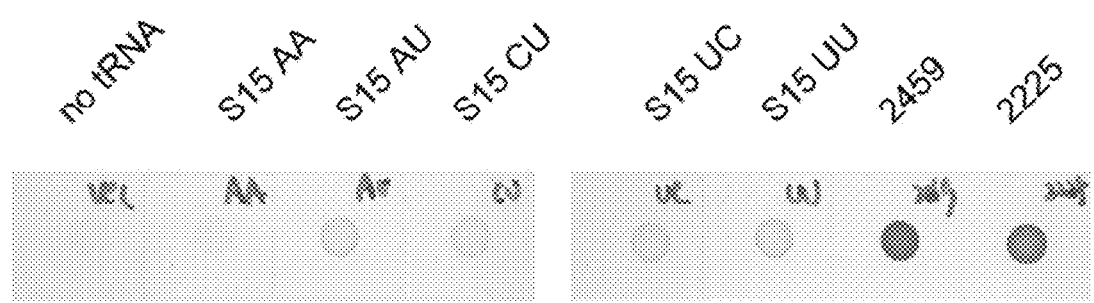

FIGS. 16A and 16B are series of images showing the results of assays testing Sec insertion suing three SelA species and seven allo-tRNA variants. Sh, As, Rx denote *Sulfurimonas honglongensis*, *Aeromonas salmonicida*, *Rubrobacter xylanophilus*, respectively. 2225, 2459, S15 were derived from 9/3-1, 9/3-2, 8/4-1, respectively. FIG. 16A shows all of the combinations of allo-tRNA and SelA inserted Sec (from the same agar plate). The fdhF (140 Amb) gene variant was used as reporter. FIG. 16B shows the two allo-tRNA$^{UTu}$ species derived from (9/3-1 and 9/3-2) were more active than the five allo-tRNA$^{UTu}$ species derived from (8/4-1) (from the same agar plate). As SelA was used. The fdhF (3 UAG codons) gene variant was used as reporter.

Figure 17:
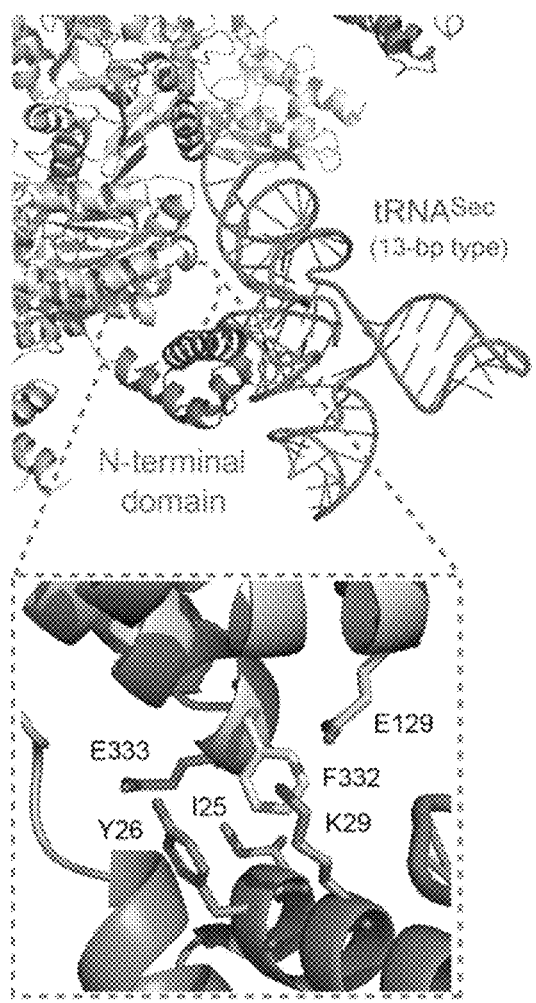

FIG. 17 is an illustration showing *A. aeolicus* SelA complexed with tRNA$^{Sec}$. Abbreviations: Aa stands for *Aquifex aeolicus*; Ec for *Escherichia coli*; Mt for *Moorella thermoacetica*; Db for *Desulfococcus biacutus*; As for *A. salmonicida*; Psp. for *Psychromonas* sp. CNPT3; Pp for *Photobacterium profundum*; Pd for *Photobacterium damselae*; Td for *Treponema denticola*; Rx for *Rubrobacter xylanophilus*.

FIG. 18A is a table of the Universal Genetic Code: Messenger RNA Codons and Amino Acids for Which They Code. FIG. 18B is a table of the anticodon diversity of allo-tRNAs. Possible codon-anticodon interactions are indicated with bars. The numbers of (8/4) and (9/3) allo-tRNA sequences are also provided.

DETAILED DESCRIPTION OF THE INVENTION

I. Definitions

Transfer RNA or tRNA refers to a set of genetically encoded RNAs that act during protein synthesis as adaptor molecules, matching individual amino acids to their corresponding codon on a messenger RNA (mRNA). In higher eukaryotes such as mammals, there is at least one tRNA for each of the 20 naturally occurring amino acids. In eukaryotes, including mammals, tRNAs are encoded by families of genes that are 73 to 150 base pairs long. tRNAs assume a secondary structure with four base paired stems known as the cloverleaf structure. The tRNA contains a stem and an anticodon. The anticodon is complementary to the codon specifying the tRNA's corresponding amino acid. The anticodon is in the loop that is opposite of the stem containing the terminal nucleotides. The 3' end of a tRNA is aminoacylated by a tRNA synthetase so that an amino acid is attached to the 3' end of the tRNA. This amino acid is delivered to a growing polypeptide chain as the anticodon sequence of the tRNA reads a codon triplet in an mRNA.

As used herein "suppressor tRNA" refers to a tRNA that alters the reading of a messenger RNA (mRNA) in a given translation system. For example, a suppressor tRNA can read through a stop codon.

As used herein, an "anticodon" refers to a unit made up of any combination of 2, 3, 4, and 5 bases (G or A or U or C), typically three nucleotides, that correspond to the three bases of a codon on an mRNA. Each tRNA contains a specific anticodon triplet sequence that can base-pair to one or more codons for an amino acid or "stop codon." Known "stop codons" include, but are not limited to, the three codon bases, UAA known as ochre, UAG known as amber and UGA known as opal, that do not code for an amino acid but act as signals for the termination of protein synthesis. tRNAs do not decode stop codons naturally, but can and have been engineered to do so. Stop codons are usually recognized by enzymes (release factors) that cleave the polypeptide as opposed to encode an AA via a tRNA. Generally the anticodon loop consists of seven nucleotides. In the 5' to 3' direction the first two positions 32 and 33 precede the anticodon positions 34 to 36 followed by two nucleotides in positions 37 and 38 (Alberts, B., et al. in *The Molecular Biology of the Cell*, 4$^{th}$ ed, Garland Science, New York, N.Y. (2002)). The size and nucleotide composition of the anticodon is generally the same as the size of the codon with complementary nucleotide composition. A four base pair codon consists of four bases such as 5'-AUGC-3' and an anticodon for such a codon would complement the codon such that the tRNA contained 5'-GCAU-3' with the anticodon starting at position 34 of the tRNA. A 5 base codon 5'-CGGUA-3' codon is recognized by the 5'-UACCG-3' anticodon (Hohsaka T., et al. *Nucleic Acids Res.* 29:3646-3651 (2001)). The composition of any such anticodon for 2 (16=any possible combination of 4 nucleotides), 3 (64), 4 (256), and 5 (1024) base codons would follow the same logical composition. The "anticodon" typically starts at position 34 of a canonical tRNA, but may also reside in any position of the "anti-codon stem-loop" such that the resulting tRNA is complementary to the "stop codon" of equivalent and complementary base composition.

As used herein, "tRNA$^{Sec}$" refers to an unaminoacylated tRNA suitable for carrying selenocysteine. Typically the anticodon sequence of the tRNA$^{Sec}$ can recognize or hybridize with an mRNA codon specific for, or designed to encode, a selenocysteine amino acid, for example UGA. In *E. coli*, the endogenous tRNA$^{Sec}$ is encoded by the selC gene.

As used herein, "tRNA$^{Ser}$" refers to an unaminoacylated tRNA suitable for carrying serine. Typically the anticodon sequence of the tRNA$^{Ser}$ can recognize or hybridize with an mRNA codon specific for, or designed to encode, a serine amino acid, for example UCU, UCC, UCA, UCG, AGU, or AGC.

As used herein, "tRNA$^{UTu}$" refers to a non-naturally occurring, unaminoacylated tRNA$^{Sec}$ suitable for carrying selenocysteine. Typically the anticodon sequence of the tRNA$^{UTu}$ can recognize or hybridize with an mRNA codon specific for, or designed to encode, a selenocysteine amino acid.

As used herein, "Sec-tRNA$^{Sec}$" refers to aminoacylated tRNA$^{Sec}$ carrying a selenocysteine amino acid.

As used herein, "Ser-tRNA$^{Sec}$" refers to aminoacylated tRNA$^{Sec}$ carrying a serine amino acid.

As used herein, "Ser-tRNA$^{Ser}$" refers to aminoacylated tRNA$^{Ser}$ carrying a serine amino acid.

As used herein, "Sep-tRNA$^{Ser}$" refers to a phosphorylated Ser-tRNA$^{Sec}$.

As used herein, "EF-Tu" refers to Elongation Factor Thermo Unstable, a prokaryotic elongation factor mediates the entry of the aminoacyl-tRNA into a free site of the ribosome.

As used herein, "SerRS" refers to Seryl-tRNA synthetase (also known as Serine-tRNA ligase) which is a prokaryotic factor that catalyzes the attachment of serine to tRNA$^{Ser}$.

As used herein "SECIS" refers to a SElenoCysteine Insertion Sequence, is an RNA element around 60 nucleotides in length that adopts a stem-loop structure which directs the cell to translate UGA codons as selenocysteines. In bacteria the SECIS can be soon after the UGA codon it affects, while in archaea and eukaryotes, it can be in the 3' or 5' UTR of an mRNA, and can cause multiple UGA codons within the mRNA to code for selenocysteine.

As used herein "SelA" refers to selenocysteine synthase, a prokaryotic pyridoxal 5-phosphate-containing enzyme which catalyzes the conversion of Ser-tRNA$^{Sec}$ into a Sec-tRNA$^{Sec}$.

As used herein "SelB" refers to selenocysteine-specific elongation factor, a prokaryotic elongation factor for delivery of Sec-tRNA$^{Sec}$ to the ribosome.

As used herein "PSTK" refers to phosphoseryl-tRNA kinase (also known as O-phosphoseryl-tRNA$^{Sec}$ kinase and L-seryl-tRNA$^{Sec}$ kinase), a kinase that phosphorylates Ser-tRNA$^{Sec}$ to O-phosphoseryl-tRNA$^{Sec}$, an activated intermediate for selenocysteine biosynthesis.

As used herein "SepSecS" refers to Sep (O-phosphoserine) tRNA:Sec (selenocysteine) tRNA synthase (also known as O-phosphoseryl-tRNA(Sec) selenium transferase and Sep-tRNA:Sec-tRNA synthase), an eukaryotic and archaeal enzyme that converts O-phosphoseryl-tRNA$^{Sec}$ to selenocysteinyl-tRNA$^{Sec}$ in the presence of a selenium donor.

As used herein "SepCysS" refers to Sep-tRNA:Cys-tRNA synthase, an archaeal/bacterial enzyme that converts O-phosphoseryl-tRNA$^{Cys}$ (Sep-tRNA$^{Cys}$) into Cys-tRNA$^{Cys}$ in the presence of a sulfur donor.

As used herein "G-C content" (or guanine-cytosine content) refers to the percentage of nitrogenous bases on a nucleic acid molecule, or fragment, section, or region thereof, that are either guanine or cytosine.

Aminoacyl-tRNA Synthetases ("AARS") are enzymes that charge (acylate) tRNAs with amino acids. These charged aminoacyl-tRNAs then participate in mRNA translation and protein synthesis. The AARS show high specificity for charging a specific tRNA with the appropriate amino acid, for example, tRNA$^{Val}$ with valine by valyl-tRNA synthetase or tRNA$^{Trp}$ with tryptophan by tryptophanyl-tRNA synthetase. In general, there is at least one AARS for each of the twenty amino acids.

As used herein "translation system" refers to the components necessary to incorporate a naturally occurring amino acid into a growing polypeptide chain (protein). Components of a translation system can include, e.g., ribosomes, tRNAs, synthetases, mRNA and the like. The components described herein can be added to a translation system, in vivo or in vitro. A translation system can be either prokaryotic, e.g., an E. coli cell, or eukaryotic, e.g., a yeast, mammal, plant, or insect or cells thereof.

A "transgenic organism" as used herein, is any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation. Techniques for transferring DNA into such organisms are widely known and provided in references such as Sambrook, et al. (2000) Molecular Cloning: A Laboratory Manual, 3' ed., vol. 1-3, Cold Spring Harbor Press, Plainview N.Y.

As used herein, the term "eukaryote" or "eukaryotic" refers to organisms or cells or tissues derived therefrom belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "non-eukaryotic organism" refers to organisms including, but not limited to, organisms of the Eubacteria phylogenetic domain, such as *Escherichia coli, Thermus thermophilus,* and *Bacillus stearothermophilus,* or organisms of the Archaea phylogenetic domain such as, *Methanocaldococcus jannaschii, Methanothermobacter thermautotrophicus, Halobacterium* such as *Haloferax volcanii* and *Halobacterium* species NRC-1, *Archaeoglobus fulgidus, Pyrococcus furiosus, Pyrococcus horikoshii,* and *Aeuropyrum pernix.*

The term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "orthologous genes" or "orthologs" refer to genes that have a similar nucleic acid sequence because they were separated by a speciation event.

The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Cofactor", as used herein, refers to a substance, such as a metallic ion or a coenzyme that must be associated with an enzyme for the enzyme to function. Cofactors work by changing the shape of an enzyme or by actually participating in the enzymatic reaction.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences The term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

"Transformed," "transgenic," "transfected" and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

The term "endogenous" with regard to a nucleic acid refers to nucleic acids normally present in the host.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction $W/Z$, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

The term "stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Third Edition, Cold Spring Harbor, N.Y. (2000).

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the terms "recoded organism" and "genomically recoded organism (GRO)" in the context of codons refer to an organism in which the genetic code of the organism has been altered such that a codon has been eliminated from the genetic code by reassignment to a synonymous or nonsynonymous codon.

Unless otherwise indicated, the disclosure encompasses conventional techniques of molecular biology, microbiology, cell biology and recombinant DNA, which are within the skill of the art. See, e.g., Sambrook and Russell, Molecular Cloning: A Laboratory Manual, 3rd edition (2001); Current Protocols In Molecular Biology [(F. M. Ausubel, et al. eds., (1987)]; Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)].

Unless otherwise noted, technical terms are used according to conventional usage. Definitions of common terms in molecular biology may be found in Lewin, Genes VII, published by Oxford University Press, 2000; Kendrew et al. (eds.), The Encyclopedia of Molecular Biology, published by Wiley-Interscience., 1999; and Robert A. Meyers (ed.), Molecular Biology and Biotechnology, a Comprehensive Desk Reference, published by VCH Publishers, Inc., 1995; Sambrook and Russell. (2001) Molecular Cloning: A Laboratory Manual 3rd. edition, Cold Spring Harbor Laboratory Press.

II. Compositions

A. tRNA tRNASec suitable for carrying selenocysteine and facilitating synthesis of selenopeptides without requiring a SECIS in the mRNA encoding the peptide are disclosed. Also disclosed are aminoacylated tRNA$^{Sec}$. Using the methods discussed in more detail below, the tRNA$^{Sec}$ disclosed herein are capable of being aminoacylated to form a Sec-tRNA$^{Sec}$ which can facilitate insertion of selenocysteine into nascent polypeptide chains. Typically, the tRNA$^{Sec}$ (1) can be recognized by SerRS and by EF-Tu, or variants thereof; and is characterized by one or more of the following elements: (2) when aminoacylated with serine the non-naturally occurring Ser-tRNA$^{Sec}$ can be converted to non-naturally occurring Sec-tRNA$^{Sec}$ by SelA, or variant thereof; (3) when aminoacylated with serine the non-naturally occurring Ser-tRNA$^{Sec}$ can be phosphorylated by PSTK or variant thereof; (4) when aminoacylated with phosphorylated serine the non-naturally occurring Sep-tRNA$^{Sec}$ can serve as a substrate for SepSecS or variant thereof; and combinations thereof. In some embodiments, the tRNA$^{Sec}$ is characterized by elements (1) and (2). In some embodiments, the tRNA$^{Sec}$ is characterized by elements (1), (3), and (4). In some embodiments, the tRNA$^{Sec}$ is characterized by elements (1), (2), (3), and (4). Typically, the non-naturally occurring Sec-tRNA$^{Sec}$ can be bound by EF-Tu. The Sec can be incorporated into a growing peptide chain at a codon of the mRNA that recognizes the anticodon of the tRNA$^{Sec}$. Preferably, EF-Tu does not bind Sep-tRNA$^{Sec}$. In some embodiments, EF-Tu is less efficient at incorporating Ser-tRNA$^{Sec}$ than Sec-tRNA$^{Sec}$ into the growing peptide chain.

Typically, the tRNA$^{Sec}$ do not require a SECIS element in an mRNA to be incorporated into a growing polypeptide chain during translation. Typically the anticodon of the tRNA$^{Sec}$ is recognized or hybridizes to a stop codon. Typically the tRNA$^{Sec}$ can facilitate incorporation of a Sec into a growing peptide chain without the activity of SelB.

Some consensus and exemplary tRNA$^{Sec}$ disclosed herein are provided as an RNA sequences, while others are provided as a DNA (e.g., the sequence encoding the tRNA$^{Sec}$). The RNA sequence is also an express disclosure of the corresponding DNA sequence wherein the "U" of the RNA are replaced with "T." The DNA sequence is also an express disclosure of the corresponding RNA sequence wherein the "T" of the DNA are replaced with "U."

1. Substrates for EF-Tu

EF-Tu is a prokaryotic elongation factor that mediates the entry of the aminoacyl-tRNA into a free site of the ribosome. Endogenous prokaryotic tRNAs, typically include an antideterminant element, which prevents recognition of a Sec-tRNA$^{Sec}$ by the elongation factor EF-Tu. In some embodiments, the disclosed tRNA can be a substrate for EF-Tu. Therefore, in some embodiments, the disclosed tRNA is a variant of an endogenous tRNA$^{Sec}$ that has been modified to inactivate the antideterminant element. The antideterminant element can be modified, mutated, or deleted so that tRNA is an acceptable substrate for EF-Tu. For example the antideterminant element in E. coli tRNA$^{Sec}$ is located in the 8th, 9th and 10th bp in the acceptor branch of tRNA$^{Sec}$ (encoded by selC), corresponding to the last base pair in the amino acid acceptor stem and the two first pairs in the T-stem (Rudinger, et al., EMBO J., 15(3):650-57 (1996), and can be referred to as C7•G66/G49•U65/C50•G64 according the numbering in Schon, et al., Nucleic Acids Res., 17(18): 7159-7165 (1989). Accordingly, in some embodiments, the tRNA$^{Sec}$ is variant of a naturally occurring tRNA$^{Sec}$ where the corresponding antideterminant sequence is mutated or deleted such that the tRNA$^{Sec}$ is a substrate for EF-Tu.

2. Substrate for SelA

SelA refers to L-seryl-tRNA(Sec) selenium transferase, which converts seryl-tRNA$^{Sec}$ to selenocysteinyl-tRNA$^{Sec}$ during selenoprotein biosynthesis. SelA utilizes selenophosphate synthesized by selenophosphate synthase (SelD) as the selenium-donor molecule. In some embodiments, the disclosed tRNA$^{Sec}$ can serve as a substrate SelA. E. coli ecodes a SelA, thus, in some embodiments, the SelA is E. coli SelA.

An exemplary protein sequence for E. coli SelA is:

```
                                            (SEQ ID NO: 77)
MTTETRFLYSQLPAIDRLLRDSSFLSLRDTYGHTRVVELLRQMLDEAREV

IRGSQTLPAWCENWAQEVDARLTKEAQSALRPVINLTGTVLHTNLGRALQ

AEAAVEAVAQAMRSPVTLEYDLDDAGRGHRDRALAQLLCRITGAEDACIV

NNNAAAVLLMLAATASGKEVVVSRGELVEIGGAFRIPDVMRQAGCTLHEV

GTTNRTHANDYRQAVNENTALLMKVHTSNYSIQGFTKAIDEAELVALGKE

LDVPVVTDLGSGSLVDLSQYGLPKEPMPQELIAAGVSLVSFSGDKLLGGP

QAGIIVGKKEMIARLQSHPLKRALRADKMTLAALEATLRLYLHPEALSEK

LPTLRLLTRSAEVIQIQAQRLQAPLAAHYGAEFAVQVMPCLSQIGSGSLP

VDRLPSAALTFTPHDGRGSHLESLAARWRELPVPVIGRIYDGRLWLDLRC

LEDEQRFLEMLLK
```

An exemplary nucleic acid sequence (cloned from E. coli DH10B genome) encoding E. coli SelA is:

```
                                            (SEQ ID NO: 78)
ATGACAACCGAAACGCGTTTCCTCTATAGTCAACTTCCGGCTATTGATCG

CTTATTGCGCGATAGCTCCTTCCTTTCTTTGCGTGATACTTATGGTCACA

CCCGCGTGGTGGAATTGTTGCGTCAGATGCTCGACGAAGCGCGAGAAGTG

ATTCGTGGCAGCCAGACGCTGCCTGCGTGGTGTGAAAACTGGGCGCAAGA

AGTCGATGCCCGGTTGACGAAAGAAGCGCAGAGCGCGCTGCGTCCGGTGA

TCAACCTGACGGGAACCGTGCTGCATACCAACCTTGGGCGAGCTTTACAG

GCGGAAGCCGCGGTGGAAGCCGTTGCGCAGGCTATGCGTTCGCCAGTGAC

CCTCGAGTATGATCTGGACGACGCCGGACGCGGACATCGCGATCGGGCGC

TGGCGCAGCTGCTGTGCCGTATTACGGGGGCGGAAGATGCCTGTATCGTC

AATAACAATGCGGCGGCGGTGTTATTGATGTTGGCGGCCACTGCCAGCGG

AAAAGAGGTGGTGGTATCTCGCGGCGAACTGGTGGAGATTGGCGGCGCGT

TTCGTATTCCCGATGTTATGCGTCAGGCAGGCTGCACCCTACACGAAGTA

GGGACCACCAACCGCACGCACGCGAATGATTATCGTCAGGCGGTGAATGA

AAATACCGCACTGTTGATGAAAGTACATACCAGTAACTACAGCATTCAGG

GGTTCACCAAAGCGATAGATGAAGCGGAACTGGTGGCGCTCGGCAAAGAG

CTGGATGTTCCCGTAGTGACTGATTTAGGCAGTGGCTCGCTGGTCGATCT

TAGCCAGTACGGTTTGCCGAAAGAGCCAATGCCGCAGGAGTTGATTGCGG

CGGGCGTCAGTCTGGTGAGTTTCTCCGGCGACAAGTTGTTAGGCGGGCCG

CAGGCAGGAATTATTGTTGGTAAAAAAGAGATGATCGCCCGCCTGCAAAG

CCACCCGCTGAAGCGTGCATTACGCGCGGATAAAATGACCCTCGCGGCGC

TGGAAGCCACGTTGCGTCTTTATTTACACCCTGAAGCTCTGAGTGAAAAA

TTACCGACCCTGCGCCTGCTTACCCGCAGCGCAGAGGTCATTCAAATCCA

GGCACAACGTTTACAGGCCCCCCTTGCCGCACATTACGGCGCGGAGTTTG

CGGTACAGGTTATGCCATGTCTTTCGCAGATTGGCAGTGGTTCGCTGCCG

GTTGATCGCCTGCCGAGCGCGGCATTAACGTTTACACCCCATGATGGACG

CGGTAGCCACCTTGAGTCATTAGCCGCCCGCTGGCGTGAATTGCCAGTGC

CGGTGATTGGTCGTATTTATGACGGACGATTGTGGCTGGATTTACGCTGC

CTTGAAGATGAGCAACGGTTTTTGGAGATGTTGTTGAAATGA
```

Other organisms also encode a SelA. Thus, in other embodiments, the SelA is not wildtype E. coli SelA. Results show wildtype E. coli SelA does not efficiently convert seryl-tRNA$^{Sec}$ to selenocysteinyl-tRNA$^{Sec}$ for at least some of the exemplary allo-tRNA disclosed in more detail below. Thus, in these embodiments, an alternative or variant SelA can be utilized for recombinant selenoprotein preparation.

SelA species which recognize 12-bp type tRNA$^{Sec}$ molecules have Pro and Ala (and Gly in a metagenome sequence) in the position for the Ile25 of Aquifex aeolicus SelA. Therefore, such SelA species can be used to convert seryl-tRNA$^{Sec}$ to selenocysteinyl-tRNA$^{Sec}$. Alternatively, SelA species which recognize 13-bp type tRNA$^{Sec}$ molecules (such as E. coli) can be engineered to have, for example, Pro, Ala, or Gly in the amino acid position corresponding to position 25 (Ile25) of Aquifex aeolicus SelA.

The amino acid residues involved in the fixation of the SelA N-terminal domain are shown in FIG. 17. The crystal structure of *Aquifex aeolicus* SelA and *Thermoanaerobacter tengcongensis* tRNA$^{Sec}$ with a 13-bp amino-acid acceptor branch (PDB accession no. 3w1k) is exemplified. Other preferred residues that in can be imported (e.g., substituted) from SelA species which recognize 12-bp type tRNA$^{Sec}$ molecules into SelA species which recognize 13-bp type tRNA$^{Sec}$ molecules include, but are not limited to those corresponding with positions 25, 26, 29, 129, 332, and 333 of *Aquifex aeolicus* SelA.

The amino acid sequence for *Aquifex aeolicus* SelA (UniProtKB-O67140 (SELA_AQUAE)) is (SEQ ID NO: 79)
MKSLLRQIPQISKVVEIFKKKYPE*IY*VV*K*AAREVAEKYRKEIIEGK

RKDLNGFLEDVERKIKSLMKPNIKRVINATGVVINTNLGRAPLSKDVINF

ISEIANGYSNLEYNLEEGKRGSRIAHIEKYLN*E*LTGAESSFVVNNNAK

GAVFLVLNTLAEGKEVIISRGELVEIGGSFRIPDIMKKSGAILREVGTTN

TKVSDYEGAINQNTALLMKVHKSNFYMEGFVEEVKLEDLVKLGHKYGIPT

YYDAGSGLLINLKEFGISVDEPNFRDCISLGIDLVSGSGDKLLGGPQAGI

IVGKKNLIEKIKKNPIARALRIDKLTLSGLEMTLKLY*FE*KRYEDIPVI

RMLTQDEKALRQKAKRLEKLLKDIPGLKISVIKDKAKPGGGSLPELELPT

YCVAIRHDRLSSQELSRRLRLAEPPIVCRIREDQLLFDMRTVFHEDLKTI

KKTLQELLSI

The amino acid of I25, Y26, K29, E129, F332, and E333 of *Aquifex aeolicus* SelA are identified with bold and italics. The corresponding amino acid residues from SelA species that recognize 12-bp type tRNA$^{Sec}$ molecules are illustrated in FIG. 17 or can be identified using sequence alignment, and can be used as a basis for reengineering SelA species that recognize 12-bp type tRNA$^{Sec}$ to variants that recognize allo-tRNAs.

Exemplary SelA proteins that recognize allo-tRNAs as illustrated in the examples below include, but are not limited to, those from *Sulfurimonas honglongensis, Aeromonas salmonicida*, and *Rubrobacter xylanophilus*. An exemplary amino acid sequence for *Aeromonas salmonicida* SelA is (SEQ ID NO: 80)
MPNSSHAPAIAHSHSQPESCPTADDSLPDSLPDSLPQPSQQQARRLPQVE

QLLQQPFLTGFIEALSRPLVTQAVRDVLSELRQSEAFRQHGVAPEQIEAL

IAKRCQQQLRQRQTRVINATGTLVHTNLGRSPLSRELWDEVRDLNTGYNN

LELDLATGKRGGRKGLIAPLLRCLTQAEDSLVVNNNAASLFLLLQEIAKG

REVIVSRGEQIQIGGGFRIPDILALSGAKLVEVGTTNITTAKDYLDAITD

QTALVLMVHRSNFAIRGFTESPDIGEVARALPEHVVLAVDQGSGLTTEEF

APDETSVRQYIKAGADLVCYSGDKLLGGPQSGIISGRSDLIKRLEKHPMM

RTFRPSRIVYSLLERLLIHKLNKSPIGEGIAQRTLSNPAAMQARADQLMA

ALPGCFVPVPAQLVVGGGTLPDEFYPAPALECTDPRPAQQLLDALRKLPV

PVIATVRQQKVLLNMATLLPTETALLIAQLKELLLPTPTTATEEP

An exemplary nucleic acid sequence (cloned from the *Aeromonas salmonicida* genome) encoding *Aeromonas salmonicida* SelA is (SEQ ID NO: 81)
ATGCCGAACTCGTCTCACGCGCCAGCCATCGCCCACTCTCACAGTCAGCC

CGAATCATGTCCCACTGCCGACGATTCACTGCCAGATTCACTGCCAGATT

CACTGCCACAGCCCAGCCAGCAACAAGCGCGCCGTCTACCGCAAGTGGAA

CAGCTGCTGCAGCAACCCTTTCTCACCGGTTTTATCGAGGCGCTGAGCCG

CCCGCTGGTGACCCAGGCGGTGCGCGATGTCCTGAGCGAATTGCGCCAGA

GCGAGGCATTTCGCCAGCATGGGGTTGCCCCCGAGCAAATCGAGGCACTG

ATTGCCAAGCGTTGCCAGCAGCAGCTGCGCCAACGTCAGACCCGGGTGAT

CAACGCCACCGGCACCCTGGTGCACACCAATCTGGGGCGCTCGCCGCTAA

GTCGCGAGCTGTGGGACGAGGTGCGCGACCTCAACACTGGCTACAACAAT

CTGGAACTGGATCTCGCCACCGGCAAGCGCGGCGGGCGCAAGGGGCTGAT

CGCCCCCCTGCTCCGTTGCCTCACCCAGGCCGAGGATTCGCTGGTGGTCA

ACAACAACGCCGCTTCGCTCTTCTTGCTGCTGCAGGAGATAGCCAAGGGG

CGCGAGGTGATCGTCTCGCGGGGCGAACAGATCCAGATTGGTGGCGGCTT

TCGCATTCCCGACATTCTGGCGCTCTCCGGCGCCAAACTGGTGGAGGTGG

GCACCACCAATATCACTACCGCCAAAGATTACCTCGATGCCATCACAGAT

CAGACCGCGCTGGTGCTGATGGTACACAGATCCAATTTCGCCATTCGCGG

CTTTACCGAATCCCCCGATATTGGCGAGGTGGCCCGCGCCCTGCCCGAGC

ACGTGGTGCTGGCGGTGGATCAGGGCTCGGGCTTGACCACCGAGGAGTTT

GCACCGGACGAAACCTCGGTGCGTCAGTACATCAAGGCGGGGGCGGATCT

GGTCTGCTACTCCGGCGACAAGCTGCTGGGTGGCCCGCAATCGGGCATCA

TCAGCGGCCGCAGCGACCTCATCAAGCGGCTGGAAAAACACCCCATGATG

CGCACCTTCCGCCCGAGCCGCATCGTCTACTCCCTGCTGGAACGCCTGCT

CATCCACAAGCTCAACAAGTCCCCCATCGGCGAGGGCATCGCCCAGCGCA

CCTTGAGCAACCCTGCCGCCATGCAGGCCCGCGCCGATCAGCTGATGGCC

GCCCTGCCCGGCTGCTTTGTGCCGGTCCCCGCCCAGCTGGTGGTGGGTGG

TGGCACCCTGCCGGACGAGTTCTACCCTGCGCCTGCGCTCGAATGCACCG

ACCCGCGTCCGGCCCAGCAGCTGCTCGATGCCCTGCGGAAACTGCCGGTG

CCGGTCATCGCCACCGTGCGCCAGCAGAAGGTGCTGCTCAATATGGCGAC

CCTGCTGCCGACCGAGATTGCACTGCTTATCGCCCAACTCAAGGAGTTGC

TACTGCCCACTCCGACCACTGCGACCGAGGAGCCCTGA

An exemplary amino acid sequence for *Rubrobacter xylanophilus* SelA is (SEQ ID NO: 82)
MLDAERQSRLRSLPAVDAVLRGPAAGLAARHGRAAVAAAVREVLEGLRRE

IAAGGSPDVSGRAVAEGAARLLSGRGLRRVVNATGVVLHTNLGRAVLSER

AAAAAARAGTSYSNLEYDLSRGRRGSRYDHAVPLLRELTGAEDALVVNNC

AGATLLALSALAGEEGEGPPEVVVSRGQLIEIGGGFRIPEVLELSGAVLR

EVGTTNRTRLSDYERALSERTRAILWVHPSNFEIRGFTESAGIAELAGLG

-continued

PPVVADLGSGALLPLGGEPLVQAALRDGAELALFSGDKLLGGPQAGIAAG

SSRLVRRMRRHPLVRALRADKLCLAALEATLRAYLEGRAEEEVPAQRMLR

EPLEGVEARARRLASALSREVPGLEVGVVPSVARSGGGTLPGYEIPSFAA

RVLGADAEALAARLRAAEPPVVGRVHEGALLLDARTLLPGDEEAVVEALR

EAARG

An exemplary nucleic acid sequence encoding *Rubrobacter xylanophilus* SelA is (SEQ ID NO: 83)
ATGCTGGATGCAGAACGTCAGAGCCGTCTGCGTAGCCTGCCTGCAGTTGA

TGCAGTTCTGCGTGGTCCGGCAGCAGGTCTGGCAGCACGTCATGGTCGTG

CAGCAGTTGCAGCAGCAGTTCGTGAAGTTCTGGAAGGTCTGCGTCGTGAA

ATTGCAGCCGGTGGTAGTCCGGATGTTAGCGGTCGTGCCGTTGCAGAAGG

TGCAGCCCGTCTGCTGAGTGGTCGTGGCCTGCGTCGCGTTGTTAATGCAA

CCGGTGTTGTTCTGCATACCAATCTGGGTCGTGCGGTTCTGAGCGAACGT

GCAGCCGCAGCAGCGGCACGTGCAGGCACCAGCTATAGCAATCTGGAATA

TGATCTGAGCCGTGGTCGTCGTGGTAGCCGTTATGATCATGCAGTTCCTC

TGCTGCGTGAACTGACCGGTGCAGAAGATGCACTGGTTGTTAATAACTGT

GCCGGTGCAACCCTGCTGGCACTGAGCGCACTGGCAGGCGAAGAAGGTGA

AGGTCCGCCTGAAGTTGTTGTTAGTCGTGGTCAGCTGATTGAAATTGGTG

GTGGTTTTCGTATTCCGGAAGTGCTGGAACTGAGTGGTGCCGTTCTGCGC

GAAGTTGGTACAACCAATCGTACCCGTCTGAGCGATTATGAACGTGCACT

GAGTGAACGTACCCGTGCAATTCTGTGGGTTCATCCGAGCAATTTTGAAA

TTCGCGGTTTTACCGAAAGCGCAGGTATTGCAGAACTGGCTGGTCTGGGT

CCTCCGGTTGTTGCAGATCTGGGTAGCGGTGCACTGCTGCCGCTGGGTGG

TGAACCGCTGGTTCAGGCAGCACTGCGTGATGGTGCCGAACTGGCACTGT

TTAGCGGTGATAAACTGCTGGGTGGACCGCAGGCTGGTATTGCCGCAGGT

AGCAGCCGTCTGGTTCGTCGTATGCGTCGTCATCCGCTGGTGCGTGCCCT

GCGTGCAGATAAACTGTGCCTGGCAGCCCTGGAAGCAACACTGCGTGCAT

ATCTGGAAGGCCGTGCCGAAGAAGAAGTTCCGGCACAGCGTATGCTGCGC

GAACCACTGGAAGGTGTTGAAGCACGTGCCCGTCGTCTGGCAAGCGCACT

GAGTCGTGAAGTGCCTGGTCTGGAAGTTGGTGTTGTGCCGAGCGTTGCAC

GTAGCGGTGGTGGCACCCTGCCTGGTTATGAAATTCCGAGCTTTGCAGCA

CGTGTTCTGGGTGCAGATGCAGAAGCCCTGGCAGCGCGTCTGCGTGCCGC

AGAACCGCCTGTTGTGGGTCGTGTTCATGAAGGTGCCCTGCTGCTGGATG

CCCGTACCCTGCTGCCAGGTGATGAAGAAGCAGTTGTTGAAGCGCTGCGT

GAGGCAGCCCGTGGTTAA

An exemplary amino acid sequence for *Sulfurimonas honglongensis* SelA is (SEQ ID NO: 84)
MFLLKSIPKVDKFIAKKEFKILGSALVMSLIKELLSELRENILNGRVITF

SEDELVKELLQRYTELTKPSLQTLINATGIIVHTNLGRSLIDADAFDRVK

ELMTNYNNLEFNLESGKRGERYSLISKSVCSLLGCEDVLIVNNNASAVFL

ILNTFARKKEVVVSRGELVEIGGSFRVPDVMKQSGAKLVEVGTTNKTHLY

DYEDAIGKKTSMLMKVHKSNYSIEGFSSDVEFGEIVKLACEKGLIDYYDM

GSGHLFDLPYGLDEPSVLDFMKLNPSLLSFSGDKLLGSVQAGIIVGKKKY

IDMLKKNQLLRMLRVDKLTLALLEESFKAILLGNKEQIPTARMLFRSTDE

LREDAMQVQQKLKKNIKTNIVDTKTLIGGGTTPNKTIPSVALVIESKNIK

VKKLQKLFRQKSIIGRIEDDEFLLDFRTIQKTQLQQVVDAIDEITDV

An exemplary nucleic acid sequence encoding *Sulfurimonas honglongensis* SelA is (SEQ ID NO: 85)
ATGTTCCTGCTGAAAAGCATTCCGAAAGTGGATAAGTTTATCGCCAAGAA

AGAGTTTAAAACCCTGGGTAGCGCACTGGTTATGAGCCTGACCAAAGAAC

TGCTGAGCGAACTGCGTGAAAACATTCTGAATGGTCGTGTTACCACCTTT

AGCGAAGATGAACTGGTTAAAGAGCTGCTGCAGCGTTATACCGAACTGAC

CAAACCGAGCCTGCAGACCCTGATTAATGCAACCGGTATTATTGTTCATA

CCAATCTGGGTCGTAGCCTGATTGATGCAGATGCATTTGATCGTGTTAAA

GAACTGATGACCAACTATAACAACCTGGAATTTAATCTGGAAAGCGGTAA

ACGTGGTGAACGCTATAGTCTGATTAGCAAAAGCGTTTGTAGCCTGCTGG

GTTGTGAAGATGTTCTGATTGTGAATAATAACGCCAGCGCAGTTTTTCTG

ATTCTGAACACCTTTGCGCGTAAAAAAGAAGTTGTTGTTAGTCGCGGTGA

ACTGGTGGAAATTGGTGGTAGCTTTCGTGTTCCGGATGTTATGAAACAGA

GCGGTGCAAAACTGGTTGAAGTTGGCACCACCAATAAAACCCATCTGTAT

GATTATGAAGATGCCATCGGTAAAAAAACGAGCATGCTGATGAAAGTGCA

CAAAAGCAACTATAGCATTGAAGGTTTTAGCAGCGACGTGGAATTTGGCG

AAATTGTTAAACTGGCATGTGAAAAAGGCCTGATCGATTATTATGATATG

GGTAGCGGTCACCTGTTTGATCTGCCGTATGGTCTGGATGAACCGAGCGT

TCTGGACTTTATGAAACTGAATCCGAGTCTGCTGAGCTTTAGCGGTGATA

AACTGCTGGGTAGTGTTCAGGCAGGCATTATTGTTGGCAAAAAAAAGTAT

ATCGACATGCTGAAGAAAAACCAGCTGCTGCGTATGCTGCGTGTGGATAA

ACTGACCCTGGCACTGCTGGAAGAAAGTTTTAAAGCAATTCTGCTGGGCA

ACAAAGAGCAGATTCCGACCGCACGTATGCTGTTTCGTAGCACCGATGAA

CTGCGCGAAGATGCAATGCAGGTTCAGCAGAAACTGAAAAAAAACATCAA

GACCAACATCGTGGATACCAAAACACTGATTGGTGGCGGTACAACCCCGA

ATAAAACCATTCCGAGCGTTGCCCTGGTTATTGAAAGCAAAAACATTAAG

GTGAAAAAACTGCAGAAGCTGTTTCGCCAGAAAAGTATTATTGGTCGCAT

```
CGAGGATGATGAATTTCTGCTGGATTTTCGTACGATTCAGAAAACCCAAC

TGCAGCAGGTTGTTGATGCAATTGATGAAATTACCGACGTGTAA
```

In some embodiments, the SelA is a variant SelA that has at least 50, 60, 70, 80, 85, 90, 95, 96, 97, 98, or 99% sequence identity to any one of SEQ ID NO:79, 80, 82, or 84.

Typically the disclosed SelA or variant SelA can convert seryl-tRNA$^{Sec}$, O-phosphoseryl-tRNA$^{Sec}$ or both to selenocysteinyl-tRNA$^{Sec}$ for one or more of the disclosed tRNA$^{Sec}$.

3. Substrates for PSTK

PSTK is a kinase in archaeal and eukaryotic systems that phosphorylates Ser-tRNA$^{Sec}$ to O-phosphoseryl-tRNA$^{Sec}$, an activated intermediate for selenocysteine biosynthesis. Accordingly, in some embodiments, once aminoacylated with serine, the non-naturally occurring tRNA can serve as a substrate for a PSTK, or variant thereof. The enzyme activity of PSTK is strictly tRNA$^{Ser}$-dependent. PSTK does not hydrolyze ATP in the absence of tRNA nor in the presence of Ser-tRNA$^{Ser}$. The binding of tRNA$^{Ser}$, however, promotes ATP hydrolysis (R. Lynn Sherrer, et al., *Nucleic Acids Res.*, 36(4): 1247-1259 (2008)). This indicates that tRNA$^{Sec}$ might play an essential role in positioning the Ser moiety for initiating phosphoryl transfer. Compared to aminoacyl-tRNA synthetases, PSTK has approximately 20-fold higher affinity toward its substrate, Ser-tRNA$^{Sec}$ (Km=40 nM) (R. Lynn Sherrer, et al., *Nucleic Acids Res.*, 36(4): 1247-1259 (2008)), which may compensate for the low abundance of tRNA$^{Sec}$ in vivo. The concentration of tRNA$^{Sec}$ in vivo is at least 10-fold lower than tRNA$^{Ser}$ in tRNA$^{Ser}$-rich tissues such as liver, kidney and testes in rat (Diamond, et al., *J. Biol. Chem.*, 268:14215-14223 (1993)).

The crystal structure of *Methanocaldococcus jannaschii* PSTK (MjPSTK) places archaeal PSTK identity elements (G2:C71 and the C3:G70) (Sherrer, et al., *Nucleic Acids Res*, 36:1871-1880 (2008)). within contact of the protein dimer interface. The second base pair in the acceptor stem is highly conserved as C2:G71 in eukaryotic tRNA$^{Sec}$, and mutation of G2:C71 to C2:G71 in archaeal tRNA$^{Sec}$ resulted in a Ser-tRNA$^{Sec}$ variant that is phosphorylated inefficiently (Sherrer, et al., *Nucleic Acids Res*, 36:1871-1880 (2008)). The A5-U68 base pair in *Methanococcus maripaludis* tRNA$^{Ser}$ has some antideterminant properties for PSTK (Sherrer, et al., *NAR*, 36(6):1871-1880 (2008)). Moreover, the eukaryotic PSTK has been reported to recognize the unusual D-arm of tRNA$^{Sec}$ as the major identity element for phosphorylation (Wu and Gross *EMBO J.*, 13:241-248 (1994)). Accordingly, in some embodiments, the disclosed tRNAs include residues in the acceptor stem, the D-arm, or combinations thereof that are necessary for the tRNA to serve as a substrate for a PSTK.

4. Substrate for SepSecS

The conversion of phosphoseryl-tRNA$^{Sec}$ (Sep-tRNA$^{Sec}$) to selenocysteinyl-tRNA$^{Sec}$ (Sec-tRNA$^{Sec}$) is the last step of Sec biosynthesis in both archaea and eukaryotes, and it is catalyzed by tetratmeric O-phosphoseryl-tRNA:selenocysteinyl-tRNA synthase (SepSecS). It is believed that one SepSecS homodimer interacts with the sugar-phosphate backbone of both the acceptor-TΨC and the variable arms of tRNA$^{Sec}$, while the other homodimer interacts specifically with the tip of the acceptor arm through interaction between the conserved Arg398 and the discriminator base G73 of human tRNA$^{Sec}$.

The co-crystal structure of SepSecS and tRNA$^{Sec}$ also shows that the 9 bp acceptor stem of tRNA$^{Sec}$ is probably important for recognition by the enzyme (Palioura, S, Sherrer, R L, Steitz, T A, Söll, D & Simonovic, M (2009) *Science* 325:321-325). According to structural analysis, the acceptor-T-variable arm elbow region of tRNA$^{Sec}$ (including bases G50, G51, C64, C65 in the human tRNA$^{Sec}$ that are recognized by SepSecS) may be important for recognition by SepSecS. Accordingly, in some embodiments, the disclosed tRNAs include residues in the acceptor-TΨC, the variable arms of tRNA$^{Sec}$, the tip of the acceptor arm, or combinations thereof necessary for the tRNA to serve as a substrate for SepSecS. In some embodiments, the G50, G51, C64, C65 elements of human tRNA$^{Sec}$ are present in the tRNA$^{Sec}$.

The SepSecS enzyme itself can also be mutated to engineer enzyme variants that accept a substrate somewhat less ideal than naturally occurring tRNA$^{Sec}$. It is believed that His30, Arg33, Lys38 in SepSecS form key interactions with the protomer and G50, U51, C64 and C65 of the tRNA. Therefore, mutation of some of these residues could result in a SepSecS variant that is better able to recognize one of the tRNA$^{Sec}$. The formed Sec-tRNA$^{Sec}$ can be screened in the formate dehydrogenase-benzyl viologen assay [e.g., (Yuan, J, Palioura, S, Salazar, J C, Su, D, O'Donoghue, P, Hohn, M J, Cardoso, A M, Whitman, W B & Söll, D (2006), *Proc Natl Acad Sci USA* 103:18923-18927; Palioura, S, Sherrer, R L, Steitz, T A, Söll, D & Simonovic, M (2009) *Science* 325: 321-325)]. Other assays include standard Wolfson assay [e.g., (Yuan, J, Palioura, S, Salazar, J C, Su, D, O'Donoghue, P, Hohn, M J, Cardoso, A M, Whitman, W B & Söll, D (2006) *Proc Natl Acad Sci USA* 103:18923-18927; Palioura, S, Sherrer, R L, Steitz, T A, Söll, D & Simonovic, M (2009) *Science* 325:321-325)], labeling with [75Se]selenite in the presence of selenophosphate synthase (SelD) [e.g., (Yuan, J, Palioura, S, Salazar, J C, Su, D, O'Donoghue, P, Hohn, M J, Cardoso, A M, Whitman, W B & Söll, D (2006) *Proc Natl Acad Sci USA* 103:18923-18927)], and using [14C] or [3H]serine in the initial charging reaction.

In some embodiments, a SepCysS is used instead of SepSecS. SepCysS is a key PLP-dependent enzyme in Cys-tRNA formation in methanogens. It converts Sep-tRNA$^{Cys}$ into Cys-tRNA$^{Cys}$ using thiophosphate as sulfur donor. The enzyme's crystal structure is established (Fukunaga, R & Yokoyama, S (2007) *Nat Struct Mol Biol* 14:272-279.) and its mechanism (Liu, Y., Dos Santos, P. C., Zhu, X., Orlando, R., Dean, D. R., Söll, D. and Yuan, J. (2012) *J. Biol. Chem.* 287, 5426-5433) is different from that of SepSecS (Palioura, S, Sherrer, R L, Steitz, T A, Söll, D & Simonovic, M (2009) *Science* 325:321-325.). The length of the acceptor stem of its tRNA substrates is not critical and acceptor helices between 7-9 bp are acceptable. Therefore, this enzyme's active site can be engineered to allow selenophosphate (instead of thiophosphate) to participate in the reaction.

Figure 2:
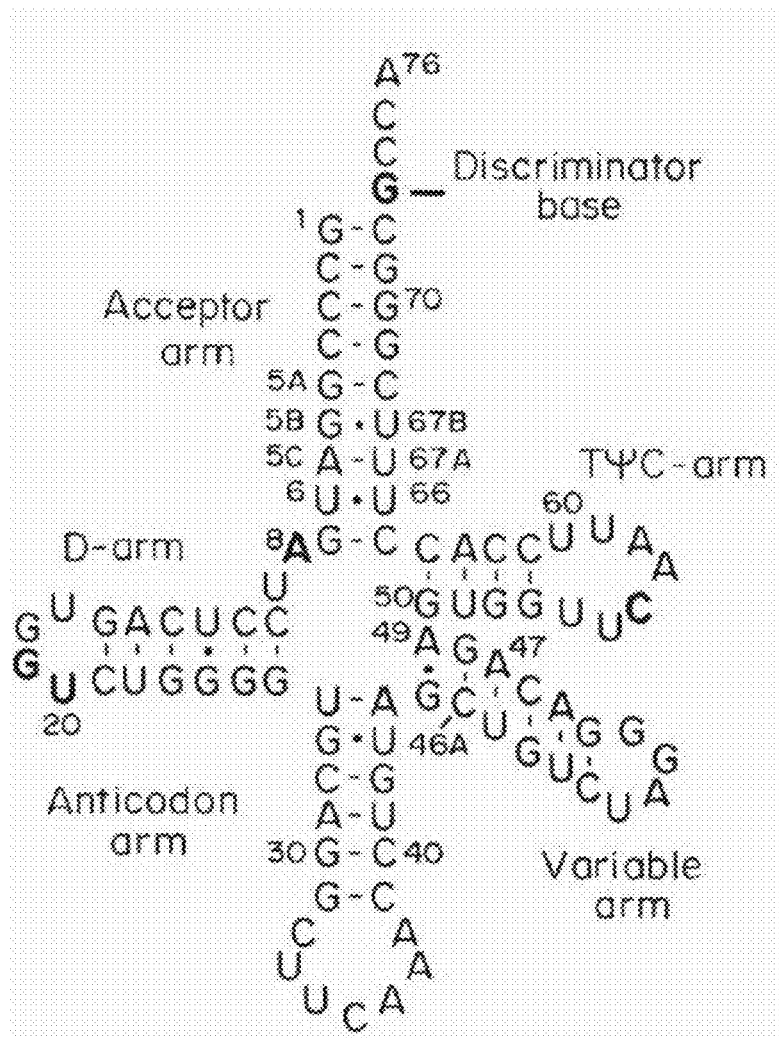
FIG. 2 is a depiction of the primary and secondary structures of human tRNA$^{Sec}$ (SEQ ID NO:3) adapted from Yuan, et al., *FEBS Lett.*, 584(2):342-349 (2010).

5. Primary Structure tRNAs can be described according to their primary structure (i.e., the sequence from 5' to 3') as well as their secondary structure. The secondary structure of tRNA is typically referred to as a "cloverleaf", which assumes a 3D L-shaped tertiary structure through coaxial stacking of the helices. FIG. 2 illustrates a typical human tRNA$^{Sec}$, which includes an acceptor arm, a D-arm, an anticodon arm, a variable arm, and a TΨC-arm.

In some embodiments the tRNA$^{Sec}$ shares sequence identity or sequence homology with a naturally occurring tRNA, for example a naturally occurring tRNA$^{Sec}$, or a naturally occurring tRNA$^{Ser}$.

a. Variants of Naturally Occurring tRNA$^{Sec}$

The non-naturally occurring tRNA$^{Sec}$ disclosed herein can be a variant of a naturally occurring tRNA$^{Sec}$. The naturally occurring tRNA$^{Sec}$ can be from a prokaryote, including but not limited to *E. coli*, an archaea, including, but not limited to, *M. maripaludis* and *M. jannaschii*, or a eukaryote including, but not limited to human.

In some embodiments, the non-naturally occurring tRNA$^{Sec}$ is a variant of an *E. coli* tRNA$^{Sec}$, for example, GGAAGAUCGUCGUCUCCGGUGAGGCGGCUGGAC-UUCAAAUCCAGUUGGGGCCGCCA GCGGU-CCCGGGCAGGUUCGACUCCUGUGAUCUUCCGCCA (SEQ ID NO:1), which is depicted in FIG. 3 (left panel).

In some embodiments, the non-naturally occurring tRNA$^{Sec}$ is a variant of an *M. maripaludis* tRNA$^{Sec}$, for example, GGCACGGGGUGCUUAUCUUGGUA-GAUGAGGGCGGACUUCAGAUCCGUCGAGUUCCG UUGGAAUUCGGGGUUCGAUUCCCCCC-CUGCGCCGCCA (SEQ ID NO:2).

In some embodiments, the non-naturally occurring tRNA$^{Sec}$ is a variant of a human tRNA$^{Sec}$, for example, GCCCGGAUGAUCCUCAGUGGUCUGGG-GUGCAGGCUUCAAACCUGUAGCUGUCUAGG GACAGAGUGGUUCAAUUCCACCUUUCGGGCGCCA (SEQ ID NO:3), which is depicted in FIG. 2.

An exemplary variant of *E. coli* tRNA$^{Sec}$ is tRNA$^{SecUX}_{am}$, described in Thyer, et al., *J. Am. Chem. Soc.*, 137:46-49 (2015) (SEQ ID NO:18), wherein the circled region of FIG. 3B was mutated in tRNA$^{Sec}$ (e.g., SEQ ID NO:1) to enable recognition by EF-Tu. The EF-Tu recognition region is very similar between tRNA$^{UTu}$ and tRNA$^{SecUX}$; residues G7, U64, G65, and C66 are shared between the two. Residues 50 and 49 are different between tRNA$^{SecUX}$ and tRNA$^{UTu}$ (discussed in more detail below).

b. Variants of Naturally Occurring tRNA$^{Ser}$

The non-naturally occurring tRNA$^{Sec}$ disclosed herein can be a variant of a naturally occurring tRNA$^{Ser}$. The naturally occurring tRNA$^{Ser}$ can be from a prokaryote, including but not limited to *E. coli*, an archaea, including, but not limited to, *M. maripaludis* and *M. jannaschii*, or a eukaryote including, but not limited to human.

Figures 3A, 3B, 3C:
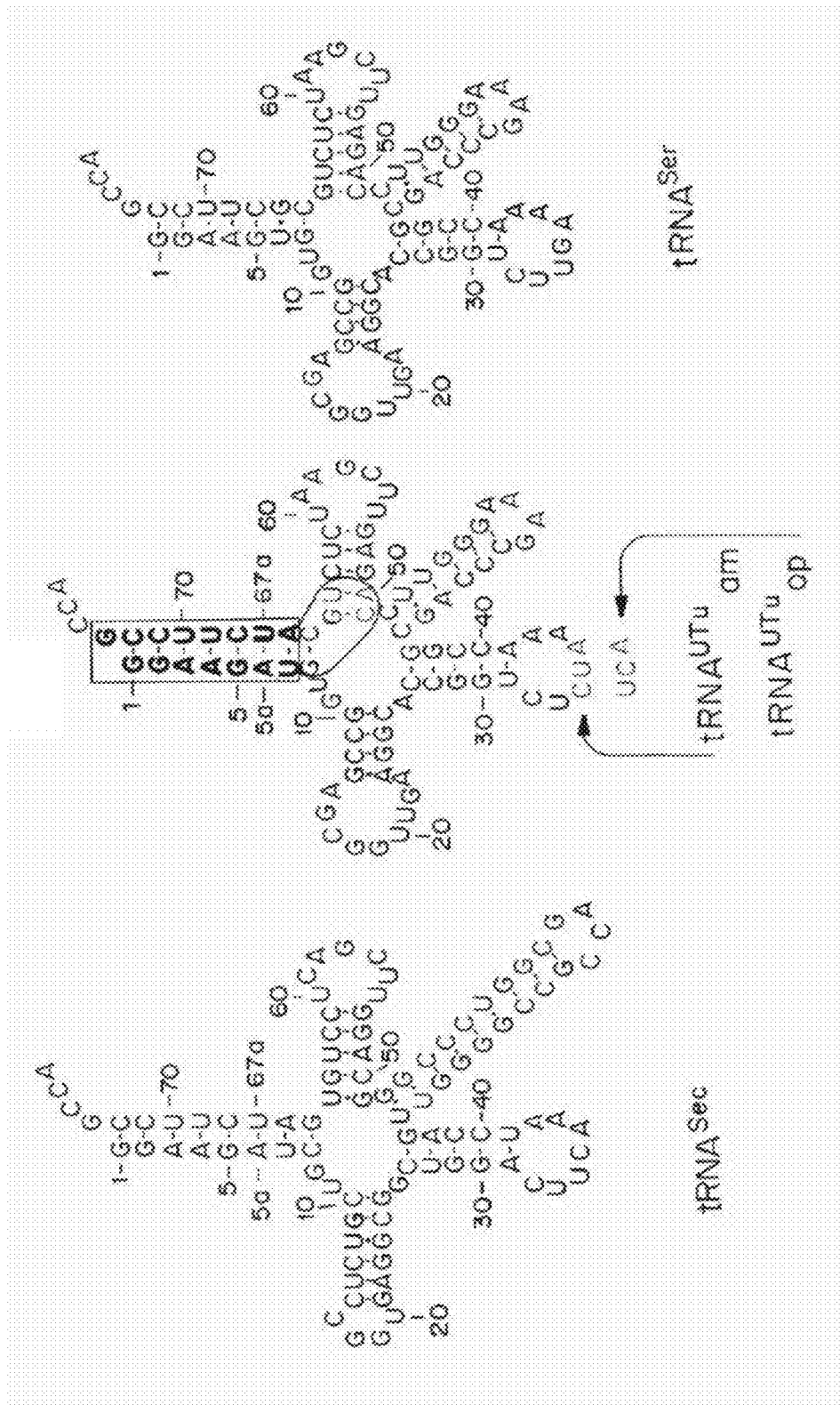
FIGS. 3A-3C are depictions of the primary and secondary structures of *E. coli* tRNA$^{Sec}$ (SEQ ID NO:1) (3A), a non-naturally occurring tRNA$^{UTu}$ with an *E. coli* body (tRNA$^{UTu}_{op}$, SEQ ID NO:6; tRNA$^{UTu}_{am}$, SEQ ID NO:7) (3B), and *E. coli* tRNA$^{Ser}$ (SEQ ID NO:4) (3C). *E. coli* tRNA$^{Ser}$ (3C) serves as a major scaffold for tRNA$^{UTu}$ (3B) with the exception of the acceptor stem that originates from *E. coli* tRNA$^{Sec}$ (boxed sequence elements). Major EF-Tu recognition elements were retained from tRNA$^{Ser}$ as well (circled sequence elements). Substitution of the amber anticodon CUA (tRNA$^{UTu}_{am}$) for the opal anti-codon UCA (tRNA$^{UTu}_{op}$) are depicted with arrows and labeling.

In some embodiments, the non-naturally occurring tRNA$^{Sec}$ is a variant of an *E. coli* tRNA$^{Ser}$, for example, GGAAGUGUGGCCGAGCGGUUGAAGGCACCGGUC-UUGAAAACCGGCGACCCGAAAGG GUUCCAGAGUUCGAAUCUCUGCGCUUCCGCCA (SEQ ID NO:4), depicted in FIG. 3C.

In some embodiments, the non-naturally occurring tRNA$^{Sec}$ is a variant of an *M. maripaludis* tRNA$^{Ser}$, for example, GCAGAGGUGGUUGAGCUUGGC-CAAAGGCGCCGGACUUGAAAUCCGGUUCUCCA-CUG GGGAGCGGGGUUCAAAUCCCUCCCU-CUGCGCCA (SEQ ID NO:5).

c. Chimeric tRNA$^{Sec}$

The non-naturally occurring tRNA$^{Sec}$ disclosed herein can also be a chimeric tRNA including sequences from two or more naturally occurring tRNAs. Some embodiments, the non-naturally occurring tRNA includes sequences from a naturally occurring tRNA$^{Sec}$ and a naturally occurring tRNA$^{Ser}$. The chimeric tRNA can include nucleic acid sequences or features, for example an antideterminant element, from a prokaryote, including but not limited to *E. coli*, an archaea, including, but not limited to, *M. maripaludis* and *M. jannaschii*, or a eukaryote including, but not limited to, human.

Examples of non-naturally occurring tRNA$^{Sec}$ that are chimeric tRNAs including sequence elements from *E. coli* include, but are not limited to GGAAGAU-GUGGCCGAGCGGUUGAAGGCACCGGUCUU-CAAAACCGGCGACCCGAAAG GGUUCCAGAGUUCGAAUCUCUGCAUCUUCCGCCA (SEQ ID NO:6; *E. coli* tRNA$^{UTu}$-opal), as depicted in FIG. 3B; GGAAGAUGUGGCCGAGCG-GUUGAAGGCACCGGUCUC-UAAAACCGGCGACCCGAAAG GGUUCCAGAGUUCGAAUCUCUGCAUCUUCCGCCA (SEQ ID NO:7; *E. coli* tRNA$^{UTu}$-amber), as depicted in FIG. 3B; and GGAAGAUGUGGCCGAGCG-GUUGAAGGCACCGGUC-UUUAAAACCGGCGACCCGAAAG GGUUCCAGAGUUCGAAUCUCUGCAUCUUCCGCCA (SEQ ID NO:8; *E. coli* tRNA$^{UTu}$-ochre).

Other examples of non-naturally occurring tRNA$^{Sec}$ that are chimeric tRNAs including sequence elements from *E. coli* include, but are not limited to GGCACU-GUGGCCGAGCGGUUGAAGGCACCGGUCUU-CAAAACCGGCGACCCGAAAGG GUUCCAGAGUUCGAAUCUCUGCGGUGCCGCCA (SEQ ID NO:9; *E. coli* tRNA$^{UTu}$-opal), as depicted in FIG. 4B;

GGCACUGUGGCCGAGCGGUUGAAGGCACCGGU-CUCUAAAACCGGCGACCCGAAAGG GUUCCAGAGUUCGAAUCUCUGCGGUGCCGCCA (SEQ ID NO:10; *E. coli* tRNA$^{UTu}$-amber), as depicted in FIG. 4B; and GGCACUGUGGCCGAGCG-GUUGAAGGCACCGGUC-UUUAAAACCGGCGACCCGAAAGG GUUCCAGAGUUCGAAUCUCUGCGGUGCCGCCA (SEQ ID NO:11; *E. coli* tRNA$^{UTu}$-ochre), which are non-naturally occurring chimeras of *E. coli* tRNA$^{Ser}$ with PSTK identity elements.

In some embodiments, the non-naturally occurring tRNA$^{Sec}$ is a variant of tRNA$^{UTu}$, for example, SEQ ID NO:7:
G$^1$GAAG$^5$A$^{5a}$UGUGG$^{10}$CCGAGCGGU$^{20}$UGAAGGCAC CGG$^{30}$UCU *CUA* AAAC$^{40}$CGGCGA CCCGAAAGGGUUCCA$^{50}$GAGUUCGAAU$^{60}$CUCUGC AU$^{67a}$CUU$^{70}$CCGCCA (SEQ ID NO:7; *E. coli* tRNA$^{UTu}$-amber) (wherein the anticodon is bolded and in italics), or the opal or ochre equivalent thereof (e.g., SEQ ID NO:6 or 8). In some embodiments, the non-naturally occurring tRNA$^{Sec}$ has at least 80, 81, 82, 83, 84, 85, 86, 97, 88, 89, 90, 91, 92, 93, 94, 95, 96, 97, 97, 98, or 99% sequence identity to SEQ ID NO: 6, 7, or 8.

The anticodon is in italics. tRNA positional markers (e.g., 1, 5, 5a, 10, 20, 30, 40, 50, 60, 67a, 70 according to the numbering of Sprinzl, et al., *Nucleic Acids Research*, 26(1): 148-153 (1998)) are provided in superscript and are not part of the tRNA sequence.

Figure 5:
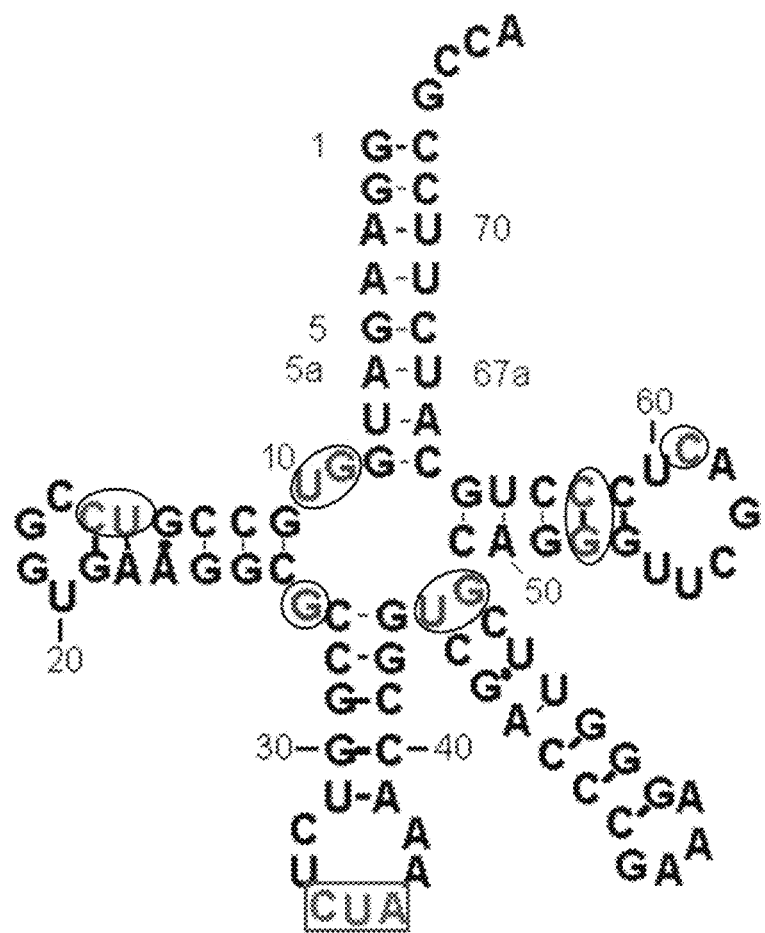
FIG. 5 is a depiction of the primary and secondary structures of a non-naturally occurring tRNA$^{UTuX}$ (SEQ ID NO:17). Nucleotides that were changed from the original tRNA$^{UTu}$ (SEQ ID NO:7) are circled and the amber anticodon is boxed. Specific mutations introduced between tRNA$^{UTu}$ and tRNA$^{UTuX}$ include U8G, G9U, and A27G in the core region; A14U and G15C in the D-arm; deletion of U21 in the D-loop; A52G and U62C in the T-arm; A59C in the T-loop; and the insertion of residues U44 and G48 in the variable arm.

An exemplary tRNA$^{UTu}$ variant is UTuX G$^1$GAAG$^5$A$^{5a}$UG<u>G</u>UG$^{10}$CCG<u>UCC</u>GGU$^{20}$GAAGGC <u>GCCGG</u>$^{30}$UCU *CUA* AAAC$^{40}$<u>C</u>GG<u>U</u>CGA CCCGAAAGG-GUUC<u>GC</u>A$^{50}$G<u>GG</u>UUCGA<u>C</u>U$^{60}$C <u>CC</u>UGCAU$^{67a}$CUU$^{70}$CCGCCA (SEQ ID NO:17; *E. coli* scaffold, tRNA$^{UTuX}$-amber, and depected in FIG. 5A), or an opal or ochre equivalent thereof.

Examples of non-naturally occurring tRNA$^{Sec}$ that are chimeric tRNAs including sequences elements from *M. maripaludis* include, but are not limited to, GGCGCGGUG-GUUGAGCUUGGCCAAAGGCGCCGGACUU-CAAAUCCGGUUCUCCACUG GGGAGCGGGGUU-CAAAUCCCUCCCGCGCCGCCA (SEQ ID NO:13; *M.*

*maripaludis* tRNA$^{UTu}$-opal), as depicted in FIG. 4A; GGCGCGGUGGUUGAGCUUGGC-CAAAGGCGCCGGACUCUAAAUCCGGUUCUCCA-CUG GGGAGCGGGGGUUCAAAUCC-CUCCCGCGCCGCCA (SEQ ID NO:14; *M. maripaludis* tRNA$^{UTu}$-amber), as depicted in FIG. 4A; GGCGCGGUG-GUUGAGCUUGGCCAAAGGCGCCGGAC-UUUAAAUCCGGUUCUCCACUG GGGAGCGGGG-GUUCAAAUCCCUCCCGCGCCGCCA (SEQ ID NO:15; *M. maripaludis* tRNA$^{UTu}$-ochre).

d. Allo-tRNA

In some embodiments, the tRNA$^{Sec}$ is a naturally occurring tRNA or a non-naturally occurring variant thereof. Thus, in some embodiments, the tRNA$^{Sec}$ includes or consists of a naturally occurring nucleic acid sequence. In other embodiments, the non-naturally occurring tRNA$^{Sec}$ includes or consists of a naturally occurring nucleic acid sequence with one or more insertions, deletions or substitutions.

In some embodiments, the tRNA$^{Sec}$ is an "allo-tRNA." Allo-tRNA are structurally similar to tRNA$^{Sec}$ as they have a long V-arm and longer anticodon and acceptor stems compared to canonical tRNAs. Moreover, the D-stem-loop of allo-tRNAs resembles that of tRNA$^{Sec}$ with its long stem and tetraloop. Allo-tRNAs typically have a 8/4 or 9/3 composition of the 12-bp amino-acid acceptor branch. As discussed in more detail in the examples below, naturally occurring allo-tRNA have been identified in, for example, Clostridia, Proteobacteria, and Acidobacteria.

Naturally occurring allo-tRNAs typically have a long V-arm and many have an identity of the discriminator base (G73 or U73) which are important for aminoacylation by seryl-tRNA synthetase (SerRS), though at least one was found to charge with alanine. Many naturally occurring allo-tRNA have an anticodon that recognizes a codon inconsistent with the amino acid charged to it. For example, some of the allo-tRNAs charge with serine, but have a leucine anticodon.

Non-naturally occurring variants of naturally occurring allo-tRNAs are also provided. The non-naturally occurring allo-tRNA typically have one or more insertions, deletions, or substitutions relative to the naturally occurring allo-tRNA. Thus in some embodiments, the only change(s) in a non-naturally occurring tRNA$^{Sec}$ is substitution of the naturally-occurring anticodon with an alternative anticodon, preferable an anticodon that recognizes a stop codon.

In some embodiments, the naturally occurring allo-tRNA can be additionally or alternatively modified to include a SerRS identity element.

In some embodiments, the variants include one more additional or alternative modifications that improve the tRNAs activity as a tRNA$^{Sec}$, for example, to improve binding to SelA, or improve binding to a EF-Tu.

i. Exemplary Consensus Allo-tRNA

Exemplary consensus primary sequences and secondary structures for allo-tRNA are provided. Exemplary consensus structures are depicted in FIGS. 6A and 6B, and 6D-6F. For the sequences provided below, N denotes A, G, T/U, or C; R denotes A or G; Y denotes T/U or C; K denotes G or T/U; and W denotes A or T/U. The anticodon is in bold and italics.

Figures 6A, 6B, 6C:
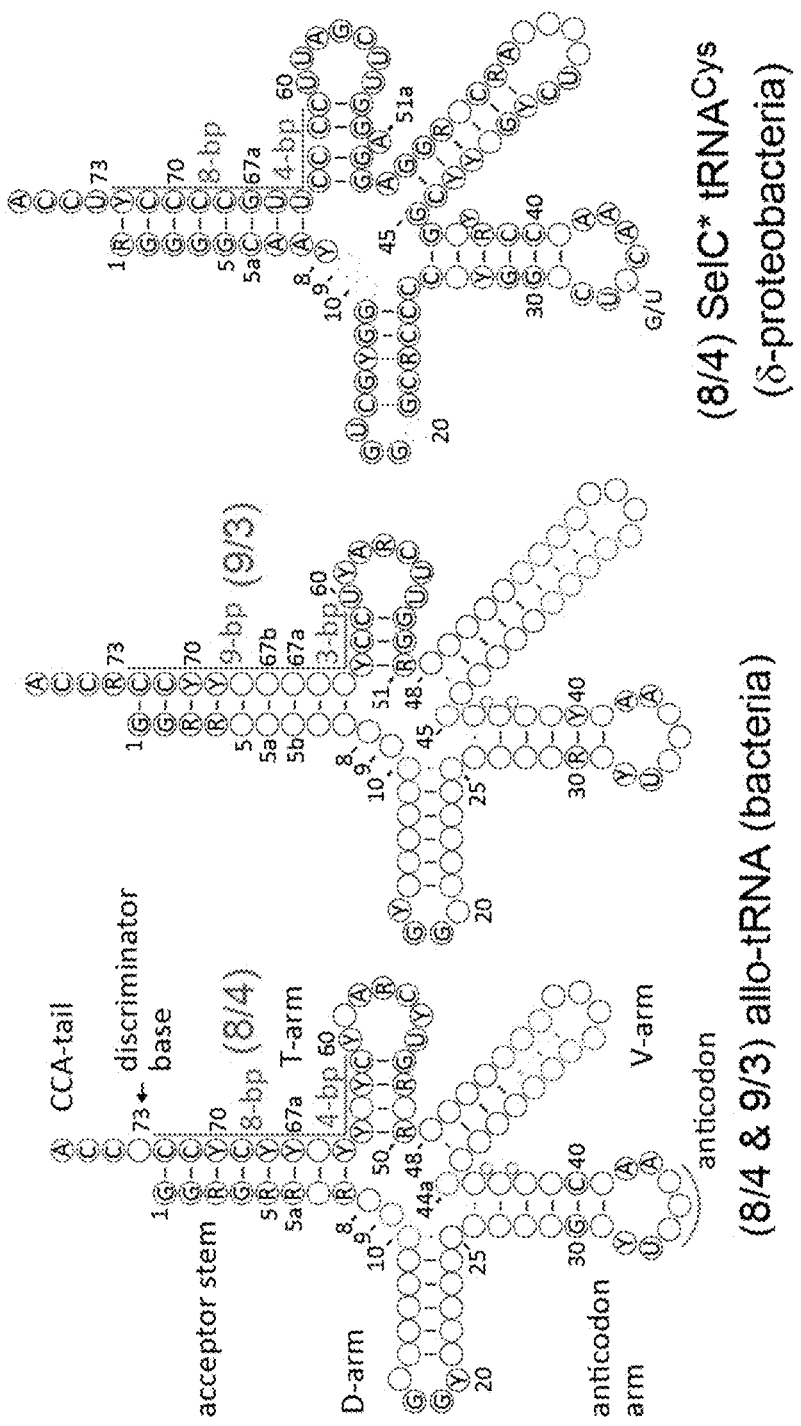
FIGS. 6A-6F are depictions of concensus primary and secondary structures of (8/4) allo-tRNA (bacteria) (SEQ ID NO:19) (6A), (9/3) allo-tRNA (bacteria) (SEQ ID NO:20)

8/4 allo-tRNA, FIG. 6A (SEQ ID NO: 19)
GGRGRRNRNNNNNNNNNNGGYNNNNNNNNNNNGNYU*NNN*AANCNNNNNNN

NNNNNNNNNNNNNNNNNRNRGUYCRANYCYNYYNYYCYCCNCCA

Typically, an Acceptor Stem can be formed by base pairing between nucleotides 1-8 with nucleotides 87-80 respectively;

a D-arm can be formed by base pairing between nucleotides 11-16 with nucleotides 26-21 respectively;

an anti-codon arm can be formed by base pairing between nucleotides 27-32 with nucleotides 45-40 respectively;

a V-arm can be formed by base pairing between nucleotides 47-53 with nucleotides 64-58 respectively;

a T-arm can be formed by base pairing between nucleotides 65-68 with nucleotides 79-76 respectively;

or a combination thereof.

9/3 Allo-tRNA (FIG. 6B)

(SEQ ID NO: 20)
GGRRNNNNNNNNNNNNNNNYGGNNNNNNNNNNNNNRNYU*NNN*AANYNNNNNN

NNNNNNNNNNNNNNNNNNNNNNRGGUUCRAYUCCYNNNNNYYCCRCCA

Typically, an Acceptor Stem can be formed by base pairing between nucleotides 1-9 with nucleotides 91-83 respectively;

a D-arm can be formed by base pairing between nucleotides 12-17 with nucleotides 27-22 respectively;

an anti-codon arm can be formed by base pairing between nucleotides 28-33 with nucleotides 46-41 respectively;

a V-arm can be formed by base pairing between nucleotides 48-56 with nucleotides 69-61 respectively;

a T-arm can be formed by base pairing between nucleotides 70-72 with nucleotides 82-80 respectively;

or a combination thereof.

Figures 6D, 6E, 6F:
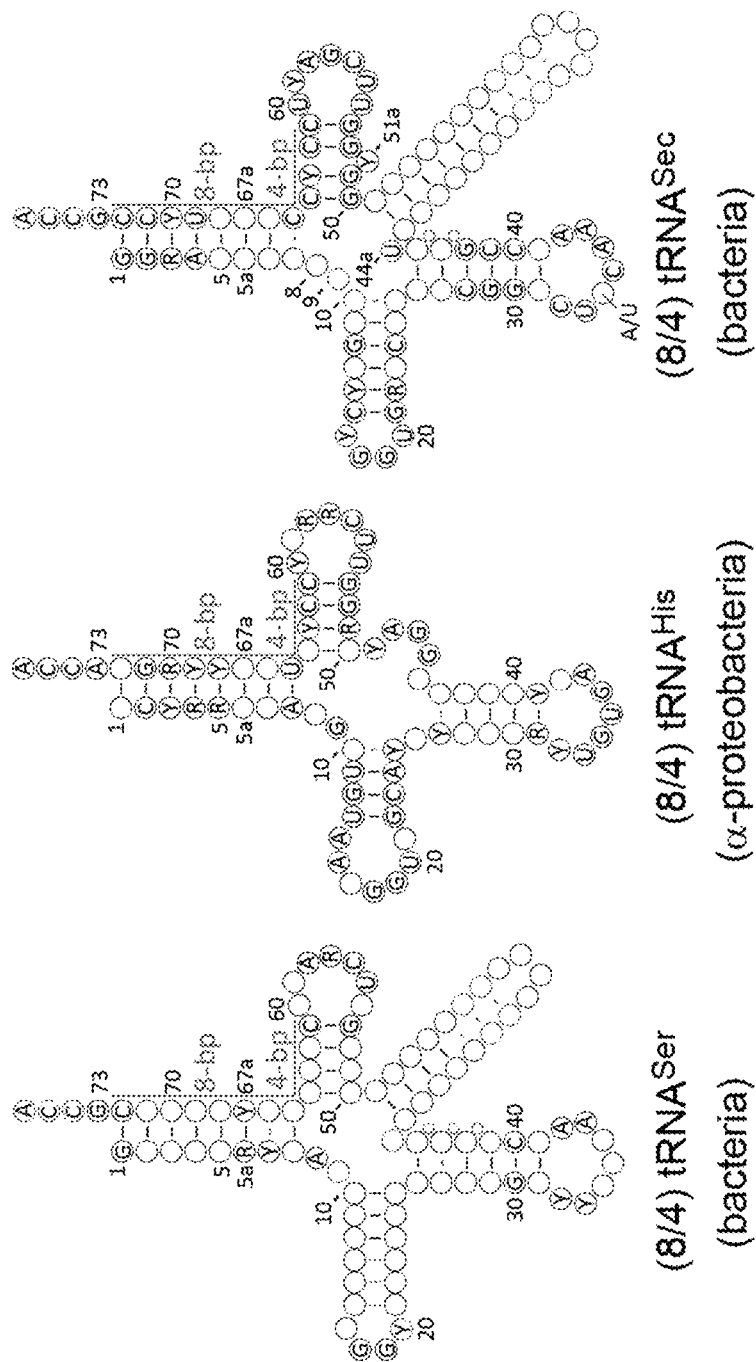

8/4 tRNASer (bacteria) (FIG. 6D)

(SEQ ID NO: 21)
GNNNNRYNANNNNNNNNGGYNNNNNNNNNNNGNYY*NNN*AANCNNNNNN

NNNNNNNNNNNNNNNNNNNGNUCRANNCNNNNNYNNNNCGCCA

Typically, an Acceptor Stem can be formed by base pairing between nucleotides 1-8 with nucleotides 87-80 respectively;

a D-arm can be formed by base pairing between nucleotides 11-16 with nucleotides 26-21 respectively;

an anti-codon arm can be formed by base pairing between nucleotides 27-32 with nucleotides 45-40 respectively;

a V-arm can be formed by base pairing between nucleotides 47-53 with nucleotides 64-58 respectively;

a T-arm can be formed by base pairing between nucleotides 65-68 with nucleotides 79-76 respectively;

or a combination thereof.

ii. Exemplary Allo-tRNA

The following table provides exemplary allo-tRNA sequences. Results show that SEQ ID NOS:24-30 can be charged with serine by SerRS. SEQ ID NO:27 cannot be charged with serine, however, its discriminator base can be substituted to a nucleotide or nucleotides that are recognized by SerRS.

TABLE 1

Exemplary Allo-tRNA

| anti-codon | codon | type | N73 | id | origin | Sequence (DNA) |
|---|---|---|---|---|---|---|
| UCU | AGA | (9/3) | G | 3300001739.u:JGI24658J20074_30893618 | Marine viral communities from the Deep Pacific Ocean-MSP-121 (Metagenome Std Draft M1679 Malaspina viral metagenome MSP-121, ASSEMBLY_DATE = 20130718) | GGGAGCAGGTATGTGTCTGGGGACACGAGCGGTCT*TCT*AAACCGCGTGGGCCGTGGTTCTGTCACGGTCGGGTTCGATTCCCCCTGCTCCCG (SEQ ID NO: 22) |
| CCU | AGG | (9/3) | G | 3300001141.u:JGI12638J13249_313825344 | Forest soil microbial communities from Davy Crockett National Forest, Groveton, Texas, USA-Texas A ecozone_OM3H0_M 2 (Texas A ecozone_OM3H0_M 2, ASSEMBLY_DATE = 20130221) | GGAGTGGTGTGCCCGGCTGGTGCCGGGAGCAGTTT*CCT*AAACTGCCGACGCTGCGAGGCGTAGGGTTCGATTCCCCACCATTCCG (SEQ ID NO: 23) |
| UAG | CUA | (9/3) | G | 3300004074.u:Ga0055518_301460185 | Wetland microbial communities from the San Francisco Bay, California, USA, that impact long-term carbon sequestration-White_ThreeSqA_D1 | GGAGGGTGGTCGCTGTTGGTGCAGCGGGCGGGCC*TAG*AACCCGCTGGAGCCTCACCGGGCTAAGGTTCGATTCCTCCACCCTCCGCCA (SEQ ID NO: 24) |
| CAG | CUG | (9/3) | G | 3300002954.u:JGI20281J44786_310361524 | Forest soil microbial communities from Harvard Forest LTER, USA-PH H12_0 (Forest soil microbial communities from Harbard Forest LTER, USA-PH H12_0, ASSEMBLY_DATE = 20140709) | GGAGAGGGCAAGAGTGACGGTTCACTCACCCGTCT*CAG*AAACGGGTAACGTCTATCCGGGCGTTGGGTTCAATTCCCGCCCTCTCCG (SEQ ID NO: 25) |
| UUA | UAA | (9/3) | G | 3300002459.u:JGI24751J29686_337535576 | Switchgrass rhizosphere microbial communities from Kellogg Biological Station, Michigan, USA-S6 (KBS Switchgrass S6, ASSEMBLY_DATE = 20140130) | GGGGTGGGGTTCCGGCTGGTGCCGGTCGCGGGCT*TTA*AACCCGTCAGGACGCTGCGACGCGTAAGGTTCGATTCCTCCCCACTCCG (SEQ ID NO: 26) |
| UUA | UAA | (9/3) | A | 3300000000.u:GPDYDRAFT_c328587791 | Soil microbail communities from Great Prairies-Wisconsin Native Prairie soli | GGGCGGGGGTTCCGTCTGGTGACGGTCGCGGGCT*TTA*AACCCGTCAGGACGCTGTGCAGGCGTTAGGTTCGATTCCTCCCCCGTCCA (SEQ ID NO: 27) |
| UAA | UUA | (9/3) | G | 3300002225.u:JGI24723J26617_313779256 | Oil polluted marine microbial communities from Coal Oil Point, Santa Barbara, California, USA-Santa Barbara | GGAGGGGAACTTCTATCTGGTGATAGACGGGAACT*TAA*AATTCCTTGAAATGCCTCGCCG |

TABLE 1-continued

Exemplary Allo-tRNA

| anti-codon | codon | type | N73 | id | origin | Sequence (DNA) |
|---|---|---|---|---|---|---|
| | | | | | Oil Seep Sample 6 (Crude oil metagenome 6, ASSEMBLY_DATE = 20131204) | CATTGGGTTC GATTCCCTTC CCCTCCGCCA (SEQ ID NO: 28) |
| CAA | UUG | (9/3) | G | 3300003 396.u:JG I26137J5 0245_30 9810974 | Arabidopsis thaliana rhizosphere microbial communities from the Joint Genome Institute, USA, that affect carbon cycling- Inoculated plant M3 PM (Arabidopsis thaliana rhizosphere microbial communities from the Joint Genome Institute, USA, that affect carbon cycling- Inoculated plant M3 PM, ASSEMBLY_DATE = 20140903) | GGAGGGCGGC TGCTGCTGGT GCAGCGGGTG GACT*CAA*AAT CCACTGGAGC CTGTCGGGGC TAGGGTTCGA TTCCCCCGCC CTCCG (SEQ ID NO: 29) |
| CAA | UUG | (9/3) | G | 3300003 218.u:JG I26339J4 6600_30 1272239 | Bog forest soil microbial communities from Calvert Island, British Columbia, Canada-ECP12_OM1 (Bog Forest metaG ECP12OM1, ASSEMBLY_DATE = 20140815) | GGAGAGTAGA TTTCATGCGG TTATGAAATG CGTCT*CAA*AA ACGCAGAGGG GGCTACACAC CCCCAGGGTT CAACTCCCCT ACTCTCCG (SEQ ID NO: 30) |

Preferred non-naturally occurring allo-tRNA$^{Sec}$ include

>allo-tRNAuTu (also referred to as "2225")
(SEQ ID NO: 31)
GGAGGGGAACTTCTATCTGGTGATAGACGGGAACT*CTA*AATTCCTTG

AAATGCCTCGCCGCATTGGGTTCGATTCCCTTCCCCTCCGCCA and variants thereof.

Other allo-tRNA$^{Sec}$ include, for example,

>allo-tRNA$^{UTu}$ (Ac-3U variant)
(SEQ ID NO: 32)
GGAGGTTGAACTTCTATCTGGTGATAGACGGGAACT*CTA*AATTCCTT

GAAATGCCTCGCCGCATTGGGTTCGATTCCCTTCTCCTCCGCCA

>allo-tRNA$^{UTu}$ (Ac-bU variant)
(SEQ ID NO: 33)
GGAGGTGGAACTTCTATCTGGTGATAGACGGGAACT*CTA*AATTCCTT

GAAATGCCTCGCCGCATTGGGTTCGATTCCCTTCCCCTCCGCCA

>allo-tRNA$^{UTu}$ (D-3b variant)
(SEQ ID NO: 34)
GGAGGGGAACTTCTGTCTGGTGGCAGACGGGAACT*CTA*AATTCCTTG

AAATGCCTCGCCGCATTGGGTTCGATTCCCTTCCCCTCCGCCA

>allo-tRNA$^{UTu2}$
(SEQ ID NO: 35)
GGACGGGGGTTCCGTCTGGTGACGGTCGCGGGCT*CTA*AACCCGTCAG

GACGCTGTGCAGGCGTTAGGTTCGATTCCTCCCCCGTCCGCCA

>allo-tRNA$^{UTu2}$ (G21 variant)
(SEQ ID NO: 36)
GGACGGGGGTTCCGTCTGGTGGCGGTCGCGGGCT*CTA*AACCCGTCAG

GACGCTGTGCAGGCGTTAGGTTCGATTCCTCCCCCGTCCGCCA

>2459
(SEQ ID NO: 37)
GGAGTGGGGTTCCGGCTGGTGCCGGTCGCGGGCT*CTA*AACCCGTCAG

GACGCTGCGACGCGTAAGGTTCGATTCCTCCCCACTCCGCCA

>S15 UU variant
(SEQ ID NO: 38)
GGAGGGCATTTTCAGTCGGTACTGGACGCCGTCT*CTA*AAACGGTTGC

AGGGTCTTAGTCAGCTCTGGGAGTTCGACTCTCCTGCCCTCCGCCA

>S15 CU variant
(SEQ ID NO: 39)
GGAGGGCACTTTCAGTCGGTACTGGACGCCGTCT*CTA*AAACGGTTGC

AGGGTCTTAGTCAGCTCTGGGAGTTCGACTCTCCTGCCCTCCGCCA

>S15 UC variant
(SEQ ID NO: 40)
GGAGGGCATCTTCAGTCGGTACTGGACGCCGTCT*CTA*AAACGGTTGC

AGGGTCTTAGTCAGCTCTGGGAGTTCGACTCTCCTGCCCTCCGCCA

>S15 AA variant
(SEQ ID NO: 41)
GGAGGGCAAATTCAGTCGGTACTGGACGCCGTCT*CTA*AAACGGTTGC

AGGGTCTTAGTCAGCTCTGGGAGTTCGACTCTCCTGCCCTCCGCCA

-continued

>S15 AU variant (SEQ ID NO: 42)
GGAGGGCAATTTCAGTCGGTACTGGACGCCGTCT*CTA*AAACGGTTGC

AGGGTCTTAGTCAGCTCTGGGAGTTCGACTCTCCTGCCCTCCGCCA

In some embodiments, the non-naturally occurring allo-tRNA$^{Sec}$ is a variant of allo-tRNA$^{UTu}$ having at least 60, 65, 70, 75, 80, 85, 86, 87, 88, 89, 90, 91, 92, 93, 94, 95, 96, 97, 98 or 99% sequence identity to SEQ ID NO:31.

In some embodiments, the variant has at least 60, 65, 70, 75, 80, 85, 86, 87, 88, 89, 90, 91, 92, 93, 94, 95, 96, 97, 98 or 99% sequence identity to any one of SEQ ID NO:22-42.

In some embodiments, the variant includes, for example, transplanting one or more features of *Aeromonas* tRNA$^{Sec}$ such as a bulged pyrimidine at position 5 or 5a in the 7-bp acceptor stem, U14:G21 wobble base pair in the D-stem of As tRNA$^{Sec}$ or a combination thereof to a disclosed tRNA$^{Sec}$. Thus mutations are designed to improve binding to *Aeromonas* SelA.

e. 8/4 SelC*tRNA (FIG. 6C)

The Examples below also describe the identification of SelC*tRNAs which were named after the selC gene, which encodes tRNA$^{Sec}$ in *E. coli*. SelC*tRNA$^{Cys}$ isoacceptors have an U73 discriminator base and cysteine GCA or opal UCA anticodons. U73 and GCA are the most important identity elements for CysRS, and certain CysRS forms are known to cysteinylate tRNA$^{Cys}$$_{UCA}$.

A consensus sequence for SelC*tRNA$^{Cys}$ is (SEQ ID NO: 43)
RGGGGCAAYGGYGCUGGGCRCCCCNYGGNCU*KCA*LANCCRYNGGCYY

NGYCUNNNNARCNRGGAGGAGGUUCGAUUCCCCUUGCCCCYUCCA

Typically, an Acceptor Stem can be formed by base pairing between nucleotides 1-8 with nucleotides 91-84 respectively;

a D-arm can be formed by base pairing between nucleotides 12-16 with nucleotides 25-21 respectively;

an anti-codon arm can be formed by base pairing between nucleotides 27-32 with nucleotides 46-45 and 43-40 respectively;

a V-arm can be formed by base pairing between nucleotides 48-53 with nucleotides 66-61 respectively;

a T-arm can be formed by base pairing between nucleotides 68-69 and 71-72 with nucleotides 83-80 respectively;

or a combination thereof.

f. Other tRNA Consensus Sequences

8/4 tRNAHis (Alpha-Proteobacteria) (FIG. 6E)

(SEQ ID NO: 44)
NCYRRNNANGNUGUAANGGUNGCAYNYNNNRYU*GUG*ANYNNNNNGGA

YNRGGUUCRRNYCCYNUNNYYRGNACCA

Typically, an Acceptor Stem can be formed by base pairing between nucleotides 1-8 with nucleotides 71-64 respectively;

a D-arm can be formed by base pairing between nucleotides 11-14 with nucleotides 25-22 respectively;

an anti-codon arm can be formed by base pairing between nucleotides 27-31 with nucleotides 43-39 respectively;

a T-arm can be formed by base pairing between nucleotides 49-52 with nucleotides 63-60 respectively;

or a combination thereof.

8/4 tRNA$^{Sec}$ (bacteria) (FIG. 6F)

(SEQ ID NO: 45)
GGRANNNNNNNNNGNYCYGGUGRNCNNNNCGGNCU*WCA*LANCCGNNUNNN

NNNNNNNNNNNNNNNNNNNNNNNNNNGGYGGUUCGAYUCCYCCNNNUYCCGCCA

Typically, an Acceptor Stem can be formed by base pairing between nucleotides 1-8 with nucleotides 87-94 respectively;

a D-arm can be formed by base pairing between nucleotides 11-16 with nucleotides 26-21 respectively;

an anti-codon arm can be formed by base pairing between nucleotides 27-32 with nucleotides 45-40 respectively;

a V-arm can be formed by base pairing between nucleotides 47-56 with nucleotides 70-61 respectively;

a T-arm can be formed by base pairing between nucleotides 71-72 and 74-75 with nucleotides 86-83 respectively;

or a combination thereof.

g. Variants and Modifications

Any of the disclosed tRNA can be further modified. Modifications can include single and combined exchanges (i.e., substitutions), one or more insertions, one or more deletions, and combinations thereof, of nucleotides in various regions of the tRNA. In some embodiments the modifications alter the variant relative to tRNA$^{UTu}$ to (i) more closely resemble the features of tRNA$^{Sec}$ that contribute to binding of SelA than tRNA$^{UTu}$. The mechanism by which SelA discriminates between tRNA$^{Ser}$ and tRNA$^{Sec}$ is described in Itoh, et al., Science, 340:75-78 (2013). In some embodiments, the important tRNA$^{UTu}$ features that (ii) provide thermodynamic binding specificity for EF-Tu [Schrader, et al., *J. Mol. Biol.*, 386:1255-1264 (2009)], (iii) contribute to reducing the incompatibility between tRNA$^{Sec}$ and EF-Tu [Rudinger, et al., *EMBO J.*, 15:650-657 (1996)], or the combination thereof are left intact. In some embodiments, the variant exhibits (i), (ii), (iii), or a combination thereof, most preferably (i), (ii), and (iii).

In some embodiments, the tRNA exhibits reduced misincorporation Ser in vivo, in vitro, or a combination thereof relative another tRNA$^{Sec}$. In some embodiments, the tRNA exhibits better interaction with SelA (e.g., tighter binding), while retaining robust Ser-tRNA formation by SerRS.

Nucleotide positions within a tRNA sequence can also be identified according to the primary sequence or based the nucleotide numbering established in Sprinzl, et al., *Nucleic Acids Research*, 26(1):148-153 (1998). As illustrated in text, figures, and sequences provide herein, this numbering system coordinates the relative locations of nucleotides and base pairs between two or more tRNA that may differ in the total number of nucleotides due to insertions and/or deletions. Thus nucleotides in any of the disclosed tRNA can be characterized based the nucleotide numbering from the terminal 5' nucleotide, or the nucleotide(s) at the base position(s) identified according to the Sprinzl numbering system.

tRNA elements that can be important for selenocysteine insertion, are illustrated with reference tRNA$^{UTu}$ in FIG. 3B. In this figure, the acceptor stem of the tRNA is highlighted as originating from tRNA$^{Sec}$, and is important for recognition by the enzyme SelA. The circled region in FIG. 3 originates from tRNA$^{Ser}$, and is important both for recognition by the enzyme EF-Tu and for its lack of recognition by the enzyme SelB. Thus in some embodiments, the tRNA (e.g., the aminoacylated tRNA) is recognized by SelA and EF-Tu, and optionally is not recognized by selB.

Some of the tRNA disclosed herein feature an anticodon that recognize a codon encoding an amino acid, some feature an anticodon that recognizes a stop codon, and some feature an "NNN" anticodon. The anticodon in any of the disclosed sequences can be substituted with any other anticodon. Anticodons are typically the reverse complement of the codon. Codons are illustrated in FIG. 18A. Thus, each of the disclosed tRNAs are expressly disclosed having every anticodon, preferably an anticodon that recognizes a stop codon. In some embodiments, the anticodon-codon interaction includes basepairing of one or more unnatural nucleobases. Thus, in some embodiments, the anticodon includes one or more unnatural bases.

A non-naturally occurring tRNA$^{Sec}$ tRNA can have a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more identical to any one or more of SEQ ID NOS:1-63. Preferably the non-naturally occurring tRNA$^{Sec}$ is characterized by one or more of the following elements: (1) the non-naturally occurring tRNA$^{Sec}$ can be recognized by SerRS and by EF-Tu, or variants thereof; (2) when aminoacylated with serine the non-naturally occurring Ser-tRNA$^{Sec}$ can be converted to non-naturally occurring Sec-tRNA$^{Sec}$ by SelA or variant thereof; (3) when aminoacylated with serine the non-naturally occurring Ser-tRNA$^{Sec}$ can be phosphorylated by PSTK or variant thereof; (4) when aminoacylated with phosphorylated serine the non-naturally occurring Sep-tRNA$^{Sec}$ can serve as a substrate for SepSecS or variant thereof.

6. Secondary Structure

The tRNAs disclosed herein typically include an acceptor arm, a D-arm, an anticodon arm, a variable arm, and a TΨC-arm, as described in more detail below.

a. Acceptor Arm

The non-naturally occurring tRNA$^{Sec}$ disclosed herein includes an acceptor arm. The acceptor arm is the end of a tRNA molecule to which an amino acid becomes bound. It contains both the 5' and 3' ends of the tRNA. The 3'-terminal sequence of cytidine-cytidine-adenosine (CCA) overhangs the end, and the terminal A is the site of 'acceptance' of the amino acid.

The acceptor stem refers to the 5' and 3' sequences to the acceptor arm that form duplex RNA. The acceptor stem can be separate from the CCA overhang by one or more nucleotides, for example one or more guanine. In some embodiments, one or more nucleotides that separate the acceptor stem and the overhang are referred to as the discriminator base(s). For some tRNAs, the discriminator base preceding the CCA sequence at the 3' end is important for aminoacylation. The discriminator base can influence the stability of the base pair of the acceptor arm onto which it is stacked which can affect the energetic cost of opening the base pair and modulate the structure of the tRNA near the site of aminoacylation. For some aminoacyl-tRNA synthetases and other proteins that interact with tRNA, these factors could be important for specific recognition and/or formation of the transition state during catalysis (Lee et al., PNAS, 90(15): 7149-52 (1993)). In some embodiments, the acceptor stem and the CCA sequence are separated by a single guanine discriminator base.

The acceptor stem of the non-naturally occurring tRNA$^{Sec}$ disclosed herein typically include 4 to 12, preferably 5 to 11, more preferably 6 to 10, most preferably 7 to 9 base pairs of duplex RNA. In some embodiments, the acceptor stem is 7, 8, or 9 base pairs of duplex RNA.

The acceptor stem can be high in G-C content. For example, in some embodiments, the G-C content is 50%, 60%, 70%, 75%, 80%, 85%, 90%, 95%, or 100% of the nucleotides of the acceptor stem. In some embodiments the G-C is lower, for example, 10%, 20%, 30%, or 40%. In some embodiments, the G-C content is between about 30% and 40%.

The 5' and 3' sequences of the tRNA that form the acceptor stem typically form a RNA duplex by Waston-Crick base pairing. The 5' and 3' sequences of the tRNA that form the acceptor stem are typically substantially complementary. Preferably, the 5' and 3' sequences of the tRNA that form the acceptor stem bind to or hybridize to each other under conditions of high stringency and specificity. In some embodiments, 5' sequence of the tRNA that forms the acceptor stem is 50%, 60%, 70%, 80%, 85%, 90%, 95%, or more complementary to the 3' sequence of the tRNA that forms the acceptor stem. In some embodiments the 5' and 3' sequences of the tRNA that form the acceptor stem are 100% complementary.

b. D-Arm

The non-naturally occurring tRNA$^{Sec}$ disclosed herein include a D-arm. The D-arm is typically composed of a D stem of duplex RNA and a D loop of non-duplex RNA. The D stem refers to the two segments of the tRNA primary sequence in the D-arm that form duplex RNA. The D stem of the non-naturally occurring tRNA$^{Sec}$ typically include 2 to 8, preferably 3 to 7, more preferably 4 to 6, base pairs of duplex RNA. In some embodiments, the D stem is 4, 5, or 6 base pairs of duplex RNA.

The D stem can be high in G-C content. For example, in some embodiments, the G-C content is 50%, 60%, 70%, 75%, 80%, 85%, 90%, 95%, or 100% of the nucleotides of the D stem.

The two segments of the tRNA that form the D stem typically form a RNA duplex by Waston-Crick base pairing. The two segments of the tRNA that form the D stem are typically substantially complementary. Preferably, the 5' and 3' sequences of the tRNA that form the acceptor stem bind to or hybridize to each other under conditions of high stringency and specificity. In some embodiments, 5' segment of the tRNA that forms the D stem is between 25% and 50% complementary to the 3' segment of the tRNA that forms the D stem. In some embodiments the 5' segment of the tRNA that forms the D stem is 50%, 60%, 70%, 80%, 85%, 90%, 95%, or more complementary to the 3' sequence of the tRNA that forms the D stem. In some embodiments the 5' and 3' sequences of the tRNA that form the D stem are 100% complementary.

The D loop refers to the part of the D-arm that does not form duplex RNA. The D loop's main function is that of recognition. The D loop can contain the base dihydrouracil. It is widely believed that it will act as a recognition site for aminoacyl-tRNA synthetase, which is an enzyme involved in the aminoacylation of the tRNA molecule. The D-loop can have between 3 and 15 nucleotides inclusive, preferably between 4 and 12 nucleotides inclusive. In some embodiments the D-loop has 4, 5, 6, 7, 8, 9, 10, 11, or 12 nucleotides.

c. Anticodon Arm

The non-naturally occurring tRNA$^{Sec}$ disclosed herein include an anticodon arm. The anticodon arm is typically composed of an anticodon stem of duplex RNA and an anticodon loop of non-duplex RNA. The anticodon stem refers to the two segments of the tRNA primary sequence in the anticodon arm that form duplex RNA. The anticodon stem of the non-naturally occurring tRNA$^{Sec}$ disclosed herein typically include 2 to 8, preferably 3 to 7, more preferably 4 to 6, base pairs of duplex RNA. In some embodiments, the anticodon stem is 4, 5, or 6 base pairs of duplex RNA.

The anticodon stem can be high in G-C content. For example, in some embodiments, the G-C content is 50%, 60%, 70%, 75%, 80%, 85%, 90%, 95%, or 100% of the nucleotides of the anticodon stem.

The two segments of the tRNA that form the anticodon stem typically form a RNA duplex by Waston-Crick base pairing. The two segments of the tRNA that form the anticodon stem are typically substantially complementary. Preferably, the 5' and 3' sequences of the tRNA that form the anticodon stem bind to or hybridize to each other under conditions of high stringency and specificity. In some embodiments the 5' segment of the tRNA that forms the anticodon stem is 50%, 60%, 70%, 80%, 85%, 90%, 95%, or more complementary to the 3' sequence of the tRNA that forms the anticodon stem. In some embodiments the 5' and 3' sequences of the tRNA that form the anticodon stem are 100% complementary.

The anticodon loop refers to the part of the anticodon-arm that does not form duplex RNA. The anticodon loop's main function is to present the anticodon sequence which can hybridize to the target codon in the mRNA sequence of interest. The anticodon sequence can be any three nucleotide sequence that binds by complementary base pairing to the target codon sequence in the mRNA of interest. In some embodiments, the anticodon pairs specifically with only one codon. Some anticodon sequences can pair with more than one codon (i.e., wobble base pairing). In some embodiments, the first nucleotide of the anticodon is inosine or pseudouridine, which can hydrogen bond to more than one base in the corresponding codon position.

In some embodiments, the anticodon hybridizes to a "stop" codon such as UAA, UAG, or UGA, preferably UAG (amber) or UGA (opal). Accordingly, in some embodiments the sequence of the anticodon is UUA, CUA, UCA, preferably CUA (amber) or UCA (opal) (in the 5' to 3' direction). The anticodon loop can have between 5 and 11 nucleotides inclusive, preferably about 7 nucleotides. In some embodiments the anticodon-loop has 5, 7, or 9 nucleotides. Typically, the three nucleotide anticodon sequence is flanked by an equal number of nucleotides both 5' and 3' of the anticodon sequence within the anticodon loop.

Although in some embodiments, the anticodon is one that recognizes a stop codon, all other possible anticodons (e.g., those that recognize an amino acid codon) are also specifically disclosed for all tRNA disclosed herein. Thus, for example, in some embodiments, a non-naturally occurring tRNA includes the sequence of any one of SEQ ID NO:1-63, or a variant there with at least 80% sequence identity, wherein the anti-codon is substituted with an alternative anti-codon. In addition of the standard A, C, G, U bases the anticodon and/or the corresponding codon of the mRNA of interest may also contain unnatural nucleotide bases. Suitable basepairing to create additional codon-anticodon interaction is described in, for example, Bain, et al., *Nature*, 356:537-539 (1992), and Malyshev, et al., *Nature*, 509:385-388 (2014), and supplemental information associated therewith, and include, but are not limited to d5SICS and dNaM (d5SICS-dNaM).

d. Variable Arm

The non-naturally occurring tRNA$^{Sec}$ disclosed herein typically include a variable arm. The variable arm is typically composed of a variable stem of duplex RNA and a variable loop of non-duplex RNA. The variable stem refers to the two segments of the tRNA primary sequence in the variable arm that form duplex RNA. The variable stem of the non-naturally occurring tRNA$^{Sec}$ typically includes 2 to 8, preferably 3 to 7, more preferably 4 to 6, base pairs of duplex RNA. In some embodiments, the variable stem is 4, 5, or 6 base pairs of duplex RNA. In some embodiments the variable stem has 9, 10, 11, or more base pairs of duplex RNA.

The variable stem can be high in G-C content. For example, in some embodiments, the G-C content is 50%, 60%, 70%, 75%, 80%, 85%, 90%, 95%, or 100% of the nucleotides of the variable stem.

The two segments of the tRNA that form the variable stem typically form a RNA duplex by Waston-Crick base pairing. The two segments of the tRNA that form the anticodon stem are typically substantially complementary. Preferably, the 5' and 3' sequences of the tRNA that form the variable stem bind to or hybridize to each other under conditions of high stringency and specificity. In some embodiments the 5' segment of the tRNA that forms the variable stem is 50%, 60%, 70%, 80%, 85%, 90%, 95%, or more complementary to the 3' sequence of the tRNA that forms the variable stem. In some embodiments the 5' and 3' sequences of the tRNA that form the variable stem are 100% complementary.

The variable loop refers to the part of the variable-arm that does not form duplex RNA. The variable loop can have between 3 and 7 nucleotides inclusive, preferably between 4 and 6 nucleotides inclusive. In some embodiments the variable loop has 3, 4, 5, 6, or 7 nucleotides.

e. TΨC-Arm

The non-naturally occurring tRNA$^{Sec}$ disclosed herein includes a TΨC-arm (also referred to herein as a T-arm). The T-arm is the region on the tRNA molecule that acts as a recognition site for the ribosome, and allows a tRNA-ribosome complex to form during the process of protein biosynthesis. The T-arm is typically composed of a T stem of duplex RNA and a T loop of non-duplex RNA. The T stem refers to the two segments of the tRNA primary sequence in the T-arm that form duplex RNA. The T stem of the non-naturally occurring tRNA$^{Sec}$ typically includes 2 to 8, preferably 3 to 7, more preferably 4 to 6, base pairs of duplex RNA. In some embodiments, the T stem is 3, 4, or 5 base pairs of duplex RNA.

The T stem can be high in G-C content. For example, in some embodiments, the G-C content is 50%, 60%, 70%, 75%, 80%, 85%, 90%, 95%, or 100% of the nucleotides of the T stem.

The two segments of the tRNA that form the T stem typically form a RNA duplex by Waston-Crick base pairing. The two segments of the tRNA that form the T stem are typically substantially complementary. Preferably, the 5' and 3' sequences of the tRNA that form the acceptor stem bind to or hybridize to each other under conditions of high stringency and specificity. In some embodiments, 5' segment of the tRNA that forms the T stem is equal to or greater than 50% complementary to the 3' segment of the tRNA that forms the T stem. In some embodiments the 5' segment of the tRNA that forms the T stem is 50%, 60%, 70%, 80%, 85%, 90%, 95%, or more complementary to the 3' sequence of the tRNA that forms the T stem. In some embodiments the 5' and 3' sequences of the tRNA that form the T stem are 100% complementary.

The T loop refers to the part of the T-arm that does not form duplex RNA. In some embodiments the T-loop includes thymidine, pseudouridine, residues, or combinations thereof. The T-loop can have between 3 and 15 nucleotides inclusive, preferably between 4 and 12 nucleotides inclusive. In some embodiments the D-loop has 4, 5, 6, 7, 8, 9, 10, 11, or 12 nucleotides.

f. Linker Nucleotides

The five arms of the tRNA can be linked directly, or can be separated by one or more linker or spacer nucleotides to ensure the tRNA assumes the proper secondary structure. For example, the acceptor arm and the D-arm can separated by 0, 1, 2, 3, or more nucleotides; the D-arm and the anticodon arm can be separated by 0, 1, 2, 3, or more nucleotides; the anticodon arm and the variable arm can be separated by 0, 1, 2, 3, or more nucleotides; the variable arm and the T-arm can be separated by 0, 1, 2, 3, or more nucleotides; and the T-arm and the acceptor arm can be separated by 0, 1, 2, 3, or more nucleotides.

B. mRNA and Polypeptides of Interest

As discussed in more detail below, the tRNA$^{Sec}$ disclosed herein can be used in combination with an mRNA to manufacture selenocysteine containing polypeptides and proteins. The mRNA does not require, and preferably does not include, a SECIS element. The mRNA, which encodes a polypeptide of interest, includes one or more codons that is recognized by the anticodon of the Sec-tRNA$^{Sec}$, referred to herein as an "tRNA$^{Sec}$ recognition codon," such that tRNA catalyzes the attachment of a selenocysteine amino acid to the growing polypeptide chain during translation.

For example, if the tRNA$^{Sec}$ recognition codon is a stop codon, such as UGA, the mRNA will contain at least one UGA codon where a selenocysteine will be added to the growing polypeptide chain during translation. The tRNA$^{Sec}$ recognition codon can be added to or inserted into any mRNA to add a codon encoding selenocysteine at any desired location in the amino acid sequence. The tRNA$^{Sec}$ recognition codon can be substituted for any existing codon in the mRNA sequence so that any one or more amino acids from a reference polypeptide sequence is substituted with selenocysteine during translation. For example, as discussed in more detail below, in some embodiments, one or more codons encoding cysteine in a reference sequence are substituted with a tRNA$^{Sec}$ recognition sequence so that the one or more cysteines are replaced with selenocysteine during translation.

Various types of mutagenesis can be used to modify the sequence of a nucleic acid encoding the mRNA of interest to generate the tRNA$^{Sec}$ recognition codon. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, and mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis and double-strand break repair.

In some embodiments, the coding sequence, excluding the tRNA$^{Sec}$ recognition site as discussed above, is further altered for optimal expression (also referred to herein as "codon optimized") in an expression system of interest. Methods for modifying coding sequences to achieve optimal expression are known in the art.

C. Isolated Nucleic Acid Molecules tRNA$^{Sec}$ and nucleic acids encoding tRNA$^{Sec}$ are disclosed. Also disclosed are mRNAs, cDNAs and other nucleic acids encoding proteins of interest that are engineered such that a tRNA$^{Sec}$, such as the tRNA$^{Sec}$ disclosed herein, "reads" at least one codon of the mRNA during translation of the protein encoded by the mRNA. As used herein, "isolated nucleic acid" refers to a nucleic acid that is separated from other nucleic acid molecules that are present in a genome, including nucleic acids that normally flank one or both sides of the nucleic acid in the genome. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule or an RNA molecule, provided one of the nucleic acid sequences normally found immediately flanking that DNA molecule in a naturally-occurring genome is removed or absent. Thus, an isolated nucleic acid includes, without limitation, a DNA molecule or RNA molecule that exists as a separate molecule independent of other sequences (e.g., a chemically synthesized nucleic acid, or a cDNA, or RNA, or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule or RNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding the tRNA$^{Sec}$ and mRNA disclosed herein may be optimized for expression in the expression host of choice. In the case of nucleic acids encoding expressed polypeptides, codons may be substituted with alternative codons encoding the same amino acid to account for differences in codon usage between the organism from which the nucleic acid sequence is derived and the expression host. In this manner, the nucleic acids may be synthesized using expression host-preferred codons.

Nucleic acids can be in sense or antisense orientation, or can be complementary to a reference sequence, for example, a sequence encoding the disclosed tRNA$^{Sec}$ and mRNA. Nucleic acids can be DNA, RNA, nucleic acid analogs, or combinations thereof. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chem. 4:5-23. In addition, the deoxyphosphate backbone can be replaced with, for example, a phosphorothioate or phosphorodithioate backbone, a phosphoroamidite, or an alkyl phosphotriester backbone.

D. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a non-naturally occurring tRNA$^{Sec}$. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995.

When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992. Examples of nucleic acid amino acid positions relative to a reference sequence that can be modified include those described herein.

E. Vectors and Host Cells

Vectors encoding tRNA$^{Sec}$ and polypeptides manufactured using the tRNA$^{Sec}$ as well as other components of the translation system including but not limited to SerRS, EF-Tu, SelA, SelD, PSTK, and SepSecS are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. Operably linked means the disclosed sequences are incorporated into a genetic construct so that expression control sequences effectively control expression of a sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II).

A "promoter" as used herein is a DNA regulatory region capable of initiating transcription of a gene of interest. Some promoters are "constitutive," and direct transcription in the absence of regulatory influences. Some promoters are "tissue specific," and initiate transcription exclusively or selectively in one or a few tissue types. Some promoters are "inducible," and achieve gene transcription under the influence of an inducer. Induction can occur, e.g., as the result of a physiologic response, a response to outside signals, or as the result of artificial manipulation. Some promoters respond to the presence of tetracycline; "rtTA" is a reverse tetracycline controlled transactivator. Such promoters are well known to those of skill in the art.

To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Likewise, although tRNA$^{Sec}$ sequences do not encode a protein, control sequence can be operably linked to a sequence encoding a tRNA$^{Sec}$, to control expression of the tRNA$^{Sec}$ in a host cell. Methods of recombinant expression of tRNA from vectors is known in the art, see for example, Ponchon and Dardel, *Nature Methods*, 4(7):571-6 (2007); Masson and Miller, J. H., Gene, 47:179-183 (1986); Meinnel, et al., *Nucleic Acids Res.*, 16:8095-6 (1988); Tisné, et al., *RNA*, 6:1403-1412 (2000).

F. Host Cells

Host cell including the nucleic acids disclosed herein are also provided. Prokaryotes useful as host cells include, but are not limited to, gram negative or gram positive organisms such as *E. coli* or Bacilli. In a prokaryotic host cell, a polypeptide may include an N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, T7 expression vectors from Invitrogen, pET vectors from Novagen and pALTER® vectors and PinPoint® vectors from Promega Corporation.

In a prokaryotic host cell, a polypeptide may include an N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include lactamase and the lactose promoter system.

In some embodiments, the host cells are *E. coli*. The *E. coli* strain can be a selA, selB, selC, deletion strain, or combinations thereof. For example, the *E. coli* can be a selA, selB, and selC deletion strain, or a selB and selC deletion strain. Examples of suitable *E. coli* strains include, but are not limited to, MH5 and ME6.

Yeasts useful as host cells include, but are not limited to, those from the genus *Saccharomyces, Pichia, K. Actinomycetes* and *Kluyveromyces*. Yeast vectors will often contain an origin of replication sequence, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991), in Li, et al., *Lett Appl Microbiol.* 40(5):347-52 (2005), Jansen, et al., *Gene* 344:43-51 (2005) and Daly and Hearn, *J. Mol. Recognit.* 18(2):119-38 (2005). Other suitable promoters and vectors for yeast and yeast transformation protocols are well known in the art.

In some embodiments, the host cells are eukaryotic cells. For example, mammalian and insect host cell culture systems well known in the art can also be employed to express non-naturally occurring tRNA$^{Sec}$ and mRNA for producing proteins or polypeptides containing selenocysteine. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

Mammalian or insect host cell culture systems well known in the art can also be employed to express ribosomes (or a ribosomal rRNA thereof), tRNAs, synthetases or a combination thereof for producing proteins or polypeptides containing one or more dipeptides, non-standard-, non-natural-, or non-α-amino acids. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

The host organism can be a genomically recoded organism "GRO." Typically, the GRO is a bacterial strain, for example, an *E. coli* bacterial strain, wherein a codon has been replaced by a synonymous codon. Because there are 64 possible 3-base codons, but only 20 canonical amino acids (plus stop codons), some amino acids are coded for by 2, 3, 4, or 6 different codons (referred to herein as "synonymous codons"). In a GRO, most or all of the iterations of a particular codon are replaced with a synonymous codon. The precursor strain of the GRO is recoded such that at least one codon is completely absent from the genome. Removal of a codon from the precursor GRO allows reintroduction of the deleted codon in, for example, a heterologous mRNA of interest. As discussed in more detail below, the reintroduced codon is typically dedicated to a non-standard amino acid, which in the presence of the appropriate translation machinery, can be incorporated in the nascent peptide chain during translation of the mRNA.

Different organisms often show particular preferences for one of the several codons that encode the same amino acid, and some codons are considered rare or infrequent. Preferably, the replaced codon is one that is rare or infrequent in the genome. The replaced codon can be one that codes for an amino acid (i.e., a sense codon) or a translation termination codon (i.e., a stop codon). GRO that are suitable for use as host or parental strains for the disclosed systems and methods are known in the art, or can be constructed using known methods. See, for example, Isaacs, et al., *Science*, 333, 348-53 (2011), Lajoie, et al., *Science* 342, 357-60 (2013), Lajoie, et al., *Science*, 342, 361-363 (2013).

Preferably, the replaced codon is one that codes for a rare stop codon. In a particular embodiment, the GRO is one in which all instances of the UAG (TAG) codon have been removed and replaced by another stop codon (e.g., TAA, TGA), and preferably wherein release factor 1 (RF1; terminates translation at UAG and UAA) has also been deleted, eliminating translational termination at UAG codons (Lajoie, et al., *Science* 342, 357-60 (2013)). In a particular embodiment, the host or precursor GRO is C321.Δ A [321 UAG→UAA conversions and deletion of prfA (encodes RF1)] (genome sequence at GenBank accession CP006698). This GRO allows the reintroduction of UAG codons in a heterologous mRNA, along with orthogonal translation machinery (i.e., aminoacyl-tRNA synthetases (aaRSs) and tRNAs as discussed in more detail below), to permit efficient and site specific incorporation of non-standard amino acids into protein encoded by the recoded gene of interest. That is, UAG has been transformed from a nonsense codon (terminates translation) to a sense codon (incorporates amino acid of choice), provided the appropriate translation machinery is present. UAG is a preferred codon for recoding because it is the rarest codon in *Escherichia coli* MG1655 (321 known instances) and a rich collection of translation machinery capable of incorporating non-standard amino acids has been developed for UAG (Liu and Schultz, *Annu. Rev. Biochem.*, 79:413-44 (2010)).

Stop codons include TAG (UAG), TAA (UAA), and TGA (UGA). Although recoding to UAG (TAG) is discussed in more detail above, it will be appreciated that either of the other stop codons (or any sense codon) can be recoded using the same strategy. Accordingly, in some embodiments, a sense codon is reassigned, e.g., AGG or AGA to CGG, CGA, CGC, or CGG (arginine), e.g., as the principles can be extended to any set of synonymous or even non-synonymous codons, that are coding or non-coding. Similarly, the cognate translation machinery can be removed/mutated/deleted to remove natural codon function (UAG-RF1, UGA-RF2). The orthogonal translation system, particularly the antisense codon of the tRNA, can be designed to match the reassigned codon.

GRO can have two, three, or more codons replaced with a synonymous or non-synonymous codon. Such GRO allow for reintroduction of the two, three, or more deleted codons in one or more recoded genes of interest, each dedicated to a different non-standard amino acid. Such GRO can be used in combination with the appropriate orthogonal translation machinery to produce polypeptides having two, three, or more different non-standard amino acids.

Another host cell system for the use of codons containing unnatural bases is *E. coli* expressing *Phaeodactylum tricornutum* nucleotide triphosphate transporters as reported (Malyshev, et al., *Nature*, 509:385-388 (2014)).

III. Methods for Manufacturing Proteins Containing Selenocysteine

A. Expression of Selenocysteine Containing Polypeptides

Generally, the canonical amino acids are charged onto their respective tRNA by their cognate aminoacyl-tRNA synthetase. The aminoacyl-tRNA is then delivered by EF-Tu to the ribosome (FIG. 1A). In contrast, the endogenous Sec pathway requires several biosynthetic steps. First, tRNA$^{Sec}$ is misacylated to Ser-tRNA$^{Sec}$ by SerRS. While in bacteria Ser-tRNA$^{Sec}$ is directly converted by SelA to Sec-tRNA$^{Sec}$, archaea and eukaryotes employ an additional phosphorylation step by PSTK to form Sep-tRNA$^{Sec}$, which is then converted by SepSecS to the final product Sec-tRNA$^{Sec}$ FIG. 1B. Sec-tRNA$^{Sec}$ is bound by elongation factor SelB and delivered to the ribosome. However, reassignment of the opal codon UGA to a Sec codon is only achieved if SelB also binds to the mRNA SECIS hairpin structure.

The compositions disclosed herein can be used to prepare polypeptides including one or more selenocysteine residues from mRNA that does not contain an SECIS element. The tRNA$^{Sec}$ disclosed herein is recognized by SerRS and misacylated to form the intermediate Ser-tRNA$^{Sec}$. Next the Ser-tRNA$^{Sec}$ is converted to Sec-tRNA$^{Sec}$ by SelA in prokaryotic system or hybrid systems, or PSTK and SepSecS in archaeal, eukaryotic, or hybrid systems. Finally, the Sec-tRNA$^{Sec}$ is delivered to the ribosome by EF-Tu, where the anticodon of the Sec-tRNA$^{Sec}$ recognizes the codon engineered to encode a Sec amino acid, and transfers the Sec onto the growing polypeptide chain. Accordingly, the non-naturally occurring tRNA$^{Sec}$ disclosed herein are typically recognized by SerRS, or a variant thereof, and when aminoacylated with serine the Ser-tRNA can (1) be a substrate for SelA or a variant thereof; or (2) be a substrate for PSTK and when aminoacylated with phosphorylated serine the Sep-tRNA can serve as a substrate for SepSecS or a variant thereof, and (3) when aminoacylated, the non-naturally occurring Sec-tRNA$^{Sec}$ is recognized by EF-Tu.

As discussed in more detail below, recombinant proteins including selenocysteine can be prepared using in vitro transcription/translation or in vivo expression systems. The system can be of prokaryotic, eukaryotic, or archaeal origin or combinations thereof. For example, the system can be hybrid system including selenocysteine biogenesis and translation factors from prokaryotic, eukaryotic, archaeal origin, or combinations thereof.

In some embodiments, the system is an in vivo prokaryotic expression including an *E. coli* strain in which the endogenous genes encoding selB, selC, or selA, selB, selC are deleted or mutated to reduce or eliminate expression of endogenous SelA, SelB, SelC or combinations thereof. The selB, selC, or selA, selB, selC mutant strains can be engineered to express a non-naturally occurring tRNA$^{Sec}$, as well as a PSTK and a SepSecS. In some embodiments recombinant SelA is expressed. The PSTK or SepSecS can of eukaryotic or archaeal origin, or a variant thereof. For example, in one embodiment, the PSTK is a *M. maripaludis* PSTK and the SepSecS is a *M. jannaschii* SepSecS.

In some embodiments, SelA, PSTK and SepSecS are all expressed in the expression system.

SelD refers to selenide, water dikinase, which synthesizes selenophosphate utilized by SelA from selenide and ATP.

An exemplary protein sequence for *E. coli* SelD is:

(SEQ ID NO: 86)
MSENSIRLTQYSHGAGCGCKISPKVLETILHSEQAKFVDPNLLVGNETRD

DAAVYDLGNGTSVISTTDFFMPIVDNPFDFGRIAATNAISDIFAMGGKPI

MAIAILGWPINKLSPEIAREVTEGGRYACRQAGIALAGGHSIDAPEPIFG

LAVTGIVPTERVKKNSTAQAGCKLFLTKPLGIGVLTTAEKKSLLKPEHQG

LATEVMCRMNIAGASFANIEGVKAMTDVTGFGLLGHLSEMCQGAGVQARV

DYEAIPKLPGVEEYIKLGAVPGGTERNFASYGHLMGEMPREVRDLLCDPQ

TSGGLLLAVMPEAENEVKATAAEFGIELTAIGELVPARGGRAMVEIR

Other organisms also encode a SelD. Thus, in other embodiments, the SelD is not from *E. coli*. Thus, in these embodiments, an alternative SelD is utilized for recombinant selenoprotein preparation. Exemplary alternative SelD proteins include, but are not limited to, SelD from *Aeromonas salmonicida*.

An amino acid sequence for *Aeromonas salmonicida* SelD is (SEQ ID NO: 87)
MSSIRLTQYSHGAGCGCKISPKVLDTILKSQIPGFDDPTLVVGNSSKDDA

AVVDIGNGQGIVSTTDFFMPIVDDPFTFGRIAATNAISDIYAMGGKPIVA

IAILGWPINTLAPEVAQQVIDGGRQVCHEAGISLAGGHSIDAPEPIFGLA

VTGIVPLNAIKQNDTAQAGDILYLTKPLGIGILTTAQKKGKLKPEHEQLA

PNAMCTLNKIGQRFAELPGVHAMTDVTGFGLAGHLLEMCEGSGVCATLDF

KALPLLDEVDYYLSEGCVPGGTLRNFDSYGAKLGAMDERTRNIMCDPQTS

GGLLVAVGKESEAELLAIATQAGLTLSPIGQLKAYTGNQFIEVIQ

A nucleic acid sequence encoding *Aeromonas salmonicida* SelD (cloned from the *Aeromonas salmonicida* genome. The AUG start codon was changed to GUG)

(SEQ ID NO: 88)

```
GTGTCTTCCATTCGTCTGACCCAATACAGCCACGGGGCTGGCTGCGGCTG

CAAAATTTCTCCCAAGGTGCTCGACACCATTCTCAAGAGCCAGATCCCGG

GCTTTGACGACCCGACCCTGGTGGTTGGCAACAGCAGCAAGGATGACGCG

GCCGTGGTCGATATCGGCAACGGTCAGGGCATTGTTTCCACCACCGACTT

CTTCATGCCCATCGTCGATGATCCCTTTACCTTTGGCCGCATCGCGGCCA

CCAACGCCATCAGCGACATCTACGCCATGGGCGGCAAGCCCATCGTTGCC

ATTGCCATCCTTGGCTGGCCCATCAACACCCTAGCCCCGGAAGTGGCCCA

GCAGGTGATAGATGGCGGCCGCCAGGTGTGCCATGAAGCGGGCATATCCT

TGGCTGGCGGCCACAGTATCGATGCCCCCGAGCCCATCTTCGGTCTTGCT

GTGACCGGTATAGTGCCGCTCAATGCCATCAAGCAGAACGACACGGCCCA

GGCGGGTGACATCCTCTACCTGACCAAGCCCCTCGGTATCGGCATCCTCA

CCACGGCCCAGAAGAAGGGCAAATTGAAGCCAGAGCATGAGCAGCTGGCC

CCCAACGCCATGTGCACCCTCAACAAGATTGGCCAGCGCTTTGCCGAACT

GCCCGGCGTGCACGCCATGACGGATGTGACCGGGTTTGGCCTGGCGGGAC

ACCTGCTTGAGATGTGCGAAGGCTCAGGGGTGTGTGCCACCCTCGATTTC

AAGGCGCTGCCACTGCTCGACGAAGTAGATTACTACCTGTCCGAGGGCTG

CGTACCGGGCGGTACCCTGCGCAACTTCGATTCCTATGGCGCCAAGCTCG

GTGCCATGGATGAACGCACCCGCAACATCATGTGCGATCCGCAGACCAGC

GGCGGCTTGCTGGTTGCCGTCGGTAAAGAAAGTGAAGCCGAGCTCCTTGC

TATCGCGACACAAGCGGGGCTGACCCTCTCCCCCATAGGCCAGCTGAAAG

CCTATACCGGAAACCAGTTTATCGAGGTTATCCAATGA
```

In some embodiments selenocysteine biogenesis and translation factors are mutated to improve their specificity or activity for $tRNA^{Sec}$. In the recombinant $tRNA^{Sec}$ biosynthetic pathway disclosed herein $tRNA^{Sec}$ is first misacylated to Ser-$tRNA^{Sec}$ by SerRS, and subsequently converted to Sec-$tRNA^{Sec}$ by SelA, or PSTK and SepSecS, or combinations thereof. Accordingly, if the SelA, or PSTK and SepSecS, enzymes are not 100% efficient at converting Ser-$tRNA^{Sec}$ to Sec-$tRNA^{Sec}$, the system may incorporate Sec or Ser at the desired position. Additionally, in some embodiments, recognition of the non-naturally occurring Sec-$tRNA^{Sec}$ by EF-Tu, is less efficient than EF-Tu recognition of other naturally occurring aminoacyl-tRNAs. Mutating the EF-Tu, SerRS, SelA, PSTK, SepSecS, or combinations thereof can improve the efficiency or recognition of the enzyme for the non-naturally occurring $tRNA^{Sec}$, the non-naturally occurring Sec-$tRNA^{Sec}$, or various intermediates thereof. In some embodiment, the EF-Tu, SerRS, SelA, PSTK, SepSecS, SelD or combinations thereof are variants of a naturally occurring protein.

In some embodiments, the variant mRNA can include or consist of replacing of the AUG start codon with GUG or UUG and optionally a UAAUU inserted in front of it. Replacing AUG with GUG or UUG can reduce the expression of the encoded protein. The corresponding DNA sequence encoding the variants are also expressly provided.

It is understood that if the $tRNA^{Sec}$ recognition codon of the mRNA of interest is one of the three mRNA stop codons (UAG, UAA, or UGA) translation of some of the mRNA of interest will terminate at each of the $tRNA^{Sec}$ recognition codons, resulting in a heterogeneous mixture of full-length and truncated proteins. The experimental results presented in the examples below show that allo-tRNA such as all-$tRNA^{UTu}$ insert a larger number of Sec amino acids into a nascent protein chain than other $tRNA^{Sec}$ including, for example, $tRNA^{SecUx}$. Thus in some embodiments, an allo-$tRNA^{Sec}$ can generate a higher yield (e.g., a higher amount) of the desired protein, particularly when the protein contains multiple Sec residues (e.g., 2, 3, 4, 5, 6, 7, 8, 9, 10, or more) compared to other $tRNA^{Sec}$ including, for example, $tRNA^{SecUx}$.

Additionally or alternatively, in some embodiments, the selenocysteine containing protein is expressed in a system that has been modified or mutated to reduce or eliminate expression of one or more translation release factors. A release factor is a protein that allows for the termination of translation by recognizing the termination codon or stop codon in an mRNA sequence. Prokaryotic release factors include RF1, RF2 and RF3; and eukaryotic release factors include eRF1 and eRF3.

Deletion of one or more release factors may result in "read-through" of the intended stop codon. Accordingly, some of recombinant proteins expressed in a system with one or more release factors may include one or more additional amino acids at the C-terminal end of the protein.

The protein of interest can be purified from the truncated proteins and other contaminants using standard methods of protein purification as discussed in more detail below.

1. In vitro Transcription/Translation

In one embodiment, the genes encoding a $tRNA^{Sec}$, mRNA encoding the protein of interest, mRNA encoding EF-Tu, SerRS, SelA, PSTK, SepSecS, SelD or combinations thereof are synthesized in vitro prior to or along with transcription and translation of the protein of interest. The synthesis of protein from a DNA sequence in vitro takes two steps. The first is transcription of an RNA copy and the second is the translation of a protein.

In vitro protein synthesis does not depend on having a polyadenylated mRNA, but if having a poly(A) tail is important for some other purpose a vector may be used that has a stretch of about 100 A residues incorporated into the polylinker region. That way, the poly(A) tail is "built in" by the synthetic method.

Eukaryotic ribosomes read RNAs more efficiently if they have a 5' methyl guanosine cap. RNA caps can be incorporated by initiation of transcription using a capped base analogue, or adding a cap in a separate in vitro reaction post-transcriptionally.

The use of in vitro translation systems can have advantages over in vivo gene expression when the over-expressed product is toxic to the host cell, when the product is insoluble or forms inclusion bodies, or when the protein undergoes rapid proteolytic degradation by intracellular proteases. Various approaches to in vitro protein synthesis are known in the art and include translation of purified RNA, as well as "linked" and "coupled" transcription:translation. In vitro translation systems can be eukaryotic or prokaryotic cell-free systems.

Combined transcription/translation systems are available, in which both phage RNA polymerases (such as T7 or SP6) and eukaryotic ribosomes are present. One example of a kit is the TNT® system from Promega Corporation.

Other suitable in vitro transcription/translation systems include, but are not limited to, the rabbit reticulocyte system, the *E. coli* S-30 transcription-translation system, and the wheat germ based translational system.

2. In Vivo Methods Transcription/Translation a. Extrachromosomal Expression

Host cells can be genetically engineered (e.g., transformed, transduced or transfected) with the vectors encoding tRNA$^{Sec}$, a nucleic acid encoding the protein of interest, EF-Tu, SerRS, SelA, PSTK, SepSecS, SelD or combinations, which can be, for example, a cloning vector or an expression vector. In some embodiments, two or more of tRNA$^{Sec}$, EF-Tu, SerRS, SelA, PSTK, SepSecS, and SelD are expressed from the same vector.

The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)). Methods of expressing recombinant proteins in various recombinant expression systems including bacteria, yeast, insect, and mammalian cells are known in the art, see for example *Current Protocols in Protein Science* (Print ISSN: 1934-3655 Online ISSN: 1934-3663, Last updated January 2012). Plasmids can be high copy number or low copy number plasmids. In some embodiments, a low copy number plasmid generates between about 1 and about 20 copies per cell (e.g., approximately 5-8 copies per cell). In some embodiments, a high copy number plasmid generates at least about 100, 500, 1,000 or more copies per cell (e.g., approximately 100 to about 1,000 copies per cell).

Kits are commercially available for the purification of plasmids from bacteria, (see, e.g., GFX™ Micro Plasmid Prep Kit from GE Healthcare; Strataprep® Plasmid Miniprep Kit and StrataPrep® EF Plasmid Midiprep Kit from Stratagene; GenElute™ HP Plasmid Midiprep and Maxiprep Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express non-naturally occurring tRNA$^{Sec}$ and mRNA for producing proteins or polypeptides containing selenocysteine. Viral based expression systems are well known in the art and include, but are not limited to, baculoviral, SV40, retroviral, or vaccinia based viral vectors.

Mammalian cell lines that stably express tRNA and proteins can be produced using expression vectors with appropriate control elements and a selectable marker. For example, the eukaryotic expression vectors pCR3.1 (Invitrogen Life Technologies) and p91023(B) (see Wong et al. (1985) *Science* 228:810-815) are suitable for expression of recombinant proteins in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

U6 and H1 are exemplary promoters that can be used for expressing bacterial tRNA in mammalian cells.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin or by metabolic selection using the Glutamine Synthetase-NS0 system). The transfected cells can be cultured such that the polypeptide of interest is expressed, and the polypeptide can be recovered from, for example, the cell culture supernatant or from lysed cells.

b. Expression by Genomic Integration

Methods of engineering a microorganism or cell line to incorporate a nucleic acid sequence into its genome are known in the art. Any one or more of tRNA$^{Sec}$, EF-Tu, SerRS, SelA, PSTK, SepSecS, SelD or combinations can be expressed from one or more genomic copies. For example, cloning vectors expressing a transposase and containing a nucleic acid sequence of interest between inverted repeats transposable by the transposase can be used to clone the stably insert the gene of interest into a bacterial genome (Barry, *Gene*, 71:75-84 (1980)). Stably insertion can be obtained using elements derived from transposons including, but not limited to Tn7 (Drahos, et al., *Bio/Tech.* 4:439-444 (1986)), Tn9 (Joseph-Liauzun, et al., *Gene*, 85:83-89 (1989)), Tn10 (Way, et al., *Gene*, 32:369-379 (1984)), and Tn5 (Berg, In *Mobile DNA.* (Berg, et al., Ed.), pp. 185-210 and 879-926. Washington, D.C. (1989)). Additional methods for inserting heterologous nucleic acid sequences in *E. coli* and other gram-negative bacteria include use of specialized lambda phage cloning vectors that can exist stably in the lysogenic state (Silhavy, et al., Experiments with gene fusions, Cold Spring Harbor Laboratory, Cold Spring Harbor, N.Y. (1984)), homologous recombination (Raibaud, et al., *Gene*, 29:231-241 (1984)), and transposition (Grinter, et al., *Gene*, 21:133-143 (1983), and Herrero, et al., *J. Bacteriology*, 172(11):6557-6567 (1990)).

Methods of engineering other microorganisms or cell lines to incorporate a nucleic acid sequence into its genome are also known in the art. Nucleic acids that are delivered to cells which are to be integrated into the host cell genome can contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome. Techniques for integration of genetic material into a host genome are also known and include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

For example, cloning vectors expressing a transposase and containing a nucleic acid sequence of interest between inverted repeats transposable by the transposase can be used to clone the stably insert the gene of interest into a bacterial genome (Barry, *Gene,* 71:75-84 (1980)). Stably insertion can be obtained using elements derived from transposons including, but not limited to Tn7 (Drahos, et al., *Bio/Tech.* 4:439-444 (1986)), Tn9 (Joseph-Liauzun, et al., *Gene,* 85:83-89 (1989)), Tn10 (Way, et al., *Gene,* 32:369-379 (1984)), and Tn5 (Berg, In *Mobile DNA.* (Berg, et al., Ed.), pp. 185-210 and 879-926. Washington, D.C. (1989)). Additional methods for inserting heterologous nucleic acid sequences in *E. coli* and other gram-negative bacteria include use of specialized lambda phage cloning vectors that can exist stably in the lysogenic state (Silhavy, et al., Experiments with gene fusions, Cold Spring Harbor Laboratory, Cold Spring Harbor, N.Y. (1984)), homologous recombination (Raibaud, et al., *Gene,* 29:231-241 (1984)), and transposition (Grinter, et al., *Gene,* 21:133-143 (1983), and Herrero, et al., *J. Bacteriology,* 172(11):6557-6567 (1990)).

Integrative plasmids can be used to incorporate nucleic acid sequences into yeast chromosomes. See for example, Taxis and Knop, *Bio/Tech.,* 40(1):73-78 (2006), and Hoslot and Gaillardin, *Molecular Biology and Genetic Engineering of Yeasts.* CRC Press, Inc. Boca Raton, Fla. (1992). Methods of incorporating nucleic acid sequence into the genomes of mammalian lines are also well known in the art using, for example, engineered retroviruses such lentiviruses.

B. Purification of Selenocysteine Containing Polypeptides

Selenocysteine containing polypeptides can be isolated using, for example, chromatographic methods such as affinity chromatography, ion exchange chromatography, hydrophobic interaction chromatography, DEAE ion exchange, gel filtration, and hydroxylapatite chromatography. In some embodiments, selenocysteine containing polypeptides can be engineered to contain an additional domain containing amino acid sequence that allows the polypeptides to be captured onto an affinity matrix. For example, an Fc-containing polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase Immunoaffinity chromatography also can be used to purify selenocysteine containing polypeptides. Selenocysteine containing polypeptides can additionally be engineered to contain a secretory signal (if there is not a secretory signal already present) that causes the protein to be secreted by the cells in which it is produced. The secreted proteins can then conveniently be isolated from the cell media.

In some embodiments, selenocysteine containing polypeptides are isolated using activated thiol SEPHAROSE®, for example, Activated Thiol SEPHAROSE® 4B. As discussed above, in the recombinant tRNA$^{Sec}$ biosynthetic pathway disclosed herein non-naturally occurring tRNA$^{Sec}$ is first misacylated to a non-naturally occurring Ser-tRNA$^{Sec}$ by SerRS, and subsequently converted to Sec-tRNA$^{Sec}$ by SelA, or PSTK and SepSecS, or combinations thereof. Accordingly, if the SelA, or PSTK and SepSecS, enzymes are not 100% efficient at converting Ser-tRNA$^{Sec}$ to Sec-tRNA$^{Sec}$, the system may incorporate Sec or Ser at the desired position, leading to a heterogeneous mixture of proteins. Activated thiol SEPHAROSE® can be incorporated into the protein purification process to purify Sec containing proteins from the Ser containing contaminants.

IV. Methods of Using Selenocysteine Containing Polypeptide

The compositions and methods disclosed herein can be used to manufacture polypeptides and proteins with one or more selenocysteine residues. In some embodiments, the mRNA encodes a polypeptide that is a naturally occurring selenocysteine containing polypeptide. In some embodiments, the mRNA encodes a polypeptide that is not a naturally occurring selenocysteine containing polypeptide. A nucleic acid sequence can include a codon that is recognized by the anticodon of a tRNA$^{Sec}$ disclosed herein, for example a nucleic acid encoding a naturally occurring selenocysteine containing protein, or can be modified to include a codon recognized by the anticodon of a tRNA$^{Sec}$. The nucleic acid sequence encoding the polypeptide can also be codon optimized for expression in the desired recombinant expression system. The nucleic acid can be expressed from a vector or incorporated into the genome of the desired expression system.

A. Recombinant Selenocysteine Containing Peptides—Naturally Occurring

The disclosed compositions and methods can be used for recombinant expression of naturally occurring selenocysteine containing peptides, or variants thereof. Selenoproteins exist in all major forms of life, including, eukaryotes, bacteria and archaea. Accordingly, in some embodiments, the mRNA of interest is an mRNA encoding a selenocysteine containing peptide from an eukaryote, a bacteria, or an archaea. The human genome encodes at least 25 naturally occurring selenocysteine containing peptides (Kryukov, et al, *Science,* 300:1439-1443 (2003)). Therefore, in some embodiments the mRNA encodes a iodothyronine deiodinase such as DIO1, DIO2, DIO3; a glutathione peroxidase such as GPX1, GPX2, GPX3, GPX4, or GPX6; a selenoprotein such as SelH, SelI, SelK, SelM, SelN, SelO, SelP, SelR, SelS, SelT, SelV, SelW, or Sel15; selenophosphate synthetase 2 (SPS2); or a thioredoxin reductase such as TXNRD1, TXNRD2, or TXNRD3.

Conditions to be Treated

In some embodiments, recombinant selenocysteine containing polypeptides prepared according to the claimed methods are administered to a subject in an effective amount to treat a disease, or one or more symptoms thereof. As discussed in Riaz and Mehmood, *JPMI,* 26(02):120-133 (2012) and Tapiero, et al., *Biomedicine & Pharmacotherapy* 57:134-144 (2003), many health effects of low selenium are thought to be due to lack of one or more specific selenocysteine containing proteins. For example, reduction or loss of one or more selenocysteine containing protein in a subject can be associated with increased oxidative stress in the subject. Accordingly, a recombinant selenocysteine containing protein can be administered to subject in an effective amount to increase antioxidant activity, or reduce oxidative stress in the subject. In some embodiments, the recombinant selenocysteine containing protein can be used to treat or prevent an age-related disorder, asthma, diabetes, an infectious disease, a cardiovascular disorder, a cancer, male infertility, pre-eclampsia, a gastrointestinal disorder, thyroid metabolism, or another diseases or condition associated with reduced levels or activity of selenocysteine containing proteins.

B. Recombinant Selenocysteine Containing Peptides—Non-Naturally Occurring

The disclosed compositions and methods can also be used for producing by recombinant expression a selenocysteine containing polypeptide variant of any polypeptide that does not naturally contain selenocysteine.

1. Insertion of Selenocysteine

One or more selenocysteines can be added to the beginning, end, and/or inserted into a polypeptide that does not typically have a selenocysteine. Adding one or more selenocysteines can change the biochemical and functional properties of the protein, for example, change the redox potential of the protein, increase the half-life of the protein, increase the stability or resistance to degradation, increase the activity of the protein (such as enzymatic activity), alter the pharmacokinetics of the protein, alter the binding affinity (such as the binding affinity of an antibody to antigen or ligand to receptor), change the folding properties of the protein, induce new epitopes onto the protein, or tag the protein for purification.

In some embodiments, the one or more selenocysteines changes the biochemical properties of the protein so it can be easily purified after recombinant expression. In some embodiments, selenocysteine can be added to a protein and used as a purification tag. For example, activated thiol SEPHAROSE®, or an equivalent thereof, can be incorporated into the protein purification process to purify Sec containing proteins from contaminants.

2. Substitution with Selenocysteine

In some embodiments, selenocysteine is substitute for one or more naturally occurring cysteines.

Reversible oxidation of thiols to disulfides or sulfenic acid residues controls biological functions in at least three general ways, by chemically altering active site cysteines, by altering macromolecular interactions, and by regulating activity through modification of allosteric Cys (reviewed in Jones, *Am. J. Physiol.*, 295(4):C849-868 (2008)). Half of all enzyme activities are sensitive to either oxidation, reaction with electrophiles, or interaction with metal ions. Enzymes with active-site Cys include caspases, kinases, phosphatases, and proteases. Cys is also a component of active sites of iron-sulfur clusters of electron transfer proteins and an element of zinc fingers in transcription factors and zinc-binding domains of metallothioneins. Cys residues are also conserved in structural proteins such as actin and docking proteins such as 14-3-3. Oxidation of Cys residues in αIIbβ3 integrin controls platelet activation. Cys-rich regions are present in plasma membrane receptors and ion channels, including the NMDA receptors, EGF receptor, and others. Thus reversible oxidation of active site thiols can provide a common and central "on-off" mechanism for control of cell functions.

β-Actin contains a conserved Cys, which results in reversible binding of proteins, S-GS-ylation, and crosslinking of actin filaments upon oxidation. Oxidation functions in glucocorticoid receptor translocation into nuclei, and oxidation controls export of yeast AP-1 (Yap-1) from nuclei. Disulfide crosslinks control fluidity of mucus. Such changes in protein structure and interaction due to reversible oxidation can provide a central mechanism for specificity in redox signaling. In addition to containing active site and/or structural thiols, many proteins contain Cys which regulate activity by an allosteric mechanism. This type of regulation can provide a "rheostat" rather than an "on-off" switch, thereby providing a means to throttle processes by GS-ylation or S-nitrosylation.

Many naturally occurring selenoproteins with known functions are oxidoreductases which contain catalytic redox-active Sec (Jacob C, et al., *Angew. Chem. Int. Ed. Engl.*, 42:4742-4758 (2003)). Variants of the naturally occurring selenoprotein in which the Sec residues are replaced with Cys residues are typically 100-1,000 times less active (Johansson L, et al, *Biochim. Biophys. Acta.*, 1726:1-13 (2005)). Furthermore, analogs of naturally occurring proteins where one or more Cys residues are replaced with Sec can generate analogs that retain the folding of the native peptides, are more potent, and have the same or greater biological activity (Raffa, *Life Sci.*, 87(15-16):451-6 (2010)).

Therefore, in some embodiments, the disclosed compositions and methods are used to manufacture recombinant variants or analogs where one or more naturally occurring Cys residues, for example Cys residues in the active site of an enzyme, are replaced with Sec residues. The methods and compositions can be used to generate analogs that retain a folding of the protein similar or the same as the native peptides, but are more potent while having the same or greater biological activity. Substituting one or more naturally occurring Cys residues with a Sec can increase the activity of the protein by 2, 5, 10, 100, 250, 500, 1,000 or more-fold over the activity of the protein that does not contain the Sec residue(s). Accordingly, the analogs can be used in therapeutic or research applications at a lower dosage, less frequently, with reduced toxicity, or combinations thereof relative to the naturally occurring protein.

In some embodiments, the disclosed compositions and methods can be used to prepare recombinant polypeptides where one or more cysteines that contributes to the formation of a disulfide bond in the protein is replaced with selenocysteine. Therefore, recombinant proteins having one or more Sec-Sec (diselenide) or Cys-Sec (selenocysteine-cysteine) bonds are disclosed.

A disulfide bond is a covalent bond, usually derived by the coupling of two thiol groups. Disulfide bonds in proteins are formed between the thiol groups of cysteine residues. A disulfide bond can stabilize the folded form of a protein in several ways. For example a disulfide bond can hold two portions of the protein together, favoring a folded topology and contributing to the formation and stability of secondary and tertiary structures. A disulfide bond can also form the center of a hydrophobic core in a folded protein, i.e., local hydrophobic residues may condense around the disulfide bond and onto each other through hydrophobic interactions. In some cases the hydrophobic core is an enzyme's active site, and the disulfide bond is necessary for enzymatic efficiency or activity.

A diselenide bond, which is formed between two selenocysteine residues, or a selenocysteine-cysteine bond between a selenocysteine and cysteine can impart similar structural and functional characteristics to the protein as a disulfide bond. Diselenide and selenocysteine-cysteine bonds are infrequent in nature, but have been reported to be in the active site of some enzymes, for example the selenocysteine protein SelL (Shchedrina, et al., *PNAS*, 104(35): 13919-13924 (2007)). Diselenide bonds have very low redox potential, but in some cases can be reduced by thioredoxin.

Therefore, in some embodiments, the disclosed compositions and methods are used to manufacture recombinant variants where one or more naturally occurring disulfide bonds are replaced with a diselenide or a selenocysteine-cysteine bond.

Replacing disulfide bonds with diselenide or selenocysteine-cysteine bonds can be used to reduce the redox potential of the bond, increase the half-life of the protein, increase the activity of the protein, alter the pharmacokinetics of the protein, for example, increase or decrease the association or dissociation constant, alter the folding and unfolding properties of the protein, or combinations thereof. For example, substituting one or more naturally occurring Cys residues with a Sec can increase the activity of the protein by 2, 5, 10, 100, 250, 500, 1,000 or more-fold over the activity of the protein that does not contain the Sec residue(s). Accordingly, the analogs can be used in therapeutic or research applications at a lower dosage, less frequently, with reduced toxicity, or combinations thereof relative to the naturally occurring protein.

Exemplary proteins where a naturally occurring Cys can be replaced with Sec according to the compositions and methods disclosed herein include, but are not limited to, caspases, kinases, phosphatases, proteases, transcription factors, metallothioneins, structural proteins such as actin and docking proteins such as 14-3-3, integrins such as αIIbβ3, plasma membrane receptors, ion channels, including the NMDA receptors, EGF receptor, and others.

The disclosed compositions and methods can be particularly useful for preparing recombinant antibodies, antigen binding fragments thereof, fusion proteins including a least one antibody domain (i.e., Ig fusion proteins) with altered properties, and receptor such as T cell receptors or receptor fragments including the binding domains. Antibodies contain inter-chain disulfide bonds which link the heavy and light chains, disulfide bonds that link two heavy chains, and disulfide bonds that link the two hinge regions. Antibodies also have disulfide bonds within the chains themselves (referred to as intra-chain disulfide bonds). The disclosed compositions and methods can be used to prepare recombinant antibodies where one or more disulfide bonds are replaced with diselenide bonds. The one or more of the inter-chain disulfide bonds which link the heavy and light chains, the disulfide bonds that link two heavy chains, the disulfide bonds that link the two hinge regions, the intra-chain disulfide bonds, or combinations thereof can be replaced with diselenide bonds.

Disulfide bonds in antibodies are important for assembly, stability and dimerization of the antibody. For example, disulfide bonds play a critical role in the stabilization of the immunoglobulin β-sandwich. Under reducing conditions, such as those characteristic of recombinant protein expression systems, disulfide bonds do not normally form and as a result most antibodies expressed in that compartment are misfolded or inactive (Seo, et al., *Protein Sci.*, 18(2): 259-267 (2009)). Furthermore, stability and homogeneity of therapeutic antibodies are important for safety and efficacy of therapeutic antibodies (McAuley, et al, *Protein Sci.*, 17(1): 95-106 (2008)). Undesired biochemical, structural, and conformational forms, such as those generated when disulfide bonds are reduced, can lead to loss of efficacy and risk of adverse side effects.

Replacing one or more of the disulfide bonds of an antibody with diselenide or selenocysteine-cysteine bonds according to the disclosed compositions and methods can improve the yield, purity, or combinations thereof, of recombinantly produced antibodies. Replacing one or more of the disulfide bonds of an antibody with diselenide or selenocysteine-cysteine bonds according to the disclosed compositions and methods can also improve stability, increase efficacy, increase half-life, reduce toxicity, alter the pharmacokinetics of the antibody, for example, increase or decrease the association or dissociation constant, or combinations thereof of antibodies, such as therapeutic antibodies.

The antibodies can be xenogeneic, allogeneic, syngeneic, or modified forms thereof, such as humanized, single chain or chimeric antibodies. Antibodies may also be anti-idiotypic antibodies specific for a idiotype of the desired antigen. The term "antibody" is also meant to include both intact molecules as well as fragments thereof that include the antigen-binding site and are capable of binding to a desired epitope. These include Fab and F(ab')$_2$ fragments which lack the Fc fragment of an intact antibody, and therefore clear more rapidly from the circulation, and may have less non-specific tissue binding than an intact antibody (Wahl et al., *J. Nuc. Med.* 24:316-325 (1983)). Also included are Fv fragments (Hochman, J. et al., *Biochemistry*, 12:1130-1135 (1973); Sharon, J. et al., *Biochemistry*, 15:1591-1594 (1976)). These various fragments can be produced using conventional techniques such as protease cleavage or chemical cleavage (see, e.g., Rousseaux et al., *Meth. Enzymol.*, 121:663-69 (1986)).

Antibody "formats" and methods of making recombinant antibodies are known in the art and reviewed in Laffly and Sodoyer, *Hum Antibodies*, 14(1-2):33-35 (2005). Methods of expressing and purifying antibodies from a recombinant expression system are known in the art, see for example, Knappik and Brundiers, "Recombinant Antibody Expression and Purification," *The Protein Protocols Handbook*, Third Edition Edited by: J. M. Walker© Humana Press, a Part of Springer Science+Business Media, LLC (2009).

Therapeutic antibodies that could benefit from replacement of one or more disulfide bonds with a diselenide or selenocysteine-cysteine bond are known in the art and include, but are not limited to, those discussed in Reichert, *Mabs*, 3(1): 76-99 (2011), for example, AIN-457, bapineuzumab, brentuximab vedotin, briakinumab, dalotuzumab, epratuzumab, farletuzumab, girentuximab (WX-G250), naptumomab estafenatox, necitumumab, obinutuzumab, otelixizumab, pagibaximab, pertuzumab, ramucirumab, REGN88, reslizumab, solanezumab, T1h, teplizumab, trastuzumab emtansine, tremelimumab, vedolizumab, zalutumumab and zanolimumab.

Other therapeutic antibodies that could benefit from replacement of one or more disulfide bonds with a diselenide bond include antibodies approved for use, in clinical trials, or in development for clinical use which include, but are not limited to, rituximab (Rituxan®, IDEC/Genentech/Roche) (see for example U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT/US2003/040426, entitled "Immunoglobulin Variants and Uses Thereof"), trastuzumab (Herceptin®, Genentech) (see for example U.S. Pat. No. 5,677,171), a humanized anti-Her2/neu antibody approved to treat breast cancer; pertuzumab (rhuMab-2C4, Omnitarge), currently being developed by Genentech; an anti-Her2 antibody described in U.S. Pat. No. 4,753,894; cetuximab (Erbitux®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Ser. No. 10/172,317), currently being developed by Genmab; 425, EMD55900, EMD62000, and EMD72000 (Merck KGaA) (U.S. Pat. No. 5,558,864; Murthy et al. 1987, Arch Biochem Biophys. 252(2):549-60; Rodeck et al., 1987, J Cell Biochem. 35(4):315-20; Kettleborough et al., 1991, Protein Eng. 4(7):773-83); 1CR62 (Institute of Cancer Research) (PCT WO 95/20045; Modjtahedi et al., 1993, J. Cell Biophys. 1993, 22(1-3):129-46; Modjtahedi et al., 1993, Br J Cancer. 1993, 67(2):247-53; Modjtahedi et al, 1996, Br J Cancer, 73(2):228-35; Modjtahedi et al, 2003, Int J Cancer, 105(2):273-80); TheraClM hR3 (YM Biosciences, Canada and Centro de Immunologia Molecular, Cuba (U.S. Pat. Nos. 5,891,996; 6,506,883; Mateo et al, 1997, Immunotechnology, 3(1):71-81); mAb-806 (Ludwig Institute for Cancer Research, Memorial Sloan-Kettering) (Jungbluth et al. 2003, Proc Natl Acad Sci USA. 100(2):639-44); KSB-102 (KS Biomedix); MRI-1 (IVAX, National Cancer Institute) (PCT WO 0162931A2); and SC100 (Scancell) (PCT WO 01/88138); alemtuzumab (Campath®, Millenium), a humanized mAb currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amcvive®), anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFalpha antibody developed by Centocor, adalimumab (Humira®), an anti-TNFalpha antibody developed by Abbott, Humicade®, an anti-TNFalpha antibody developed by Celltech, golimumab (CNTO-148), a fully human TNF antibody developed by Centocor, etanercept (Enbrel®), an p75 TNF receptor Fc fusion developed by Immunex/Amgen, lenercept, an p55 TNF receptor Fc fusion previously developed by Roche, ABX-CBL, an anti-CD 147 antibody being developed by Abgenix, ABX-IL8, an anti-IL8 antibody being developed by Abgenix, ABX-MAI, an anti-MUC18 antibody being developed by Abgenix, Pemtumomab (R1549,90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegrene (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-.beta.2 antibody being developed by Cambridge Antibody Technology, ABT 874 (J695), an anti-IL-12 p40 antibody being developed by Abbott, CAT-192, an anti-TGF.beta.1 antibody being developed by Cambridge Antibody Technology and Genzyme, CAT-213, an anti-Eotaxinl antibody being developed by Cambridge Antibody Technology, LyntphoStat-B® an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc. Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech. Xolair® (Omalizurnab), an anti-IgE antibody being developed by Genentech, Raptiva® (Efalizurnab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDFC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (labetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-I), and anti-Her2 antibody being developed by Medarex and Immuno-Designed Molecules, HuMaxe-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J. CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAFO, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, Xolair® (Omalizumab) a humanized anti-IgE antibody developed by Genentech and Novartis, and MLN01, an anti-Beta2 integrin antibody being developed by Xoma. In another embodiment, the therapeutics include KRN330 (Kirin); huA 33 antibody (A33, Ludwig Institute for Cancer Research); CNTO 95 (alpha V integrins, Centocor); MEDI-522 (alpha V133 integrin, Medimmune); volociximab (αVβ1 integrin, Biogen/PDL); Human mAb 216 (B cell glycosolated epitope, NCI); BiTE MT103 (bispecific CD19×CD3, Medimmune); 4G7× H22 (Bispecific BcellxFcgammaRl, Meclarex/Merck KGa); rM28 (Bispecific CD28×MAPG, U.S. Patent No. EP1444268); MDX447 (EMD 82633) (Bispecific CD64×EGFR, Medarex); Catumaxomab (removah) (Bispecific EpCAMxanti-CD3, Trion/Fres); Ertumaxomab (bispecific HER2/CD3, Fresenius Biotech); oregovomab (OvaRex) (CA-125, ViRexx);

Rencarex® (WX G250) (carbonic anhydrase IX, Wilex); CNTO 888 (CCL2, Centocor); TRC105 (CD105 (endoglin), Tracon); BMS-663513 (CD137 agonist, Brystol Myers Squibb); MDX-1342 (CD19, Medarex); Siplizumab (MEDI-507) (CD2, Medimmune); Ofatumumab (Humax-CD20) (CD20, Genmab); Rituximab (Rituxan) (CD20, Genentech); THIOMAB (Genentech); veltuzumab (hA20) (CD20, Immunomedics); Epratuzumab (CD22, Amgen); lumiliximab (IDEC 152) (CD23, Biogen); muromonab-CD3 (CD3, Ortho); HuM291 (CD3 fc receptor, PDL Biopharma); HeFi-1, CD30, NCI); MDX-060 (CD30, Medarex); MDX-1401 (CD30, Medarex); SGN-30 (CD30, Seattle Genetics); SGN-33 (Lintuzumab) (CD33, Seattle Genetics); Zanolimumab (HuMax-CD4) (CD4, Genmab); HCD 122 (CD40, Novartis); SGN-40 (CD40, Seattle Genetics); Campathlh (Alemtuzumab) (CD52, Genzyme); MDX-1411 (CD70, Medarex); hLL1 (EPB-I) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Brystol Myers Squibb); Tremelimumab (Ticilimumab, CP-675,2) (CTLA4, Pfizer); 1-IGS-ETR1 (Mapatumumab) (DR4TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DRSTRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 AVANT Immunotherapeutics); adecatumumab (MT201) (Epcam, Merck); edrecolomab (Panorex, 17-1A) (Epcam Glaxo/Centocor); MORAb-003 (folate receptor a, Morphotech); KW-2871 (ganglioside GD3, Kyowa); MORAb-009 (GP-9, Morphotech); CDX-1307 (MDX-1307) (hCGb, Celldex); Trastuzumab (Herceptin) (HER2, Celldex); Pertuzumab (rhuMAb 2C4) (HER2 (DI), Genentech); apolizumab (HLA-DR beta chain, PDL Pharma); AMG-479 (IGF-1R, Amgen); anti-IGF-1R R1507 (IGF1-R, Roche); CP 751871 (IGF 1-R, Pfizer); IMC-A12 (IGF1-R, Imclone); B1111022 Biogen); Mik-beta-1 (IL-2Rb (CD122), Hoffman LaRoche); CNTO 328 (IL6, Centocor); Anti-MR (1-7F9) (Killer cell Ig-like Receptor (KIR), Novo); Hu3S193 (Lewis (y), Wyeth, Ludwig Institute of Cancer Research); hCBE-11 (LTβR, Biogen); HuHMFG1 (MUC1, Antisoma/NCI); RAV 12 (N-linked carbohydrate epitope, Raven); CAL (parathyroid hormone-related protein (PTHrP), University of California); CT-011 (PD1, CtireTech); MDX-1106 (ono-4538) (PDL Nileclarox/Ono); MAb CT-011 (PD1, Curetech); IMC-3G3 (PDGFRa, Imclone); bavituximab (phosphatidylserine, Peregrine); huJ591 (PSMA, Cornell Research Foundation); muJ591 (PSMA, Cornell Research Foundation); GC1008 (TGFb (pan) inhibitor (IgG4), Genzyme); Infliximab (Remicade) (TNFα, Centocor); A27.15 (transferrin receptor, Salk Institute, INSERN WO 2005/111082); E2.3 (transferrin receptor, Salk Institute); Bevacizumab (Avastin) (VEGF, Genentech); HuMV833 (VEGF, Tsukuba Research Lab-WO/2000/034337, University of Texas); IMC-18F1 (VEGFR1, Imclone); IMC-1121 (VEGFR2, Imclone)

In another embodiment, the recombinant protein is a fusion protein having a least one Cys, preferably at least one Cys-Cys bond. In some embodiments, the fusion protein is a fusion protein containing an antibody domain, for example an Ig fusion protein. A fusion protein typically includes two or more domains, where a first domain including a peptide of interest is fused, directly or indirectly to a second polypeptide. In some embodiments, the second domain includes one or more domains of an Ig heavy chain constant region, preferably having an amino acid sequence corresponding to the hinge, $C_{H2}$ and $C_{H3}$ regions of a human immunoglobulin Cγ1 chain. Construction of immunoglobulin fusion proteins is discussed in *Current Protocols in Immunology*, (ed. Diane Hollenbaugh, Alejandro Aruffo) UNIT 10.19A, Published May 1, 2002, by John Wiley and Sons, Inc.

3. Selenocysteine-Containing Polypeptide Conjugates

In some embodiments, the addition of one or more selenocysteines can be used to facilitate linkage of second therapeutic, prophylactic or diagnostic agent to the selenocysteine containing polypeptide. Methods of utilizing cysteines as reactive sites for attachment of a second agent, for example, via a disulfide bridge, are known in the art. See for example, Ritter, *Pharmaceutical Technology*, 42-47 (2012), Miao, et al., *Bioconjug. Chem.*, 19(1):15-19 (2008); and Dosio, et al., *Toxins (Basel)*, 3(7):848-83 (2011). Accordingly, one or more selenocysteines can be added to a recombinant polypeptide, or substitute for an existing amino acid such as cysteine, to create or replace a reactive site for conjugation of the second agent. The recombinant polypeptide and the second agent can be conjugated via a linker. In a preferred embodiment, the recombinant polypeptide engineered to a contain one or more selenocysteines is an antibody, for example a therapeutic antibody.

In some embodiments, the second agent is a toxin, diagnostic imaging agent, purification ligand or other engineered element that modifies the stability, activity, pharmacokinetics, or other properties of the protein. The second agent can be a small molecule.

In a preferred embodiment, the second agent is a therapeutic agent. For example, the second agent can be a chemotherapeutic drug. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

In some preferred embodiments, recombinant antibody including one or more selenocysteine polypeptides manufactured according to the disclosed methods is conjugated with second therapeutic agent such as a chemotherapeutic drug.

Conditions to be Treated

As discussed above, substituting one or more naturally occurring Cys residues with a Sec can increase activity, lower dosage, reduce toxicity, improve stability, increase efficacy, increase half-life or combinations thereof of a selenocysteine containing protein relative to its cysteine containing counterpart. Accordingly, therapeutic proteins containing one or more selenocysteine residues can be prepared according to the compositions and methods disclosed herein and administered to a subject in need thereof in an effective amount to reduce or alleviate one or more symptoms of a disease or disorder. Therapeutic proteins such as enzymes and antibodies which contain one or more cysteine residues or disulfide bonds can be replaced with Sec to increase activity, lower dosage, reduce toxicity, improve stability, increase efficacy, increase half-life, or attach a second agent or combinations thereof are discussed above and known in the art, and can be administered to subject to treat diseases or disorders including, but not limited to, infectious diseases, cancers, metabolic disorders autoimmune disorders, inflammatory disorders, and age-related disorders.

C. Administration

The recombinant selenocysteine containing polypeptides disclosed herein can be part of a pharmaceutical composition. The compositions can be administered in a physiologically acceptable carrier to a host. Preferred methods of administration include systemic or direct administration to a cell. The compositions can be administered to a cell or patient, as is generally known in the art for protein therapy applications.

The compositions can be combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween®, Pluronics® or PEG.

The compositions can be administered parenterally. As used herein, "parenteral administration" is characterized by administering a pharmaceutical composition through a physical breach of a subject's tissue. Parenteral administration includes administering by injection, through a surgical incision, or through a tissue-penetrating non-surgical wound, and the like. In particular, parenteral administration includes subcutaneous, intraperitoneal, intravenous, intraarterial, intramuscular, intrasternal injection, and kidney dialytic infusion techniques.

Parenteral formulations can include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Parenteral administration formulations include suspensions, solutions, emulsions in oily or aqueous vehicles, pastes, reconstitutable dry (i.e. powder or granular) formulations, and implantable sustained-release or biodegradable formulations. Such formulations may also include one or more additional ingredients including suspending, stabilizing, or dispersing agents. Parenteral formulations may be prepared, packaged, or sold in the form of a sterile injectable aqueous or oily suspension or solution. Parenteral formulations may also include dispersing agents, wetting agents, or suspending agents described herein.

Methods for preparing these types of formulations are known. Sterile injectable formulations may be prepared using non-toxic parenterally-acceptable diluents or solvents, such as water, 1,3-butane diol, Ringer's solution, isotonic sodium chloride solution, and fixed oils such as synthetic monoglycerides or diglycerides. Other parentally-administrable formulations include microcrystalline forms, liposomal preparations, and biodegradable polymer systems. Compositions for sustained release or implantation may include pharmaceutically acceptable polymeric or hydrophobic materials such as emulsions, ion exchange resins, sparingly soluble polymers, and sparingly soluble salts.

Pharmaceutical compositions may be prepared, packaged, or sold in a buccal formulation. Such formulations may be in the form of tablets, powders, aerosols, atomized solutions, suspensions, or lozenges made using known methods, and may contain from about 0.1% to about 20% (w/w) active ingredient with the balance of the formulation containing an orally dissolvable or degradable composition and/or one or more additional ingredients as described herein. Preferably, powdered or aerosolized formulations have an average particle or droplet size ranging from about 0.1 nanometers to about 200 nanometers when dispersed.

As used herein, "additional ingredients" include one or more of the following: excipients, surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which may be included in the pharmaceutical compositions are known. Suitable additional ingredients are described in Remington's Pharmaceutical Sciences, Mack Publishing Co., Genaro, ed., Easton, Pa. (1985).

Dosages and desired concentrations of the pharmaceutical compositions disclosed herein may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

EXAMPLES

Mukai, et al., "Transfer RNAs with novel cloverleaf structures," *Nucleic Acids Research*, 45(5):2776-2785 (2017), and all of the associated Supplementary Data and materials, doi: 10.1093/nar/gkw898 is specifically incorporated by reference in their entirety.

Example 1: tRNA$^{Sec}$-Like tRNAs are Widespread in Bacteria

Since the discovery of tRNA in the late-1950s (Hoagland, et al., *J Biol Chem*, 231:241-257 (1958)), its role as an adaptor molecule during translation of the genetic information has been extensively investigated (RajBhandary, et al., *American Society for Microbiology*, Washington, DC (1995)). While recent research has focused on the non-translational functions of tRNAs (Keam, et al., *Life (Basel)*, 5:1638-1651 (2015); Raina, et al., *Front Genet*, 5:Article 171 (2014); Hamashima, et al., *Biomol Concepts*, 4:309-318 (2013); Katz, et al., *Mol Microbiol*, doi: 10.1111/mmi 13419 (2016)), the rapidly increasing expanse of genomic and metagenomic sequence information has revived the interests in the canonical function of tRNAs (Ling, et al., *Nat Rev Microbiol*, 13:707-721 (2015)). Recent studies have identified a number of non-canonical tRNA species that were previously mis-annotated or undetected due to their unusual recognition elements, anticodon sequences, and irregular secondary structures (Katz, et al., *Mol Microbiol*, doi: 10.1111/mmi 13419 (2016); Ling, et al., *Nat Rev Microbiol*, 13:707-721 (2015); Hamashima, et al., *Mol Biol Evol*, 33:530-540 (2016); Marck, et al., *RNA*, 8:1189-1232 (2002); Campbell, et al., *Proc Natl Acad Sci USA*, 110:5540-5545 (2013); Borrel, et al., *Archaea*, 374146 (2014); Ivanova, et al., *Science*, 344:909-913 (2014); Mukai, et al., *Angew Chem Int Ed Engl*, 55:5337-5341 (2016); Mühlhausen, et al., *Genome Res*, 26:945-955 (2016); Swart, et al., *Cell*, 166:691-702 (2016)). Interestingly, although the function of many of them remains unknown (Hamashima, et al., *Biomol Concepts*, 4:309-318 (2013); Katz, et al., *Mol Microbiol*, doi: 10.1111/mmi 13419 (2016); Hamashima, et al., *Mol Biol Evol*, 33:530-540 (2016)), some of these non-canonical tRNAs are known to be responsible for changes to the universal meaning of the genetic code (Ling, et al., *Nat Rev Microbiol*, 13:707-721 (2015); Campbell, et al., *Proc Natl Acad Sci USA*, 110:5540-5545 (2013); Borrel, et al., *Archaea*, 374146 (2014); Ivanova, et al., *Science*, 344:909-913 (2014); Mukai, et al., *Angew Chem Int Ed Engl*, 55:5337-5341 (2016); Mühlhausen, et al., *Genome Res*, 26:945-955 (2016); Swart, et al., *Cell*, 166:691-702 (2016)). Therefore, proper identification of tRNA genes is important to identify genetic code variations in nature (Campbell, et al., *Proc Natl Acad Sci USA*, 110:5540-5545 (2013); Mukai, et al., *Angew Chem Int Ed Engl*, 55:5337-5341 (2016)).

All tRNAs fold into an L-shaped tertiary structure which physically links the amino acid moiety attached to one end (amino-acid acceptor branch) to the genetic information of the anticodon sequence on the other end (the anticodon branch) (RajBhandary, et al., *American Society for Microbiology*, Washington, D C (1995); Katz, et al., *Mol Microbiol*, doi: 10.1111/mmi 13419 (2016)). The amino-acid acceptor branch consists of a 7-bp acceptor stem and a 5-bp T-stem, and this 12-bp branch is recognized by the elongation factor (EF-Tu), whereas the anticodon branch consists of the D-arm, V-arm, and anticodon arm. The size and structure of tRNAs are normally standardized in a particular genetic code system, as they share the same apparatus such as processing RNases, base modification enzymes, CCA-adding enzyme, EF-Tu, and the ribosome. Although tRNA size reduction is common in the mitochondrial genomes, all prokaryotic and eukaryotic tRNA species are believed to have a 12-bp amino-acid acceptor branch (7/5) with a few exceptions. To date such exceptions are known for selenocysteine (Sec) tRNAs and histidine (His) tRNAs. Most tRNA$^{His}$ species have an additional guanosine at the 5'-end (G-1) that produces a non-canonical 7/5 structure (Cooley, et al., *Proc Natl Acad Sci USA*, 79:6475-6479 (1982); Orellana, et al., *Mol Cell Biol*, 6:525-529 (1986)). In contrast, tRNA$^{Sec}$ has a 13-bp amino-acid acceptor branch (8/5 or 9/4) (Hubert, et al., *RNA*, 4:1029-1033 (1998); Schön, et al., *Nucleic Acids Res*, 17:7159-7165 (1989)) and are actually longer than the other tRNA species. Bacterial tRNA$^{Sec}$ species with 12-bp amino-acid acceptor branches have also been identified (Mukai, et al., *Angew Chem Int Ed Engl*, 55:5337-5341 (2016); Cravedi, et al., *Genome Biol Evol*, 7:2692-2704 (2015)). Among these, tRNA$^{Sec}$ species with a 12-bp amino-acid acceptor branch composed of an 8-bp acceptor stem and a 4-bp T-stem and a bulge nucleotide at position 51a were identified. The existence of such 8/4 tRNA$^{Sec}$ structure in two different bacterial phyla (Actinobacteria and Chloroflexi) prompted a search for other previously unidentified or mischaracterized tRNAs with an 8/4 structure. In the results below, a large number of bacterial tRNA sequences with different secondary structures were identified, annotated, and classified, and their translational functions in *Escherichia coli* evaluated.

Materials and Methods

Identification of tRNA Sequences

The false positive sequences of a previous tRNA$^{Sec}$ search study (Mukai, et al., *Angew Chem Int Ed Engl*, 55:5337-5341 (2016)) were re-analyzed, and tRNA$^{Sec}$-like sequences with a non-canonical composition of the amino-acid acceptor branch were manually collected with the aid of the ARAGORN server (Laslett, et al., *Nucleic Acids Res*, 32:11-16 (2004)) and the Clustal X program (Larkin, et al., *Bioinformatics*, 23:2947-2948 (2007)). Next, a BLAST search of some soil and sediment metagenome data was performed in the Integrated Microbial Genomes (IMG) system (Markowitz, et al., *Nucleic Acids Res*, 42:D568-573 (2014)) and the National Center for Biotechnology Information (NCBI) for more allo-tRNA sequences. A number of metagenomic contigs were found to contain up to two allo-tRNA genes and frequently annotated as belonging to Acidobacteria.

The resulting allo-tRNA sequences were classified into several groups, and representative sequences were used as query for BLAST searches of acidobacterial genomes. Acidobacterium strain C40 was renamed in this study as *Edaphobacter* strain C40, based on the 99.4% 16S rRNA sequence similarity with *Edaphobacter modestus* Jbg-1$^T$ (Koch, et al., *Int J Syst Evol Microbiol*, 58:1114-1122 (2008)). Some of the selC*tRNA sequences were found in the false positive sequences of the tRNA$^{Sec}$ search. By using them as query for BLAST, most of the selC*tRNA sequences were detected. The resulting selC*tRNA sequences were classified into several groups with the aid of the ARAGORN server (Laslett, et al., *Nucleic Acids Res*, 32:11-16 (2004)) and the Clustal X program (Larkin, et al., *Bioinformatics*, 23:2947-2948 (2007)). A few allo-tRNA sequences with a serine anticodon were found in tRNA gene clusters of unknown bacteriophages in the Macroalgal surface ecosystem from Botany Bay, Sydney, Australia. The secondary structures of all tRNAs were manually predicted in the clusters and found (8/4) tRNA$^{Ser}$ and (8/4) tRNA$^{His}$ species. Next, a BLAST search of all metagenomic assembled sequence data was performed in IMG and NCBI for more (8/4) tRNA$^{Ser}$ and (8/4) tRNA$^{His}$ sequences. Some allo-tRNA sequences missing nucleotides 9-11 were found in some metatranscriptome reads of the Harvard Forest Long Term Ecological Research site (Petersham, Mass., USA) and from the Peat soil microbial communities from Weissenstadt, Germany. The secondary structures of these tRNAs were predicted BLAST searches of all metatranscriptome datasets were performed in IMG for more read sequences containing even a part of these tRNAs.

Results

The tRNA$^{Sec}$ search pipeline used previously (Mukai, et al., *Angew Chem Int Ed Engl,* 55:5337-5341 (2016)) produced tRNA sequences with high similarity to the tRNA$^{Sec}$ covariance model, but they were considered false positives after further curation. Upon re-analysis a series of tRNA sequences with non-canonical secondary structures were identified. These tRNA genes were classified into two groups: "allo-tRNA" (named after their irregular appearance) and "SelC*tRNA$^{Cys}$" (FIG. 6A-6F). While allo-tRNA genes belong to bacteria from Clostridia, Proteobacteria, and Acidobacteria, selC*genes were found in anaerobic bacteria from the phyla Firmicutes, Thermodesulfobacteria, Nitrospirae, and Proteobacteria. Both tRNA groups are structurally similar to tRNA$^{Sec}$ as they have a long V-arm and longer anticodon and acceptor stems compared to canonical tRNAs (FIGS. 6A-6F). Moreover, the D-stem-loop of allo-tRNAs resembles that of tRNA$^{Sec}$ with its long stem and tetraloop (FIG. 6A-6B). The most striking feature of allo-tRNAs is their 8/4 or 9/3 composition of the 12-bp amino-acid acceptor branch (FIG. 6A-6B), whereas SelC*tRNA$^{Cys}$ species of certain δ-proteobacteria may have a modified 8/4 structure with a bulge base A51a (FIG. 6C).

The presence of a long V-arm and the identity of the discriminator base (G73 or U73) in most allo-tRNAs indicate that these tRNAs may be serine tRNA isoacceptors, since these unique elements are essential for aminoacylation by seryl-tRNA synthetase (SerRS) (Wu, et al., *Nucleic Acids Res,* 21:5589-5594 (1993); Suzuki, et al., *EMBO J,* 16:1122-1134 (1997); Himeno, et al., *Nucleic Acids Res,* 18:6815-6819 (1990); Tukalo, et al., *Biopolymers and Cell,* 29:311-323 (2013); Biou, et al., *Science,* 263:1404-1410 (1994)). In addition, SerRS also recognizes not only (7/5) tRNA$^{Ser}$ but also (8/5, 9/4, and 8/4) tRNA$^{Sec}$ and even a variant of tRNA$^{Sec}$ with a 9/3 structure (Mizutani, et al., *Mol Biol Rep,* 25:211-216 (1998)). SelC*tRNAs were named after the selC gene, which encodes tRNA$^{Sec}$ in *E. coli*. SelC*tRNA$^{Cys}$ isoacceptors have an U73 discriminator base and cysteine GCA or opal UCA anticodons (FIG. 6C). U73 and GCA are the most important identity elements for CysRS (Pallanck, et al., *J Biol Chem,* 267:7221-7223 (1992); Komatsoulis, et al., *Biochemistry,* 32:7435-7444 (1993)), and certain CysRS forms are known to cysteinylate tRNA$^{Cys}_{UCA}$ (Turanov, et al., *Science,* 323:259-261 (2009)).

Next metagenomic contigs containing allo-tRNA genes were analyzed and tRNA$^{Ser}$ and tRNA$^{His}$ species with 8/4 structure (FIG. 6A-6E) and polycistrons of irregular tRNAs with 7/5 and 8/4 structures were discovered. (8/4) tRNA$^{Ser}$ was found in bacteriophages, proteobacteria, and bovine rumen bacteria such as Clostridia, while (8/4) tRNA$^{His}$ was found in bacteriophages and an α-proteobac-terium. Interestingly, (8/4) tRNA$^{Ser}$ and (8/4) tRNA$^{His}$ genes coexist in the same tRNA gene clusters of α-proteobacterial phages. The (8/4) tRNA$^{Ser}$ species are included in the (8/4) allo-tRNA group or in the Y20-lacking (8/4) allo-tRNA derivative group. The (8/4) tRNA$^{His}$ species lack G-1 and have A73 (or U73), which is characteristic of the (7/5) tRNA$^{His}$ species of a group of α-proteobacteria (41). The polycistrons of irregular tRNAs are discussed below.

Example 2: tRNA have Extensive Structural Plasticity

The structural features that enable these tRNAs to be folded into a standardized tertiary tRNA structure were examined. In most cases, the cloverleaf-like secondary structure of (8/4) and (9/3) tRNAs could not be predicted properly by any of the commonly used RNA folding prediction programs (Laslett, et al., *Nucleic Acids Res,* 32:11-16 (2004)). Therefore, the cloverleaf structures of (8/4 and 9/3) allo-tRNAs and SelC*tRNAs were manually curated and predicted using structural alignments guided by tRNA$^{Sec}$ crystal structures, an approach typically used for predicting tRNA$^{Sec}$ cloverleaf structures (Itoh, et al., *Nucleic Acids Res,* 41:6729-6738 (2013)).

Allo-tRNAs are generally similar to archaeal and eukaryotic (9/4) tRNA$^{Sec}$ (Hubert, et al., *RNA,* 4:1029-1033 (1998)), except for the lengths of acceptor- and T-stems. A more detailed analysis of the secondary structure shows that a few nucleotides at junctions may be involved in the tertiary structures of allo-tRNAs. The base at position 48 may be involved in the V-stem structure in most cases (FIG. 1B), similar to (9/4) tRNA$^{Sec}$ (Hubert, et al., *RNA,* 4:1029-1033 (1998)). Some (8/4 and 9/3) allo-tRNA and (8/4) tRNA$^{Ser}$ species lack the nucleotide at position 10 (FIG. 6A-6B) and may require, at least, one or two linker nucleotides between the acceptor arm and D-arm. Such alternative folding was observed in the crystal structure of a pyrrolysine tRNA (tRNA$^{Pyl}$), where the nucleotides at positions 25 and 44a form a non-WC base pair (Ambrogelly, et al., *Proc Natl Acad Sci USA,* 104:3141-3146 (2007); Nozawa, et al., *Nature,* 457:1163-1167 (2009); Mustoe, et al., *J Am Chem Soc,* 137:3592-3599 (2015)). Thus, tRNAs missing N10 might form similar tertiary arrangement (FIG. 6A-6B). *Rubrobacter* tRNA$^{Sec}$ also lacks nucleotides at positions 9 and 10 and has U44a (FIG. 6E). The unpaired nucleotide at position 45 found in some (9/3) allo-tRNAs (FIG. 6B) might fill the space between the L-shaped tRNA body and the V-stem, which is occupied by the G45-A48 pair in human tRNA$^{Sec}$ (Itoh, et al., *Nucleic Acids Res,* 37:6259-6268 (2009)).

The selC*tRNA$^{Cys}$ species of certain δ-proteobacteria (FIG. 6C) can in theory have three alternative cloverleaf structures, two of which are 7/5. However, the 8/4 structure with a bulge nucleotide at position 51a (FIG. 6E) may be more energetically favorable, since the other two possible structures, 7/5 and 7/5 with the bulge nucleotide, eliminate two and five hydrogen bonds, respectively. In the 8/4 structure, residues at positions 9 and 10 are missing, which might be compensated by G45 (FIG. 6C), as discussed above. In contrast, the structure of the D-stem-loop is more difficult to predict since WC and G:U wobble base pairing patterns leads to a sterically unfavorable tri-loop. The D-stem-loop may have either a triloop hairpin structure or a larger loop with a shorter stem. Thus, the hypothetical three successive WC and G:U wobble base pairs between bases at positions 13-15 and 20a-23 were indicated by dashed lines on the predicted cloverleaf structure (FIG. 6C). Actually, GGG-triloop is not observed in the D-stem-loop of *Archaeoglobus fulgidus* tRNA$^{Cys}$ crystal structure (Fukunaga, et al., *Nat Struct Mol Biol,* 14:272-279 (2007)), while a CGG-triloop may form in the D-stem-loop of *Candidatus Methanomassiliicoccus* intestinalis tRNA$^{Pyl}$ (Borrel, et al., *Archaea,* 374146 (2014)).

Example 3: Allo-tRNAs have Diverse Anticodon Sequences

Although the (8/4) tRNA$^{Ser}$ species have anticodons corresponding to serine codons, most of allo-tRNA species have non-serine anticodons (FIG. 18B). In fact, their anticodon sequences are highly diverse and correspond to 35 distinct codons (FIG. 18B). Among them, the UAU, GCG, and GUC anticodons corresponding to the AUA isoleucine (Ile) codon, the CGC arginine (Arg) codon, and the GAC aspartic acid (Asp) codon, respectively, are predominant, whereas (8/4) allo-tRNAs with anticodons corresponding to phenylalanine (Phe), valine (Val), His, and lysine (Lys) codons were only found once in the examined metagenomic dataset (FIG. 18B). In contrast, the (9/3) allo-tRNA species have anticodons corresponding to the AGA/AGG Arg codons, the UUA/UUG/CUA/CUG leucine (Leu) codons, and the UAA stop codon (FIG. 18B).

Example 4: Allo-tRNAs are Fully Compatible with a Bacterial Translation System

Materials and Methods

Plasmids and *E. coli* Strains

Plasmid pGFiB (Normanly, et al., *Proc Natl Acad Sci USA*, 83:6548-6552 (1986)) was used for cloning the *Desulfococcus biacutus* selC*tRNA$^{Cys}$ sequence and its variants using EcoRI and BamHI sites. The arabinose promoter cassette of pBAD-myc-HisA (Invitrogen) was previously transplanted into pRSFDuet1 (Haruna, et al., *Nucleic Acids Res*, 42:9976-9983 (2014)) to make pBAD-RSF. The open reading frame (ORF) of the Desulfomonile tiedjei cysS gene was cloned from the genomic DNA obtained from DSMZ (German Collection of Microorganisms and Cell Cultures, Braunschweig, Germany) and fused directly downstream of the kan marker gene of pBAD-RSF with a weak Shine-Dalgarno sequence of the *E. coli* prfA gene [TTTA-CAGGGTGCATTTACGCCT (SEQ ID NO:64)]. The cloned cysS gene was mutated using Infusion (Clontech) to make the cysS variant genes. The multiple cloning site (MCS) of pBAD-RSF was replaced by the MCS and the rrnC terminator sequence of pGFiB with a modification of BamHI site to BglII site using Infusion to make pBAD-RSFS. Allo-tRNA sequences were cloned into the MCS of pBAD-RSFS using EcoRI and BglII sites. Plasmid pBAD-sfGFP (Fan, et al., *Nucleic Acids Res*, 43:e156 (2015)) was mutated using Infusion to make the sfGFP variant genes. Plasmid pACYC184 was mutated using Infusion to make the cat variant genes. The ORF of the cat marker gene in pACYC184 was replaced using Infusion with the ORF of *D. tiedjei* selD gene cloned from the genomic DNA to make pACYC-DtselD. The *E. coli* strain DH10B was used for allo-tRNA experiments. The *E. coli* WL400 (MC4100 selD204:cat+) (Leinfelder, et al., *Proc Natl Acad Sci USA*, 87:543-547 (1990)) cells harboring pACYC-DtselD corresponded to *E. coli* ΔselD with *D. tiedjei* selD.

Mass Analysis sfGFP variants encoding a C-terminal His-tag were purified using nickel-nitrilotriacetic acid agarose (QIAGEN). Purified sfGFP solutions were concentrated by centrifugation using Amicon Ultra 10k (Merck Millipore) and subjected to peptide mass fingerprinting (PMF) analysis by liquid chromatography coupled to tandem mass spectrometry (LC-MS/MS) performed by the Keck Foundation Biotechnology Resource Laboratory (Yale University).

tRNA Sequences for FIGS. 7A-7E

FIG. 7A (SEQ ID NO: 46)
GGAGGGCAUCUUCAGUAGGUACUGGACGCCGUCUGAGAAACGGUUGCAGG

GUCUUAGUCAGCUCUGGGAGUUCGACUCUCCUGCCCUCCG

FIG. 7B (SEQ ID NO: 47)
GGAGGGGAACUUCUAUCUGGUGAUAGACGGGAACUUAAAAUUCCUUGAAAU

GCCUCGCCGCAUUGGGUUCGAUUCCCUUCCCCUCCGCCA

FIG. 7C (SEQ ID NO: 48)
GGGGAGUAAUGUGCGGUGGUCCGCACCGUAGUCUGCGAAACUAUUGGUUCG

UUUAUACGAAUGGGGUUCAAUUCCCCUGCUCUCCACCA

FIG. 7D (SEQ ID NO: 49)
GGGGUGGGGUUCCGGCUGGUGCCGGUCGCGGGCUUUAAACCCGUCAGGACG

CUGCGACGCGUAAGGUUCGAUUCCUCCCCACUCCG

FIG. 7E (SEQ ID NO: 50)
GGGCGGGGUUCCGUCUGGUGACGGUCGCGGGCUUUAAACCCGUCAGGACG

CUGUGCAGGCGUUAGGUUCGAUUCCUCCCCGUCCA

Results

To investigate whether allo-tRNAs are active translational adaptors, super-folder green fluorescent protein (sfGFP) were used as a reporter in *E. coli*. The Ser codon at position 2 of wild-type (WT) sfGFP was mutated to either CUC or UUA and the resulting mutants were expressed together with *Silvibacterium bohemicum* (8/4) allo-tRNA$_{GAG}$ (Llado, et al., *Syst Appl Microbiol*, 39:14-19 (2016)) or (9/3) allo-tRNA$_{UAA}$ in *E. coli* (FIG. 7A-7B). Interestingly, both tRNAs efficiently inserted Ser in response to the CUC and UUA Leu codons, respectively, as confirmed by the liquid chromatography (LC) coupled with tandem mass spectrometry (LC-MS/MS) and peptide mass fingerprinting (PMF) analyses of purified sfGFP. Furthermore, induction of the allo-tRNA expression from the araBAD promoter led to severe cell growth arrest and ultimately to cell death, which is possibly caused by global mis-incorporation of Ser at Leu codons in the *E. coli* proteome.

(8/4) and (9/3) allo-tRNAs with a G3:U70 wobble pair, the most important structural element for aminoacylation by alanyl-tRNA synthetase (AlaRS) were also identified (Hou, et al., *Nature*, 333:140-145 (1988); McClain, et al., *Science*, 240:793-796 (1988); Naganuma, et al., *Nature*, 510:507-511 (2014)). To test whether these allo-tRNAs can be acylated by AlaRS in vivo, three examples were chosen, and their wild-type anticodons (GCG and UUA) replaced with the amber anticodon CUA (FIG. 7C-7E) and mutated the Ser2 codon of sfGFP to an amber stop codon. The mutant sfGFP was then co-expressed with one of the three allo-tRNAs in *E. coli*. The three amber suppressor tRNAs efficiently translated the amber codon, leading to expression of the full-length sfGFP variant, and producing as much fluorescence as did cells expressing WT sfGFP (FIG. 7F). The sfGFP variants were then purified, and the identity of the amino acid incorporated at position 2 was revealed by LC-MS/MS and PMF analyses (FIG. 3D). The amber codon was mainly translated as Ala and Ser, as judged by the probability scores. Insertion of Asn, Gln, Lys, and possibly Cys, Ile, and Glu was also detected. Only the allo-tRNA 9/3-2 variant inserted Ser, probably due to its discriminator base G73.

To further confirm the allo-tRNA-mediated incorporation of Ala and Ser, the chloramphenicol (Cm) acetyltransferase (CAT) gene was used as a reporter since it contains an important catalytic Ser residue at position 146 that only tolerates substitutions with Ala (Lewendon, et al., *Biochemistry*, 29:2075-2080 (1990)). Replacing Ser146 with Asn, Gln, or Lys produced an inactive CAT, while the Ser146Ala CAT mutant retained activity. Then, an amber codon was substituted for Ser146 and the resulting CAT variant was expressed with any of the three allo-tRNA variants. The allo-tRNAs suppressed the amber codon and conferred Cm resistance to the *E. coli* cells with the Ser146TAG cat gene (FIG. 7G). However, only the allo-tRNA 9/3-2 variant conferred the resistance at a Cm concentration of 100 μg/mL, which corroborates that only this tRNA incorporates Ser. Together, these results clearly demonstrated that these allo-tRNA (both 8/4 and 9/3) sequences were properly folded, processed, aminoacylated, and delivered to the ribosomes by EF-Tu in *E. coli*.

Example 5: Active and Inactive Allo-tRNAs are Associated with Toxin-Antitoxin Systems Materials and Methods In Vitro Aminoacylation with *E. coli* Aminoacyl-tRNA Synthetases

*E. coli* cells harboring expression plasmids for *E. coli* threonyl-tRNA synthetase (ThrRS), glycyl-tRNA synthetase (GlyRS) (glyQ and glyS subunits), and histidyl-tRNA synthetase (HisRS) were obtained from the ASKA collections (Kitagawa, et al., (*A Complete Set of E. coli K-12 ORF Archive*): Unique Resources for Biological Research. *DNA Research*, 12:291-299 (2006)). Overnight-night cultures for each protein were used to inoculate 1 L of fresh LB media containing chloramphenicol. Cells were grown to an A600 of 0.6 and protein overexpression was induced with 0.1 mM IPTG overnight at 25° C. Cells were harvested by centrifugation and the resulting pellet was lysed with buffer containing 50 mM Tris (pH 8), 300 mM NaCl, and protease inhibitor cocktail tablets (cOmplete, Roche). Lysed cells were then centrifuged at 4° C. for 45 min at 18,000×g. The lysate was loaded on a TALON metal affinity resin (Clontech), and the protein was eluted with varying concentrations of imidazole. The protein-containing fractions were pooled and stored in buffer containing 50 mM HEPES (pH 7.3) and 150 mM NaCl. tRNA genes were cloned into pUC18 using Gibson Assembly (New England Biolabs), and the tRNAs were prepared using in vitro transcription as previously described (Ahel, et al., *J. Biol. Chem.*, 277: 34743-34748 (2002)). Aminoacylation assays were carried out with 5 μM tRNA and 0.5 μM tRNA synthetase in buffer containing 50 mM Hepes (pH 7.3), 4 mM ATP, 10 mM MgCl$_2$, 0.1 mg/mL BSA, 1 mM dithiothreitol, and 20 μM [$^{14}$C]His (590 cpm/pmol) (PerkinElmer), 100 μM [$^{14}$C]Gly (146 cpm/pmol) (PerkinElmer) or 25 μM [$^{3}$H]Thr (7779 cpm/mol) (American Radiolabeled Chemicals). Reactions were incubated at 37° C. and after 15 min, 10 μL of the reaction mixture was spotted on Whatman 3MM filters pre-soaked with 5% trichloroacetic acid (TCA). Filters were washed three times with 5% TCA, and the remaining radioactivity was quantified using a scintillation counter.

tRNA Sequences for FIGS. 8C-8I

FIG. 8C (SEQ ID NO: 51)
GGAGGGCGUCUCGCUGGCGCGAGAAGCGGUCUUAUAAACCGCAAAUGUCU

UGACGGGCAUUGGGGUCCGAUCCCCCGCCCUCCG

FIG. 8D (SEQ ID NO: 52)
GGAGGGCGACAGGCCGGUGCCUGGAGCCGACUUAUAAUCGGCGAAUCCUU

CGCAGGGGAUAGCGGUUCGACUCCGCCGCCCUCCG

FIG. 8E (SEQ ID NO: 53)
GGAGGGAGAUCCCGGCUGGUGCCUGGAGCCGACUUAUAAUCGGUCGAUCCC

GUUCCGGGGAUCGCGGUUCAAAUCCGCCUCCCUCCGCCA

FIG. 8F (SEQ ID NO: 54)
GGAGGGUGUCACGCUGGUGCGUGGGCCGGUCUUAUAAACCGGAGAUUCCUU

GCCGGGAAUGGAGUUCGAUUCUCCCACCCUCCGCCA

FIG. 8G (SEQ ID NO: 55)
GGGGGACACAACUCGUGGGUGCGAGAGUUGGUCUUAUAAACCAAUGGCGUC

GUUGCAGCGACGCAAGGUUCAAUUCCUUUGUCCCCCG

FIG. 8H (SEQ ID NO: 56)
GGAGGGUGUCUAGCUGGUGCUAGGACCGGCCUUAUAAGCCGGAUUACCUUC

CACGGGUAUUGGGGUCCGAUCCCCCCACCCUCCGCCA

FIG. 9A (SEQ ID NO: 57)
GGAGGGGAACUUCUAUCUGGUGAUAGACGGGAACUCUAAAUUCCUUGAAAU

GCCUCGCCGCAUUGGGUUCGAUUCCCUUCCCUCCGCCA

Results

Although the *S. bohemicum* allo-tRNA$^{Ser}_{GAG}$ gene is in a metabolic gene cluster, the *Edaphobacter* strain C40 has an allo-tRNA$_{UAU}$u pseudogene overlapping with the ORF of a transposon-related protein. In soil and sediment metagenomic sequences, allo-tRNA genes are often found in the vicinity of a variety of toxin-antitoxin systems (Wen, et al., *Pathog Dis*, 70:240-249 (2014)). Among others, allo-tRNA$_{UAU}$ species compose the most abundant allo-tRNA group (FIG. 18B). Interestingly, they have cloverleaf structures slightly different from that of the standard allo-tRNA$^{Ser}$, stem-destabilizing mutations as in the *Edaphobacter* strain C40 allo-tRNA$_{UAU}$, and a variety of possible five-stem-junction structures (FIGS. 8A-8H). To assess their ability to serve in translation, six allo-tRNA$_{UAU}$ species with a potential Ser identity were converted to allo-tRNA$_{CUA}$ and examined their activity in *E. coli* using the CAT (Ser146TAG) reporter. However, none of the six variants conferred Cm resistance in response to the amber codon, and two of them caused cell death (FIG. 8I). Thus, it is possible that most of the allo-tRNA$_{UAU}$ species are not used for translation and instead may be associated with transposable elements or toxin-antitoxin systems.

In addition to 9/3-2 (in FIG. 7G), the amber suppressor variants of 8/4-1 and 9/3-1 allo-tRNAs translated the amber codon in *E. coli*. The 9/3-1 (CUA) is corresponding to allo-tRNA$^{UTu1}$ (in FIG. 9A).

>8/4-1 (CUA)
(SEQ ID NO: 61)
GGAGGGCATCTTCAGTAGGTACTGGACGCCGTCTCTAAAACGGTTGCAGG

GTCTTAGTCAGCTCTGGGAGTTCGACTCTCCTGCCCTCCGCCA

>9/3-2
(SEQ ID NO: 62)
GGGGTGGGGTTCCGGCTGGTGCCGGTCGCGGGCTCTAAACCCGTCAGGAC

GCTGCGACGCGTAAGGTTCGATTCCTCCCCACTCCGCCA

>9/3-1 (CUA) equals to allo-tRNAUTu1
(SEQ ID NO: 31)
GGAGGGGAACTTCTATCTGGTGATAGACGGGAACTCTAAATTCCTTGAAA

TGCCTCGCCGCATTGGGTTCGATTCCCTTCCCCTCCGCCA

Polycistrons formed by allo-tRNA-like sequences and other irregular tRNA sequences were discovered in metatranscriptome sequences of two forest/peat soil metatranscriptome projects. Both might be nonsense or missense suppressor tRNA, and may also be associated with a toxin-antitoxin system. Among the polycistronic tRNA groups (tRNA0, tRNA1, and tRNA2), 8/4 structures were predicted for tRNA$_{GGU}$ species containing a G-1 and a group of tRNAs containing an extra-loop (E-loop).

Three tRNA1 species from the polycistrons were examined; a (8/4) tRNA1 with an E-loop and two tRNA1 with G-1, one of which has an 8/4 structure. The two G-1 tRNA1 species with GGU anticodon were thought to be substrates for histidyl-tRNA synthetase (HisRS), whereas the E-loop tRNA1 with U73 and GCU anticodon were thought to be a poor substrate for *E. coli* threonyl-tRNA synthetase (ThrRS) and/or glycyl-tRNA synthetase (GlyRS). The three tRNAs were transcribed in vitro and tested for aminoacylation with *E. coli* HisRS, GlyRS, and ThrRS. The two G-1 tRNA1 species were aminoacylated by *E. coli* HisRS, even more efficiently than *E. coli* tRNA$^{His}$, despite the Thr GGU anticodon. The GUG triplet at positions 35-37 (but not the anticodon positions 34-36 in tRNA$^{His}$) of the two G-1 tRNA1 species might have recognized by HisRS (Tukalo, et al., *Biopolymers and Cell*, 29:311-323 (2013); Biou, et al., *Science*, 263:1404-1410 (1994); Mizutani, et al., *Mol Biol Rep*, 25:211-216 (1998)). Interestingly, the two G-1 tRNA1 species did not insert His in response to the ACC Thr codon at position 2 in a sfGFP variant gene in *E. coli*. Thus, G-1 tRNA1 species may be charged, but not used for translation. In contrast, the E-loop tRNA1 was not aminoacylated either by *E. coli* GlyRS or ThrRS in vitro. However, it is possible that the organisms encoding these irregular tRNAs encode a GlyRS and ThrRS capable of charging them. Alternatively, another aminoacyl-tRNA synthetase or homolog might charge them in a non-canonical manner, similar to the aminoacylation of a tRNA-like small RNA (tRNA$^{Other}$) by a complex of class I and II lysyl-tRNA synthetases in *Bacillus cereus* (Ataide, et al., *EMBO Rep*, 6:742-747 (2005)).

Example 6: selC*tRNA$^{Cys}$ Functions in Translation

Materials and Methods
Identification and Analysis of Protein Sequences
BLASTp search were preformed of all genomic and metagenomic protein sequence data in the IMG and NCBI systems in order to identify cysS, selA, selB and selD genes and their homologs. To manually enlarge a metagenomic contig containing a selC*gene from Wastewater microbial communities from Syncrude, Ft. McMurray, Alberta—Microbes from Suncor tailings pond 6 2012TP6_6, BLAST searches of the raw data (SRR943333) were performed using NCBI short read archive (SRA) BLAST. Likewise, the amino-acid sequences for the selB* and cysS* genes of *Desulfonema limicola* Jadebusen DSM 2076 were identified by filling the gaps of the partially-sequenced genome using the raw data (SRR058919) in the NCBI SRA database. Sequence alignments and phylogenetic trees (Bootstrap N-J Tree) were made using Clustal X 2.1. The BoxShade Server was also used for the alignments.

selD Reporter Assay
WL400 [pACYC-DtselD] cells were transformed with pGFiB or one of the tRNA-expressing plasmids together with pBAD-RSF or one of the *D. tiedjei* cysS-expressing plasmids. Their overnight cultures were spotted onto LB agar plates supplemented with 1 µM Na$_2$MoO$_4$, 1 µM Na$_2$SeO$_3$, 50 mM sodium formate, 100 µg/mL carbenicillin, 30 µg/mL kanamycin, 100 µg/mL spectinomycin, and 0.1% 1-arabinose and grown anaerobically at 37° C. overnight. These plates were overlaid under anaerobic condition with a 0.75% top agar containing 1 mg/mL benzyl viologen, 250 mM sodium formate, and 25 mM KH$_2$PO$_4$ (pH 7.0). Within a few seconds or less than a minute, spots on the plates became dark or light purple, depending on the formate dehydrogenase activity of cells.

In Vitro Cysteinylation Assay
*D. tiedjei* selC*tRNA$^{Cys}$ was prepared by T7 RNA polymerase transcription, purified in preparative 10% urea PAGE and electroeluted. The tRNA was refolded by heating at 95° C. for 3 min followed by cooling to 65° C. at a rate of 0.5° C./s. During a 3 min hold at 65° C., MgCl$_2$ was added to a final concentration of 10 mM. The refolding was completed by cooling to 30° C. at 0.2° C./s. tRNA was radiolabelled at the 3'-end using [α-$^{32}$P]ATP and *E. coli* CCA-adding enzyme as previously described (Ledoux, et al., *Methods*, 44:74-80 (2008)). *D. tiedjei* cysteinyl-tRNA synthetase (CysRS) with a His-tag was recombinantly obtained using *E. coli* Aminoacylation reactions were performed in [50 mM HEPES-NaOH, pH 7.2, 50 mM KCl, 10 mM MgCl$_2$, 10 mM ATP, 1 mM cysteine, 1 mM DTT]. At the indicated time points, 10 µL aliquots were removed and digested by nuclease P1. 1 µL of the quenched reaction was spotted on PEI cellulose plates. [$^{32}$P]AMP and [$^{32}$P]AMP-Cys were separated with 100 mM ammonium acetate-5% acetic acid. The plates were analyzed using a PhosphorImager.

Results
selC*genes were found in isolated genomic sequences of Clostridia, Bacilli, Thermodesulfobacteria, Thermodesulfovibrio, δ-proteobacteria, a composite genome of Smithella, and a few metagenomic contigs, probably derived from Nitrospirae or δ-proteobacteria. Interestingly, selC*tRNA$^{Cys}$ species belonging to a particular phylum or class show a unique conserved secondary arrangement. Furthermore, complete selenocysteine-inserting apparatus (consisting of the selA, selB, selC and selD genes) was identified in all selC*-containing genomes, whereas incomplete selenocysteine systems were also found in the metagenomic contigs. Strikingly, in two δ-proteobacterial subgroups, Syntrophobacterales and Desulfobacterales, a second copy of selB, referred to here as selB*, was found downstream of the selC*genes. Because selB encodes the Sec-tRNA$^{Sec}$-specific elongation factor, it is possible that selC*tRNA$^{Cys}$ mimics tRNA$^{Sec}$, both structurally and functionally, and is recognized by SelB*.

In addition to selB*, in a subgroup of Desulfobacterales, an additional copy of the cysS gene was discovered, which encodes CysRS, downstream of the selB* genes (FIG. 5A). This second copy, named cysS*, lacks the region that encodes the anticodon binding domain (ABD) of CysRS. Intriguingly, genomes with cysS* genes appear to always encode selC*tRNA$^{Cys}$ species containing an A1:U72 base pair and an opal anticodon (UCA).

To assess the ability of selC*tRNA$^{Cys}_{UCA}$ to suppress opal codons, a reporter system was developed using the Desulfomonile tiedjei (Dt) selD gene, which has a naturally occurring UGA selenocysteine codon at position 15. The Dt selD gene was expressed together with *Desulfococcus biacutus* (Db) tRNA$^{Cys}_{UCA}$ in an *E. coli* ΔselD strain. Only when the UGA codon is translated as either Sec or Cys, functional selenophosphate synthase (SelD) is produced. SelD then catalyzes the synthesis of the selenophosphate necessary for the conversion of Ser-tRNA$^{Sec}$ to Sec-tRNA$^{Sec}$ by selenocysteine synthase (SelA), which allows synthesis of selenoproteins. The overall suppression efficiency of Db tRNA$^{Cys}_{UCA}$ can then be evaluated by monitoring the activity of the Sec-containing formate dehydrogenase H (FDH$_H$) through the FDH$_H$-catalyzed reduction of benzyl viologen that results in a purple dye (Lacourciere, et al., *Proc Natl Acad Sci USA*, 99:9150-9153 (2002)). Expression of Db CysRS* as well as two other CysRS* did not lead to suppression of the selD opal codon.

Because Dt CysRS efficiently aminoacylated Dt selC*tRNA$^{Cys}_{GCA}$ in vitro, a series of Dt CysRS variants were created that may recapitulate the activity of CysRS*. Because the main difference between Db CysRS* and Dt CysRS is the presence of an ABD, Dt CysRS mutant lacking the ABD (Dt CysRS ΔABD) was created. However, Dt CysRS ΔABD did not efficiently aminoacylate Db tRNA$^{Cys}_{UCA}$ as indicated by the light purple color (FIG. 5E). Multiple sequence alignments of canonical CysRS and CysRS* revealed that a highly conserved and critical Gly residue of the canonical CysRS CP1 domain (Liu, et al., *RNA*, 18:213-221 (2012)) was not conserved in CysRS*. This Gly is responsible for accurate recognition of first base pair of tRNA$^{Cys}$ acceptor stem (Liu, et al., *RNA*, 18:213-221 (2012)), which is typically G1:C72. In Dt CysRS, this Gly residue is part of the "MSGA" motif, whereas the "MSGA" is mutated to "PTVS" in Db CysRS*.

Therefore, to test the role of this motif in the activity of Dt CysRS, the "MSGA" sequence was mutated to "PTVS" to construct the Dt CysRS PTVS mutant. Expression of Dt CysRS PTVS and Dt selD in the *E. coli* ΔselD strain produced a dark purple color indicating efficient aminoacylation of Db tRNA$^{Cys}_{UCA}$. Furthermore, a Dt CysRS variant containing the ΔABD and PTVS (ΔABD/PTVS) was more efficient than the Dt CysRS PTVS as confirmed by the saturated purple color. These results show that CysRS* may have evolved to specifically aminoacylate selC*tRNA$^{Cys}_{UCA}$ species with A1:U72. This hypothesis was explored by using a Db tRNA$^{Cys}_{UCA}$ variant in which the A1:U72 base pair was mutated to G1:C72. The CysRS ΔABD/PTVS was unable to efficiently aminoacylate the G1:C72 Db tRNA$^{Cys}_{UCA}$ mutant. Lastly, the 8/4 conformation of Db tRNA$^{Cys}_{UCA}$ was experimentally confirmed by employing a previously developed method used to confirm the 9/4 structure of eukaryotic tRNA$^{Sec}$ (Mizutani, et al., *FEBS Lett*, 466:359-362 (2000). The 8-bp acceptor stem was important for efficient opal suppression, whereas the bulge structure was dispensable.

In sum, a large number of tRNAs with new secondary structures have been identified. The function of these tRNAs is still uncharted: some of them may be involved in the translation of Ser and His codons, in opal suppression or recoding with Cys, and in mis-translation of diverse codons with Ser or Ala; others may have non-translational roles. The (8/4) tRNACys species may have co-evolved with its dedicated aminoacyl-tRNA synthetase and elongation factor. Future studies should elucidate the biological functions of these non-canonical tRNAs and protein components, and structural studies of these tRNAs will add to the knowledge of the structural plasticity of tRNA.

Example 7: Allo-tRNA can Incorporate SEC in a Nascent Protein

Selenocysteine (Sec), the 21$^{st}$ amino acid, is a fascinating building block of recombinant proteins (Metanis, et al., *Angew Chem Int Ed Engl* (2017)), because Sec is more active and oxygen-resistant than cysteine (Cys) (Reich, et al., *ACS Chem Biol*, 11:821-841 (2016); Marques, et al., *Nat Chem Biol*, 13, 544-550 (2017)) and is chemically modifiable (Liu, et al., *J Am Chem Soc*, 139, 3430-3437 (2017); Rakauskaite, et al., *Chem Commun (Camb)*, 51, 8245-8248 (2015)), and because a diselenide bond is more stable than a disulfide bond in proteins (Arai, et al., *Angew Chem Int Ed Engl*, 56, 5522-5526 (2017)). Furthermore, Sec residues can be chemically converted to another side chain via dehydroalanine intermediate (Liu, et al., *J Am Chem Soc*, 139, 3430-3437 (2017); Wright, et al., *Science*, 354 (6312), aag1465 (2016)). Recent advances in the genetic code expansion field allows one to site-specifically insert Sec into recombinant proteins in response to the amber UAG codon in *E. coli* via the elongation factor Tu (EF-Tu), without relying on the dedicated elongation factor (SelB) and Sec-insertion sequence (SECIS element) (Aldag, et al., *Angew Chem Int Ed Engl*, 52:1441-1445 (2013); Haruna, et al., *Nucleic Acids Res*, 42:9976-9983 (2014); Thyer, et al., *J Am Chem Soc*, 137:46-49 (2015); Miller, et al., *FEBS Lett*, 589:2194-2199 (2015); Fan, et al., *ACS Synth Biol*. (2017)). Although wildtype tRNA$^{Sec}$ species have antideterminants against EF-Tu (Rudinger, et al., *EMBO J*, 15:650-657 (1996)), a few point mutations in the acceptor stem and the T-stem of tRNA$^{Sec}$ are sufficient to remove these antideterminants (Thyer, et al., *J Am Chem Soc*, 137:46-49 (2015); Rudinger, et al., *EMBO J*, 15:650-657 (1996)). Thus, EF-Tu-compatible variants of *E. coli* tRNA$^{Sec}$ enabled the production of bacterial and human selenoproteins using *E. coli* cells (Aldag, et al., *Angew Chem Int Ed Engl*, 52:1441-1445 (2013); Haruna, et al., *Nucleic Acids Res*, 42:9976-9983 (2014); Thyer, et al., *J Am Chem Soc*, 137:46-49 (2015); Miller, et al., *FEBS Lett*, 589:2194-2199 (2015); Fan, et al., ACS Synth Biol. (2017)). However, this Sec-insertion technology has a room for improvement in as far as product yield and the extent of Sec insertion is concerned.

Materials and Methods

Escherichia coli Strains

The ΔselABC ΔfdhF ME6 strain of Escherichia coli was reported previously (Mukai, et al., Angew Chem Int Ed Engl, 55, 5337-5341 (2016)). E. coli HST08 strain (Clontech) was mainly used for plasmid construction.

Construction of Plasmids

The native E. coli fdhF gene was cloned into the pACYC184 plasmid by replacing the chloramphenicol acetyltransferase (cat) gene in a similar manner with a reference (Thyer, et al., J Am Chem Soc, 137:46-49 (2015) The UGA codon and four cysteine codons of fdhF were then mutated to UAG or AGC codons by Infusion (Clontech). All tRNA sequences were cloned between the EcoRI and BglII sites into the pBAD-RSFS plasmid (Mukai, et al., Nucleic Acids Res, 45:2776-2785 (2017)). The ORF of Aeromonas salmonicida subsp. pectinolytica 34mel SelA was amplified by PCR from the genomic DNA and cloned together with the EM7 promoter (Thyer, et al., J Am Chem Soc, 137:46-49 (2015)) immediately downstream of the kan marker gene (Mukai, et al., Nucleic Acids Res, 45:2776-2785 (2017)) in pBAD-RSFS carrying allo-tRNA$^{UTu}$ to produce pSecUAG-A.

Sequence

>allo-tRNA$^{UTu}$ (SEQ ID NO: 31)
GGAGGGGAACTTCTATCTGGTGATAGACGGGAACTCTAAATTCCTTGAAA

TGCCTCGCCGCATTGGGTTCGATTCCCTTCCCCTCCGCCA,

In Vivo FDH$_H$ Activity Assay in E. coli

E. coli ME6 strain was transformed with indicated plasmids. The concentrations of the antibiotics were 5 or 7 μg/ml for tetracycline, 30 μg/ml for kanamycin, 34 μg/ml for chloramphenicol and 100 μg/ml for carbenicillin. Overnight cultures of transformed ME6 cells were spotted onto LB agar plates supplemented with 1 μM Na$_2$MoO$_4$, 1 μM Na$_2$SeO$_3$ unless otherwise noted, 50 mM sodium formate, 0.1% L-arabinose, and antibiotics and grown anaerobically (90% N$_2$, 5% H2, 5% CO$_2$) at the room temperature for two days in an anaerobic tent (Coy Laboratories). When necessary, IPTG at final concentrations of 0.01 and 0.1 mM was also added into the agar plates. After incubation, these agar plates were overlaid with a top agar (0.75%) containing 1 mg/mL benzyl viologen, 250 mM sodium formate, and 25 mM KH$_2$PO$_4$ (pH 7.0) in the tent.

Results

E. coli tRNA$^{Sec}$ and its EF-Tu-compatible variants (UTu, UTuX, UTu6, and SecUx) (Aldag, et al., Angew Chem Int Ed Engl, 52:1441-1445 (2013); Thyer, et al., J Am Chem Soc, 137:46-49 (2015); Miller, et al., FEBS Lett, 589:2194-2199 (2015); Fan, et al., ACS Synth Biol. (2017)) have a non-canonical 13-base pair (13-bp) amino-acid acceptor branch that is one of the essential identity elements for E. coli selenocysteine synthase (SelA) that produces Sec-tRNA$^{Sec}$ (Itoh, et al., Science, 340:75-78 (2013)). Sec-tRNA$^{Sec}$ is synthesized in two steps in bacteria; seryl-tRNA synthetase (SerRS) attaches serine (Ser) to tRNA$^{Sec}$; SelA converts the Ser moiety to Sec by using selenophosphate synthesized by selenophosphate synthase (SelD) (Silva, et al., J Biol Chem, 290:29178-29188 (2015)). While SelB rejects Ser-tRNA$^{Sec}$, EF-Tu accepts both Ser-tRNA and Sec-tRNA molecules. Therefore, the Ser-tRNAs must be quickly converted to Sec-tRNA to prevent Ser-tRNA translating UAG codons via EF-Tu (Thyer, et al., J Am Chem Soc, 137:46-49 (2015)). Although several studies improved the purity and the yield of recombinant selenoproteins (Aldag, et al., Angew Chem Int Ed Engl, 52:1441-1445 (2013); Haruna, et al., Nucleic Acids Res, 42:9976-9983 (2014); Thyer, et al., J Am Chem Soc, 137:46-49 (2015); Miller, et al., FEBS Lett, 589:2194-2199 (2015); Fan, et al., ACS Synth Biol. (2017)), these tRNAs with a 13-bp branch may be less compatible than canonical tRNAs having a 12-bp branch in EF-Tu-mediated translation by the ribosome.

To overcome this drawback, experiments were designed to investigate another SelA species which can recognize tRNA$^{Sec}$ with a 12-bp branch. A close relative of E. coli, Aeromonas salmonicida subsp. pectinolytica 34mel, has one of such SelA and tRNA$^{Sec}$ pairs (Mukai, et al., Angew Chem Int Ed Engl, 55, 5337-5341 (2016)). EF-Tu-compatible variants of A. salmonicida tRNA$^{Sec}$ were designed, however, they were not good amber suppressors, probably because the tRNA$^{Sec}$ tertiary structure may not be suitable for canonical translation via EF-Tu but is optimized for SelB-mediated codon recoding (Fischer, et al., Nature, 540:80-85 (2016)). Therefore, a search for tRNA$^{Ser}$ species which may be recognized by A. salmonicida SelA was conducted. Bacterial tRNA$^{Sec}$ species have a characteristic tRNA elbow structure composed of the D-loop (YGGU) and the T-loop (UUCR-AYU) (Y denotes C/U, while R denotes G/A; the two Ys are either C-C or U-U pairs) (Mukai, et al., Angew Chem Int Ed Engl, 55, 5337-5341 (2016); Santesmasses, et al., PLoS Comput Biol, 13, e1005383 (2017)). This elbow structure is recognized by the N-terminal domain of SelA. The Examples above identified a new group of tRNA$^{Sec}$-like tRNAs ("allo-tRNAs" named after their non-canonical cloverleaf structures), some of which were revealed as tRNA$^{Ser}$ (Mukai, et al., Nucleic Acids Res, 45:2776-2785 (2017)) (see also Examples above). Among them, one allo-tRNA species (referred to as "9/3-1" and "allo-tRNA$^{UTu}$") (FIG. 9A), derived from a metagenomic sequence, has a 12-bp branch and tRNA$^{Sec}$-like D- and T-loops and functioned as active tRNA$^{Ser}$ in E. coli (Mukai, et al., Nucleic Acids Res, 45:2776-2785 (2017)) (see also Examples above).

The E. coli fdhF gene encoding formate dehydrogenase H (FDH$_H$) (FIG. 9C), one of the three selenoproteins in E. coli, was used as a reporter gene to check EF-Tu-mediated Sec incorporation (Aldag, et al., Angew Chem Int Ed Engl, 52:1441-1445 (2013); Thyer, et al., J Am Chem Soc, 137: 46-49 (2015); Miller, et al., FEBS Lett, 589:2194-2199 (2015)). The UGA codon 140 encoding the catalytic Sec140 residue was changed to UAG (FIG. 9C). Coexpression of the amber suppressor variant of allo-tRNA (9/3-1) (renamed "allo-tRNA$^{UTu}$") and A. salmonicida SelA (FIG. 1A) inserted Sec into the UAG 140 position and expressed wildtype FDH$_H$ which reduced benzyl viologen into a purple dye (FIG. 9C).

In order to further estimate the activity of allo-tRNA$^{UTu}$, four Cys codons were changed at positions 8, 11, 15 and 42 to UAG in fdhF. These four Cys residues are accommodating an essential iron sulfur cluster (FIG. 1B) (Boyington, et al., Science, 275:1305-1308 (1997)). A preliminary study revealed that each of the four Cys residues can be separately replaced by Sec without impairing the FDH$_H$ activity but cannot be replaced by Ser (FIG. 9C). Thus, the reporter fdhF gene variants have one to five UAG codons which must be translated as Sec; premature translation stop by release factor 1 (RF-1) and Ser incorporation by Ser-allo-tRNA$^{UTu}$ make inactive FDH$_H$. The allo-tRNA$^{UTu}$ and A. salmonicida SelA pair enabled the translation of up to five UAG codons in the reporter fdhF gene variants (FIG. 9C). Thus, the FDH$_H$ variants may have up to five Sec residues. However, premature stop or Ser incorporation was also occurring, since increasing the number of UAG codons in the fdhF reading frame decreased the FDH$_H$ activity of the cell spots (FIG. 9C).

Example 8: Allo-tRNA$^{UTu}$ Improves Yield of Proteins Containing Multiple Sec Residues Relative to Other tRNA$^{Sec}$ Materials and Methods >tRNA$^{UTuX}$
(SEQ ID NO: 63)
GGAAGATGGTGCCGTCCGGTGAAGGCGCCGGTCTCTAAAACCGGTCGACC

CGAAAGGGTTCGCAGGGTTCGACTCCCTGCATCTTCCGCCA

>tRNA$^{SecUx}$
(SEQ ID NO: 18)
GGAAGATGGTCGTCTCCGGTGAGGCGGCTGGACTCTAAATCCAGTTGGGG

CCGCCAGCGGTCCCGGTCAGGTTCGACTCCTTGCATCTTCCGCCA

Results

Next allo-tRNA$^{UTu}$ with tRNA$^{UTuX}$ (Miller, et al., *FEBS Lett*, 589:2194-2199 (2015)) and tRNA$^{SecUX}$ (Thyer, et al., *J Am Chem Soc*, 137:46-49 (2015)). For proper comparison, the two tRNA sequences were first cloned the under the araBAD promoter in the same manner as allo-tRNA$^{UTu}$ (Mukai, et al., *Nucleic Acids Res*, 45:2776-2785 (2017)). The expression level of *E. coli* SelA for each of the tRNA$^{U}_{TuX}$ and tRNA$^{SecUx}$ species were optimized, because excess SelA molecules completely sequestered these tRNA molecules (FIG. 11A-11C). After the optimization step, it was revealed that tRNA$^{SecUx}$ is more active than tRNA$^{UTuX}$ and translated two UAG codons in an fdhF variant gene (FIGS. 11A-11C and 9D). The FDH$_H$ activities of cell spots expressing tRNA$^{SecUX}$+fdhF(2 UAG codons) and tRNA$^{UTuX}$+fdhF(1 UAG codon) were comparable (FIG. 11A-11C). Next, the allo-tRNA$^{UTu}$+As SelA pair and the tRNA$^{SecUx}$+Ec SelA pair were compared. The *E. coli* pair hardly translated three UAG codons in an fdhF variant gene (FIG. 9D), probably due to the competition with RF-1 (Cheng, et al., *J Biol Chem*, 292:5476-5487 (2017)) which terminates translation at UAG and UAA. The FDH$_H$ activity of cell spots expressing allo-tRNA$^{UTu}$+fdhF(4 UAG codons) was higher than that of cells expressing tRNA$^{SecUx}$ fdhF(2 UAG codons) (FIG. 9D). Thus, allo-tRNA$^{UTu}$ is apparently the best in terms of the yield of proteins containing multiple Sec residues. However, tRNA$^{SecUx}$ might be superior to allo-tRNA$^{UTu}$ in terms of the purity of yielded selenoproteins, because 100% pure (no Ser incorporation) recombinant selenoproteins were obtained in some cases under optimal conditions by using tRNA$^{SecUX}$ (Thyer, et al., *J Am Chem Soc*, 137:46-49 (2015)).

Example 9: The Conversion Rate of Ser-Allo-tRNA$^{UTu}$ to Sec-Allo-tRNA$^{UTu}$ can be Improved by Modifying the Translation System Materials and Methods
Construction of Plasmids The *A. salmonicida* 34mel selD gene with its native promoter was amplified by PCR from the same genomic DNA and cloned immediately downstream of the SelA ORF of pSecUAG-A together with an intervening *E. coli* trp terminator sequence. The AUG start codon of the *A. salmonicida* selD gene was changed to GUG (designated as As selD') by Infusion to produce pSecUAG-AD. The allo-tRNA$^{UTu}$ sequence of pSecUAG-AD was mutated by Infusion to make allo-tRNA$^{UTu}$ variants. The *A. salmonicida* SelA expression cassette (but not the Ttrp) was removed from these allo-tRNA$^{UTu}$ variant-carrying plasmids. Thus, the Ttrp is remaining between the kan gene and the As selD' gene in these SelA-lacking plasmids. Alternatively, the As selD' gene of pSecUAG-AD (together with the intervening Ttrp) was cloned into the allo-tRNA$^{UTu2}$-carrying plasmid. The G21 variant of allo-tRNA$^{UTu2}$ was made by Infusion from allo-tRNA$^{UTu2}$-carrying plasmids. The ORF of *Treponema denticola* Trx1(32UAG) (Kim, et al., *Biochem Biophys Res Commun*, 461:648-652 (2015)) was cloned immediately downstream of the As selD' gene together with a linker sequence including a ribosome binding site (TCACACAGGAAACAGACC (SEQ ID NO:76)) in pSecUAG-AD to make pSecUAG-ADT. The allo-tRNA$^{UTu}$ sequence of pSecUAG-ADT was mutated to the D-3b variant by Infusion to make pSecUAG-AD3T. A low-copy-number plasmid pMW219 (NIPPON GENE) was modified to carry a cat gene instead of the kan marker and the multiple cloning site to make pMWcat by Infusion using the following primer sets (5'-ccactccaagaattgCAAAAAGGC-CATCCGTCAGG-3' (SEQ ID NO:65) and 5'-cgtgtgcttct-caaaGAGCGCAACGCAATTAATGTG-3' (SEQ ID NO:66)) and (5'-TTTGAGAAGCACACGGTCAC-3' (SEQ ID NO:67) and 5'-CAATTCTTGGAGTGGTGAATC-3' (SEQ ID NO:68)). The *A. salmonicida* SelA expression cassette (with the Ttrp) was cloned in front of the cat gene in pMWcat to make pMWcat-AsSelA(AUG) by Infusion using the following primer sets (5'-TCC-CACAGCCGCCAGTTCCGCTGGCGGCATTT-TACCCGACGCACTTTGCGCCG-3' (SEQ ID NO:69) and 5'-AGGCCCTTTCGTCTTCAAG-3' (SEQ ID NO:70)) and (5'-aagacgaaagggcctCACGTGTTGACAATTAATCATCG-3' (SEQ ID NO:71)) and 5'-ctggcggctgtgg-gaTCAGGGCTCCTCGGTCGCAG-3' (SEQ ID NO:72)). The AUG start codon for the *A. salmonicida* SelA gene on pMWcat-AsSelA(AUG) was changed to GUG to make pMWcat-AsSelA(GUG). The *E. coli* selA gene with its native promoter was amplified by PCR from a genomic DNA and cloned immediately downstream of the kan marker gene together with an intervening *E. coli* trp terminator sequence in pBAD-RSFS carrying tRNA$^{UTuX}$ or tRNA$^{SecUx}$. The start codon of the *E. coli* selA gene was mutated by Infusion. In particular, pSecUx-A has tRNA$^{SecUX}$ and an *E. coli* selA gene variant carrying a GUG start codon with a short insertion "UAAUU" in front of it. The plasmid vector pTrc99A was used for the inducible expression of a few enzymes. For cloning the ORFs of *A. salmonicida* SelA and phosphoseryl-tRNA kinases (PTSKs) of *Trypanosoma brucei* (Aeby, et al., *Proc Natl Acad Sci USA*, 106:5088-5092 (2009)) and *Homo sapiens*, they were cloned between CACACAGGAAACAGACC (SEQ ID NO:73) and TGTTTTGGCGGATGAGAGAAG (SEQ ID NO:74). The codon usage of the human PSTK was partially optimized for use in *E. coli* (see below). The ORF of Sep-tRNA:Cys-tRNA synthetase (SepCysS) from the Parcubacteria DG_74_2 bin (Mukai, et al., *MBio*, 8, e00561-00517 (2017)) was cloned after the PSTK ORFs with a short upstream sequence including a ribosome binding site (TTT-TAAGAAGGAGATATACAT (SEQ ID NO:75)). The plasmid vector pETDuet-1 (Novagen) was used for the inducible expression of selenoproteins. The ORF of a human GPx1 (49UAG) variant having additional N-terminal MetGly sequence (for NcoI site) and a C-terminal Leu-Glu-His-His-His-His-His-His (SEQ ID NO:95) tag (Aldag, et al., *Angew Chem Int Ed Engl*, 52:1441-1445 (2013)) was transferred from pRSFDuet-1 plasmids into the NcoI and HindIII sites of pETDuet-1.

Sequences

>*Trypanosoma brucei* pstk
(SEQ ID NO: 89)
ATGACAGTTTGTCTTGTTCTACTAACTGGGCTGCCAGGAGCGGGGAAGAC
GACACTAGGCAAGGCTCTTAAACAGTTGGGGGATCACATAACCCATGAAC
TCTCCCTCATAGTCACGGCAGTGGTGGAATTAGATGACTTTATGTGTAAC
GTCGGTGCGAGTAATGGGTCCCGTGTAGAGAGTACCGTTTTCGATCCAAG
TCGGTGGCGAGAGGCGTTCGAAGCGGCTCGTCAGGCAACTCGCCAGGAGT
TGGAGCGGTGCCTAATGATGGAGAGGAATAAAGCGGTAATGCACTTGGTT
TTTCTGGTGGATCCGCTGCCATATAGGAGTATGAGAGCATCGTACTGGAA
AATGTGCAAGGAATTAAGTGCCAAGTGTGCTGAGACTCACTTTCATGATT
CATGGGAAGTGCAGAGCATTGTTGTCTTGTTGGAGGTGCGGATGAACACC
CCGGAGGAGGTTTGTCTCCAACGCAATGAGCTCCGCGCCGGAACCCCGCA
GTATATTCCCCGTATGTTATTAAGGGGATAAGTGACTCGTTTGACCGTG
GTGACCTCACTGCTGTGCTGCTGGGTACAGACGGAAATATGTGGGCCGTA
CTTCCCGGGCAGAAGTCGGCACCGTGGCCCGTTCTTTTACTGGTTGATGA
AGTGAGATGCTGCGCGTCACCACCCAATTTGTTGGCCACGCAGTTGCTGG
AGCGTATCCGAGGGGAAGACATAATGCGTGAGATGACGGAACAACAAGTA
AGTGTTTTTAATTATTACAAGTGCCAAGTGGAAGGGGGGAAGTCGAAGTG
TTTGGCGAGTGGAGAAGCACATGACAACGTTAACAACTGTCTTCATCAAG
TGGACCTCCACATGCGGGCAGTTGTGGGACATTACATGGTCGAGCGGCAG
AGTAGTGGTTCACTGAAGCCAGGCACTGGGCAACGCGTAAGCAAATGTCG
GTCGACCCACTACGCGGGAATTCGCGCAGCAATCACGAAGGGAACGAGAA
ACACAGGAGGATCTTTTTCCGAAGTGCAAGGACTACTGCAGCAGTTACTT
TTGGAATTCGAGCATGCCTTAGTAGATCTTTAA >*Homo sapiens* pstk isoform X1
(SEQ ID NO: 90)
ATGAAAACCGCAGAAAATATTCGTGGCACCGGTTCAGATGGTCCGCGTAA
ACGTGGTCTGTGTGTTCTGTGTGGTCTGCCTGCAGCAGGTAAAAGCACCT
TTGCACGTGCCCTGGCACATCGTCTGCAGCAAGAACAAGGTTGGGCAATT
GGTGTTGTTGCATATGATGATGTTATGCCGGATGCATTTCTGGCAGGCGC
ACGCGCACGTCCGGCACCGAGTCAGTGGAAACTGCTGCGTCAAGAACTGC
TGAAATATCTGGAATATTTCCTGATGGCCGTGATTAATGGTTGTCAGATG AGCGTTCCGCCTAATCGTACCGAAGCAATGTGGGAAGATTTTATCACCTG
TCTGAAAGATCAGGACCTGATTTTTAGCGCAGCATTTGAAGCACAGAGCT
GTTATCTGCTGACCAAAACAGCAGTTAGCCGTCCGCTGTTTCTGGTTCTG
GATGATAATTTCTATTATCAGAGCATGCGCTATGAGGTTTATCAGCTGGC
ACGTAAATATAGCCTGGGTTTTTGTCAGCTGTTCCTGGATTGTCCGCTGG
AAACCTGTCTGCAGCGTAATGGTCAGCGTCCGCAGGCACTGCCTCCGGAA
ACCATTCATCTGATGGGTCGTAAACTGGAAAAACCGAATCCGGAAAAAAA
TGCCTGGGAACATAATAGCCTGACCATTCCGAGTCCGGCATGTGCAAGCG
AAGCAAGCCTGGAAGTTACCGATCTGCTGCTGACCGCACTGGAAAATCCG
GTTAAATATGCCGAAGATAACATGGAACAGAAAGATACCGATCGCATTAT
TTGCAGCACCAACATTCTGCATAAAACCGATCAGACCCTGCGTCGTATTG
TTAGCCAGACCATGAAAGAAGCAAAAGATGAACAGGTTCTGCCGCATAAT
CTGAAACTGCTGGCAGAAGAACTGAATAAACTGAAAGCAGAATTCCTTGA
GGATCTGAAACAGGGCAATAAAAAGTATCTGTGTTTTCAGCAGACCATCG
ATATTCCGGATGTGATCAGCTTTTTCCACTATGAGAAAGATAACATCGTG
CAGAAATACTTCAGCAAGCAGCATTAA >*Treponema denticola* Trx1(32UAG)
(SEQ ID NO: 91)
ATGATTATGGCAGTATTGGATATTACAAATGCTAATTTTGATGAAACCGT
tAAgACCGCCAAGCCCGTTTTAATTGACTTTTGGGCACCGTGGTAGCCGG
GATGCGTACAGCTCAGTCCTGAGCTGCAGGCTGCCGAGGCGGAACTCGGC
GACAAGGCTGTGATAGCACAGTCTAACGTGGATAATGCACGTGAATTGGC
AGTAAAATTTAAGTTTATGTCAATACCTACCCTCATCGTTTTAAAAGACG
GAAAAGAGGTGGACAGGCACACAGGCTATATGGATAAgAAGAGCCTTGTA
AACTTTGTTTCAAAGCATATCTAA >pSecUAG-AD Plasmid Annotation
  misc_feature complement(5998 . . . 6876)
  /label=araC
  misc_feature 6906 . . . 127
  /label=ParaBAD
  misc_feature 151 . . . 240
  /label=allo-tRNA$^{UTu}$
  misc_feature 262 . . . 290
  /label=TrrnC
  misc_feature 366 . . . 523
  /label=rrnB T1 and T2
  misc_feature join(946 . . . 1982, 1984 . . . 2116)
  /label=As selD with a GUG start codon
  misc_feature complement(2117 . . . 2149)
  /label=Ttrp
  misc_feature complement(2150 . . . 3708)
  /label=As SelA with an EM7 promoter >pSecUAG-AD
(SEQ ID NO: 92)
GTCTATAATCACGGCAGAAAAGTCCACATTGATTATTTGCACGGCGTCACACTTTG
CTATGCCATAGCATTTTTATCCATAAGATTAGCGGATCCTACCTGACGCTTTTTAT
CGCAACTCTCTACTGTTTCTCCATACCCGTTTGAATTCggaggggaacttctatct
ggtgatagacgggaactctaaattccttgaaatgcctcgccgcattgggttcgatt -continued

```
ccccttccctccgccaGGATCTAGAGTCGACCTGCAGATCCTTAGCGAAAGCTAAG
GATTTTTTTAGGAATTAACCATGGATCCGAGCAGCCTGATACAGATTAAATCAGA
ACGCAGAAGCGGTCTGATAAAACAGAATTTGCCTGGCGGCAGTAGCGCGGTGGTCC
CACCTGACCCCATGCCGAACTCAGAAGTGAAACGCCGTAGCGCCGATGGTAGTGTG
GGGTCTCCCCATGCGAGAGTAGGGAACTGCCAGGCATCAAATAAAACGAAAGGCTC
AGTCGAAAGACTGGGCCTTTCGTTTTATCTGTTGTTTGTCGGTGAACGCTCTCCTG
AGTAGGACAAATCCGCCGGGAGCGGATTTGAACGTTGCGAAGCAACGGCCCGGAGG
GTGGCGGGCAGGACGCCCGCCATAAACTGCCAGGCATCAAATTAAGCAGAAGGCCA
TCCTGACGGATGGCcgcggccGCCTCTAAACGGGTCTTGAGGGGTTTTTTGCTGAA
ACCTCAGGCATTTGAGAAGCACACGGTCACACTGCTTCCGGTAGTCAATAAACCGG
TAAACCAGCAATAGACATAAGCGGCTATTTAACGACCCTGCCCTGAACCGACGACA
AGCTGACGACCGGGTCTCCGCAAGTGGCACTTTTCGGGGAAATGTGCGCGGAACCC
CTATTTGTTTATTTTTCTAAATACATTCAAATATGTATCCGCTCATGAATCATTGG
ATAACCTCGATAAACTGGTTTCCGGTATAGGCTTTCAGCTGGCCTATGGGGGAGAG
GGTCAGCCCCGCTTGTGTCGCGATAGCAAGGAGCTCGGCTTCACTTTCTTTACCGA
CGGCAACCAGCAAGCCGCCGCTGGTCTGCGGATCGCACATGATGTTGCGGGTGCGT
TCATCCATGGCACCGAGCTTGGCGCCATAGGAATCGAAGTTGCGCAGGGTACCGCC
CGGTACGCAGCCCTCGGACAGGTAGTAATCTACTTCGTCGAGCAGTGGCAGCGCCT
TGAAATCGAGGGTGGCACACACCCCTGAGCCTTCGCACATCTCAAGCAGGTGTCCC
GCCAGGCCAAACCCGGTCACATCCGTCATGGCGTGCACGCCGGGCAGTTCGGCAAA
GCGCTGGCCAATCTTGTTGAGGGTGCACATGGCGTTGGGGGCCAGCTGCTCATGCT
CTGGCTTCAATTTGCCCTTCTTCTGGGCCGTGGTGAGGATGCCGATACCGAGGGGC
TTGGTCAGGTAGAGGATGTCACCCGCCTGGGCCGTGTCGTTCTGCTTGATGGCATT
GAGCGGCACTATACCGGTCACAGCAAGACCGAAGATGGGCTCGGGGGCATCGATAC
TGTGGCCGCCAGCCAAGGATATGCCCGCTTCATGGCACACCTGGCGGCCGCCATCT
ATCACCTGCTGGGCCACTTCCGGGGCTAGGGTGTTGATGGGCCAGCCAAGGATGGC
AATGGCAACGATGGGCTTGCCGCCCATGGCGTAGATGTCGCTGATGGCGTTGGTGG
CCGCGATGCGGCCAAAGGTAAAGGGATCATCGACGATGGGCATGAAGAAGTCGGTG
GTGGAAACAATGCCCTGACCGTTGCCGATATCGACCACGGCCGCGTCATCCTTGCT
GCTGTTGCCAACCACCAGGGTCGGGTCGTCAAAGCCCGGGATCTGGCTCTTGAGAA
TGGTGTCGAGCACCTTGGGAGAAATTTTGCAGCCGCAGCCAGCCCCGTGGCTGTAT
TGGGTCAGACGAATGGAAGACACgattaccccttgtttggctgtttctcaagatga
aacagcgtatatcaggcaaaaggagatgaccctgagcgggccattggacagggcat
tatgccacaaggactctgcgggttcgaatcacaatagcctgtcgAAAATGCCGCCA
GCGGAACTGGCGGCTGTGGGAtcagggctcctcggtcgcagtggtcggagtgggca
gtagcaactccttgagttgggcgataagcagtgcaatctcggtcggcagcagggtc
gccatattgagcagcaccttctgctggcgcacggtggcgatgaccggcaccggcag
tttccgcagggcatcgagcagctgctgggccggacgcgggtcggtgcattcgagcg
caggcgcagggtagaactcgtccggcagggtgccaccacccaccaccagctgggcg
gggaccggcacaaagcagccgggcagggcggccatcagctgatcggcgcgggcctg
```

-continued

```
catggcggcagggttgctcaaggtgcgctgggcgatgccctcgccgatggggact tgttgagcttgtggatgagcaggcgttccagcagggagtagacgatgcggctcggg cggaaggtgcgcatcatggggtgtttttccagccgcttgatgaggtcgctgcggcc gctgatgatgcccgattgcgggccacccagcagcttgtcgccggagtagcagacca gatccgccccgccttgatgtactgacgcaccgaggtttcgtccggtgcaaactcc tcggtggtcaagcccgagccctgatccaccgccagcaccacgtgctcgggcagggc gcgggccacctcgccaatatcggggattcggtaaagccgcgaatggcgaaattgg atctgtgtaccatcagcaccagcgcggtctgatctgtgatggcatcgaggtaatct ttggcggtagtgatattggtggtgcccacctccaccagtttggcgccggagagcgc cagaatgtcgggaatgcgaaagccgccaccaatctggatctgttcgccccgcgaga cgatcacctcgcgcccttggctatctcctgcagcagcaagaagagcgaagcggcg ttgttgttgaccaccagcgaatcctcggcctgggtgaggcaacggagcaggggggc gatcagcccttgcgcccgccgcgcttgccggtggcgagatccagttccagattgt tgtagccagtgttgaggtcgcgcacctcgtcccacagctcgcgacttagcggcgag cgccccagattggtgtgcaccagggtgccggtggcgttgatcacccgggtctgacg ttggcgcagctgctgctggcaacgcttggcaatcagtgcctcgatttgctcggggg caaccccatgctggcgaaatgcctcgctctggcgcaattcgctcaggacatcgcgc accgcctgggtcaccagcgggcggctcagcgcctcgataaaaccggtgagaaaggg ttgctgcagcagctgttccacttgcggtagacggcgcgcttgttgctggctgggct gtggcagtgaatctggcagtgaatctggcagtgaatcgtcggcagtgggacatgat tcgggctgactgtgagagtgggcgatggctggcgcgtgagacgagttcggcatggt ttagttcctcaccttgtcgtattatactatgccgatatactatgccgatgattaat tgtcaacacgtgTTAATTCTTAGAAAAACTCATCGAGCATCAAATGAAACTGCAAT

TTATTCATATCAGGATTATCAATACCATATTTTTGAAAAAGCCGTTTCTGTAATGA

AGGAGAAAACTCACCGAGGCAGTTCCATAGGATGGCAAGATCCTGGTATCGGTCTG

CGATTCCGACTCGTCCAACATCAATACAACCTATTAATTTCCCCTCGTCAAAAATA

AGGTTATCAAGTGAGAAATCACCATGAGTGACGACTGAATCCGGTGAGAATGGCAA

AAGTTTATGCATTTCTTTCCAGACTTGTTCAACAGGCCAGCCATTACGCTCGTCAT

CAAAATCACTCGCATCAACCAAACCGTTATTCATTCGTGATTGCGCCTGAGCGAGA

CGAAATACGCGGTCGCTGTTAAAAGGACAATTACAAACAGGAATCGAATGCAACCG

GCGCAGGAACACTGCCAGCGCATCAACAATATTTTCACCTGAATCAGGATATTCTT

CTAATACCTGGAATGCTGTTTTCCCGGGGATCGCAGTGGTGAGTAACCATGCATCA

TCAGGAGTACGGATAAAATGCTTGATGGTCGGAAGAGGCATAAATTCCGTCAGCCA

GTTTAGTCTGACCATCTCATCTGTAACATCATTGGCAACGCTACCTTTGCCATGTT

TCAGAAACAACTCTGGCGCATCGGGCTTCCCATACAATCGATAGATTGTCGCACCT

GATTGCCCGACATTATCGCGAGCCCATTTATACCCATATAAATCAGCATCCATGTT

GGAATTTAATCGCGGCCTAGAGCAAGACGTTTCCCGTTGAATATGGCTCATACTCT

TCCTTTTTCAATATTATTGAAGCATTTATCAGGGTTATTGTCTCATGAGCGGATAC

ATATTTGAATGTATTTAGAAAAATAAACAAATAGGCATGCAGCGCTCTTCCGCTTC

CTCGCTCACTGACTCGCTACGCTCGGTCGTTCGACTGCGGCGAGCGGTGTCAGCTC

ACTCAAAAGCGGTAATACGGTTATCCACAGAATCAGGGGATAAAGCCGGAAAGAAC
```

-continued

```
ATGTGAGCAAAAAGCAAAGCACCGGAAGAAGCCAACGCCGCAGGCGTTTTTCCATA
GGCTCCGCCCCCCTGACGAGCATCACAAAAATCGACGCTCAAGCCAGAGGTGGCGA
AACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGG
GAAGCGTGGCGCTTTCTCATAGCTCACGCTGTTGGTATCTCAGTTCGGTGTAGGTC
GTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCAC
TGGCAGCAGCCATTGGTAACTGATTTAGAGGACTTTGTCTTGAAGTTATGCACCTG
TTAAGGCTAAACTGAAAGAACAGATTTTGGTGAGTGCGGTCCTCCAACCCACTTAC
CTTGGTTCAAAGAGTTGGTAGCTCAGCGAACCTTGAGAAAACCACCGTTGGTAGCG
GTGGTTTTTCTTTATTTATGAGATGATGAATCAATCGGTCTATCAAGTCAACGAAC
AGCTATTCCgggccggcCGGAGCCTATGGAAAAACGCCAGCAACGCGGCCTTTTTA
CGGTTCCTGGCCTTTTGCTGGCCTTTTGCTCACATGTTCTTTCCTGCGTTATCCCC
TGATTCTGTGGATAACCGTATTACCGCCTTTGAGTGAGCTGATACCGCTCGCCGCA
GCCGAACGACCGAGCGCAGCGAGTCAGTGAGCGAGGAAGCGGAAGAGCGCCTGATG
CGGTATTTTCTCCTTACGCATCTGTGCGGTATTTCACACCGCATATGGTGCACTCT
CAGTACAATCTGCTCTGATGCCGCATAGTTAAGCCAGTATACACTCCGCTATCGCT
ACGTGACTGGGTCATGGCTGCGCCCCGACACCCGCCAACACCCGCTGACGCGCCCT
GACGGGCTTGTCTGCTCCCGGCATCCGCTTACAGACAAGCTGTGACCGTCTCCGGG
AGCTGCATGTGTCAGAGGTTTTCACCGTCATCACCGAAACGCGCGAGGCAGCAGAT
CAATTCGCGCGCGAAGGCGAAGCGGCATGCATAATGTGCCTGTCAAATGGACGAAG
CAGGGATTCTGCAAACCCTATGCTACTCCGTCAAGCCGTCAATTGTCTGATTCGTT
ACCAATTATGACAACTTGACGGCTACATCATTCACTTTTTCTTCACAACCGGCACG
GAACTCGCTCGGGCTGGCCCCGGTGCATTTTTAAATACCCGCGAGAAATAGAGTT
GATCGTCAAAACCAACATTGCGACCGACGGTGGCGATAGGCATCCGGGTGGTGCTC
AAAAGCAGCTTCGCCTGGCTGATACGTTGGTCCTCGCGCCAGCTTAAGACGCTAAT
CCCTAACTGCTGGCGGAAAAGATGTGACAGACGCGACGGCGACAAGCAAACATGCT
GTGCGACGCTGGCGATATCAAAATTGCTGTCTGCCAGGTGATCGCTGATGTACTGA
CAAGCCTCGCGTACCCGATTATCCATCGGTGGATGGAGCGACTCGTTAATCGCTTC
CATGCGCCGCAGTAACAATTGCTCAAGCAGATTTATCGCCAGCAGCTCCGAATAGC
GCCCTTCCCCTTGCCCGGCGTTAATGATTTGCCCAAACAGGTCGCTGAAATGCGGC
TGGTGCGCTTCATCCGGGCGAAAGAACCCCGTATTGGCAAATATTGACGGCCAGTT
AAGCCATTCATGCCAGTAGGCGCGCGGACGAAAGTAAACCCACTGGTGATACCATT
CGCGAGCCTCCGGATGACGACCGTAGTGATGAATCTCTCCTGGCGGGAACAGCAAA
ATATCACCCGGTCGGCAAACAAATTCTCGTCCCTGATTTTTCACCACCCCCTGACC
GCGAATGGTGAGATTGAGAATATAACCTTTCATTCCCAGCGGTCGGTCGATAAAAA
AATCGAGATAACCGTTGGCCTCAATCGGCGTTAAACCCGCCACCAGATGGGCATTA
AACGAGTATCCCGGCAGCAGGGGATCATTTTGCGCTTCAGCCATACTTTTCATACT
CCCGCCATTCAGAGAAGAAACCAATTGTCCATATTGCATCAGACATTGCCGTCACT
```

```
GCGTCTTTTACTGGCTCTTCTCGCTAACCAAACCGGTAACCCCGCTTATTAAAAGC

ATTCTGTAACAAAGCGGGACCAAAGCCATGACAAAAACGCGTAACAAAAGT
```

>Homo sapiens GPx1(49UAG)-6His (SEQ ID NO: 93)

```
ATGGGCATGTGTGCTGCTCGGCTAGCGGCGGCGGCGGCGGCCCAGTCGGTGTA

TGCCTTCTCGGCGCGCCCGCTGGCCGGCGGGGAGCCTGTGAGCCTGGGCTCCCTGC

GGGGCAAGGTACTACTTATCGAGAATGTGGCGTCCCTCTAGGGCACCACGGTCCGG

GACTACACCCAGATGAACGAGCTGCAGCGGCGCCTCGGACCCCGGGGCCTGGTGGT

GCTCGGCTTCCCGTGCAACCAGTTTGGGCATCAGGAGAACGCCAAGAACGAAGAGA

TTCTGAATTCCCTCAAGTACGTCCGGCCTGGTGGTGGGTTCGAGCCCAACTTCATG

CTCTTCGAGAAGTGCGAGGTGAACGGTGCGGGGGCGCACCCTCTCTTCGCCTTCCT

GCGGGAGGCCCTGCCAGCTCCCAGCGACGACGCCACCGCGCTTATGACCGACCCCA

AGCTCATCACCTGGTCTCCGGTGTGTCGCAACGATGTTGCCTGGAACTTTGAGAAG

TTCCTGGTGGGCCCTGACGGTGTGCCCCTACGCAGGTACAGCCGCCGCTTCCAGAC

CATTGACATCGAGCCTGACATCGAAGCCCTGCTGTCTCAAGGGCCCAGCTGTGCCC

TCGAGCACCACCACCACCACCACTAA
```

>Parcubacteria DG_74_2 bin SepCysS (SEQ ID NO: 94)

```
ATGATCTACAAACGCCAGAACAAAAACAAAATTAACATCAACCCGATTCAGGCAGG

CGGTATTCTGACCAAAGATGCACGTAAAACCCTGATTGAATGGGGTGATGGTTATA

GCGTTTGCGATATTTGGTATAGCGGCAAAATCGATAAAATCGAAAATCCGCAGATC

CGCAAATTCATCAATGAAGATCTGCCGAAATTTCTGGGTAGCGATATTGCACGTAT

TATTGGTGGTGCACGTGAAGGTATTTGTGCAATTATGCATGCAGTTGCAAAACCGG

GTGATATTATTCTGGTGGATGAGAACAAACACTATACCACCATTCTGGCAGCAGAA

AAAAATGGTCTGAAAGTTGTTGAAGTTCCGAATAGCGGTCATCCGGAATACAAAAT

TGATGTGCGCGATTATGAAAAACTGATCAAAAAACATAAACCGGCACTGATCCTGC

TGACCTATCCGGATGGTAATTATGGTAATATGCCGGATGCAAAAAAACTGGGCGAA

ATCGTGATCAAATATAACATTCCGTATCTGCTGAATGCAGCATATAGCGCAGGTCG

TCTGCCGGTTGATCTGATTGCAATTAATGGTGATTTTATTGTGGCCAGCGGTCATA

AAAGCATGGCAGCAAGCGAACCGATTGGTGTTCTGGGTTTTCGTAAAAAATGGAAA

GACACCCTGTTCAAAAAAAGCTTCTTCTATCCGGACAAAGAGATTGAATTCCTGGG

CCATTATCAGAAAGGTGCACCGATGATGACCCTGATGGCAAGCTTTCCGTATGTGA

AAAAACGTGTTGAAGAGTGGGAAAAACAAATCGAGAAAGCACGTTGGTTTAGCGCA

GAAATGGAAAAACTGGGTTTTAAACAGCTGGGTGAAAAACCGCATAATCACGATCT

GCTGTTTTTCGAATCACCGCAGCTGTACAAAATTAGCCAGAAACATAAAGAGGGTC

GGTTTTTCCTGTACAAAGAACTGAAAAAAAAAGGCATCTACGGCATTAAACCGGGT

CTGACGAAACATTTTAAACTGAGCACCTTTGCAGCCAGCAAAGAGGAACTGAAAAA

ACTGCTGGAAGTGTTCAAAGAGATCCTGATTAAATAA
```

GPx1 Expression and Purification

E. coli ME6 cells transformed with pSecUAG-AD and pET-GPx1(49UAG) were grown in LB media containing 50 µg/ml ampicillin, 25 µg/ml kanamycin, 10 µM or 100 µM Na$_2$SeO$_3$ at 37° C. until the A600 reached 0.8. In order to raise the Na$_2$SeO$_3$ concentration to 100 µM, a solution of 50 mg/ml L-cystine in 1N HCl was made and added into the growth medium at a final concentration of 100 µg/ml together with 1/5 volume of 5N NaOH for the neutralization of the medium (31). The culture was then induced by the addition of 1 mM IPTG and 0.1% L-arabinose, and then shifted to 25° C. for approximately 16 h before harvesting. The cells were harvested and resuspended in buffer A [50 mM Tris-HCl (pH 8.5), 300 mM NaCl, 5 mM MgCl$_2$, 10% glycerol, 2 mM 2-mercaptoethanol (or 1 mM DTT), 0.5 mg/ml lysozyme, 0.1 mg/ml DNase]. After the cell disruption by BugBuster (Millipore), the His6-tagged protein was purified by immobilized metal-ion affinity chromatography using a Ni-NTA (Qiagen). The protein bound to the column was washed with buffer B [20 mM Tris-HCl (pH 8.5), 300 mM NaCl, 10% glycerol, 2 mM 2-mercaptoethanol with 5 mM $MgCl_2$ (or 1 mM DTT without $MgCl_2$), 15 mM imidazole] and eluted by buffer B containing 250 mM imidazole. Eluted proteins were buffer exchanged into water using 10 kDa molecular weight cut off filters (Millipore).

Mass Spectrometry

Electrospray mass spectrometry analyses were done at the W.M. Keck Biotechnology Resource Laboratory at Yale. The procedure of Keck: Intact proteins samples were diluted in 50% acetonitrile containing 0.1% formic acid and loaded into glass nanospray emitters. The samples were analyzed by direct infusion on an Orbitrap Fusion Tribrid mass spectrometer (ThermoFisher Scientific, San Jose, Calif.). The mass spectrometer was operated in Intact Protein mode with an ion routing multipole pressure of 3 mTorr or 8 mTorr. Spectra were acquired at 120K resolution. The isotopically resolved data were processed using Protein Deconvolution 4.0 software (ThermoFisher Scientific).

Results

In order to improve the conversion rate of Ser-allo-tRNA$^{UTu}$ to Sec-allo-tRNA$^{UTu}$, five modifications to the original pSecUAG-A system were made (FIG. 9A). Open reading frames for As SelA and phosphoseryl-tRNA kinase (PTSK) of *Trypanosoma brucei* (Aeby, et al., *Proc Natl Acad Sci USA*, 106:5088-5092 (2009)) or *Homo sapiens* (Carlson, et al., *Proc Natl Acad Sci USA*, 101:12848-12853 (2004)) were cloned under the trc promoter in the pTrc99A plasmid vector. The selD gene of As 34mel was cloned into pSecUAG-A and the start codon was changed from AUG to GUG to reduce the expression level of As SelD to produce pSecUAG-AD (FIG. 9E). In addition, an ORF for *Treponema denticola* Trx1 (Sec-containing thioredoxin) (Kim, et al., *Biochem Biophys Res Commun*, 461:648-652 (2015)) was cloned after the As SelD ORF of pSecUAG-AD with a Shine-Dalgarno (SD) sequence. The original UGA Sec codon of Td Trx1 ORF was mutated to UAG for its allo-tRNA$^{UTu}$-mediated expression. Previous studies indicate that thioredoxin may be involved in Se-transfer in the cytoplasm of bacteria (Tamura, et al., *Biosci Biotechnol Biochem*, 75:1184-1187 (2011); Kumar, et al., *Eur J Biochem*, 207:435-439 (1992)) and that recombinant expression of Td Trx1 in *E. coli* may modulate Sec incorporation in the *E. coli* proteome (Kim, et al., *Biochem Biophys Res Commun*, 461:648-652 (2015)).

It was revealed that As SelA should be expressed at a proper level, because excess As SelA molecules sequestered allo-tRNA$^{UTu}$ molecules in a dose-dependent manner (FIG. 12A-12B). PSTK might prevent Ser-allo-tRNA$^{UTu}$ translating UAG codons (Aldag, et al., *Angew Chem Int Ed Engl*, 52:1441-1445 (2013)), because PSTK can convert Ser-tRNA to phosphoseryl-tRNA which is a poor substrate of EF-Tu but is a good substrate of SelA (Aldag, et al., *Angew Chem Int Ed Engl*, 52:1441-1445 (2013); Xu, et al., *PLoS Biol*, 5, e4 (2007)). Both PSTK species recognized Ser-allo-tRNA$^{UTu}$ according to the observation that their co-expression with a Sep-tRNA:Cys-tRNA synthase (SepCysS) (Yuan, et al., *FEBS Lett*, 584:2857-2861 (2010); Mukai, et al., *MBio*, 8, e00561-00517 (2017)) resulted in the formation of Cys-allo-tRNA$^{UTu}$ which inserted Cys into the UAG position of FDH$_H$ (FIG. 12C). The FDH$_H$ (Cys140) variant retains the activity (Yuan, et al., *FEBS Lett*, 584:2857-2861 (2010); Axley, et al., *Proc Natl Acad Sci USA*, 88:8450-8454 (1991)). T. brucei PSTK molecules sequestered allo-tRNA$^{UTu}$ molecules in a dose-dependent manner, whereas *H. sapiens* PSTK did not affect the pSecUAG-A system (FIG. 12A-12B). Therefore, application of PSTK does not help.

Experiments were also designed to determine whether As SelD improved the expression levels of the FDH$_H$ variants carrying four or five Sec residues. Note that the *E. coli* strain tested has its own selD gene in the chromosome. The new pSecUAG-AD system (FIG. 9E) drastically improved the yield of the FDH$_H$ variant carrying five Sec residues and also improved the yield of the four Sec variants. The FDH$_H$ activities of cell spots carrying pSecUAG-A+fdhF(4 UAG codons) and pSecUAG-AD+fdhF(5 UAG codons) were comparable. The cells carrying pSecUAG-AD+fdhF(5 UAG codons) became darkened within a few minutes, whereas cells carrying pSecUAG-A+fdhF(5 UAG codons) were colorless within a short incubation time. Thus, supply of selenophosphate from SelD to SelA was revealed as a limiting step. While the wildtype As selD gene carrying the AUG start codon gave similar results (FIG. 13A), its effect was not robust (FIG. 13B), possibly due to the SelD overexpression. Since three Sec residues plus one Ser residue failed to properly accommodate the iron-sulfur cluster in FDH$_H$ variants (FIG. 13C), the pSecUAG-AD system actually produced FDH$_H$ with five Sec residues.

Figure 14A:
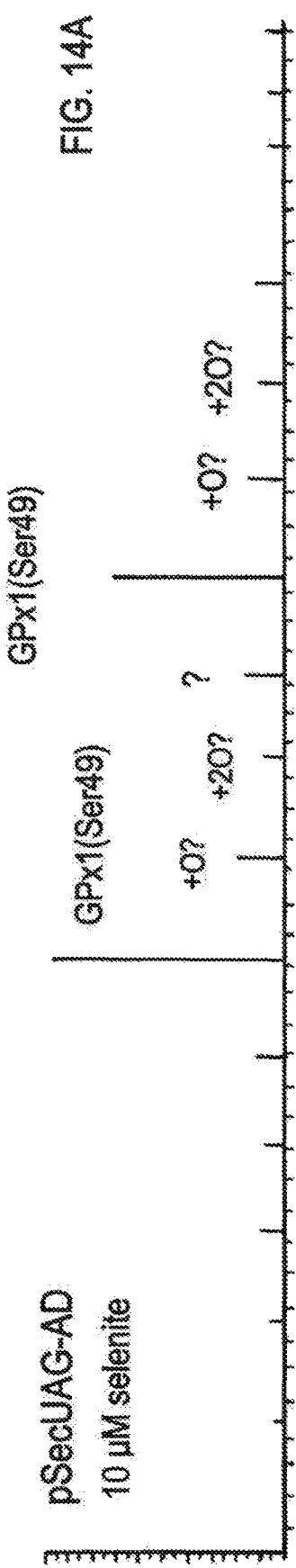
Figure 14B:
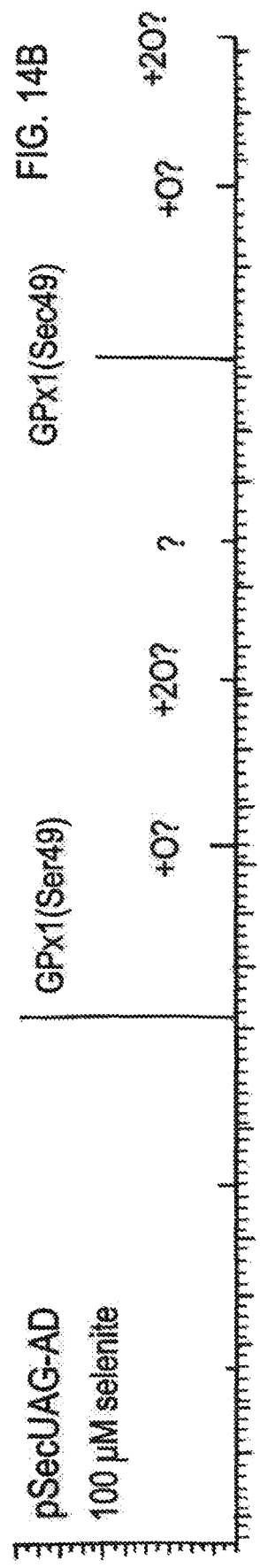
Figure 14C:
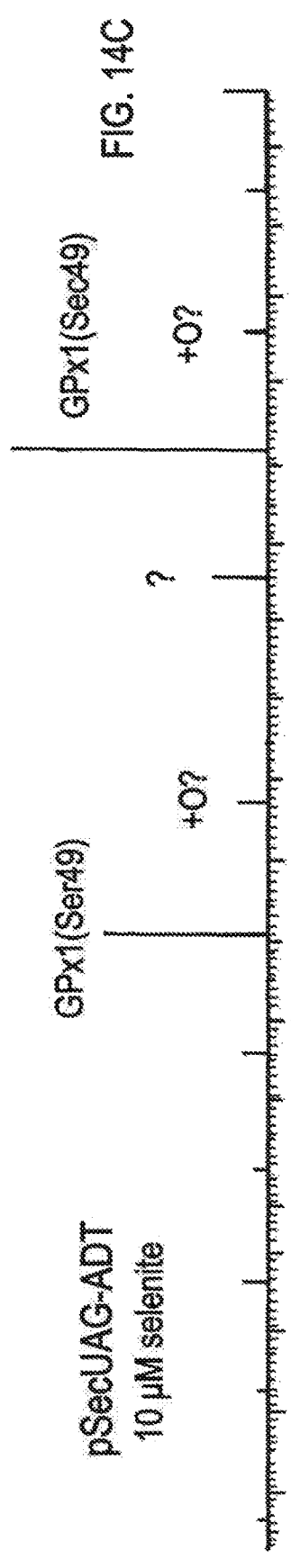
Figure 14D:
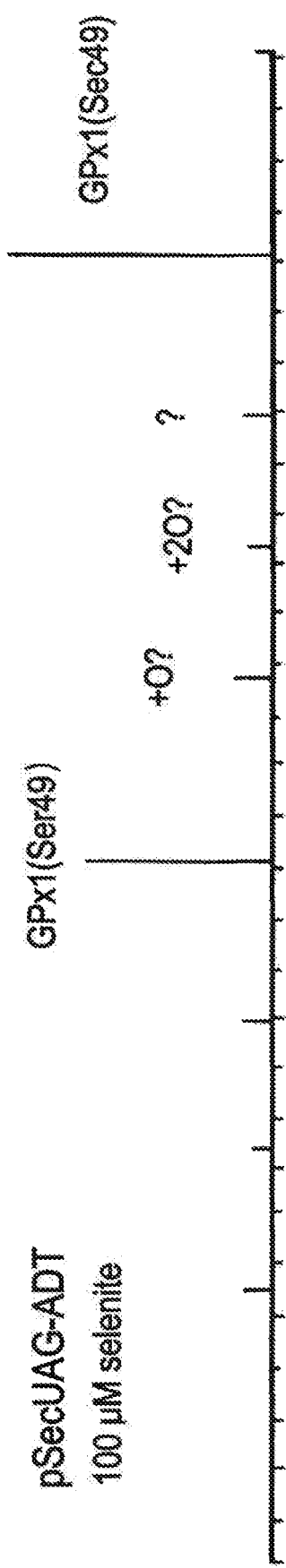

Human selenoprotein glutathione peroxidase 1, or GPx1 (Sec49), was expressed and analyzed by mass analysis. The pSecUAG-AD system fully supported the overexpression of GPx1 proteins by the standard pET expression system. Intact mass spectrometry confirmed Sec incorporation (FIGS. 9F and 14A-14F). However, Ser was also incorporated at a significant rate because the peak for GPx1(Ser49) is higher than that for GPx1(Sec49) (FIGS. 9F and 14A). Increasing the concentration of sodium selenite (selenium source) in the growth medium from 10 µM to 100 µM did not improve the Sec incorporation ratio (FIG. 14B). In order to facilitate continuous selenium supply to SelD, pSecUAG-AD was modified to additionally encode the Sec-containing thioredoxin of *T. denticola* (Kim, et al., *Biochem Biophys Res Commun*, 461:648-652 (2015)). The developed pSecUAG-ADT system produced mixtures of GPx1(Sec49) and GPx1(Ser49) in which the former is the major product (FIGS. 9G and 14C, 14D). Thus, selenium supply to SelD was revealed as a limiting step.

Example 10: Variants of allo-tRNA$^{UTu}$ are Also Functional

Materials and Methods

Sequences

```
>allo-tRNA^UTu (Ac-3U variant)
                                   (SEQ ID NO: 32)
GGAGGTTGAACTTCTATCTGGTGATAGACGGGAACTCTAAATTCCTTGAA

ATGCCTCGCCGCATTGGGTTCGATTCCCTTCTCCTCCGCCA

>allo-tRNA^UTu (Ac-bU variant)
                                   (SEQ ID NO: 33)
GGAGGTGGAACTTCTATCTGGTGATAGACGGGAACTCTAAATTCCTTGAA

ATGCCTCGCCGCATTGGGTTCGATTCCCTTCCCCTCCGCCA
```

>allo-tRNA^UTu (D-3b variant)
(SEQ ID NO: 34)
GGAGGGGAACTTCTGTCTGGTGGCAGACGGGAACTCTAAATTCCTTGAAA

TGCCTCGCCGCATTGGGTTCGATTCCCTTCCCCTCCGCCA

>allo-tRNA^UTu2
(SEQ ID NO: 35)
GGACGGGGGTTCCGTCTGGTGACGGTCGCGGGCTCTAAACCCGTCAGGAC

GCTGTGCAGGCGTTAGGTTCGATTCCTCCCCCGTCCGCCA

>allo-tRNA^UTu2 (G21 variant)
(SEQ ID NO: 36)
GGACGGGGGTTCCGTCTGGTGGCGGTCGCGGGCTCTAAACCCGTCAGGAC

GCTGTGCAGGCGTTAGGTTCGATTCCTCCCCCGTCCGCCA

>2225 (also referred to as allo-tRNA^UTu)
(SEQ ID NO: 31)
GGAGGGGAACTTCTATCTGGTGATAGACGGGAACTCTAAATTCCTTGAAA

TGCCTCGCCGCATTGGGTTCGATTCCCTTCCCCTCCGCCA

>2459
(SEQ ID NO: 37)
GGAGTGGGGTTCCGGCTGGTGCCGGTCGCGGGCTCTAAACCCGTCAGGAC

GCTGCGACGCGTAAGGTTCGATTCCTCCCCACTCCGCCA

>S15 UU variant
(SEQ ID NO: 38)
GGAGGGCATTTTCAGTCGGTACTGGACGCCGTCTCTAAAACGGTTGCAGG

GTCTTAGTCAGCTCTGGGAGTTCGACTCTCCTGCCCTCCGCCA

>S15 CU variant
(SEQ ID NO: 39)
GGAGGGCACTTTCAGTCGGTACTGGACGCCGTCTCTAAAACGGTTGCAGG

GTCTTAGTCAGCTCTGGGAGTTCGACTCTCCTGCCCTCCGCCA

>S15 UC variant
(SEQ ID NO: 40)
GGAGGGCATCTTCAGTCGGTACTGGACGCCGTCTCTAAAACGGTTGCAGG

GTCTTAGTCAGCTCTGGGAGTTCGACTCTCCTGCCCTCCGCCA

>S15 AA variant
(SEQ ID NO: 41)
GGAGGGCAAATTCAGTCGGTACTGGACGCCGTCTCTAAAACGGTTGCAGG

GTCTTAGTCAGCTCTGGGAGTTCGACTCTCCTGCCCTCCGCCA

>S15 AU variant
(SEQ ID NO: 42)
GGAGGGCAATTTCAGTCGGTACTGGACGCCGTCTCTAAAACGGTTGCAGG

GTCTTAGTCAGCTCTGGGAGTTCGACTCTCCTGCCCTCCGCCA

The nucleotide sequences of Rx and Sh SelA were optimized for use in *E. coli*:

>Rubrobacter xylanophilus SelA
(SEQ ID NO: 83)
ATGCTGGATGCAGAACGTCAGAGCCGTCTGCGTAGCCTGCCTGCAGTTGA

TGCAGTTCTGCGTGGTCCGGCAGCAGGTCTGGCAGCACGTCATGGTCGTG

CAGCAGTTGCAGCAGCAGTTCGTGAAGTTCTGGAAGGTCTGCGTCGTGAA

ATTGCAGCCGGTGGTAGTCCGGATGTTAGCGGTCGTGCCGTTGCAGAAGG

TGCAGCCCGTCTGCTGAGTGGTCGTGGCCTGCGTCGCGTTGTTAATGCAA

CCGGTGTTGTTCTGCATACCAATCTGGGTCGTGCGGTTCTGAGCGAACGT

GCAGCCGCAGCAGCGGCACGTGCAGGCACCAGCTATAGCAATCTGGAATA

TGATCTGAGCCGTGGTCGTCGTGGTAGCCGTTATGATCATGCAGTTCCTC

TGCTGCGTGAACTGACCGGTGCAGAAGATGCACTGGTTGTTAATAACTGT

GCCGGTGCAACCCTGCTGGCACTGAGCGCACTGGCAGGCGAAGAAGGTGA

AGGTCCGCCTGAAGTTGTTGTTAGTCGTGGTCAGCTGATTGAAATTGGTG

GTGGTTTTCGTATTCCGGAAGTGCTGGAACTGAGTGGTGCCGTTCTGCGC

GAAGTTGGTACAACCAATCGTACCCGTCTGAGCGATTATGAACGTGCACT

GAGTGAACGTACCCGTGCAATTCTGTGGGTTCATCCGAGCAATTTTGAAA

TTCGCGGTTTTACCGAAAGCGCAGGTATTGCAGAACTGGCTGGTCTGGGT

CCTCCGGTTGTTGCAGATCTGGGTAGCGGTGCACTGCTGCCGCTGGGTGG

TGAACCGCTGGTTCAGGCAGCACTGCGTGATGGTGCCGAACTGGCACTGT

TTAGCGGTGATAAACTGCTGGGTGGACCGCAGGCTGGTATTGCCGCAGGT

AGCAGCCGTCTGGTTCGTCGTATGCGTCGTCATCCGCTGGTGCGTGCCCT

GCGTGCAGATAAACTGTGCCTGGCAGCCCTGGAAGCAACACTGCGTGCAT

ATCTGGAAGGCCGTGCCGAAGAAGAAGTTCCGGCACAGCGTATGCTGCGC

GAACCACTGGAAGGTGTTGAAGCACGTGCCCGTCGTCTGGCAAGCGCACT

GAGTCGTGAAGTGCCTGGTCTGGAAGTTGGTGTTGTGCCGAGCGTTGCAC

GTAGCGGTGGTGGCACCCTGCCTGGTTATGAAATTCCGAGCTTTGCAGCA

CGTGTTCTGGGTGCAGATGCAGAAGCCCTGGCAGCGCGTCTGCGTGCCGC

AGAACCGCCTGTTGTGGGTCGTGTTCATGAAGGTGCCCTGCTGCTGGATG

CCCGTACCCTGCTGCCAGGTGATGAAGAAGCAGTTGTTGAAGCGCTGCGT

GAGGCAGCCCGTGGTTAA

>Sulfurimonas honlongensis SelA
(SEQ ID NO: 85)
ATGTTCCTGCTGAAAAGCATTCCGAAAGTGGATAAGTTTATCGCCAAGAA

AGAGTTTAAAACCCTGGGTAGCGCACTGGTTATGAGCCTGACCAAAGAAC

TGCTGAGCGAACTGCGTGAAAACATTCTGAATGGTCGTGTTACCACCTTT

AGCGAAGATGAACTGGTTAAAGAGCTGCTGCAGCGTTATACCGAACTGAC

CAAACCGAGCCTGCAGACCCTGATTAATGCAACCGGTATTATTGTTCATA

CCAATCTGGGTCGTAGCCTGATTGATGCAGATGCATTTGATCGTGTTAAA

GAACTGATGACCAACTATAACAACCTGGAATTTAATCTGGAAAGCGGTAA

ACGTGGTGAACGCTATAGTCTGATTAGCAAAAGCGTTTGTAGCCTGCTGG

GTTGTGAAGATGTTCTGATTGTGAATAATAACGCCAGCGCAGTTTTTCTG

ATTCTGAACACCTTTGCGCGTAAAAAAGAAGTTGTTGTTAGTCGCGGTGA

ACTGGTGGAAATTGGTGGTAGCTTTCGTGTTCCGGATGTTATGAAACAGA

GCGGTGCAAAACTGGTTGAAGTTGGCACCACCAATAAAACCCATCTGTAT

GATTATGAAGATGCCATCGGTAAAAAAACGAGCATGCTGATGAAAGTGCA

CAAAAGCAACTATAGCATTGAAGGTTTTAGCAGCGACGTGGAATTTGGCG

AAATTGTTAAACTGGCATGTGAAAAAGGCCTGATCGATTATTATGATATG

GGTAGCGGTCACCTGTTTGATCTGCCGTATGGTCTGGATGAACCGAGCGT

TCTGGACTTTATGAAACTGAATCCGAGTCTGCTGAGCTTTAGCGGTGATA

AACTGCTGGGTAGTGTTCAGGCAGGCATTATTGTTGGCAAAAAAAGTAT

-continued
ATCGACATGCTGAAGAAAAACCAGCTGCTGCGTATGCTGCGTGTGGATAA

ACTGACCCTGGCACTGCTGGAAGAAAGTTTTAAAGCAATTCTGCTGGGCA

ACAAAGAGCAGATTCCGACCGCACGTATGCTGTTTCGTAGCACCGATGAA

CTGCGCGAAGATGCAATGCAGGTTCAGCAGAAACTGAAAAAAAACATCAA

GACCAACATCGTGGATACCAAAACACTGATTGGTGGCGGTACAACCCCGA

ATAAAACCATTCCGAGCGTTGCCCTGGTTATTGAAAGCAAAAACATTAAG

GTGAAAAAACTGCAGAAGCTGTTTCGCCAGAAAAGTATTATTGGTCGCAT

CGAGGATGATGAATTTCTGCTGGATTTTCGTACGATTCAGAAAACCCAAC

TGCAGCAGGTTGTTGATGCAATTGATGAAATTACCGACGTGTAA

FIG. 15A (SEQ ID NO: 57)
GGAGGGGAACUUCUAUCUGGUGAUAGACGGGAACUCUAAAUUCCUUGAAA

UGCCUCGCCGCAUUGGGUUCGAUUCCCUUCCCCUCCGCCA

FIG. 15B (SEQ ID NO: 58)
GGACGGGGGUUCCGUCUGGUGACGGUCGCGGGCUCUAAACCCGUCAGGAC

GCUGUGCAGGCGUUAGGUUCGAUUCCUCCCCCGUCCGCCA

Results

Variants of the nucleotide sequence of allo-tRNA$^{UTu}$ and the amino acid sequence of As SelA were engineered. Since allo-tRNA$^{UTu}$ is not the original substrate of As SelA, there maybe room for improvement (Miller, et al., *FEBS Lett,* 589:2194-2199 (2015)). Some characteristic features of *Aeromonas* tRNA$^{Sec}$ were each transplanted to allo-tRNA$^{UTu}$ (FIG. 15A-15B). The tRNA$^{Sec}$ species of *Aeromonas* and some other bacteria have a bulged pyrimidine at position 5 or 5a in the 7-bp acceptor stem (Mukai, et al., *Angew Chem Int Ed Engl,* 55, 5337-5341 (2016); Santesmasses, et al., *PLoS Comput Biol,* 13, e1005383 (2017)). Two allo-tRNA$^{UTu}$ variants having a bulged 5aU were made (FIG. 15A-15B). The U14:G21 wobble base pair in the D-stem of As tRNA$^{Sec}$ was transplanted to make variant D-3b (FIGS. 10A and 15A-15B).

Another type of UTu tRNA from an alanine-accepting allo-tRNA species (named 9/3-3, see also Examples above) (Mukai, et al., *Nucleic Acids Res,* 45:2776-2785 (2017)) to make allo-tRNA$^{UTu2}$ (FIG. 15A-15B). Effects of allo-tRNA engineering were assessed by observing the yields of the FDH$_H$ variant carrying five Sec residues (FIG. 15C).

Figure 14E:
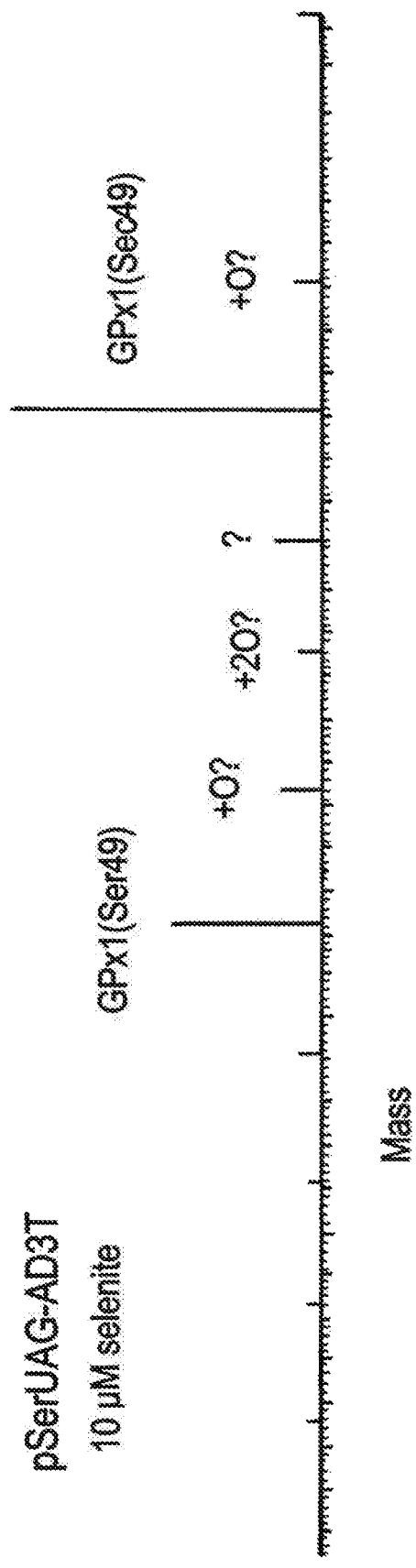
Figure 14F:
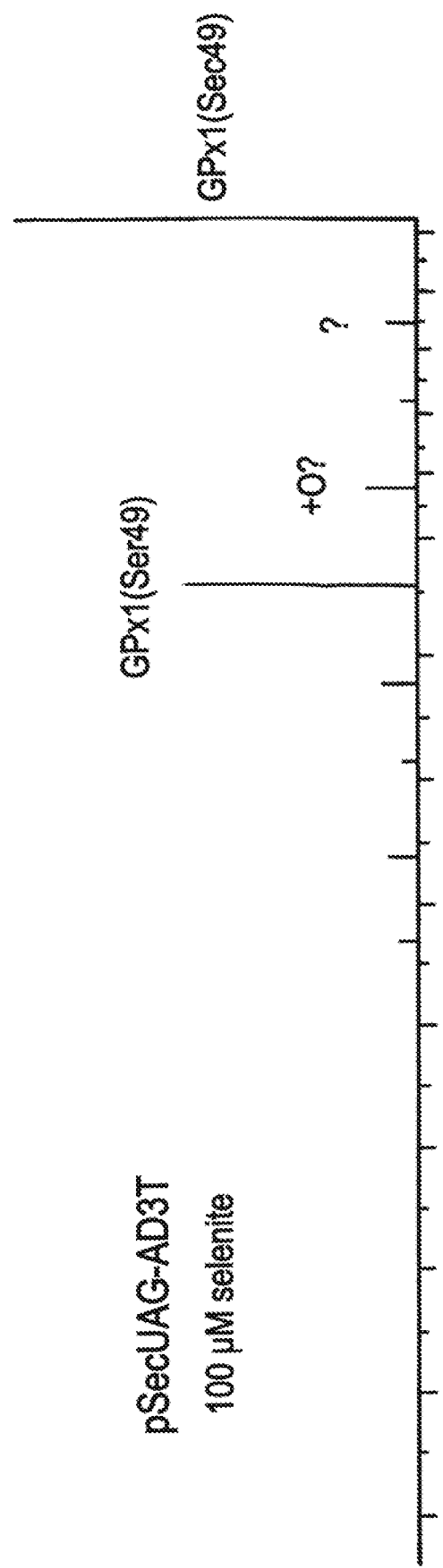

To facilitate experiments, the expression level of As SelA was significantly reduced. First, the As SelA expression cassette of pSecUAG-AD (100 copies per cell) was removed and transferred to a low-copy-number plasmid (5-8 copies per cell). Then the AUG start codon for As SelA was mutated to GUG to further decrease its translation level. With these limited amounts of As SelA molecules, the D-3b variant produced the largest amount of the FDH$_H$ variant carrying five Sec residues (FIG. 15C). On the other hand, allo-tRNA$^{UTu2}$ and its variant carrying U14:G21 were less active than the original allo-tRNA$^{UTu}$ (FIG. 15D), probably because they are not an inherent substrate of SerRS. Intact mass analysis was performed using the same GPx1 reporter. A modified pSecUAG-ADT system (FIG. 10B) (named pSecUAG-AD3T) expressing the D-3b variant instead of allo-tRNA$^{UTu}$ gave similar results as those obtained with the original pSecUAG-ADT system (FIGS. 10C and 14C-14F). A small improvement was observed (FIGS. 10C and 14E).

Two other SelA species from *Rubrobacter xylanophilus* and *Sulfurimonas honglongensis* and six other allo-tRNA variants were also tested. *R. xylanophilus* and *S. honglongensis* have a small tRNA$^{Sec}$ like *A. salmonicida*.

The results are shown in FIGS. 16A-16B. Sh, As, Rx denote *Sulfurimonas honglongensis, Aeromonas salmonicida, Rubrobacter xylanophilus*, respectively. 2225, 2459, S15 were derived from 9/3-1, 9/3-2, 8/4-1, respectively (Mukai, et al., *Nucleic Acids Res,* 45:2776-2785 (2017)). FIG. 16A shows that all of the combinations of allo-tRNA and SelA inserted Sec. The fdhF(140 Amb) gene variant was used as reporter. FIG. 16B shows that the two allo-tRNA$^{UTu}$ species derived from (9/3-1 and 9/3-2) were more active than the five allo-tRNA$^{UTu}$ species derived from (8/4-1). As SelA was used. The fdhF(3 UAG codons) gene variant was used as reporter.

The results indicated that diverse SelA species can be used for selenocysteinylation of allo-tRNA (FIG. 16A) and that allo-tRNA with a 9/3 structure is more active than allo-tRNA with an 8/4 structure (FIG. 16B).

We claim:

1. A nucleic acid comprising a heterologous expression control sequence operably linked to a nucleic acid sequence encoding a tRNA$^{Sec}$, the tRNA$^{Sec}$ comprising
a twelve base pair acceptor branch comprising a nine base pair acceptor stem and a three base pair T stem or an eight base pair acceptor stem and a four base pair T stem, and
wherein the tRNA$^{Sec}$ is recognized by a SerRS, when aminoacylated with serine the Ser-tRNA$^{Sec}$ is a substrate for a SelA, and when aminoacylated with seleocysteine the Sec-tRNA$^{Sec}$ is recognized by an EF-Tu.

2. The nucleic acid of claim 1, wherein the amino acid acceptor branch comprises an eight base pair acceptor stem and a four base pair T stem.

3. The nucleic acid of claim 1, wherein the amino acid acceptor branch comprises a nine base pair acceptor stem and a three base pair T stem.

4. The nucleic acid of claim 1, wherein the SerRS, the EF-Tu, or both are from *E. coli*.

5. The nucleic acid of claim 1, wherein the SelA is not wildtype *E. coli* SelA.

6. The nucleic acid of claim 1, wherein the SelA is from Sulfurimonas *hongkongensis*, Aeromonas *salmonicida*, or Rubrobacter *xylanophilus*.

7. The nucleic acid of claim 1, wherein the tRNA$^{Sec}$ is not a substrate for SelB.

8. The nucleic acid of claim 1, wherein the nucleic acid comprises a nucleic acid sequence comprising at least 85% sequence identity to any one of SEQ ID NOS:22-42, 61, or 62.

9. The nucleic acid of claim 8, wherein the nucleic acid comprises at least 85% sequence identity to SEQ ID NO:36.

10. The nucleic acid of claim 1, wherein the nucleic acid is DNA or RNA.

11. An expression vector comprising the nucleic acid of claim 1.

12. A host cell comprising the nucleic acid of claim 1.

13. The host cell of claim 12, wherein the host cell is a prokaryote, archaeon, or eukaryote.

14. The host cell of claim 13, wherein the prokaryote is *E. coli*.

15. The host cell of claim 12, wherein the nucleic acid is incorporated into the genome of the cell.

16. The host cell of claim 15, wherein the host cell is a genetically recoded organism.

17. A method of making a recombinant selenocysteine containing protein comprising co-expressing the nucleic acid of claim 1 in a host cell also expressing a SerRS, an EF-Tu, and a SelA with a polynucleotide comprising a codon that hybridizes with the anticodon of the tRNA$^{Sec}$.

18. The nucleic acid of claim 1, wherein the anticodon of the tRNA$^{Sec}$ recognizes a stop codon.

19. The nucleic acid of claim 1, wherein the variable arm comprises five base pairs, the anticodon arm comprises five base pairs, the D-arm comprises four base pairs, or a combination thereof.

20. The nucleic acid of claim 19, wherein the variable arm comprises six base pairs, the anticodon arm comprises five base pairs, and the D-arm comprises four base pairs.

21. A nucleic acid comprising a heterologous expression control sequence operably linked to a nucleic acid sequence encoding a tRNA$^{Sec}$, the nucleic acid sequence comprising at least 85% sequence identity to any one of SEQ ID NO:22-42, 61, or 62.

22. A nucleic acid comprising a heterologous expression control sequence operably linked to a nucleic acid sequence encoding a tRNA$^{Sec}$, the nucleic acid sequence comprising SEQ ID NO:31, 33, 34, 35, 36, 37, or 62, or a variant thereof with an alternative anticodon.

* * * * *